United States Patent
De Haro Garcia et al.

(10) Patent No.: US 11,479,546 B2
(45) Date of Patent: Oct. 25, 2022

(54) ANTIMALARIAL HEXAHYDROPYRIMIDINE ANALOGUES

(71) Applicant: UCB Biopharma SRL, Brussels (BE)

(72) Inventors: Teresa De Haro Garcia, Brussels (BE); Lloyd Malcolm King, Slough (GB); Martin Alexander Lowe, Slough (GB); Malcolm Maccoss, Seabrook Island (SC); Richard David Taylor, Slough (GB); Zhaoning Zhu, Slough (GB)

(73) Assignee: UCB Biopharma SRL

( * ) Notice: Subject to any disclaimer, the term of this patent is extended or adjusted under 35 U.S.C. 154(b) by 34 days.

(21) Appl. No.: 17/044,550

(22) PCT Filed: Apr. 2, 2019

(86) PCT No.: PCT/EP2019/058249
§ 371 (c)(1),
(2) Date: Oct. 1, 2020

(87) PCT Pub. No.: WO2019/192992
PCT Pub. Date: Oct. 10, 2019

(65) Prior Publication Data
US 2021/0094941 A1    Apr. 1, 2021

(30) Foreign Application Priority Data
Apr. 6, 2018   (GB) .................................... 1805816

(51) Int. Cl.
| | |
|---|---|
| A61P 33/06 | (2006.01) |
| C07D 403/12 | (2006.01) |
| C07D 493/08 | (2006.01) |
| C07D 471/04 | (2006.01) |
| C07D 239/22 | (2006.01) |
| C07D 401/12 | (2006.01) |
| C07D 413/14 | (2006.01) |
| C07D 405/06 | (2006.01) |
| C07D 405/14 | (2006.01) |
| C07D 405/04 | (2006.01) |

(52) U.S. Cl.
CPC .......... *C07D 405/14* (2013.01); *C07D 239/22* (2013.01); *C07D 401/12* (2013.01); *C07D 403/12* (2013.01); *C07D 405/04* (2013.01); *C07D 405/06* (2013.01); *C07D 413/14* (2013.01); *C07D 471/04* (2013.01); *C07D 493/08* (2013.01)

(58) Field of Classification Search
CPC ..... A61P 33/06; C07D 403/12; C07D 493/08; C07D 471/04; C07D 239/22; C07D 401/12; C07D 413/12; C07D 405/06; C07D 405/14; C07D 405/04; Y02A 50/30
See application file for complete search history.

(56) References Cited

U.S. PATENT DOCUMENTS 10,870,635 B2 * 12/2020 Cherukury ......... C07D 491/048

FOREIGN PATENT DOCUMENTS

| WO | WO2017/089453 | 6/2017 |
| WO | WO2017/142825 | 8/2017 |
| WO | WO2017/144517 | 8/2017 |

OTHER PUBLICATIONS

Charlton et al., 2017, caplus abstract of WO 2017089453.*
International Search Report dated Jul. 2, 2019 for International Application No. PCT/EP2019/058249, 2 pages.

* cited by examiner

*Primary Examiner* — Sun Jae Yoo
(74) *Attorney, Agent, or Firm* — McDonnell Boehnen Hulbert & Berghoff LLP

(57) ABSTRACT

The application relates to a series of 2-imino-6-methylhexahydropyrimidin-4-one derivatives and 3-imino-5-methyl-1,2,4-thiadiazinane 1,1-dioxide derivatives of formula (I), substituted by an arylaminophenyl or heteroarylaminophenyl moiety. The compounds are potent inhibitors of the growth and propagation of the *Plasmodium falciparum* parasite in human blood and thus useful as pharmaceutical agents for the treatment of malaria.

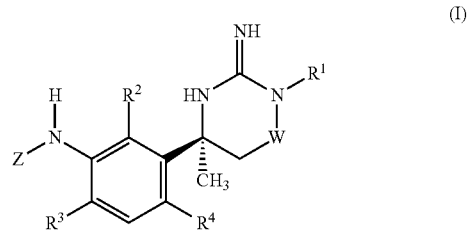

18 Claims, No Drawings

ANTIMALARIAL HEXAHYDROPYRIMIDINE ANALOGUES

CROSS-REFERENCE TO RELATED APPLICATIONS

This application is a U.S. national phase of International Application No. PCT/EP2019/058249, filed Apr. 2, 2019, which claims priority from Great Britain Application No GB1805816.4, filed Apr. 6, 2018, the disclosure of each of which is hereby incorporated by reference in its entirety.

The present invention relates to a class of heterocyclic compounds, and to their use in therapy. More particularly, this invention is concerned with pharmacologically active substituted hexahydropyrimidine derivatives, and analogues thereof. These compounds are potent inhibitors of the growth and propagation of the *Plasmodium falciparum*: parasite in human blood, and are accordingly of benefit as pharmaceutical agents, especially in the treatment of malaria.

Malaria is a mosquito-borne infectious disease, caused by a parasite of the genus *Plasmodium*, which has devastating consequences. In 2010, an estimated 225 million cases were reported, with 610,000 to 971,000 deaths, approximately 80% of which occurred in sub-Saharan Africa, mostly in young children (aged 5 years or less).

The compounds in accordance with the present invention, being potent inhibitors of the growth and propagation of the *P. falciparum* parasite in human blood, are therefore beneficial in the treatment of malaria.

In addition, the compounds in accordance with the present invention may be beneficial as pharmacological standards for use in the development of new biological tests and in the search for new pharmacological agents. Thus, the compounds of this invention may be useful as radioligands in assays for detecting pharmacologically active compounds.

WO 2017/142825 describes a family of heterocyclic compounds which are stated to be potent inhibitors of *P. falciparum* growth in vitro that may be useful for the treatment of malaria.

WO 2017/089453 and WO 2017/144517 describe heterocyclic compounds which are stated to be potent and selective inhibitors of plasmepsin V activity that are beneficial in the treatment of malaria.

WO 2016/172255, WO 2016/118404 and WO 2011/044181 describe certain classes of heterocyclic compounds which are stated to be BACE inhibitors that may be useful for treating Aβ-related pathologies including Alzheimer's disease.

WO 2008/103351, WO 2006/065277 and WO 2005/058311 describe a family of heterocyclic compounds that are stated to be aspartyl protease inhibitors. The compounds described in those publications are also stated to be effective in a method of inhibiting inter alia plasmepsins (specifically plasmepsins I and II) for treatment of malaria.

The present invention provides a compound of formula (I) or a pharmaceutically acceptable salt thereof:

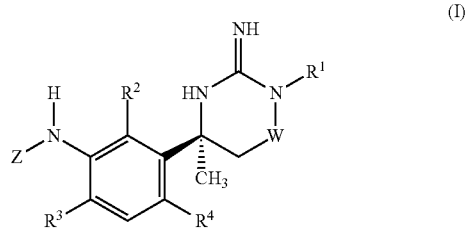

(I)

wherein

W represents C(O) or S(O)$_2$;

Z represents aryl or heteroaryl, either of which groups may be optionally substituted by one or more substituents;

R$^1$ represents C$_{2-6}$ alkyl, optionally substituted by hydroxy; or R$^1$ represents C$_{3-7}$ cycloalkyl, C$_{3-7}$ cycloalkyl(C$_{1-6}$)alkyl, aryl(C$_{1-6}$)alkyl, C$_{3-7}$ heterocycloalkyl, C$_{3-7}$ heterocycloalkyl(C$_{1-6}$)alkyl, C$_{4-9}$ heterobicycloalkyl, C$_{4-9}$ spiroheterocycloalkyl or heteroaryl(C$_{1-6}$)alkyl, any of which groups may be optionally substituted by one or more substituents; and R$^2$, R$^3$ and R$^4$ independently represent hydrogen, halogen or trifluoromethyl.

The compounds in accordance with the present invention are encompassed within the broadest generic scope of WO 2016/172255, WO 2016/118404, WO 2011/044181, WO 2008/103351, WO 2006/065277 and WO 2005/058311. There is, however, no specific disclosure in any of those publications of a compound of formula (I) as defined above, or a pharmaceutically acceptable salt thereof.

The present invention also provides a compound of formula (I) as defined above, or a pharmaceutically acceptable salt thereof, for use in therapy.

The present invention also provides a compound of formula (I) as defined above, or a pharmaceutically acceptable salt thereof, for use in the treatment and/or prevention of malaria.

The present invention also provides a method for the treatment and/or prevention of malaria which comprises administering to a patient in need of such treatment an effective amount of a compound of formula (I) as defined above, or a pharmaceutically acceptable salt thereof.

The present invention also provides the use of a compound of formula (I) as defined above, or a pharmaceutically acceptable salt thereof, for the manufacture of a medicament for the treatment and/or prevention of malaria.

Where any of the groups in the compounds of formula (I) above is stated to be optionally substituted, this group may be unsubstituted, or substituted by one or more substituents. Typically, such groups will be unsubstituted, or substituted by one, two or three substituents, generally by one or two substituents.

For use in medicine, the salts of the compounds of formula (I) will be pharmaceutically acceptable salts. Other salts may, however, be useful in the preparation of the compounds of use in the invention or of their pharmaceutically acceptable salts.

Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002.

Suitable alkyl groups which may be present on the compounds of use in the invention include straight-chained and branched C$_{1-6}$ alkyl groups, for example C$_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "C$_{1-6}$ alkoxy", "C$_{1-6}$ alkylthio", "C$_{1-6}$ alkylsulfonyl" and "C$_{1-6}$ alkylamino" are to be construed accordingly.

The term "C$_{3-7}$ cycloalkyl" as used herein refers to monovalent groups of 3 to 7 carbon atoms derived from a saturated monocyclic hydrocarbon, and may comprise benzo-fused analogues thereof. Suitable C$_{3-7}$ cycloalkyl groups include cyclopropyl, cyclobutyl, benzocyclobutenyl, cyclopentyl, indanyl, cyclohexyl and cycloheptyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzo-furanyl, dihydrobenzothienyl, pyrrolidinyl, indolinyl, isoindolinyl, oxazolidinyl, thiazolidinyl, isothiazolidinyl, imidazolidinyl, tetrahydropyranyl, chromanyl, dioxanyl, tetrahydrothiopyranyl, piperidinyl, 1,2,3,4-tetrahydroquinolinyl, 1,2,3,4-tetrahydro-isoquinolinyl, piperazinyl, 1,2,3,4-tetrahydroquinoxalinyl, hexahydro-[1,2,5]thiadiazolo-[2,3-a]pyrazinyl, homopiperazinyl, morpholinyl, benzoxazinyl, thiomorpholinyl, azepanyl, oxazepanyl, diazepanyl, thiadiazepanyl and azocanyl.

The term "$C_{4-9}$ heterobicycloalkyl" as used herein refers to monovalent groups of 4 to 9 carbon atoms derived from a saturated bicyclic hydrocarbon, comprising one or more heteroatoms selected from oxygen, sulphur and nitrogen. Typical heterobicycloalkyl groups include 3-azabicyclo[3.1.0]hexanyl, 2-oxa-5-azabicyclo[2.2.1]heptanyl, 7-oxabicyclo[2.2.1]hexanyl, 6-azabicyclo[3.2.0]heptanyl, 3-azabicyclo[3.1.1]heptanyl, 6-oxa-3-azabicyclo[3.1.1]heptanyl, 3-azabicyclo[4.1.0]heptanyl, 2-oxabicyclo[2.2.2]octanyl, quinuclidinyl, 2-oxa-5-azabicyclo[2.2.2]octanyl, 3-azabicyclo[3.2.1]octanyl, 8-oxabicyclo-[3.2.1]octanyl, 8-azabicyclo[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo[3.3.1]nonanyl, 3,7-dioxa-9-azabicyclo[3.3.1]nonanyl and 3,9-diazabicyclo[4.2.1]nonanyl.

The term "$C_{4-9}$ spiroheterocycloalkyl" as used herein refers to saturated bicyclic ring systems containing 4 to 9 carbon atoms and at least one heteroatom selected from oxygen, sulphur and nitrogen, in which the two rings are linked by a common atom. Suitable spiroheterocycloalkyl groups include 5-azaspiro[2.3]hexanyl, 5-azaspiro[2.4]-heptanyl, 2-oxaspiro[3.3]heptanyl, 2-azaspiro[3.3]heptanyl, 2-oxa-6-azaspiro[3.3]-heptanyl, 3-oxa-6-azaspiro[3.3]heptanyl, 6-thia-2-azaspiro[3.3]heptanyl, 2-oxa-6-azaspiro-[3.4]octanyl, 2-oxa-6-azaspiro[3.5]nonanyl, 7-oxa-2-azaspiro[3.5]nonanyl, 2-oxa-7-azaspiro[3.5]nonanyl and 2,4,8-triazaspiro[4.5]decanyl.

The term "heteroaryl" as used herein refers to monovalent aromatic groups containing at least five atoms derived from a single ring or multiple condensed rings, wherein one or more carbon atoms have been replaced by one or more heteroatoms selected from oxygen, sulfur and nitrogen. Suitable heteroaryl groups include furyl, benzofuryl, dibenzofuryl, thienyl, benzothienyl, thieno[2,3-c]pyrazolyl, thieno[3,2-c]-pyridinyl, dibenzothienyl, pyrrolyl, indolyl, pyrrolo[2,3-b]pyridinyl, pyrrolo[3,2-c]-pyridinyl, pyrrolo[3,4-b]pyridinyl, pyrazolyl, pyrazolo[1,5-a]pyridinyl, pyrazolo[3,4-d]-pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]-thiazolyl, imidazo[1,2-a]pyridinyl, imidazo[4,5-b]pyridinyl, purinyl, imidazo[1,2-a]-pyrimidinyl, imidazo[1,2-a]pyrazinyl, oxadiazolyl, thiadiazolyl, triazolyl, [1,2,4]triazolo-[1,5-a]pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups. Additional groups include pyrazolo[3,4-b]pyridinyl, imidazo[1,5-a]pyridinyl and [1,2,4]triazolo[1,5-a]pyridinyl.

The term "halogen" as used herein is intended to include fluorine, chlorine, bromine and iodine atoms, typically fluorine, chlorine or bromine.

The absolute stereochemical configuration of the chiral carbon atom in the W-containing six-membered ring of the compounds according to the invention is as depicted in formula (I) above. Generally, the compounds in accordance with the invention are at least 51% enantiomerically pure (by which it is meant that a sample thereof comprises a mixture of enantiomers containing 51% or more of the enantiomer depicted in formula (I) and 49% or less of the opposite antipode). Typically, the compounds in accordance with the invention are at least 60% enantiomerically pure. Appositely, the compounds in accordance with the invention are at least 75% enantiomerically pure. Suitably, the compounds in accordance with the invention are at least 80% enantiomerically pure. More suitably, the compounds in accordance with the invention are at least 85% enantiomerically pure. Still more suitably, the compounds in accordance with the invention are at least 90% enantiomerically pure. Even more suitably, the compounds in accordance with the invention are at least 95% enantiomerically pure. Preferably, the compounds in accordance with the invention are at least 99% enantiomerically pure. Ideally, the compounds in accordance with the invention are at least 99.9% enantiomerically pure.

Where the compounds of formula (I) have one or more additional asymmetric centres, they may accordingly exist as enantiomers. Where the compounds in accordance with the invention possess one or more additional asymmetric centres, they may also exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)↔enol ($CH=CHOH$) tautomers or amide ($NHC=O$)↔hydroxyimine ($N=COH$) tautomers or imide ($NHC=NH$)↔aminoimine ($N=CNH_2$) tautomers. Formula (I) and the formulae depicted hereinafter are intended to represent all individual tautomers and all possible mixtures thereof, unless stated or shown otherwise. In addition, under certain circumstances, e.g. where $R^2$ represents halogen, compounds of formula (I) may exist as atropisomers. Formula (I) and the formulae depicted hereinafter are intended to represent all individual atropisomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium; D) or $^3H$ (tritium; T) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

In a first embodiment, W represents C(O). In a second embodiment, W represents S(O)$_2$.

In a first embodiment, the present invention provides a compound of formula (IA) or a pharmaceutically acceptable salt thereof:

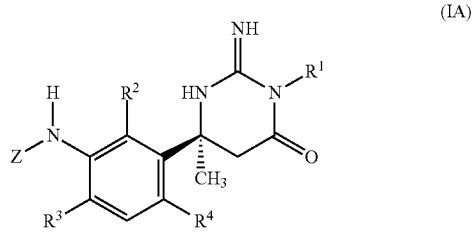

(IA)

wherein

Z, R$^1$, R$^2$, R$^3$ and R$^4$ are as defined above.

In a second embodiment, the present invention provides a compound of formula (IB) or a pharmaceutically acceptable salt thereof:

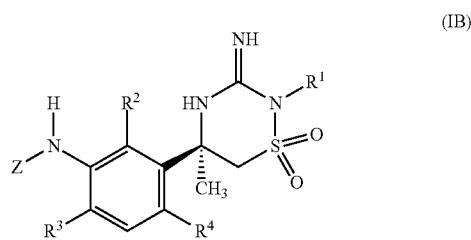

(IB)

wherein

Z, R$^1$, R$^2$, R$^3$ and R$^4$ are as defined above.

In a first embodiment, Z represents aryl, which group may be optionally substituted by one or more substituents. In a second embodiment, Z represents heteroaryl, which group may be optionally substituted by one or more substituents.

Typically, Z represents phenyl, naphthyl, furyl, benzofuryl, dibenzofuryl, thienyl, benzothienyl, thieno[2,3-c]pyrazolyl, thieno[3,2-c]pyridinyl, dibenzothienyl, pyrrolyl, indolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-d]pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]-pyridinyl, imidazo[4,5-b]pyridinyl, purinyl, imidazo[1,2-a]pyrimidinyl, imidazo[1,2-a]-pyrazinyl, oxadiazolyl, thiadiazolyl, triazolyl, [1,2,4]triazolo[1,5-a]pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl or chromenyl, any of which groups may be optionally substituted by one or more substituents. Additionally, Z may represent 2,3-dihydroindolyl, 2,3-dihydrobenzoxazinyl, pyrazolo[3,4-b]pyridinyl, imidazo[1,5-a]pyridinyl or [1,2,4]triazolo[1,5-a]-pyridinyl, any of which groups may be optionally substituted by one or more substituents.

Appositely, Z represents phenyl, naphthyl, 2,3-dihydroindolyl, 2,3-dihydrobenzoxazinyl, pyrazolyl, pyrazolo[1,5-a]pyridinyl, pyrazolo[3,4-b]pyridinyl, indazolyl, imidazo[1,2-a]pyridinyl, imidazo[1,5-a]pyridinyl, imidazo[4,5-b]pyridinyl, [1,2,4]-triazolo[1,5-a]pyridinyl, pyridinyl, quinolinyl, isoquinolinyl, pyridazinyl, pyrimidinyl or pyrazinyl, any of which groups may be optionally substituted by one or more substituents.

More particularly, Z represents phenyl, pyridinyl, pyridazinyl, pyrimidinyl or pyrazinyl, any of which groups may be optionally substituted by one or more substituents.

Suitably, Z represents phenyl or pyridinyl, either of which groups may be optionally substituted by one or more substituents.

In a first embodiment, Z represents phenyl, which group may be optionally substituted by one or more substituents. In a second embodiment, Z represents pyridinyl, which group may be optionally substituted by one or more substituents. In a third embodiment, Z represents pyridazinyl, which group may be optionally substituted by one or more substituents. In a fourth embodiment, Z represents pyrimidinyl, which group may be optionally substituted by one or more substituents. In a fifth embodiment, Z represents pyrazinyl, which group may be optionally substituted by one or more substituents.

Typical examples of optional substituents on Z include one, two or three substituents independently selected from halogen, cyano, nitro, $C_{1-6}$ alkyl, difluoromethyl, trifluoromethyl, hydroxy, hydroxy($C_{1-6}$)alkyl, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, amino($C_{1-6}$)alkyl, di($C_{1-6}$)alkylamino($C_{1-6}$)alkyl, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl. Additional examples include trifluoroethyl, cyclopropyl, cyclobutyl, cyanocyclobutyl, phenyl, azetidinyl, oxopyrrolidinyl, morpholinyl, oxazolyl, methyloxadiazolyl, triazolyl, methyltetrazolyl, difluoroethoxy, trifluoroethoxy, phenoxy, methylenedioxy, difluoromethylenedioxy and di($C_{1-6}$)alkylsulfoximino.

Selected examples of optional substituents on Z include one, two or three substituents independently selected from halogen, cyano, $C_{1-6}$ alkyl, difluoromethyl, trifluoromethyl, trifluoroethyl, cyclopropyl, cyclobutyl, cyanocyclobutyl, phenyl, azetidinyl, oxopyrrolidinyl, morpholinyl, oxazolyl, methyloxadiazolyl, triazolyl, methyltetrazolyl, oxo, $C_{1-6}$ alkoxy, difluoromethoxy, trifluoromethoxy, difluoroethoxy, trifluoroethoxy, phenoxy, methylenedioxy, difluoromethylenedioxy, $C_{1-6}$ alkylsulfonyl, di($C_{1-6}$)alkylamino, $C_{2-6}$ alkylcarbonyl, $C_{2-6}$ alkoxycarbonyl and di($C_{1-6}$)alkylsulfoximino.

Suitable examples of optional substituents on Z include one, two or three substituents independently selected from halogen, cyano, $C_{1-6}$ alkyl and trifluoromethyl.

Typical examples of particular substituents on Z include one, two or three substituents independently selected from fluoro, chloro, bromo, cyano, nitro, methyl, ethyl, isopropyl, difluoromethyl, trifluoromethyl, hydroxy, hydroxymethyl, hydroxyethyl, hydroxyisopropyl, oxo, methoxy, difluoromethoxy, trifluoromethoxy, methylthio, methylsulfinyl, methylsulfonyl, amino, methylamino, dimethylamino, aminomethyl, dimethylaminomethyl, acetylamino, methoxycarbonylamino, methylsulfonylamino, formyl, acetyl, carboxy, methoxycarbonyl, ethoxycarbonyl, aminocarbonyl, methylaminocarbonyl, dimethylaminocarbonyl, aminosulfonyl, methylaminosulfonyl and dimethylaminosulfonyl. Additional examples include tert-butyl, trifluoroethyl, cyclopropyl, cyclobutyl, cyanocyclobutyl, phenyl, azetidinyl, oxopyrrolidinyl, morpholinyl, oxazolyl, methyloxadiazolyl, triazolyl, methyltetrazolyl, isopropoxy, difluoroethoxy, trifluoroethoxy, phenoxy, methylenedioxy, difluoromethylenedioxy and dimethylsulfoximino.

Selected examples of particular substituents on Z include one, two or three substituents independently selected from fluoro, chloro, cyano, methyl, ethyl, tert-butyl, difluoromethyl, trifluoromethyl, trifluoroethyl, cyclopropyl, cyclobutyl, cyanocyclobutyl, phenyl, azetidinyl, oxopyrrolidinyl, morpholinyl, oxazolyl, methyloxadiazolyl, triazolyl, methyltetrazolyl, oxo, methoxy, isopropoxy, difluoromethoxy, trifluoromethoxy, difluoroethoxy, trifluoroethoxy, phenoxy, methylenedioxy, difluoromethylenedioxy, methylsulfonyl, dimethylamino, acetyl, methoxycarbonyl and dimethylsulfoximino.

Representative examples of particular substituents on Z include one, two or three substituents independently selected from methyl, cyclopropyl, difluoromethoxy and difluoroethoxy.

Suitable examples of particular substituents on Z include one, two or three substituents independently selected from fluoro, chloro, cyano, methyl and trifluoromethyl.

Selected values of Z include phenyl, fluorophenyl, chlorophenyl, cyanophenyl, methylphenyl, tert-butylphenyl, trifluoromethylphenyl, biphenylyl, oxopyrrolidinyl-phenyl, oxazolylphenyl, methyloxadiazolylphenyl, methoxyphenyl, isopropoxyphenyl, difluoromethoxyphenyl, trifluoromethoxyphenyl, phenoxyphenyl, methylenedioxyphenyl, difluoromethylenedioxyphenyl, methylsulfonylphenyl, methoxycarbonylphenyl, dimethylsulfoximinophenyl, difluorophenyl, (chloro)(fluoro)phenyl, (cyano)(fluoro)-phenyl, (fluoro)(methyl)phenyl, (fluoro)(methoxy)phenyl, (fluoro)(difluoromethoxy)-phenyl, (fluoro)(trifluoromethoxy)phenyl, (fluoro)(methylsulfonyl)phenyl, (chloro)-(cyano)phenyl, (chloro)(methylsulfonyl)phenyl, (cyano)(trifluoromethyl)phenyl, (cyano)(methoxy)phenyl, (cyano)(difluoromethoxy)phenyl, dimethylphenyl, dimethoxy-phenyl, trifluorophenyl, naphthyl, acetyl-2,3-dihydroindolyl, methyl-2,3-dihydrobenzoxazinyl, (dimethyl)(phenyl)pyrazolyl, pyrazolo[1,5-a]pyridinyl, fluoropyrazolo[1,5-a]pyridinyl, methylpyrazolo[3,4-b]pyridinyl, methylindazolyl, imidazo[1,2-a]pyridinyl, imidazo[1,5-a]pyridinyl, methylimidazo[4,5-b]pyridinyl, [1,2,4]triazolo[1,5-a]pyridinyl, pyridinyl, fluoropyridinyl, chloropyridinyl, cyanopyridinyl, methylpyridinyl, ethyl-pyridinyl, tert-butylpyridinyl, difluoromethylpyridinyl, trifluoromethylpyridinyl, trifluoroethylpyridinyl, cyclopropylpyridinyl, cyclobutylpyridinyl, cyanocyclobutyl-pyridinyl, azetidinylpyridinyl, morpholinylpyridinyl, triazolylpyridinyl, methyltetrazolyl-pyridinyl, methoxypyridinyl, difluoromethoxypyridinyl, trifluoromethoxypyridinyl, difluoroethoxypyridinyl, trifluoroethoxypyridinyl, dimethylaminopyridinyl, (fluoro)-(methoxy)pyridinyl, (chloro)(methyl)pyridinyl, (chloro)(trifluoromethyl)pyridinyl, (cyano)(methyl)pyridinyl, (cyano)(difluoromethyl)pyridinyl, (methyl)(trifluoromethyl)-pyridinyl, (methyl)(oxo)pyridinyl, (cyclopropyl)(oxo)pyridinyl, (methoxy)(methyl)-pyridinyl, (difluoromethoxy)(methyl)pyridinyl, quinolinyl, cyanoquinolinyl, difluoromethoxy-quinolinyl, isoquinolinyl, methylisoquinolinyl, difluoromethoxyisoquinolinyl, methylpyridazinyl, cyclopropylpyridazinyl, trifluoroethoxypyridazinyl, methyl-pyrimidinyl, tert-butylpyrimidinyl, trifluoromethylpyrimidinyl, cyclopropylpyrimidinyl, methylpyrazinyl, tert-butylpyrazinyl, cyclopropylpyrazinyl and difluoromethoxypyrazinyl.

Representative values of Z include methylpyridinyl, cyclopropylpyridinyl, difluoromethoxypyridinyl, difluoroethoxypyridinyl, (difluoromethoxy)(methyl)pyridinyl, cyclopropylpyridazinyl, cyclopropylpyrimidinyl and difluoromethoxypyrazinyl.

Typical values of Z include phenyl, fluorophenyl, chlorophenyl, cyanophenyl, methylphenyl, trifluoromethylphenyl, (fluoro)(methyl)phenyl and methylpyridinyl.

Appositely, $R^1$ represents $C_{3-7}$ cycloalkyl, $C_{3-7}$ cycloalkyl($C_{1-6}$)alkyl, aryl($C_{1-6}$)-alkyl, $C_{3-7}$ heterocycloalkyl, $C_{3-7}$ heterocycloalkyl($C_{1-6}$)alkyl, $C_{4-9}$ heterobicycloalkyl, $C_{4-9}$ spiroheterocycloalkyl or heteroaryl($C_{1-6}$)alkyl, any of which groups may be optionally substituted by one or more substituents.

Generally, $R^1$ represents $C_{2-6}$ alkyl, optionally substituted by hydroxy; or $R^1$ represents $C_{3-7}$ cycloalkyl, $C_{3-7}$ cycloalkyl($C_{1-6}$)alkyl, aryl($C_{1-6}$)alkyl, $C_{3-7}$ heterocycloalkyl, $C_{3-7}$ heterocycloalkyl($C_{1-6}$)alkyl or heteroaryl($C_{1-6}$)alkyl, any of which groups may be optionally substituted by one or more substituents.

More particularly, $R^1$ represents $C_{3-7}$ cycloalkyl, $C_{3-7}$ cycloalkyl($C_{1-6}$)alkyl, aryl-($C_{1-6}$)alkyl, $C_{3-7}$ heterocycloalkyl, $C_{3-7}$ heterocycloalkyl($C_{1-6}$)alkyl or heteroaryl($C_{1-6}$)-alkyl, any of which groups may be optionally substituted by one or more substituents.

Suitably, $R^1$ represents $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, $C_{4-9}$ heterobicycloalkyl or $C_{4-9}$ spiroheterocycloalkyl, any of which groups may be optionally substituted by one or more substituents.

Typically, $R^1$ represents $C_{3-7}$ cycloalkyl, $C_{3-7}$ cycloalkyl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Suitable values of $R^1$ include cyclobutyl, cyclohexyl, cyclopropylmethyl, tetrahydrofuranyl, tetrahydropyranyl, oxetanylmethyl, tetrahydropyranylmethyl, 7-oxabicyclo[2.2.1]heptanyl, 8-oxabicyclo[3.2.1]octanyl and 2-oxaspiro[3.3]heptanyl, any of which groups may be optionally substituted by one or more substituents.

Typical values of $R^1$ include cyclobutyl, cyclohexyl, cyclopropylmethyl, tetrahydrofuranyl, tetrahydropyranyl and tetrahydropyranylmethyl, any of which groups may be optionally substituted by one or more substituents.

A particular value of $R^1$ is tetrahydropyranyl, which group may be optionally substituted by one or more substituents.

Typical examples of optional substituents on $R^1$ include one, two or three substituents independently selected from halogen, cyano, nitro, $C_{1-6}$ alkyl, difluoromethyl, trifluoromethyl, hydroxy, hydroxy($C_{1-6}$)alkyl, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, amino($C_{1-6}$)alkyl, di($C_{1-6}$)alkylamino($C_{1-6}$)alkyl, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Selected examples of optional substituents on $R^1$ include one, two or three substituents independently selected from halogen, cyano, $C_{1-6}$ alkyl, trifluoromethyl and hydroxy.

Suitable examples of optional substituents on $R^1$ include one, two or three substituents independently selected from $C_{1-6}$ alkyl and hydroxy.

Typical examples of particular substituents on $R^1$ include one, two or three substituents independently selected from fluoro, chloro, bromo, cyano, nitro, methyl, ethyl, isopropyl, difluoromethyl, trifluoromethyl, hydroxy, hydroxymethyl, hydroxyethyl, hydroxyisopropyl, oxo, methoxy, difluoromethoxy, trifluoromethoxy, methylthio, methylsulfinyl, methylsulfonyl, amino, methylamino, dimethylamino, aminomethyl, dimethylaminomethyl, acetylamino, methoxycarbonylamino, methylsulfonylamino, formyl, acetyl, carboxy, methoxycarbonyl, ethoxycarbonyl, aminocarbonyl, methylaminocarbonyl, dimethylaminocarbonyl, aminosulfonyl, methylaminosulfonyl and dimethylaminosulfonyl.

Selected examples of particular substituents on $R^1$ include one, two or three substituents independently selected from fluoro, cyano, methyl, ethyl, isopropyl, trifluoromethyl and hydroxy.

Suitable examples of particular substituents on $R^1$ include one, two or three substituents independently selected from methyl and hydroxy.

Selected values of $R^1$ include (cyano)(methyl)cyclobutyl, (hydroxy)(methyl)-cyclobutyl, (ethyl)(hydroxy)cyclobutyl, (hydroxy)(isopropyl)cyclobutyl, (hydroxy)-(trifluoromethyl)cyclobutyl, cyclohexyl, difluorocyclohexyl, hydroxycyclopropylmethyl, tetrahydrofuranyl, tetrahydropyranyl, methyltetrahydropyranyl, dimethyltetrahydropyranyl, methyloxetanylmethyl, tetrahydropyranylmethyl, 7-oxabicyclo[2.2.1]heptanyl, 8-oxabicyclo[3.2.1]octanyl and 2-oxaspiro[3.3]heptanyl.

Particular values of $R^1$ include tetrahydropyranyl, methyltetrahydropyranyl and dimethyltetrahydropyranyl. In a first embodiment, $R^1$ represents tetrahydropyranyl. In a second embodiment, $R^1$ represents methyltetrahydropyranyl. In a third embodiment, $R^1$ represents dimethyltetrahydropyranyl.

Suitable values of $R^1$ include (hydroxy)(methyl)cyclobutyl, cyclohexyl, hydroxycyclopropylmethyl, tetrahydrofuranyl, tetrahydropyranyl and tetrahydropyranylmethyl.

Generally, $R^2$, $R^3$ and $R^4$ independently represent hydrogen or halogen.

Generally, $R^2$ represents hydrogen or halogen.

In a first embodiment, $R^2$ represents hydrogen. In a second embodiment, $R^2$ represents halogen, especially fluoro or chloro. In one aspect of that embodiment, $R^2$ represents fluoro. In another aspect of that embodiment, $R^2$ represents chloro. In a third embodiment, $R^2$ represents trifluoromethyl.

Selected values of $R^2$ include hydrogen, fluoro and chloro.

Suitably, $R^2$ represents chloro.

Generally, $R^3$ represents hydrogen or halogen.

In a first embodiment, $R^3$ represents hydrogen. In a second embodiment, $R^3$ represents halogen, especially fluoro or chloro. In one aspect of that embodiment, $R^3$ represents fluoro. In another aspect of that embodiment, $R^3$ represents chloro. In a third embodiment, $R^3$ represents trifluoromethyl.

Selected values of $R^3$ include hydrogen, fluoro and chloro.

Suitably, $R^3$ represents hydrogen or fluoro.

Generally, $R^4$ represents hydrogen or halogen.

In a first embodiment, $R^4$ represents hydrogen. In a second embodiment, $R^4$ represents halogen, especially fluoro or chloro. In one aspect of that embodiment, $R^4$ represents fluoro. In another aspect of that embodiment, $R^4$ represents chloro. In a third embodiment, $R^4$ represents trifluoromethyl.

Suitably, $R^2$ represents hydrogen or halogen; $R^3$ represents hydrogen or halogen; and $R^4$ represents hydrogen.

Appositely, $R^2$ represents halogen; $R^3$ represents hydrogen or halogen; and $R^4$ represents hydrogen.

Generally, $R^2$ represents hydrogen or halogen; and $R^3$ and $R^4$ both represent hydrogen.

One sub-class of compounds according to the invention is represented by the compounds of formula (IIA), and pharmaceutically acceptable salts thereof:

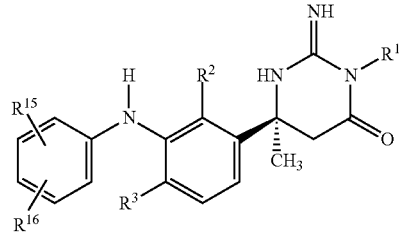

(IIA)

wherein $R^{15}$ and $R^{16}$ independently represent hydrogen, halogen, cyano, nitro, $C_{1-6}$ alkyl, difluoromethyl, trifluoromethyl, phenyl, oxopyrrolidinyl, oxazolyl, methyloxadiazolyl, hydroxy, hydroxy($C_{1-6}$)alkyl, $C_{1-6}$ alkoxy, difluoromethoxy, trifluoromethoxy, phenoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, amino($C_{1-6}$)alkyl, di($C_{1-6}$)alkylamino($C_{1-6}$)alkyl, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl, di($C_{1-6}$)alkylaminosulfonyl or di($C_{1-6}$)alkylsulfoximino; and $R^1$, $R^2$ and $R^3$ are as defined above.

Generally, $R^{15}$ and $R^{16}$ independently represent hydrogen, halogen, cyano, nitro, $C_{1-6}$ alkyl, difluoromethyl, trifluoromethyl, hydroxy, hydroxy($C_{1-6}$)alkyl, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$) alkylamino, amino($C_{1-6}$)alkyl, di($C_{1-6}$)alkylamino($C_{1-6}$)-alkyl, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl.

Suitably, $R^{15}$ and $R^{16}$ independently represent hydrogen, halogen, cyano, $C_{1-6}$ alkyl, trifluoromethyl, phenyl, oxopyrrolidinyl, oxazolyl, methyloxadiazolyl, $C_{1-6}$ alkoxy, difluoromethoxy, trifluoromethoxy, phenoxy, $C_{1-6}$ alkylsulfonyl, $C_{2-6}$ alkoxycarbonyl and di($C_{1-6}$)alkylsulfoximino.

Typically, $R^{15}$ and $R^{16}$ independently represent hydrogen, halogen, cyano, $C_{1-6}$ alkyl and trifluoromethyl.

In general, $R^{15}$ and $R^{16}$ may independently represent hydrogen, fluoro, chloro, bromo, cyano, nitro, methyl, ethyl, isopropyl, tert-butyl, difluoromethyl, trifluoromethyl, phenyl, oxopyrrolidinyl, oxazolyl, methyloxadiazolyl, hydroxy, hydroxymethyl, hydroxyethyl, hydroxyisopropyl, methoxy, isopropoxy, difluoromethoxy, trifluoromethoxy, phenoxy, methylthio, methylsulfinyl, methylsulfonyl, amino, methylamino, dimethylamino, aminomethyl, dimethylaminomethyl, acetylamino, methoxycarbonylamino, methylsulfonylamino, formyl, acetyl, carboxy, methoxycarbonyl, ethoxycarbonyl, aminocarbonyl, methylaminocarbonyl, dimethylaminocarbonyl, aminosulfonyl, methylaminosulfonyl, dimethylaminosulfonyl or dimethylsulfoximino.

In particular, $R^{15}$ and $R^{16}$ may independently represent hydrogen, fluoro, chloro, bromo, cyano, nitro, methyl, ethyl, isopropyl, difluoromethyl, trifluoromethyl, hydroxy, hydroxymethyl, hydroxyethyl, hydroxyisopropyl, methoxy, difluoromethoxy, trifluoromethoxy, methylthio, methylsulfinyl, methylsulfonyl, amino, methylamino, dimethylamino, aminomethyl, dimethylaminomethyl, acetylamino, methoxycarbonylamino, methylsulfonylamino, formyl, acetyl, carboxy, methoxycarbonyl, ethoxycarbonyl, aminocarbonyl, methylaminocarbonyl, dimethylaminocarbonyl, aminosulfonyl, methylaminosulfonyl or dimethylaminosulfonyl.

Appropriately, $R^{15}$ and $R^{16}$ may independently represent hydrogen, fluoro, chloro, cyano, methyl, tert-butyl, trifluoromethyl, phenyl, oxopyrrolidinyl, oxazolyl, methyloxadiazolyl, methoxy, isopropoxy, difluoromethoxy, trifluoromethoxy, phenoxy, methylsulfonyl, methoxycarbonyl or dimethylsulfoximino.

More particularly, $R^{15}$ and $R^{16}$ may independently represent hydrogen, fluoro, chloro, cyano, methyl or trifluoromethyl.

Suitable values of $R^{15}$ include hydrogen, halogen, cyano, $C_{1-6}$ alkyl, trifluoromethyl, phenyl, oxopyrrolidinyl, oxazolyl, methyloxadiazolyl, $C_{1-6}$ alkoxy, difluoro-methoxy, trifluoromethoxy, phenoxy, $C_{1-6}$ alkylsulfonyl, $C_{2-6}$ alkoxycarbonyl and di-($C_{1-6}$)alkylsulfoximino.

Typical values of $R^{15}$ include hydrogen, halogen, cyano, $C_{1-6}$ alkyl and trifluoromethyl.

In a first embodiment, $R^{15}$ represents hydrogen. In a second embodiment, $R^{15}$ represents halogen. In a first aspect of that embodiment, $R^{15}$ represents fluoro. In a second aspect of that embodiment, $R^{15}$ represents chloro. In a third embodiment, $R^{15}$ represents cyano. In a fourth embodiment, $R^{15}$ represents $C_{1-6}$ alkyl. In a first aspect of that embodiment, $R^{15}$ represents methyl. In a second aspect of that embodiment, $R^{15}$ represents tert-butyl. In a fifth embodiment, $R^{15}$ represents trifluoromethyl. In a sixth embodiment, $R^{15}$ represents phenyl. In a seventh embodiment, $R^{15}$ represents oxopyrrolidinyl (especially 2-oxopyrrolidin-1-yl). In an eighth embodiment, $R^{15}$ represents oxazolyl (especially oxazol-5-yl). In a ninth embodiment, $R^{15}$ represents methyloxadiazolyl (especially 2-methyl-1,3,4-oxadiazol-5-yl). In a tenth embodiment, $R^{15}$ represents $C_{1-6}$ alkoxy. In a first aspect of that embodiment, $R^{15}$ represents methoxy. In a second aspect of that embodiment, $R^{15}$ represents isopropoxy. In an eleventh embodiment, $R^{15}$ represents difluoromethoxy. In a twelfth embodiment, $R^{15}$ represents trifluoromethoxy. In a thirteenth embodiment, $R^{15}$ represents phenoxy. In a fourteenth embodiment, $R^{15}$ represents $C_{1-6}$ alkylsulfonyl. In a first aspect of that embodiment, $R^{15}$ represents methylsulfonyl. In a fifteenth embodiment, $R^{15}$ represents $C_{2-6}$ alkoxycarbonyl. In a first aspect of that embodiment, $R^{15}$ represents methoxycarbonyl. In a sixteenth embodiment, $R^{15}$ represents di($C_{1-6}$)alkylsulfoximino. In a first aspect of that embodiment, $R^{15}$ represents dimethylsulfoximino.

Particular values of $R^{15}$ include hydrogen, fluoro, chloro, cyano, methyl, tert-butyl, trifluoromethyl, phenyl, oxopyrrolidinyl, oxazolyl, methyloxadiazolyl, methoxy, isopropoxy, difluoromethoxy, trifluoromethoxy, phenoxy, methylsulfonyl, methoxycarbonyl and dimethylsulfoximino.

Specific values of $R^{15}$ include hydrogen, fluoro, chloro, cyano, methyl and trifluoromethyl.

Selected values of $R^{16}$ include hydrogen, halogen, cyano, $C_{1-6}$ alkyl, trifluoromethyl and $C_{1-6}$ alkoxy.

Typical values of $R^{16}$ include hydrogen and halogen.

In a first embodiment, $R^{16}$ represents hydrogen. In a second embodiment, $R^{16}$ represents halogen. In a first aspect of that embodiment, $R^{16}$ represents fluoro. In a second aspect of that embodiment, $R^{16}$ represents chloro. In a third embodiment, $R^{16}$ represents cyano. In a fourth embodiment, $R^{16}$ represents $C_{1-6}$ alkyl. In a first aspect of that embodiment, $R^{16}$ represents methyl. In a fifth embodiment, $R^{16}$ represents trifluoromethyl. In a sixth embodiment, $R^{16}$ represents $C_{1-6}$ alkoxy. In a first aspect of that embodiment, $R^{16}$ represents methoxy.

Specific values of $R^{16}$ include hydrogen, fluoro, chloro, cyano, methyl, trifluoromethyl and methoxy.

Apposite values of $R^{16}$ include hydrogen, fluoro and chloro.

Suitable values of $R^{16}$ include hydrogen and fluoro.

Another sub-class of compounds according to the invention is represented by the compounds of formula (IIB), and pharmaceutically acceptable salts thereof:

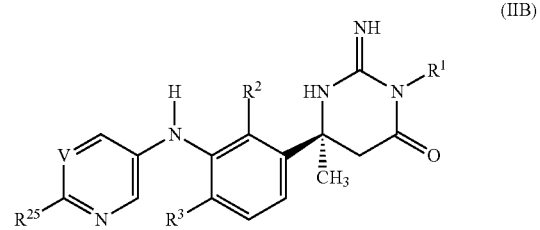

wherein

V represents N or CH;

$R^{25}$ represents methyl, cyclopropyl, difluoromethoxy or difluoroethoxy; and $R^1$, $R^2$ and $R^3$ are as defined above.

In a first embodiment, V represents N. In a second embodiment, V represents CH.

In a first embodiment, $R^{25}$ represents methyl. In a second embodiment, $R^{25}$ represents cyclopropyl. In a third embodiment, $R^{25}$ represents difluoromethoxy. In a fourth embodiment, $R^{25}$ represents difluoroethoxy (especially 2,2-difluoroethoxy).

A further sub-class of compounds according to the invention is represented by the compounds of formula (IIC), and pharmaceutically acceptable salts thereof:

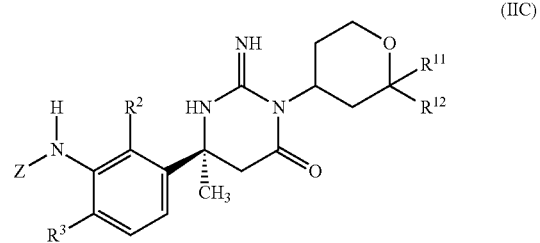

wherein $R^{11}$ represents hydrogen or methyl;

$R^{12}$ represents hydrogen or methyl; and

Z, $R^2$ and $R^3$ are as defined above.

In a first embodiment, $R^{11}$ represents hydrogen. In a second embodiment, $R^{11}$ represents methyl.

In a first embodiment, $R^{12}$ represents hydrogen. In a second embodiment, $R^{12}$ represents methyl.

In a first embodiment, $R^{11}$ and $R^{12}$ both represent hydrogen. In a second embodiment, $R^{11}$ represents hydrogen and $R^{12}$ represents methyl. In a third embodiment, $R^{11}$ and $R^{12}$ both represent methyl.

Specific novel compounds in accordance with the present invention include each of the compounds whose preparation is described in the accompanying Examples, and pharmaceutically acceptable salts thereof.

The present invention also provides a pharmaceutical composition which comprises a compound in accordance with the invention as described above, or a pharmaceutically acceptable salt thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

General methods for the preparation of the compounds of formula (I) as defined above are described in WO 2016/172255, WO 2016/118404, WO 2011/044181 and WO 2008/103351.

The compounds in accordance with the invention may be prepared by a process which comprises reacting a compound of formula Z—B(OH)$_2$ with a compound of formula (III):

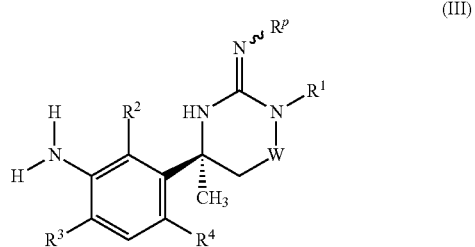

wherein W, Z, $R^1$, $R^2$, $R^3$ and $R^4$ are as defined above, and $R^p$ represents hydrogen or an N-protecting group; in the presence of a transition metal catalyst; followed, as necessary, by removal of the N-protecting group $R^p$.

Suitably, the transition metal catalyst of use in the above reaction is a copper(II) salt, e.g. copper(II) acetate. Suitably, the reaction is performed in the presence of a base, typically an organic base such as triethylamine.

The reaction between the compound of formula Z—B(OH)$_2$ and compound (III) is conveniently accomplished at ambient temperature in a suitable solvent, e.g. a chlorinated solvent such as dichloromethane.

Suitably, the N-protecting group R$^p$ is tert-butoxycarbonyl (BOC).

Where the N-protecting group R$^p$ is BOC, subsequent removal of the BOC group may suitably be accomplished by treatment with an acid, e.g. a mineral acid such as hydrochloric acid, or an organic acid such as trifluoroacetic acid, typically at ambient temperature in a suitable solvent, e.g. a chlorinated solvent such as dichloromethane, or a cyclic ether such as 1,4-dioxane.

In an alternative procedure, the compounds in accordance with the invention may be prepared by a process which comprises reacting a compound of formula (III) as defined above with a compound of formula Z-L$^1$, wherein Z is as defined above, and L$^1$ represents a suitable leaving group; in the presence of a transition metal catalyst; followed, as necessary, by removal of the N-protecting group R$^p$.

Suitably, the leaving group L$^1$ is a halogen atom, e.g. chloro, bromo or iodo.

Suitably, the transition metal catalyst of use in the reaction between the compound of formula Z—L$^1$ and compound (III) is a palladium-containing catalyst. Typical palladium-containing catalysts include tris(dibenzylideneacetone)dipalladium(0); palladium(II) acetate; chloro[2-(dicyclohexylphosphino)-3,6-dimethoxy-2',4',6'-tri-isopropyl-1,1'-biphenyl][2-(2-aminoethyl)phenyl]palladium(II) (BrettPhos Pd G1); [(2-dicyclohexylphosphino-3,6-dimethoxy-2',4',6'-triisopropyl-1,1'-biphenyl)-2-(2'-amino-1,1'-biphenyl)]palladium(II) methanesulfonate (BrettPhos Pd G3); and (2-dicyclohexyl-phosphino-2',6'-diisopropoxy-1,1'-biphenyl)[2-(2'-amino-1,1'-biphenyl)]palladium(II) methanesulfonate (RuPhos Pd G3).

Suitably, the reaction is performed in the presence of an organophosphorus reagent (phosphine ligand). Typical phosphine ligands include 2-dicyclohexylphosphino-2',4',6'-triisopropylbiphenyl (XPhos); 4,5-bis(diphenylphosphino)-9,9-dimethylxanthene (XantPhos); (±)-2,2'-bis(diphenylphosphino)-1,1'-binaphthalene (rac-BINAP); and 2-(dicyclohexylphosphino)-3,6-dimethoxy-2',4',6'-triisopropyl-1,1'-biphenyl (BrettPhos).

Suitably, the reaction is performed in the presence of a base. Typical bases include phosphate salts, e.g. an alkali metal phosphate such as potassium phosphate; alkoxide salts, e.g. an alkali metal alkoxide such as sodium tert-butoxide; and carbonate salts, e.g. an alkaline earth metal carbonate such as cesium carbonate.

The reaction is conveniently accomplished at an elevated temperature in a suitable solvent, e.g. an aromatic solvent such as toluene; or a cyclic ether such as 1,4-dioxane.

In an alternative procedure, the compounds in accordance with the invention may be prepared by a two-step process which comprises: (i) treating a compound of formula (III) as defined above with a base; and (ii) reacting the resulting material with a compound of formula Z-L$^2$, wherein Z is as defined above, and L$^2$ represents a suitable leaving group; followed, as necessary, by removal of the N-protecting group R$^p$.

Suitably, the leaving group L$^2$ is a halogen atom, e.g. fluoro.

Step (i) comprises treating compound (III) with a base. Suitably, the base may be an alkyllithium, e.g. tert-butyllithium.

The process is conveniently performed under low temperature conditions, e.g. at a temperature in the region of −78° C., in a suitable solvent, e.g. a cyclic ether such as tetrahydrofuran.

The intermediates of formula (III) above wherein W represents C(O) may be prepared by treating a compound of formula (IV):

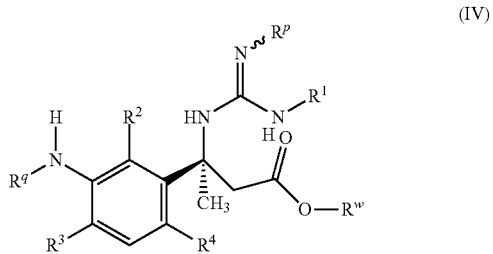

wherein R$^1$, R$^2$, R$^3$, R$^4$ and R$^p$ are as defined above, R$^q$ represents an N-protecting group, and R$^w$ represents C$_{1-4}$ alkyl, especially methyl; with a base; followed by removal of the N-protecting group R$^q$.

Suitably, the base of use in the above reaction is a C$_{1-4}$ alkoxide salt, typically an alkali metal alkoxide such as potassium tert-butoxide. The reaction is conveniently accomplished at ambient temperature in a suitable solvent, e.g. a cyclic ether such as tetrahydrofuran.

Suitably, the N-protecting group R$^q$ is benzyloxycarbonyl.

Where the N-protecting group R$^q$ is benzyloxycarbonyl, subsequent removal of the benzyloxycarbonyl group may suitably be accomplished by catalytic hydrogenation. Typically, this will involve treatment with gaseous hydrogen in the presence of a hydrogenation catalyst such as palladium on charcoal.

The intermediates of formula (IV) above may be prepared by reacting a compound of formula (V) with a compound of formula (VI):

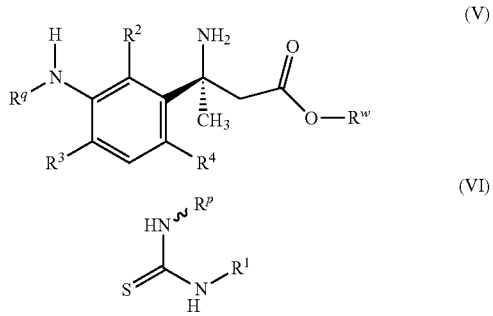

wherein R$^1$, R$^2$, R$^3$, R$^4$, R$^p$, R$^q$ and R$^w$ are as defined above.

Generally, the reaction between compounds (V) and (VI) is performed in the presence of a coupling agent. A suitable coupling agent is N-(3-dimethylaminopropyl)-N'-ethylcarbodiimide hydrochloride (EDC.HCl). Suitably, the reaction is performed in the presence of a base, typically an organic base such as N,N-diisopropylethylamine.

The reaction between compounds (V) and (VI) is conveniently accomplished at ambient temperature in a suitable solvent, e.g. a dipolar aprotic solvent such as N,N-dimethylformamide.

Under certain circumstances, the reaction between compounds (V) and (VI) will proceed directly to the corresponding compound of formula (III).

In an alternative procedure, the intermediates of formula (III) above may be prepared by treating a compound of formula (VII):

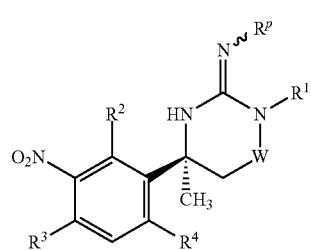

(VII)

wherein W, $R^1$, $R^2$, $R^3$, $R^4$ and $R^p$ are as defined above; with a reducing agent.

Suitably, the reducing agent of use in the above reaction may be a mixture of zinc and ammonium formate, in which case the reaction may conveniently be accomplished at ambient temperature in a suitable solvent, e.g. a $C_{1-4}$ alkanol such as methanol.

Alternatively, the reducing agent may be tin(II) chloride, in which case the reaction may conveniently be accomplished at an elevated temperature in a suitable solvent, e.g. a $C_{1-4}$ alkanol such as ethanol.

Alternatively, the compound of formula (VII) may be reduced by conventional catalytic hydrogenation, in which case the reaction may conveniently be accomplished by treating compound (VII) with hydrogen gas in the presence of a hydrogenation catalyst, e.g. palladium on charcoal. The reaction will typically be performed at ambient temperature in a suitable solvent, e.g. a $C_{1-4}$ alkanol such as methanol.

The intermediates of formula (VII) above wherein W represents C(O) may be prepared by treating a compound of formula (VIII):

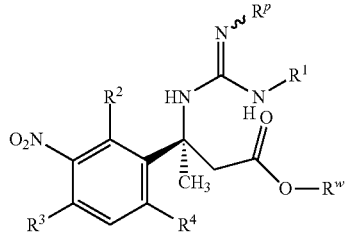

(VIII)

wherein $R^1$, $R^2$, $R^3$, $R^4$, $R^p$ and $R^w$ are as defined above; with a base; as described above for compound (IV).

The intermediates of formula (VIII) above may be prepared by reacting a compound of formula (VI) as defined above with a compound of formula (IX):

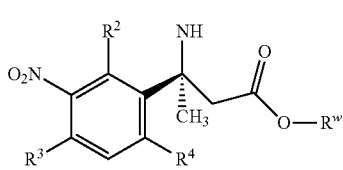

(IX)

wherein $R^2$, $R^3$, $R^4$ and $R^w$ are as defined above; employing conditions analogous to those described above for the reaction between compounds (V) and (VI).

In an alternative procedure, the compounds in accordance with the invention may be prepared by a process which comprises reacting a compound of formula Z—$NH_2$ with a compound of formula (X):

(X)

wherein W, Z, $R^1$, $R^2$, $R^3$, $R^4$ and $R^p$ are as defined above, and $L^3$ represents a suitable leaving group; employing conditions analogous to those described above for the reaction between compound (III) and a compound of formula Z-L; followed, as necessary, by removal of the N-protecting group $R^p$.

Suitably, the leaving group $L^3$ is a halogen atom, e.g. iodo.

The intermediates of formula (X) above wherein $L^3$ is iodo may be prepared by reacting a compound of formula (III) as defined above with copper(I) iodide in the presence of an alkyl nitrite, e.g. tert-butyl nitrite. The reaction is conveniently performed at ambient temperature in a suitable solvent, e.g. a nitrile solvent such as acetonitrile.

Where they are not commercially available, the starting materials of formula (V), (VI) and (IX) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, $3^{rd}$ edition, 1999. The protecting groups may be removed at any convenient subsequent stage utilising methods known from the art.

The following Examples illustrate the preparation of compounds according to the invention.

The compounds of the present invention are potent inhibitors of the growth and propagation of the *Plasmodium falciparum* parasite in human blood. As such, they are active in a *P. falciparum* 3D7 asexual blood stage assay, exhibiting $IC_{50}$ values of 50 µM or less, generally of 20 µM or less, usually of 5 µM or less, typically of 1 µM or less, suitably of 500 nM or less, ideally of 100 nM or less, and preferably of 20 nM or less (the skilled person will appreciate that a lower $IC_{50}$ figure denotes a more active compound).

Asexual Blood Stage Assay

The assay used to measure the effect of test compounds on a bloodstream stage of *Plasmodium falciparum* 3D7 strain employs SYBR green as the readout. This is a dye that binds to double stranded deoxyribonucleic acid (DNA) with a resulting increase in fluorescence, allowing detection of *P. falciparum* DNA in infected erythrocytes, and thereby providing a measure of parasite growth and propagation.

*P. falciparum* Culture Maintenance

Erythrocytes (A+blood) were prepared for both parasite culture and assay by washing 4 times with incomplete media (15.9 g RPMI 1640 (25 mM HEPES, L-glutamine), 1 g NaHCO$_3$, 2 g glucose, 400 µL gentacin (500 mg/mL), 2 mL hypoxanthine solution (13.6 g/L in 0.1M NaOH pH 7.3) in 1 litre of media). The cells were centrifuged at 1800 g for 5 minutes, before decanting the supernatant and re-suspending in fresh incomplete media. On the final wash, the cells were re-suspended in complete media (incomplete media with 5 g/L AlbumaxII), and centrifuged at 1800 g for 3 minutes. This cell sediment was treated as 100% haematocrit.

*P. falciparum* 3D7 was cultured in erythrocytes at 5% haematocrit in complete media at 37° C. (1% $O_2$, 3% $CO_2$, balance $N_2$). Cultures were split on a weekly basis to achieve a 1% parasitaemia in erythrocites at 5% haematocrit in fresh media. Culture media is replaced by fresh media every other day (2 times during the week).

Assay Procedure—Version 1

On day 1, test compounds were added to assay plates using Echo dispensing technology (3 fold dilution and 10 points titration). 50 nL of each compound dilution was added to 50 µL of culture (5% haematocrit, 0.5% parasitaemia) and incubated for 72 h at 37° C. (1% $O_2$, 3% $CO_2$, balance $N_2$). Final concentrations of test compounds ranged from 10,000 nM to 0.51 nM, in 0.5% DMSO.

On day 4, 10 µL SYBR green (Invitrogen S7563 supplied as 10,000×concentrate in DMSO) pre-diluted to 3× concentrate with Lysis buffer (20 mM Tris pH 7.9, 5% EDTA, 0.16% w/v, 1.6% TX100 v/v) was added to the cultures and incubated in the dark, overnight, at room temperature.

On day 5, fluorescent signal was measured using a BioTek plate reader (excitation 485 nm, emission 528 nm). All data were processed using IDBS ActivityBase [10]. Raw data were converted into percent inhibition through linear regression by setting the high inhibition control as 100% and the no inhibition control as 0%. Quality control criteria for passing plates were as follows: Z'>0.5, S:B>3, % $CV_{(no\ inhibition\ control)}$<15. The formula used to calculate Z' is $$1 - \frac{3\times(\text{StDev\_high}+\text{StDev\_low})}{\text{ABS}(\text{Mean\_high}-\text{Mean\_low})}.$$

All $EC_{50}$ curve fitting was undertaken using the following 4 parametric equation:

$$y = A + \frac{B-A}{1+(C/x)^D},$$

where A=% inhibition at bottom; B=% inhibition at top; C=$EC_{50}$; D=slope; x=inhibitor concentration; and y=% inhibition. If curve did not reach 100% of inhibition, B was fixed to 100 when at least 50% of inhibition was reached.

Assay Procedure—Version 2

On day 1, test compounds were added to assay plates using Echo dispensing technology (1.5 fold dilution and 20 points titration). 50 nL of each compound dilution was added to 50 µL of culture (5% haematocrit, 0.5% parasitaemia) and incubated for 72 h at 37° C. (1% $O_2$, 3% $CO_2$, balance $N_2$). Final concentrations of test compounds ranged from 50,000 nM to 15 nM, in 0.5% DMSO.

On day 4, 10 µL SYBR green (Invitrogen S7563 supplied as 10,000× concentrate in DMSO) pre-diluted to 3× concentrate with Lysis buffer (20 mM Tris pH 7.9, 5% EDTA, 0.16% w/v, 1.6% TX100 v/v) was added to the cultures and incubated in the dark, overnight, at room temperature.

On day 5, fluorescent signal was measured using a BioTek plate reader (excitation 485 nm, emission 528 nm). All data were processed using IDBS ActivityBase. Raw data were converted into percent inhibition through linear regression by setting the high inhibition control (mefloquine) as 100% and the no inhibition control (DMSO) as 0%. Quality control criteria for passing plates were as follows: Z'>0.5, S:B>3, % $CV_{(no\ inhibition\ control)}$<15. The formula used to calculate Z' is:

$$1 - \frac{3(\sigma p + \sigma n)}{(\mu p - \mu n)}$$

where µ denotes the mean; σ denotes the standard deviation; p denotes the positive control; and n denotes the negative control.

All $EC_{50}$ curve fitting was undertaken using the following bi-phasic two site dose response using XLfit model 300 (IDBS):

$$y = \frac{A}{1+10^{(C-\log 10(Bx))}} + \frac{100-A}{1+10^{(D-\log 10(Bx))}}$$

where A=100 minus the top of the upper curve 1 and the bottom of lower curve; B=Hill slope; log(C)=$IC_{50}$ concentration at lower site; log(D)=$IC_{50}$ concentration at upper site; x=inhibitor concentration; and y=% inhibition.

When tested in the *P. falciparum* 3D7 asexual blood stage assay (Version 1 or Version 2) as described above, the compounds of the accompanying Examples were found to exhibit the following $IC_{50}$ values.

Quoted $IC_{50}$ values indicated by an asterisk (*) were obtained from Version 2 of the assay procedure. All other quoted $IC_{50}$ values were obtained from Version 1 of the assay procedure.

| Example | $IC_{50}$ (nM) |
| --- | --- |
| 1 | 400 |
| 2 | 150 |
| 3 | 80 |
| 4 | 75 |
| 5 | 120 |
| 6 | 70 |
| 7 | 334 |
| 8 | 330 |
| 9 | 333 |
| 10 | 690 |
| 11 | 820 |
| 12 | 200 |
| 13 | 230 |
| 14 | 280 |
| 15 | 1530 |
| 16 | 2290 |
| 17 | 270 |
| 18 | 534 |
| 19 | 996 |
| 20 | 2306 |
| 21 | 1182 |
| 22 | 1520 |
| 23 | 1336 |
| 24 | 1672 |
| 25 | 821 |
| 26 | 331 |
| 27 | 236 |
| 28 | 2962 |
| 29 | 539 |
| 30 | 640 |
| 31 | 430 |
| 32 | 851 |
| 33 | 1813 |
| 34 | 790 |
| 35 | 2376 |
| 36 | 2898 |
| 37 | 1150 |
| 38 | 811 |
| 39 | 2091 |
| 40 | 1510 |
| 41 | 1950 |
| 42 | 269* |
| 43 | 63* |
| 44 | 815* |
| 45 | 305* |
| 46 | 425* |
| 47 | 171* |
| 48 | 386* |
| 49 | 468* |
| 50 | 373* |
| 51 | 370* |
| 52 | 680* |
| 53 | 212* |
| 54 | 655* |
| 55 | 433* |
| 56 | 253* |
| 57 | 600* |
| 58 | 1630* |
| 59 | 365* |
| 60 | 269* |
| 61 | 753* |
| 62 | 226* |
| 63 | 916* |
| 64 | 1759* |
| 65 | 458* |
| 66 | 217* |
| 67 | 2579* |
| 68 | 524* |
| 69 | 579* |
| 70 | 478* |
| 71 | 3534* |
| 72 | 325* |
| 73 | 10416* |
| 74 | 1288* |
| 75 | 1456* |
| 76 | 757* |
| 77 | 791* |
| 78 | 1415* |
| 79 | 401* |
| 80 | 652* |
| 81 | 425* |
| 82 | 137* |
| 83 | 357* |
| 84 | 1541* |
| 85 | 1786* |
| 86 | 658* |
| 87 | 666* |
| 88 | 532* |
| 89 | 232* |
| 90 | 3112* |
| 91 | 896* |
| 92 | 461* |
| 93 | 70* |
| 94 | 34* |
| 95 | 456* |
| 96 | 195* |
| 97 | 216* |
| 98 | 224* |
| 99 | 66* |
| 100 | 347* |
| 101 | 97* |
| 102 | 193* |
| 103 | 551* |
| 104 | 131* |
| 105 | 318* |
| 106 | 374* |
| 107 | 863* |
| 108 | 2038* |
| 109 | 814* |
| 110 | 227* |
| 111 | 248* |
| 112 | 642* |
| 113 | 225* |
| 114 | 519* |
| 115 | 668* |
| 116 | 556* |
| 117 | 707* |
| 118 | 138* |
| 119 | 237* |
| 120 | 652 |
| 121 | 1655 |
| 122 | 4508* |
| 123 | 552* |
| 124 | 509* |
| 125 | 1097* |
| 126 | 1749* |
| 127 | 184* |
| 128 | 717* |
| 129 | 1333* |
| 130 | 744* |
| 131 | 18348* |
| 132 | 623* |
| 133 | 562* |
| 134 | 3971* |
| 135 | 21* |
| 136 | 249* |
| 137 | 158* |
| 138 | 19* |
| 139 | 132* |
| 140 | 704* |

-continued

| Example | IC$_{50}$ (nM) |
|---|---|
| 141 | 180* |
| 142 | 232* |
| 143 | 996* |
| 144 | 493* |
| 145 | 1263* |
| 146 | 425* |
| 147 | 287* |
| 148 | 368* |
| 149 | 1383* |
| 150 | 622* |
| 151 | 707* |
| 152 | 613* |
| 153 | 3218* |
| 154 | 884* |
| 155 | 71* |
| 156 | 2982* |
| 157 | 3856* |
| 158 | 1734* |
| 159 | 2275 |
| 160 | 1685 |
| 161 | 1684 |
| 162 | 905 |
| 163 | 913 |
| 164 | 2204 |
| 165 | 890 |
| 166 | 1783 |
| 167 | 627 |
| 168 | 252 |
| 169 | 323 |
| 170 | 492 |
| 171 | 1136 |
| 172 | 228 |
| 173 | 1541 |
| 174 | 764* |
| 175 | 2822 |
| 176 | 460* |
| 177 | 2446* |
| 178 | 428* |
| 179 | 381* |
| 180 | 629* |
| 181 | 201* |
| 182 | 466* |
| 183 | 582* |
| 184 | 217* |
| 185 | 565* |
| 186 | 456* |
| 187 | 385* |
| 188 | 3465 |
| 189 | 820 |
| 190 | 2583 |
| 191 | 363* |
| 192 | 3705* |
| 193 | 148* |
| 194 | 747* |
| 195 | 244* |
| 196 | 552* |
| 197 | 536* |
| 198 | 22* |
| 199 | 309* |
| 200 | 45* |
| 201 | 102* |
| 202 | 112* |
| 203 | 57* |
| 204 | 31 |
| 205 | 6210* |
| 206 | 243 |
| 207 | 659 |

EXAMPLES

Abbreviations

DCM: dichloromethane EtOAc: ethyl acetate
DMSO: dimethyl sulfoxide THF: tetrahydrofuran
MeOH: methanol DMF: N,N-dimethylformamide
DIPEA: N,N-diisopropylethylamine TFA: trifluoroacetic acid
TBAF: tetrabutylammonium fluoride TFAA: trifluoroacetic anhydride
EtOH: ethanol DEA: diethylamine
mCPBA: 3-chloroperbenzoic acid
EDC.HCl: N-(3-dimethylaminopropyl)-N'-ethylcarbodiimide hydrochloride
KHMDS: potassium bis(trimethylsilyl)amide
Pd$_2$(dba)$_3$: tris(dibenzylideneacetone)dipalladium(0)
BrettPhos Pd G1: chloro[2-(dicyclohexylphosphino)-3,6-dimethoxy-2',4',6'-triisopropyl-1,1'-biphenyl][2-(2-aminoethyl)phenyl]palladium(II)
BrettPhos Pd G3: [(2-dicyclohexylphosphino-3,6-dimethoxy-2',4',6'-triisopropyl-1,1'-biphenyl)-2-(2'-amino-1,1'-biphenyl)]palladium(II) methanesulfonate
RuPhos Pd G3: (2-dicyclohexylphosphino-2',6'-diisopropoxy-1,1'-biphenyl)[2-(2'-amino-1,1'-biphenyl)]palladium(II) methanesulfonate
XPhos: 2-dicyclohexylphosphino-2',4',6'-triisopropylbiphenyl
XantPhos: 4,5-bis(diphenylphosphino)-9,9-dimethylxanthene
rac-BINAP: (±)-2,2'-bis(diphenylphosphino)-1,1'-binaphthalene
BrettPhos: 2-(dicyclohexylphosphino)-3,6-dimethoxy-2',4',6'-triisopropyl-1,1'-biphenyl
h: hour M: mass
r.t.: room temperature RT: retention time
DAD: Diode Array Detector
HPLC: High Performance Liquid Chromatography
LCMS: Liquid Chromatography Mass Spectrometry
ESI: Electrospray Ionisation

Nomenclature

Compounds were named with the aid of ACD/Name Batch (Network) version.

Materials

Commercially available Zn dust was activated by stirring with dilute 1N HCl, then washing with water, methanol and acetone, followed by drying under vacuum at 100-120° C. for 15 minutes.

Analytical Conditions

Employed to obtain LCMS data and QC data.
Method 1
Column: Waters×Bridge C18, 2.1×30 mm, 2.5 m

| Injection Volume | 5.0 µL |
|---|---|
| Flow Rate | 1.00 mL/minute |

Detection:
 MS—ESI+m/z 150 to 800
 UV—DAD 220-400 nm
Solvent A 5 mM ammonium formate in water+0.1% ammonia
Solvent B acetonitrile+5% Solvent A+0.1% ammonia
Gradient Program:
 5% B to 95% B in 4.0 minutes; hold until 5.00 minutes; at 5.10 minutes concentration of B is 5%; hold up to 6.5 minutes
Method 2
Instrument name: LCMS/MS API 2000
Instrument manufacturer: Applied Biosystem
HPLC: Shimadzu Prominence Column (name, size, type): Zorbax Extend (C18, 4.6×50 mm, 5 micron)
Eluent (solvent): Channel A: 10 mM ammonium acetate in water
  Channel B: acetonitrile (organic phase)
Dual Wavelength: at 220 and 260 nm
Detector: UV
Gradient condition: Solvent A: buffer 10 mM ammonium acetate in water
  Solvent B: acetonitrile
Flow rate: 1.2 mL/minute
LC-MS gradient:
Mobile phase: from 90% buffer 10 mM ammonium acetate in water and 10% acetonitrile to 70% buffer 10 mM ammonium acetate in water and 30% acetonitrile in 1.5 minutes; further to 10% buffer 10 mM ammonium acetate in water and 90% acetonitrile in 3.0 minutes; hold this mobile phase composition to 4 minutes and finally back to initial condition in 5 minutes.

| Time | Module | % A | % B |
| --- | --- | --- | --- |
| 0.01 | Pumps | 90 | 10 |
| 1.50 | Pumps | 70 | 30 |
| 3.00 | Pumps | 10 | 90 |
| 4.00 | Pumps | 10 | 90 |
| 5.00 | Pumps | 90 | 10 |
| 5.10 | System Controller | Stop | |

Mass Conditions
Ionization technique: ESI (Electron Spray Ionization) using API (Atmospheric Pressure Ionization) source
Declustering Potential: 10-70 V depending on the ionization of compound
Mass range: 100-800 amu
Scan type: Q1
Polarity: +ve
Ion Source: Turbo spray
Ion spray voltage: +5500 for +ve mode
Mass Source temperature: 200° C.
Method 3
Column: Waters UPLC X Bridge BEH (C18, 2.1×50 mm, 2.5 μm)
Temperature: 45° C.
Injection volume: 1.0 μL
Flow rate: 1.00 mL/minute
Detection: Mass spectrometry—+/−detection in the same run
PDA: 210 to 400 nm
Solvent A: 10 mM ammonium formate in water+0.1% ammonia
Solvent B: 95% acetonitrile+5% $H_2O$+0.1% ammonia

| Time | % A | % B |
| --- | --- | --- |
| 0 | 95 | 5 |
| 0.10 | 95 | 5 |
| 2.10 | 5 | 95 |
| 2.35 | 5 | 95 |
| 2.80 | 95 | 5 |

Method 4
Column: Waters UPLC X Bridge BEH (C18, 2.1×50 mm, 2.5 μm)
Temperature: 45° C.
Injection volume: 1.0 μL
Flow rate: 1.00 mL/minute
Detection: Mass spectrometry—+/−detection in the same run
PDA: 210 to 400 nm
Solvent A: 10 mM ammonium formate in water+0.1% formic acid
Solvent B: 95% acetonitrile+5% $H_2O$+0.1% formic acid

| Time | % A | % B |
| --- | --- | --- |
| 0 | 95 | 55 |
| 0.10 | 95 | 5 |
| 2.10 | 5 | 95 |
| 2.35 | 5 | 95 |
| 2.80 | 95 | 5 |

Method 5
Column: Zorbax Extend C18 (50×4.6 mm, 5μ, 80 A)
Mobile phase: 50:50 [10 mM ammonium acetate in water]:acetonitrile to 5:95 [10 mM ammonium acetate in water]:acetonitrile gradient over 1.5 minutes, then continue elution to 4 minutes.
Flow rate: 1.2 mL/minute Intermediate 1

N-[1-(2-Chloro-3-nitrophenyl)ethylidene]-(R)-2-methylpropane-2-sulfinamide

To a solution of 1-(2-chloro-3-nitrophenyl)ethanone (10.5 g, 5.1 mmol) and (R)-2-methyl-2-propanesulfinamide (11.2 g, 5.1 mmol) in dry THF (100 mL) was added titanium(IV) ethoxide (23.2 g, 10.5 mmol). The reaction mixture was heated at 75° C. for 12 h, then quenched with $H_2O$ (500 mL), stirred at room temperature for 1 h and filtered through a pad of Celite. The aqueous layer was extracted with EtOAc (2×150 mL). The organic layer was separated and dried over anhydrous sodium sulfate, then concentrated in vacuo. The crude residue was purified by column chromatography (silica, 100-200 mesh, 30% EtOAc in hexanes) to afford the title compound (10.0 g, 63%) as a red liquid. LCMS (Method 1, ESI) 303.00 [MH]$^+$, RT 3.02 minutes.

Intermediate 2

N-[1-(3-Amino-2-chlorophenyl)ethylidene]-2-(R)-methylpropane-2-sulfinamide

To a solution of Intermediate 1 (10.0 g, 33.2 mmol) in MeOH (100 mL) was added Raney Ni (10.0 g) at room temperature. The reaction mixture was stirred at room temperature for 6 h under hydrogen pressure, then filtered through a pad of Celite and washed with MeOH (150 mL). The filtrate was concentrated in vacuo to afford the title compound (8.80 g, 98%) as a colourless liquid, which was utilised without further purification. LCMS (Method 1, ESI) 273.00 [MH], RT 2.58 minutes.

Intermediate 3

Benzyl N-(3-{N—[(R)-tert-butylsulfinyl]-C-methyl-carbonimidoyl}-2-chlorophenyl)-carbamate To a solution of Intermediate 2 (10.0 g, 36.7 mmol) in THF (100 mL) were added DIPEA (32.5 mL, 183.0 mmol) and benzyl chloroformate (12.5 g, 73.5 mmol) at 0° C. The reaction mixture was stirred at room temperature for 16 h, then quenched with $H_2O$ (500 mL) and extracted with EtOAc (3×250 mL). The organic layer was separated and dried over anhydrous sodium sulfate, then concentrated in vacuo. The crude residue was purified by column chromatography (silica, 100-200 mesh, 30% EtOAc in n-hexanes) to afford the title compound (12.5 g, 84%) as a yellow liquid. LCMS (Method 1, ESI) 407.00 [MH]$^+$, RT 3.43 minutes.

Intermediate 4

Methyl (3S)-3-[3-(benzyloxycarbonylamino)-2-chlorophenyl]-3-{[(R)-tert-butylsulfinyl]-amino}butanoate A suspension of CuCl (4.37 g, 44.2 mmol) and Zn (14.4 g, 221.0 mmol) in THF (90 mL) was heated at 50° C. for 30 minutes. Methyl bromoacetate (11.0 g, 66.0 mmol) was added dropwise at 80° C., then the reaction mixture was heated at 50° C. for 1 h. Intermediate 3 (9.00 g, 22.0 mmol) was added at 0° C. The reaction mixture was stirred at room temperature for 16 h, then filtered through a pad of Celite. The filtrate was washed with brine (300 mL). The organic layer was separated and dried over anhydrous sodium sulfate, then concentrated in vacuo. The crude residue was purified by column chromatography (silica, 100-200 mesh, 40% EtOAc in hexanes) to afford the title compound (7.50 g, 70%) as a yellow liquid. $\delta_H$ (400 MHz, DMSO-d$_6$) 9.09 (s, 1H), 7.54 (d, J8.0 Hz, 1H), 7.29-7.43 (m, 7H), 5.39 (s, 1H), 5.14 (s, 2H), 3.47 (s, 3H), 3.31 (s, 2H), 1.86 (s, 3H) 1.13 (s, 9H). LCMS (Method 1, ESI) 481.00 [MH], RT 3.43 minutes.

Intermediate 5

Methyl (3S)-3-amino-3-[3-(benzyloxycarbonylamino)-2-chlorophenyl]butanoate

To a solution of Intermediate 4 (7.50 g, 15.6 mmol) in MeOH (80 mL) was added 4M HCl in 1,4-dioxane (15.6 mL, 62.5 mmol) at 0° C. The reaction mixture was stirred at room temperature for 6 h, then concentrated in vacuo. The residue was basified with saturated aqueous NaHCO$_3$ solution (200 mL) and extracted with EtOAc (2×250 mL). The organic layer was separated and dried over anhydrous sodium sulfate, then concentrated in vacuo, to afford the title compound (5.18 g, 90%) as a yellow liquid, which was utilised without further purification.

Intermediate 6 tert-Butyl N-(tetrahydropyran-4-ylcarbamothioyl)carbamate

To a solution of N,N'-bis-tert-butoxycarbonylthiourea (12.3 g, 44.5 mmol) in THF (100 mL) under nitrogen was added 60% NaH (5 g, 124.5 mmol) portionwise over a period of 10 minutes at 0° C. The mixture was stirred for 1 h, then TFAA (11.2 mL, 80.1 mmol) was added dropwise at 0° C. The mixture was stirred for 1 h, then a solution of tetrahydropyran-4-amine (4.5 g, 44.5 mmol) in THF (20 mL) was added. The reaction mixture was stirred at r.t. for 2 h, then quenched with ice-cold water and extracted with EtOAc (2×500 mL). The combined organic layers were dried over sodium sulfate, then the solvent was evaporated under reduced pressure. The crude residue was purified by column chromatography (silica gel, 100-200 mesh, 3% ethyl acetate/hexane) to afford the title compound (9.0 g, 77%) as a pale yellow solid. $\delta_H$ (400 MHz, CDCl$_3$) 9.68 (br s, 1H), 7.81 (br s, 1H), 4.46-4.44 (m, 1H), 3.95 (d, J 11.6 Hz, 2H), 3.52 (t, J 11.6 Hz, 2H), 2.07 (d, J11.6 Hz, 2H), 1.61-1.53 (m, 2H), 1.47 (s, 9H).

Intermediate 7

Methyl (3S)-3-[3-(benzyloxycarbonylamino)-2-chlorophenyl]-3-{[N'-tert-butoxy-carbonyl-N-(tetrahydropyran-4-yl)carbamimidoyl]amino}butanoate To a solution of Intermediate 5 (14 g, 33.9 mmol) and Intermediate 6 (9 g, 33.9 mmol) in DMF (100 mL) were added DIPEA (24 mL, 135.9 mmol) and EDC.HCl (13 g, 67.9 mmol) at 0° C. The reaction mixture was stirred at r.t. for 16 h, then diluted with ice-cold water and extracted with EtOAc (2×800 mL). The combined organic layers were washed with brine and dried over sodium sulfate, then the solvent was evaporated under reduced pressure. The crude residue was purified by column chromatography (silica gel, 100-200 mesh, 30% EtOAc/hexane) to afford the title compound (9 g, 44%) as an off-white solid. LCMS (Method 1, ESI) 603.85 [MH]$^+$, RT 2.14 minutes.

Intermediate 8 tert-Butyl N-{(4S)-4-[3-(benzyloxycarbonylamino)-2-chlorophenyl]-4-methyl-6-oxo-1-(tetrahydropyran-4-yl)hexahydropyrimidin-2-ylidene}carbamate To a solution of Intermediate 7 (9 g, 14.9 mmol) in THF (100 mL) was added potassium tert-butoxide in THF (1M, 29.84 mL, 29.8 mmol) under nitrogen at 0° C. over a period of 10 minutes. The reaction mixture was stirred at r.t. for 45 minutes, then quenched with aqueous ammonium chloride solution and extracted with EtOAc (2×800 mL). The combined organic layers were washed with brine and dried over sodium sulfate, then the solvent was evaporated under reduced pressure. The crude residue was purified by column chromatography (silica gel, 100-200 mesh, 30% EtOAc/hexane) to afford the title compound (7.5 g, 88%) as an off-white solid. LCMS (Method 1, ESI) 571.75 [MH]$^+$, RT 2.21 minutes.

Intermediate 9 tert-Butyl N-(cyclohexylcarbamothioyl)carbamate

Prepared from N,N'-bis-tert-butoxycarbonylthiourea (6.5 g, 23.5 mmol) and cyclohexanamine (4.3 g, 42.4 mmol) in accordance with the method described for Intermediate 6. The crude material was purified by column chromatography (silica gel, 100-200 mesh, 3% ethyl acetate/hexane) to afford the title compound (3.9 g, 64%) as an off-white solid. LCMS (Method 2, ESI) 259.20 [MH]$^+$, RT 1.94 minutes.

Intermediate 10

Methyl (3S)-3-[3-(benzyloxycarbonylamino)-2-chlorophenyl]-3-{[N'-tert-butoxy-carbonyl-N-(cyclohexyl)carbamimidoyl]amino}butanoate Prepared from Intermediate 5 (3.9 g, 10.3 mmol) and Intermediate 9 (3.3 g, 12.4 mmol) in accordance with the method described for Intermediate 7. The crude material was purified by column chromatography (silica gel, 100-200 mesh, 10% EtOAc/hexane) to afford the title compound (3.0 g, 48%) as a yellow sticky solid. LCMS (Method 2, ESI) 600. 6 [MH]+, RT 3.99 minutes.

Intermediate 11 tert-Butyl N-{(4S)-4-[3-(benzyloxycarbonylamino)-2-chlorophenyl]-1-cyclohexyl-4-methyl-6-oxohexahydropyrimidin-2-ylidene}carbamate Prepared from Intermediate 10 (3.0 g, 5.0 mmol) in accordance with the method described for Intermediate 8. The crude material was purified by column chromatography (silica gel, 100-200 mesh, 15% EtOAc/hexane) to afford the title compound (2.1 g, 73%) as a white solid. LCMS (Method 2, ESI) 569. 2 [MH]+, RT 4.38 minutes.

Intermediate 12

{1-[tert-Butyl(dimethyl)silyloxy]cyclopropyl}methanamine

To a solution of 1-(aminomethyl)cyclopropanol (6.00 g, 68.9 mmol) in DCM (100 mL) was added triethylamine (13.9 g, 138.0 mmol) at 0° C. The reaction mixture was stirred at 0° C. for 10 minutes, then tert-butyldimethylsilyl chloride (12.4 g, 82.6 mmol) was added at 0° C. The reaction mixture was stirred at room temperature for 16 h, then quenched with $H_2O$ (50 mL). The organic layer was separated, washed with $H_2O$ (3×50 mL) and brine (100 mL), then dried over anhydrous sodium sulfate and concentrated in vacuo. The crude residue was purified by column chromatography (silica, 100-200 mesh, 5% MeOH in DCM) to afford the title compound (11.0 g, 79%) as a yellow liquid. $\delta_H$ (400 MHz, CDCl$_3$) 2.67 (s, 2H), 1.52 (br s, 2H), 0.88 (s, 9H), 0.73-0.77 (m, 2H), 0.49-0.54 (m 2H), 0.12 (s, 6H).

Intermediate 13

N-({1-[tert-Butyl(dimethyl)silyloxy]cyclopropyl}methylcarbamothioyl)benzamide

To a solution of Intermediate 12 (11.0 g, 54.6 mmol) in THF (250 mL) was added benzoyl isothiocyanate (8.91 g, 54.6 mmol) at room temperature. The reaction mixture was heated at 70° C. for 2 h, then quenched with $H_2O$ (100 mL) and extracted with EtOAc (3×200 mL). The organic layer was separated and washed with brine (100 mL), then dried over anhydrous sodium sulfate and concentrated in vacuo. The crude residue was purified by column chromatography (silica, 100-200 mesh, 10% EtOAc in hexanes) to afford the title compound (12.0 g, 60%) as a yellow liquid. $\delta_H$ (400 MHz, CDCl$_3$) 11.10 (br s, 1H), 9.01 (br s, 1H), 7.88 (d, J7.3 Hz, 2H), 7.61-7.66 (m, 1H), 7.50-7.56 (m, 2H), 3.79 (d, J4.4 Hz, 2H), 0.90 (s, 9H), 0.87-0.89 (m, 2H), 0.69-0.77 (m, 2H), 0.15 (s, 6H). LCMS (Method 1, ESI) 365.00 [MH]+, RT 2.61 minutes.

Intermediate 14

{1-[tert-Butyl(dimethyl)silyloxy]cyclopropyl}methylthiourea

To a solution of Intermediate 13 (12.0 g, 32.9 mmol) in MeOH (70 mL) was added a solution of $K_2CO_3$ (9.09 g, 65.8 mmol) in $H_2O$ (35 mL) at 0° C. The reaction mixture was stirred at room temperature for 16 h, then extracted with EtOAc (3×100 mL). The organic layer was separated and washed with brine (50 mL), then dried over anhydrous sodium sulfate and concentrated in vacuo. The crude residue was purified by column chromatography (silica, 100-200 mesh, 20% EtOAc in n-hexanes) to afford the title compound (7.25 g, 85%) as an off-white solid. LCMS (Method 1, ESI) 261.00 [MH]+, RT 2.03 minutes.

Intermediate 15 tert-Butyl N-({1-[tert-butyl(dimethyl)silyloxy]cyclopropyl}methylcarbamothioyl)-carbamate To a solution of Intermediate 14 (7.25 g, 27.8 mmol) in THF (200 mL) was added 60% NaH (2.00 g, 83.5 mmol) at 0° C. The reaction mixture was stirred at 0° C. for 40 minutes, then at room temperature for 10 minutes. A solution of di-tert-butyl dicarbonate (7.29 g, 33.4 mmol) in THF (10 mL) was added. The reaction mixture was stirred at room temperature for 16 h, then quenched with ice-cold $H_2O$ (100 mL) and extracted with EtOAc (3×100 mL). The organic layer was separated and washed with brine (100 mL), then dried over anhydrous sodium sulfate and concentrated in vacuo. The crude residue was purified by column chromatography (silica, 100-200 mesh, 10% EtOAc in hexanes) to afford the title compound (8.0 g, 80%) as a colourless liquid. $\delta_H$ (400 MHz, DMSO-d$_6$) 10.74 (s, 1H), 10.21 (t, J4.2 Hz, 1H), 3.60 (d, J4.4 Hz, 2H), 1.44 (s, 9H), 0.81 (s, 9H), 0.66-0.73 (m, 4H), 0.08 (s, 6H). LCMS (Method 1, ESI) 361.00 [MH]+, RT 2.41 minutes.

Intermediate 16

Methyl (3S)-3-{[(R)-tert-butylsulfinyl]amino}-3-(2-chloro-3-nitrophenyl)butanoate Prepared from Intermediate 1 (11 g, 36.8 mmol) in accordance with the method described for Intermediate 4. The crude residue was purified by column chromatography (silica, 100-200 mesh, 50% EtOAc in hexanes) to afford the title compound (9.00 g, 60%) as a yellow semi-solid. $\delta_H$ (400 MHz, DMSO-d$_6$) 7.85-7.92 (m, 2H), 7.55-7.61 (m, 1H), 5.54 (s, 1H), 3.48 (s, 3H), 3.29-3.36 (m, 2H), 1.91 (s, 3H), 1.13 (s, 9H). LCMS (Method 1, ESI) 377.00 [MH]+, RT 1.85 minutes.

Intermediate 17

Methyl (3S)-3-amino-3-(2-chloro-3-nitrophenyl)butanoate

Prepared from Intermediate 16 (6.5 g, 16.0 mmol) in accordance with the method described for Intermediate 5 to afford the title compound (5.2 g, 95%) as a yellow liquid, which was utilised without further purification. LCMS (Method 1, ESI) 273.00 [MH]+, RT 1.86 minutes.

Intermediate 18

Methyl (3S)-3-{[N'-tert-butoxycarbonyl-N-({1-[tert-butyl(dimethyl)silyloxy]-cyclopropyl}methyl)carbamimidoyl]amino}-3-(2-chloro-3-nitrophenyl)butanoate Prepared from Intermediate 17 (1.70 g, 5.45 mmol) and Intermediate 15 (2.58 g, 6.54 mmol) in accordance with the method described for Intermediate 7. The crude material was purified by column chromatography (silica, 100-200 mesh,

Intermediate 19 tert-Butyl (NZ)—N-[(6S)-6-(2-chloro-3-nitrophenyl)-6-methyl-4-oxo-3-({1-[tert-butyl-(dimethyl)silyloxy]cyclopropyl}methyl)hexahydropyrimidin-2-ylidene]carbamate Prepared from Intermediate 18 (3.0 g, 4.9 mmol) in accordance with the method described for Intermediate 8. The crude material was purified by column chromatography (silica, 100-200 mesh, 20% EtOAc in n-hexanes) to afford the title compound (2.40 g, 82%) as a yellow solid. LCMS (Method 1, ESI) 567.15 [MH]+, RT 2.61 minutes.

Intermediate 20 tert-Butyl N-(tetrahydropyran-4-ylmethylcarbamothioyl)carbamate

Prepared from N,N'-bis-tert-butoxycarbonylthiourea (10.0 g, 36.2 mmol) and tetrahydropyran-4-ylmethanamine (5 g, 43.47 mmol) in accordance with the method described for Intermediate 6. The crude material was purified by column chromatography (silica gel, 100-200 mesh, 15-20% EtOAc/hexane) to afford the title compound (7.8 g, 78%) as an off-white solid. LCMS (Method 2, ESI) 275.0 [MH]+, RT 3.20 minutes.

Intermediate 21 tert-Butyl N-{(4S)-4-[3-(benzyloxycarbonylamino)-2-chlorophenyl]-4-methyl-6-oxo-1-(tetrahydropyran-4-ylmethyl)hexahydropyrimidin-2-ylidene}carbamate To a solution of Intermediate 5 (4.0 g, 10.6 mmol) and Intermediate 20 (3.49 g, 12.7 mmol) in DMF (30 mL) were added EDC.HCl (2.65 g, 13.8 mmol) and DIPEA (4.64 mL, 26.6 mmol) at 0° C. The reaction mixture was stirred at room temperature for 16 h, then quenched with cold water (150 mL) and extracted with EtOAc (2×200 mL). The organic layer was washed with brine, then dried over anhydrous sodium sulfate and concentrated under reduced pressure. The crude residue was purified by column chromatography (silica gel, 100-200 mesh, 20-25% EtOAc/hexane) to afford the title compound (3.2 g, 52%) as an off-white solid. LCMS (Method 2, ESI) 585.3 [MH]+, 3.56 minutes.

Intermediate 22 tert-Butyl N-(tetrahydrofuran-3-ylcarbamothioyl)carbamate

The title compound was prepared from N,N'-bis-tert-butoxycarbonylthiourea (17.5 g, 63.4 mmol) and tetrahydrofuran-3-amine (6.62 g, 76.1 mmol) in accordance with the method described for Intermediate 6. The crude material was purified by column chromatography (silica gel, 100-200 mesh, 30% ethyl acetate/hexane) to afford the title compound (racemic mixture) (7.0 g, 44%) as an off-white solid.

Intermediate 23

Methyl (3S)-3-[3-(benzyloxycarbonylamino)-2-chlorophenyl]-3-{[N'-tert-butoxy-carbonyl-N-(tetrahydrofuran-3-yl)carbamimidoyl]amino}butanoate Prepared from Intermediate 5 (8.0 g, 21.3 mmol) and Intermediate 22 (6.29 g, 25.6 mmol) in accordance with the method described for Intermediate 7. The crude material was purified by column chromatography (silica gel, 100-200 mesh, 30% ethyl acetate/hexane) to afford the title compound (diastereomeric mixture) (4 g, impure, mixture with Intermediate 24) as a thick red liquid, which was utilised without further purification.

Intermediate 24 tert-Butyl N-{(4S)-4-[3-(benzyloxycarbonylamino)-2-chlorophenyl]-4-methyl-6-oxo-1-(tetrahydrofuran-3-yl)hexahydropyrimidin-2-ylidene}carbamate Prepared from Intermediate 23 (4.0 g, 6.8 mmol) in accordance with the method described for Intermediate 8 to afford the title compound (diastereomeric mixture) (3.4 g, 89%) as an off-white solid. LCMS (Method 2, ESI) 557. 3 [MH]+, RT 3.79 minutes.

Intermediate 25 tert-Butyl N-[(3-hydroxy-3-methylcyclobutyl)carbamothioyl]carbamate

The title compound was prepared from N,N'-bis-tert-butoxycarbonylthiourea (10 g, 36.2 mmol) and 3-amino-1-methylcyclobutanol (4.4 g, 43.5 mmol) in accordance with the method described for Intermediate 6. The crude material was purified by column chromatography (silica gel, 100-200 mesh, 30% ethyl acetate/hexane) to afford the title compound (racemic mixture) (5.5 g, 58%) as a brown solid. LCMS (Method 2, ESI) 261.2 [MH]+, RT 2.99 minutes.

Intermediate 26

Methyl (3S)-3-[3-(benzyloxycarbonylamino)-2-chlorophenyl]-3-{[N'-tert-butoxy-carbonyl-N-(3-hydroxy-3-methylcyclobutyl)carbamimidoyl]amino}butanoate Prepared from Intermediate 5 (5.0 g, 13.3 mmol) and Intermediate 25 (4.16 g, 15.9 mmol) in accordance with the method described for Intermediate 7. The reaction mixture was diluted with water and extracted with ethyl acetate (2×300 mL), then washed with water and brine. The solvent was evaporated under reduced pressure to afford the title compound (impure, crude mixture with Intermediate 27), which was utilised without further purification.

Intermediate 27 tert-Butyl N-{(4S)-4-[3-(benzyloxycarbonylamino)-2-chlorophenyl]-1-(3-hydroxy-3-methylcyclobutyl)-4-methyl-6-oxohexahydropyrimidin-2-ylidene}carbamate (syn isomer)

Prepared from Intermediate 26 (8.0 g) in accordance with the method described for Intermediate 8. The crude material was purified by column chromatography (silica, 100-200 mesh, 10-50% ethyl acetate/hexane) to afford, as the first-eluting isomer, the title compound (2.5 g, 33% after two steps) as an off-white solid. The syn configuration between the hydroxy and the amino group was confirmed by nOE spectroscopy. $\delta_H$ (400 MHz, DMSO-$d_6$) 10.31 (s, 1H), 9.24 (s, 1H), 7.60-7.58 (d, J8 Hz, 1H), 7.41-7.32 (m, 6H), 7.19-7.17 (d, J8 Hz, 1H), 5.14 (s, 2H), 4.73 (s, 1H), 4.13-4.09 (m, 1H), 3.61-3.57 (d, J17 Hz, 1H), 3.19-3.15 (d, J17 Hz, 1H), 2.24-2.09 (m, 4H), 1.75 (s, 3H), 1.43 (s, 9H), 1.14 (s, 3H). LCMS (Method 2, ESI) 571.1 [MH]$^+$, RT 3.69 minutes.

Intermediate 28 tert-Butyl N-[(4S)-4-(3-amino-2-chlorophenyl)-4-methyl-6-oxo-1-(tetrahydropyran-4-yl)-hexahydro-pyrimidin-2-ylidene]carbamate To a solution of Intermediate 8 (8.0 g, 14.0 mmol) in methanol (100 mL) was added 10% Pd/C (800 mg). The reaction mixture was stirred under hydrogen balloon pressure at r.t. for 30 minutes, then filtered through celite and washed with methanol. The filtrate was concentrated under reduced pressure. The crude residue was purified by column chromatography (silica gel, 100-200 mesh, 30% EtOAc/hexane) to afford the title compound (5.5 g, 89%) as an off-white solid. $\delta_H$ (400 MHz, CDCl$_3$) 10.53 (br s, 1H), 6.99-7.05 (m, 1H), 6.75 (d, J7.8 Hz, 1H), 6.68 (d, J7.83 Hz, 1H), 4.74-4.85 (m, 1H), 4.20 (br s, 2H), 3.97 (dd, J 11.2, 4.4 Hz, 1H), 3.90 (dd, J11.2, 4.40 Hz, 1H), 3.67 (dd, J 16.1, 1.5 Hz, 1H), 3.42-3.48 (m, 1H), 3.31-3.39 (m, 1H), 2.81 (d, J16.63 Hz, 1H), 2.62-2.68 (m, 1H), 2.53-2.58 (m, 1H), 1.84 (s, 3H), 1.54 (s, 9H), 1.47-1.50 (m, 1H), 1.09-1.13 (m, 1H). LCMS (Method 1, ESI) 437.20 [MH]$^+$, RT 2.08 minutes.

Intermediate 29 tert-Butyl N-[(4S)-4-(3-amino-2-chlorophenyl)-1-cyclohexyl-4-methyl-6-oxohexahydro-pyrimidin-2-ylidene]carbamate Prepared from Intermediate 11 (2 g, 3.6 mmol) in accordance with the method described for Intermediate 28. The crude material was purified by column chromatography (silica gel, 100-200 mesh, 15% EtOAc/hexane) to afford the title compound (1.4 g, 89%) as a white solid. LCMS (Method 2, ESI) 434. 9 [MH]$^+$, RT 3.82 minutes.

Intermediate 30 tert-Butyl N-[(6S)-6-(3-amino-2-chlorophenyl)-6-methyl-4-oxo-3-({1-[tert-butyl-(dimethyl)silyloxy]cyclopropyl}methyl)hexahydropyrimidin-2-ylidene}carbamate To a solution of Intermediate 19 (2.40 g, 4.1 mmol) in MeOH (30 mL) were added ammonium formate (1.28 g, 20.2 mmol) and Zn (1.31 g, 20.2 mmol) at 0° C. The reaction mixture was stirred at room temperature for 2 h, then quenched with H$_2$O (200 mL) and extracted with EtOAc (3×100 mL). The organic layer was separated, then dried over anhydrous sodium sulfate and concentrated in vacuo. The crude residue was purified by column chromatography (silica, 100-200 mesh, 20% EtOAc in hexanes) to afford the title compound (1.90 g, 87%) as an off-white solid. H (400 MHz, CDCl$_3$) 10.52 (br s, 1H), 7.04 (t, J8.1 Hz, 1H), 6.75-6.78 (m, 2H), 4.38 (d, J 13.7 Hz, 1H), 4.19 (br s, 2H), 4.03 (d, J 13.7 Hz, 1H), 3.69 (d, J 16.1 Hz, 1H), 2.81 (d, J 16.1 Hz, 1H), 1.87 (s, 3H), 1.53 (s, 9H), 0.77 (s, 9H), 0.53-0.56 (m, 1H), 0.37-0.46 (m, 3H), 0.09 (s, 3H), 0.06 (s, 3H). LCMS (Method 1, ESI) 537.7 [MH]$^+$, RT 2.653 minutes.

Intermediate 31 tert-Butyl N-[(4S)-4-(3-amino-2-chlorophenyl)-4-methyl-6-oxo-1-(tetrahydropyran-4-yl-methyl)hexa-hydropyrimidin-2-ylidene]carbamate Prepared from Intermediate 21 (2.2 g, 3.7 mmol) in accordance with the method described for Intermediate 28. The crude material was purified by column chromatography (silica gel, 100-200 mesh, 30% EtOAc/hexane) to afford the title compound (1.4 g, 82%) as an off-white solid. $\delta_H$ (400 MHz, DMSO-$d_6$) 10.44 (s, 1H), 6.97 (t, J7.8 Hz, 1H), 6.77-6.75 (d, J7.7 Hz, 1H), 6.50-6.48 (d, J7.3 Hz, 1H), 5.52 (s, 2H), 3.73-3.49 (m, 5H), 3.14-3.10 (d, J16.4 Hz, 1H), 2.98 (m, 2H), 1.74 (s, 3H), 1.52-1.50 (m, 1H), 1.43 (s, 9H), 0.93-0.88 (m, 4H). LCMS (Method 2, ESI) 450.7 [MH]$^+$, RT 3.36 minutes.

Intermediates 32 & 33 tert-Butyl N-[(1S,4S)-4-(3-amino-2-chlorophenyl)-4-methyl-6-oxo-1-(tetrahydrofuran-3-yl)hexahydro-pyrimidin-2-ylidene]carbamate and tert-Butyl N-[(1R,4S)-4-(3-amino-2-chlorophenyl)-4-methyl-6-oxo-1-(tetrahydrofuran-3-yl)hexahydropyrimidin-2-ylidene]-carbamate Prepared from Intermediate 24 (5.4 g, 9.7 mmol) in accordance with the method described for Intermediate 28. The crude material was purified by column chromatography (silica gel, 100-200 mesh 40% ethyl acetate/hexane) to afford an off-white solid (diastereomeric mixture) (3.7 g, 92%). The diasteromeric mixture was separated by preparative chiral HPLC to give the title compounds as white solids. The absolute stereochemistry is unknown.

Separation of the stereoisomers was performed by Agilent Prep-HPLC using the following conditions:
Column: Chiralpak IC (21.0×250 mm), 5μ
Mobile phase: n-hexane/ethanol/isopropylamine (80:20:0.1)
Flow rate: 21.0 mL/minute
Run time: 20 minutes
Wavelength: 242 nm
Solubility: methanol
Analytical Conditions
Column: Chiralpak IC (4.6×250 mm), 5μ
Mobile phase: n-hexane/ethanol/isopropylamine (80:20:0.1)
Flow rate: 1.0 mL/minute
Run time: 25 minutes
Wavelength: 242 nm
Solubility: methanol
Analytical data of first-eluting isomer (Peak 1):
$\delta_H$ (400 MHz, DMSO-$d_6$) 10.44 (s, 1H), 7.03-6.99 (t, J7.9 Hz, 1H), 6.79-6.78 (d, J7.5 Hz, 1H), 6.47-6.45 (d, J7.2 Hz, 1H), 5.53 (s, 2H), 5.23 (m, 1H), 3.97-3.95 (m, 1H), 3.71-3.70 (m, 1H), 3.54-3.50 (m, 2H), 3.36 (m, 1H), 3.15-3.11 (d, J 16.1 Hz, 1H), 2.02-1.91 (m, 2H), 1.74 (s, 3H), 1.43 (s, 9H). LCMS (Method 2, ESI) 423.2 [MH]$^+$, RT 3.38 minutes.
Analytical data of second-eluting isomer (Peak 2):
$\delta_H$ (400 MHz, DMSO-$d_6$) 10.45 (s, 1H), 7.03-6.99 (t, J7.9 Hz, 1H), 6.79-6.78 (d, J7.5 Hz, 1H), 6.49-6.47 (d, J7.2 Hz, 1H), 5.54 (s, 2H), 5.18-5.14 (m, 1H), 3.93-3.89 (m, 1H), 3.74-3.67 (m, 2H), 3.59-3.50 (m, 2H), 3.14-3.10 (d, J16.32 Hz, 1H), 1.73 (s, 5H), 1.43 (s, 9H). LCMS (Method 2, ESI) 423.1 [MH]⁺, RT 3.35 minutes.

Intermediate 34 tert-Butyl N-[(4S)-4-(3-amino-2-chlorophenyl)-1-(3-hydroxy-3-methylcyclobutyl)-4-methyl-6-oxohexahydropyrimidin-2-ylidene]carbamate (syn isomer)

Prepared from Intermediate 27 (2.3 g, 4.0 mmol) in accordance with the method described for Intermediate 28. The reaction mixture was filtered through a pad of Celite, then the filtrate was concentrated under reduced pressure. The crude residue was triturated with pentane to afford the title compound (1.47 g, 85%) as an off-white solid. $\delta_H$ (400 MHz, DMSO-d₆) 10.29 (s, 1H), 7.01 (t, J7.9 Hz, 1H), 6.80-6.78 (d, J7.4 Hz, 1H), 6.49-6.48 (d, J7.5 Hz, 1H), 5.52 (s, 2H), 4.75 (s, 1H), 4.17-4.13 (m, 1H), 3.53-3.48 (d, J16.8 Hz, 1H), 3.10-3.06 (d, J 16.6 Hz, 1H), 2.24-2.17 (m, 4H), 1.72 (s, 3H), 1.42 (s, 9H), 1.14 (s, 3H). LCMS (Method 2, ESI) 437.0 [MH]⁺, RT 3.14 minutes.

Intermediates 35 to 47 (General Method 1)

To a solution of the appropriate aniline intermediate (1 equiv.) in DCM (0.06 mol/L) were added the appropriate arylboronic acid (2 equiv.), copper(II)acetate (3 equiv.) and triethylamine (3 equiv.). The reaction mixture was stirred at room temperature for 35 h, then diluted with H₂O (20 mL) and extracted with DCM (2×30 mL). The organic layer was separated, washed with H₂O (50 mL) and brine (60 mL), then dried over anhydrous sodium sulfate and concentrated in vacuo. The crude residue was purified to afford Intermediates 35 to 47 as indicated in the following Table.

| Int. | Aniline | Aryl boronic acid | Product | LCMS RT (min) | LCMS [MH]⁺ (method 1) |
|---|---|---|---|---|---|
| 35 | 30 | Phenylboronic acid | tert-Butyl N-[(4S)-4-(3-anilino-2-chlorophenyl)-1-({1-[tert-butyl-(dimethyl)silyloxy]cyclopropyl}-methyl)-4-methyl-6-oxohexahydropyrimidin-2-ylidene]-carbamate | 2.76 | 613.50 |
| 36 | 28 | Phenylboronic acid | tert-Butyl N-[(4S)-4-(3-anilino-2-chlorophenyl)-4-methyl-6-oxo-1(tetrahydropyran-4-yl)hexahydropyrimidin-2-ylidene]carbamate | 2.34 | 513.30 |
| 37 | 31 | Phenylboronic acid | tert-Butyl N-[(4S)-4-(3-anilino-2-chlorophenyl)-4-methyl-6-oxo-1-(tetrahydropyran-4-ylmethyl)-hexahydropyrimidin-2-ylidene]-carbamate | 2.37 | 527.25 |
| 38 | 29 | Phenylboronic acid | tert-Butyl N-[(4S)-4-(3-anilino-2-chlorophenyl)-1-cyclohexyl-4-methyl-6-oxohexahydropyrimidin-2-ylidene]carbamate | 2.63 | 511.00 |
| 39 | 32 | Phenylboronic acid | tert-Butyl N-{(4S)-4-(3-anilino-2-chlorophenyl)-4-methyl-6-oxo-1-[(3S or 3R*)-tetrahydrofuran-3-yl]-hexahydropyrimidin-2-ylidene}-carbamate | 2.37 | 499.20 |
| 40 | 33 | Phenylboronic acid | tert-Butyl N-{(4S)-4-(3-anilino-2-chlorophenyl)-4-methyl-6-oxo-1-[(3S or 3R*)-tetrahydrofuran-3-yl]-hexahydropyrimidin-2-ylidene}-carbamate | 2.38 | 499.00 |
| 41 | 28 | (3-Chlorophenyl)-boronic acid | tert-Butyl N-{(4S)-4-[2-chloro-3-(3-chloroanilino)phenyl]-4-methyl-6-oxo-1-(tetrahydropyran-4-yl)-hexahydropyrimidin-2-ylidene}-carbamate | 2.47 | 547.20 |
| 42 | 28 | m-Tolylboronic acid | tert-Butyl N-{(4S)-4-[2-chloro-3-(3-methylanilino)phenyl]-4-methyl-6-oxo-1-(tetrahydropyran-4-yl)hexahydropyrimidin-2-ylidene]carbamate | 2.58 | 527.70 |
| 43 | 28 | (3-Cyanophenyl)-boronic acid | tert-Butyl N-{(4S)-4-[2-chloro-3-(3-cyanoanilino)phenyl]-4-methyl-6-oxo-1-(tetrahydropyran-4-yl)-hexahydropyrimidin-2-ylidene}-carbamate | 2.41 | 538.75 |
| 44 | 28 | (4-Fluoro-3-methyl-phenyl) boronic acid | tert-Butyl N-{(4S)-4-[2-chloro-3-(4-fluoro-3-methylanilino)phenyl]-4-methyl-6-oxo-1-(tetrahydropyran-4-yl)hexahydropyrimidin-2-ylidene}carbamate | 2.44 | 545.20 |
| 45 | 28 | [4-(Trifluoromethyl)-phenyl]boronic acid | tert-Butyl N-[(4S)-4-{2-chloro-3-[4-(trifluoromethyl)anilino]-phenyl}-4-methyl-6-oxo-1-(tetrahydropyran-4-yl)hexahydropyrimidin-2-ylidene]carbamate | 2.43 | 581.20 |

| Int. | Aniline | Aryl boronic acid | Product | LCMS RT (min) | LCMS [MH]+ (method 1) |
|---|---|---|---|---|---|
| 46 | 28 | (4-Fluorophenyl)-boronic acid | tert-Butyl N-{(4S)-4-[2-chloro-3-(4-fluoroanilino)phenyl]-4-methyl-6-oxo-1-(tetrahydropyran-4-yl)-hexahydropyrimidin-2-ylidene}-carbamate | 2.37 | 531.20 |
| 47 | 34 | Phenylboronic acid | tert-Butyl N-[(4S)-4-(3-anilino-2-chlorophenyl)-1-(3-hydroxy-3-methylcyclobutyl)-4-methyl-6-oxohexahydropyrimidin-2-ylidene]carbamate | 2.34 | 513.25 |

Intermediate 48 tert-Butyl N-{(4S)-4-(3-anilino-2-chlorophenyl)-1-[(1-hydroxycyclopropyl)methyl]-4-methyl-6-oxo-hexahydropyrimidin-2-ylidene}carbamate To a solution of Intermediate 35 (0.15 g, 0.24 mmol) in THF (2 mL) was added a solution of TBAF in THF (1M, 0.24 mL, 0.24 mmol) at 0° C. The reaction mixture was stirred at room temperature for 2 h, then quenched with $H_2O$ (20 mL) and extracted with EtOAc (3×30 mL). The organic layer was separated, then dried over anhydrous sodium sulfate and concentrated in vacuo. The crude residue was purified by column chromatography (silica, 100-200 mesh, 30% EtOAc in hexanes) to afford the title compound as an off-white solid. LCMS (Method 1, ESI) 499.35 [MH]+, RT 2.33 minutes.

Intermediate 49 tert-Butyl N-[(4S)-4-{2-chloro-3-[(6-methylpyridin-3-yl)amino]phenyl}-4-methyl-6-oxo-1-(tetrahydro-pyran-4-yl)hexahydropyrimidin-2-ylidene]carbamate To a solution of Intermediate 28 (0.30 g, 0.69 mmol) in toluene (10 mL) were added 5-bromo-2-methylpyridine (0.18 g, 1.03 mmol) and $K_3PO_4$ (0.44 g, 2.06 mmol). The reaction mixture was purged with argon for 30 minutes, then tris(dibenzylidene-acetone)dipalladium(0) (0.03 g, 0.03 mmol) and XPhos (0.07 g, 0.14 mmol) were added. The reaction mixture was stirred at 90° C. for 4 h, then cooled and concentrated in vacuo. The crude residue was purified by column chromatography (silica, 100-200 mesh, 10-60% EtOAc in hexanes), then preparative HPLC, to afford the title compound (0.028 g, 7%) as an off-white solid. LCMS (Method 1, ESI) 528.1 [MH], 2.06 minutes.

Intermediate 50

1-Bromo-4-(difluoromethoxy)benzene

To a solution of 4-bromophenol (2.50 g, 14.5 mmol) in acetonitrile (100 mL) were added a solution of KOH (16.2 g, 289 mmol) in $H_2O$ (20 mL), and diethyl (bromo-difluoromethyl)phosphonate (10.3 mL, 57.8 mmol), at 0° C. The reaction mixture was stirred at room temperature for 10 h, then diluted with $H_2O$ (100 mL) and extracted with EtOAc (3×100 mL). The organic layer was separated, washed with $H_2O$ (3×200 mL) and brine (200 mL), then dried over anhydrous $Na_2SO_4$ and concentrated in vacuo. The crude residue was purified by column chromatography (silica, 100-200 mesh, 2-5% EtOAc in hexanes) to afford the title compound (2.00 g, 62%) as a colourless oil. $\delta_H$ (400 MHz, $CDCl_3$) 6.46 (t, J72 Hz, 1H), 7.00 (d, J8.3 Hz, 2H), 7.46 (d, J8.8 Hz, 2H).

Intermediate 51 tert-Butyl (NE)-N-[(4S)-4-(2-chloro-3-iodophenyl)-4-methyl-6-oxo-1-(tetrahydropyran-4-yl)hexahydro-pyrimidin-2-ylidene]carbamate To a solution of Intermediate 28 (1.00 g, 2.29 mmol) in acetonitrile (15 mL) was added tert-butyl nitrite (0.41 mL, 3.43 mmol) at 0° C., followed by the addition of CuI (0.65 g, 3.43 mmol). The reaction mixture was stirred at room temperature for 16 h, then diluted with $H_2O$ (200 mL) and extracted with EtOAc (2×100 mL). The organic layer was separated, dried over anhydrous $Na_2SO_4$ and concentrated in vacuo. The crude residue was purified by column chromatography (silica, 100-200 mesh, 25% EtOAc in hexanes) to afford the title compound (0.38 g, 26%) as an off-white solid. $\delta_H$ (400 MHz, $CDCl_3$) 1.07 (d, J 12.7 Hz, 1H), 1.47 (d, J 12.2 Hz, 1H), 1.54 (s, 9H), 1.84 (s, 3H), 2.51-2.67 (m, 2H), 2.82 (d, J 16.1 Hz, 1H), 3.29-3.46 (m, 2H), 3.69 (d, J 16.1 Hz, 1H) 3.87-3.93 (m, 1H), 3.94-4.01 (m, 1H), 4.74-4.82 (m, 1H), 6.94 (t, J8.1 Hz, 1H), 7.31 (d, J7.8 Hz, 1H), 7.89 (d, J7.3 Hz, 1H), 10.58 (br s, 1H). MS (ESI, Method 1) 548.3 [M+H]+, RT 2.29 minutes.

Intermediate 52

3-Bromo-6-methylpyridine-2-carbonitrile

To a solution of 5-bromo-2-methylpyridine (1.00 g, 5.81 mmol) in $CHCl_3$ (15 mL) was added mCPBA (1.10 g, 6.39 mmol). The reaction mixture was stirred at room temperature for 4 h, then washed with saturated aqueous $Na_2CO_3$ solution (50 mL) and extracted with DCM (2×40 mL). The organic layer was separated, dried over anhydrous $Na_2SO_4$ and concentrated in vacuo. The resulting pale yellow solid was redissolved in acetonitrile (28 mL) at room temperature, then trimethylsilyl cyanide (2.24 mL, 17.9 mmol) and triethylamine (1.10 mL, 13.4 mmol) were added. The reaction mixture was stirred at 100° C. for 16 h, then cooled to room temperature and concentrated in vacuo. The crude residue was purified by column chromatography (silica, 100-200 mesh, 20% EtOAc in hexanes) to afford the title compound (0.7 g, 66%) as a pale yellow solid. $\delta_H$ (400 MHz, $CDCl_3$) 2.58 (s, 3H), 7.26 (d, J8.8 Hz, 1H), 7.88 (d, J8.4 Hz, 1H).

Intermediate 53

3-Bromoquinoline-4-carbonitrile

Prepared from 3-bromoquinoline in accordance with the method described for Intermediate 52 to afford the title compound (0.30 g, 69%) as a pale yellow solid. $\delta_H$ (400 MHz, CDCl$_3$) 7.68-7.78 (m, 1H), 7.80-7.90 (m, 2H), 8.18-8.22 (m, 1H), 8.52 (s, 1H).

Intermediate 54

3-Bromo-2-(difluoromethoxy)-6-methylpyridine

To a solution of 3-bromo-6-methylpyridin-2-ol (0.50 g, 2.66 mmol) in acetonitrile (25 mL) at 0° C. was added NaH (60%, 0.32 g, 7.98 mmol) portionwise. The reaction mixture was stirred at room temperature for 30 minutes, then 2,2-difluoro-2-(fluoro-sulfonyl)acetic acid (0.41 mL, 4.00 mmol) was added dropwise. The reaction mixture was stirred at room temperature for 16 h, then poured into ice-cold H$_2$O (40 mL) and extracted with EtOAc (2×25 mL). The organic layer was washed with brine (40 mL) and separated, then dried over anhydrous Na$_2$SO$_4$ and concentrated in vacuo. The crude residue was purified by column chromatography (silica, 100-200 mesh, 10% EtOAc in hexanes) to afford the title compound (0.52 g, 79%) as a pale yellow oil. $\delta_H$ (400 MHz, DMSO-d$_6$) 2.41 (s, 3H), 7.10 (d, J 8.3 Hz, 1H), 7.71 (t, J 74 Hz, 1H), 8.09 (d, J 7.8 Hz, 1H).

Intermediate 55

4-Bromo-1-(difluoromethoxy)isoquinoline

Prepared from 4-bromoisoquinolin-1-ol (0.3 g, 1.34 mmol) in accordance with the method described for Intermediate 54 to afford the title compound (0.21 g, 57%) as an off-white solid. $\delta_H$ (400 MHz, DMSO-d$_6$) 7.85-7.90 (m, 2H), 8.02-8.13 (m, 2H), 8.22 (d, J 8.4 Hz, 1H), 8.39 (s, 1H).

Intermediate 56

4-Bromo-3-(difluoromethoxy)benzonitrile

Prepared from 4-bromo-3-hydroxybenzonitrile (0.5 g, 2.53 mmol) in accordance with the method described for Intermediate 50 to afford the title compound (0.4 g, 64%) as a white solid. $\delta_H$ (400 MHz, DMSO-d$_6$) 7.35 (t, J 72 Hz, 1H), 7.66 (dd, J 8.2, 1.7 Hz, 1H), 7.86 (s, 1H), 7.96 (d, J 7.98 Hz, 1H).

Intermediate 57 tert-Butyl (NE)-N-{(4S)-4-[3-(benzyloxycarbonylamino)-2-chlorophenyl]-4-methyl-6-oxo-1-(tetrahydropyran-3-yl)hexahydropyrimidin-2-ylidene}carbamate Prepared from tetrahydropyran-3-amine (5.56 g, 19.8 mmol) in accordance with the sequence of methods described for Intermediate 6, Intermediate 7 and Intermediate 8 to afford the title compound (2.2 g, 28%) as an off-white solid. $\delta_H$ (400 MHz, CDCl$_3$) (signals for isomers are in italics) 1.51, 1.52 (s, 9H), 1.79, 1.80 (s, 3H), 2.26-2.34 (m, 1H), 2.38-2.49 (m, 1H), 2.79 (d, J 16.1 Hz, 1H), 3.20-3.35 (m, 2H), 3.57-3.66 (m, 1H), 3.68-3.76 (m, 1H), 3.79-3.81 (m, 1H), 3.94 (t, J 10.5 Hz, 1H), 4.05 (t, J 10.5 Hz, 1H), 4.72-4.84 (m, 1H), 5.21 (s, 2H), 6.96-7.03 (m, 1H), 7.33-7.42 (m, 5H), 8.17, 8.19 (s, 1H), 10.50, 10.52 (s, 1H) (2H merged into solvent peak). MS (ESI, Method 1) 571.45 [M+H]$^+$, RT 2.31 minutes.

Intermediate 58 tert-Butyl (NE)-N-[(4S)-4-(3-amino-2-chlorophenyl)-4-methyl-6-oxo-1-(tetrahydropyran-3-yl)hexahydropyrimidin-2-ylidene]carbamate To a solution of Intermediate 57 (2.20 g, 3.77 mmol) in MeOH (50 mL) at 0° C. was added 10% Pd/C (0.48 g, 4.52 mmol). The reaction mixture was degassed and stirred at room temperature for 1 h under H$_2$ pressure (1 atm), then filtered through a pad of celite and washed with MeOH (100 mL). The filtrate was concentrated in vacuo. The crude residue was purified by column chromatography (silica, 100-200 mesh, 30% EtOAc in hexanes) to afford the title compound (1.5 g, 91%) as an off-white solid. $\delta_H$ (400 MHz, CDCl$_3$) (signals for isomers are in italics) 1.54, 1.55 (s, 9H), 1.83, 1.84 (s, 3H), 2.31-2.40 (m, 1H), 2.45-2.53 (m, 1H), 2.79 (d, J 16.1 Hz, 1H), 3.25-3.39 (m, 2H), 3.63-3.70 (m, 1H), 3.74 (dd, J10.27, 2.93 Hz, 1H), 3.82-3.85 (m, 1H), 3.98 (t, J10.51 Hz, 1H), 4.07-4.16 (m, 1H), 4.21 (s, 2H), 4.78-4.88 (m, 1H), 6.63-6.70 (m, 1H), 6.73-6.78 (m, 1H), 7.01-7.05 (m, 1H), 10.48, 10.51 (br s, 1H). MS (ESI, Method 1) 437.2 [M+H]$^+$, RT 2.14 minutes.

Intermediates 59 & 60 tert-Butyl (NE)-N-{(4S)-4-[2-chloro-3-(4-fluoroanilino)phenyl]-4-methyl-6-oxo-1-[(3R*)-tetrahydropyran-3-yl]hexahydropyrimidin-2-ylidene}carbamate (isomers 1 & 2)

To a solution of Intermediate 58 (0.80 g, 1.83 mmol) in DCM (15 mL) were added 4-fluorophenylboronic acid (0.51 g, 3.65 mmol), copper(II) acetate (1.00 g, 5.48 mmol) and triethylamine (0.76 mL, 5.48 mmol) at room temperature. The reaction mixture was stirred at room temperature for 35 h, then diluted with H$_2$O (150 mL) and extracted with DCM (2×200 mL). The organic layer was separated, washed with H$_2$O (150 mL) and brine (160 mL), then dried over anhydrous Na$_2$SO$_4$ and concentrated in vacuo. The crude residue was purified by preparative HPLC, followed by chiral SFC purification, to afford the title compounds (Peak 1 diastereomer 0.190 g; Peak 2 diastereomer 0.150 g) as off-white solids.

Intermediate 59 (Peak 1): $\delta_H$ (400 MHz, CDCl$_3$) 1.56 (s, 9H), 1.64-1.68 (m, 1H), 1.74-1.80 (m, 2H), 1.88 (s, 3H), 2.50 (dd, J12.47, 4.1 Hz, 1H), 2.83 (d, J16.1 Hz, 1H), 3.26-3.38 (m, 2H), 3.72 (d, J 16.1 Hz, 1H), 3.81-3.87 (m, 1H), 4.00 (t, J10.5 Hz, 1H), 4.81-4.91 (m, 1H), 6.19 (s, 1H), 6.74 (d, J7.8 Hz, 1H), 6.97-7.01 (m, 1H), 7.03-7.10 (m, 3H), 7.13-7.17 (m, 2H), 10.56 (s, 1H). MS (ESI, Method 1) 531.30 [M+H]$^+$, RT 2.37 minutes. Intermediate 60 (Peak 2): $\delta_H$ (400 MHz, CDCl$_3$) 1.32-1.35 (m, 1H), 1.55 (s, 9H), 1.61 (s, 1H), 1.66-1.71 (m, 1H), 1.88 (s, 3H), 2.34-2.44 (m, 1H), 2.83 (d, J16.6 Hz, 1H), 3.30-3.38 (m, 1H), 3.66-3.71 (m, 1H), 3.74-3.77 (m, 1H), 3.85 (dd, J11.00, 3.6 Hz, 1H), 4.11 (t, J10.5 Hz, 1H), 4.80-4.88 (m, 1H), 6.20 (s, 1H), 6.74-6.78 (m, 1H), 6.98-7.01 (m, 1H), 7.04-7.10 (m, 3H), 7.13-7.18 (m, 2H), 10.53 (s, 1H). MS (ESI, Method 1) 531.25 [M+H]$^+$, RT 2.36 minutes.

Intermediate 61 tert-Butyl (NE)-N-{(4S)-4-[3-(benzyloxycarbonylamino)-2-chlorophenyl]-4-methyl-1-(2-oxaspiro[3.3]heptan-6-yl)-6-oxohexahydropyrimidin-2-ylidene}carbamate To a solution of Intermediate 5 (1.00 g, 2.42 mmol) in DMF (20 mL) were added Intermediate 101 (0.66 g, 2.18 mmol), EDC.HCl (0.69 g, 3.63 mmol) and DIPEA (0.85 mL, 4.84 mmol) at 0° C. The reaction mixture was stirred at room temperature for 24 h, then quenched with $H_2O$ (200 mL) and extracted with EtOAc (3×100 mL). The organic layer was separated, dried over anhydrous $Na_2SO_4$ and concentrated in vacuo. The crude residue was purified by column chromatography (silica, 100-200 mesh, 80% EtOAc in n-hexanes). An aliquot of the resulting off-white solid (1.0 g) was re-dissolved in THF (15 mL) and potassium tert-butoxide (0.33 g, 2.92 mmol) was added at 0° C. The reaction mixture was stirred for 30 minutes, then diluted with $H_2O$ (300 mL) and extracted with EtOAc (3×100 mL). The organic layer was separated, washed with $H_2O$ (100 mL) and brine (100 mL), then dried over anhydrous $Na_2SO_4$ and concentrated in vacuo. The crude residue was purified by column chromatography (silica, 100-200 mesh, 80% EtOAc in n-hexanes) to afford the title compound (0.81 g) as an off-white solid. $\delta_H$ (400 MHz, $CDCl_3$) 1.53 (s, 9H), 1.83 (s, 3H), 2.47-2.55 (m, 2H), 2.60-2.66 (m, 2H), 2.82 (d, J 16.6 Hz, 1H), 3.65 (d, J 16.6 Hz, 1H), 4.64 (d, J2.9 Hz, 2H), 4.66 (s, 2H), 4.88 (t, J8.56 Hz, 1H), 5.24 (s, 2H), 7.01-7.04 (m, 1H), 7.36-7.46 (m, 7H), 8.22 (d, J8.31 Hz, 1H), 10.52 (s, 1H). MS (ESI, Method 1) m/e 583.25 [M+H]$^+$, RT 2.22 minutes.

Intermediate 62 tert-Butyl (NE)-N-[(4S)-4-(3-amino-2-chlorophenyl)-4-methyl-1-(2-oxaspiro[3.3]heptan-6-yl)-6-oxohexahydropyrimidin-2-ylidene]carbamate Prepared from Intermediate 61 (0.80 g, 1.35 mmol) in accordance with the method described for Intermediate 28 to afford the title compound (0.60 g, 97%) as an off-white solid. $\delta_H$ (400 MHz, $CDCl_3$) 1.54 (s, 9H), 1.84 (s, 3H), 2.50-2.56 (m, 2H), 2.60-2.70 (m, 2H), 2.80 (d, J 16.6 Hz, 1H), 3.66 (d, J 16.6 Hz, 1H), 4.17-4.26 (s, 2H), 4.62-4.64 (m, 2H), 4.66 (s, 2H), 4.88-4.95 (m, 1H), 6.68 (d, J7.8 Hz, 1H), 6.77 (d, J7.82 Hz, 1H), 7.04 (t, J7.8 Hz, 1H), 10.48 (br s, 1H). LCMS (ESI, Method 1) m/e 449.15 [M+H]$^+$, RT 1.93 minutes.

Intermediate 63 tert-Butyl N-(7-oxabicyclo[2.2.1]heptan-2-ylcarbamothioyl)carbamate

Prepared from 7-oxabicyclo[2.2.1]heptan-2-amine (1.00 g, 8.84 mmol) in accordance with the procedure described for Intermediate 6 to afford the title compound (0.45 g, 14%) as an off-white solid. LCMS (ESI, Method 1) m/e 273.1 [M+H]$^+$, RT 1.89 minutes.

Intermediate 64 tert-Butyl (NE)-N-{(4S)-4-[3-(benzyloxycarbonylamino)-2-chlorophenyl]-4-methyl-1-(7-oxabicyclo[2.2.1]heptan-2-yl)-6-oxohexahydropyrimidin-2-ylidene}carbamate Prepared from Intermediate 63 (0.43 g, 1.20 mmol) in accordance with the procedure described for Intermediate 61 to afford the title compound (0.86 g, 85%) as an off-white solid. LCMS (ESI, Method 1) m/e 583.2 [M+H]$^+$, RT 2.31 minutes.

Intermediate 65 tert-Butyl (NE)-N-[(4S)-4-(3-amino-2-chlorophenyl)-4-methyl-1-(7-oxabicyclo[2.2.1]-heptan-2-yl)-6-oxohexahydropyrimidin-2-ylidene]carbamate Prepared from Intermediate 64 (0.80 g, 1.23 mmol) in accordance with the procedure described for Intermediate 28 to afford the title compound (0.58 g, 100%) as an off-white solid. LCMS (ESI, Method 1) m/e 449.2 [M+H]$^+$, RT 2.00 minutes.

Intermediate 66 tert-Butyl (NE)-N-{(4S)-4-[2-chloro-3-(4-fluoroanilino)phenyl]-4-methyl-1-[(1R,2S,4S or 1S,2R,4R)-7-oxabicyclo[2.2.1]heptan-2-yl]-6-oxo-hexahydropyrimidin-2-ylidene}-carbamate Prepared from Intermediate 65 (0.60 g, 1.27 mmol) in accordance with General Method 1 followed by SFC purification. Separation of the diastereomers was achieved using a Chiralpak IG column (250×4.6 mm, 5 g; flow rate 3 mL/minute; mobile phase A $CO_2$; mobile phase B 0.1% $NH_3$ in methanol; 90% A to 50% A gradient elution over 9 minutes). The first peak was collected to afford the title compound. $\delta_H$ (400 MHz, $CDCl_3$) 0.90-1.00 (m, 2H), 1.37-1.47 (m, 3H), 1.53 (s, 9H), 1.88 (s, 3H), 2.22-2.29 (m, 1H), 2.87 (d, J 17.1 Hz, 1H), 3.63 (d, J16.6 Hz, 1H), 4.25-4.33 (m, 1H), 4.40 (t, J4.40 Hz, 1H), 5.11-5.17 (m, 1H), 6.24 (s, 1H), 6.82 (d, J7.34 Hz, 1H), 7.00-7.15 (m, 6H), 10.55 (br s, 1H). LCMS (ESI, Method 1) m/e 543.2 [M+H]$^+$, RT 2.36 minutes.

Intermediate 67 tert-Butyl N-[(3-methyloxetan-3-yl)methylcarbamothioyl]carbamate

Prepared from (3-methyloxetan-3-yl)methanamine (7.11 g, 24.7 mmol) in accordance with the procedure described for Intermediate 6 to afford the title compound (1.80 g, 25%) as an off-white solid. LCMS (ESI, Method 1) m/e 261.0 [M+H]$^+$, RT 1.79 minutes.

Intermediate 68 tert-Butyl (NE)-N-{(4S)-4-[3-(benzyloxycarbonylamino)-2-chlorophenyl]-4-methyl-1-[(3-methyloxetan-3-yl)methyl]-6-oxohexahydropyrimidin-2-ylidene}carbamate Prepared from Intermediate 67 (1.50 g, 3.63 mmol) in accordance with the procedure described for Intermediate 61 to afford the title compound (0.90 g, 41%) as an off-white solid. LCMS (ESI, Method 1) m/e 571.3 [M+H]$^+$, RT 2.10 minutes.

Intermediate 69 tert-Butyl (NE)-N-{(4S')-4-(3-amino-2-chlorophenyl)-4-methyl-1-[(3-methyloxetan-3-yl)-methyl]-6-oxohexahydropyrimidin-2-ylidene}carbamate Prepared from Intermediate 68 (0.90 g, 1.50 mmol) in accordance with the procedure described for Intermediate 28 to afford the title compound (0.35 g, 50%) as an off-white solid. $\delta_H$ (400 MHz, CDCl$_3$) 1.49 (s, 9H), 1.54 (s, 3H), 1.83 (s, 3H), 2.80 (d, J 16.1 Hz, 1H), 3.68-3.74 (m, 1H), 3.91-4.00 (m, 3H), 4.15 (s, 1H), 4.19 (s, 2H), 4.54 (d, J 6.3 Hz, 1H), 4.58 (d, J5.8 Hz, 1H), 6.67 (d, J7.8 Hz, 1H), 6.74 (d, J8.3 Hz, 1H), 7.00 (t, J7.8 Hz, 1H), 10.47 (br s, 1H). LCMS (ESI, Method 1) m/e 437.1 [M+H]$^+$, RT 2.72 minutes.

Intermediate 70 tert-Butyl N-(3-ethylidenecyclobutyl) carbamate

To a solution of ethyltriphenylphosphonium bromide (4.51 g, 12.1 mmol) in THF (40 mL) at −78° C. was added KHMDS (1M solution in THF, 12.1 mL, 12.1 mmol). The mixture was stirred for 30 minutes, then tert-butyl N-(3-oxocyclobutyl)carbamate (1.50 g, 8.10 mmol) in THF (20 mL) was added dropwise at −78° C. The reaction mixture was stirred at room temperature for 2 h, then quenched with saturated brine (100 mL) and extracted with EtOAc (2×100 mL). The organic layer was washed with H$_2$O (100 mL) and brine (100 mL), then separated, dried over anhydrous Na$_2$SO$_4$ and concentrated in vacuo. The crude residue was purified by column chromatography (silica, 100-200 mesh, 10% EtOAc in hexanes) to afford the title compound (0.62 g, 39%) as an off-white solid. $\delta_H$ (400 MHz, DMSO-d$_6$) 1.37 (s, 9H), 1.45 (d, J6.8 Hz, 3H), 2.72-2.87 (m, 2H), 3.86-3.97 (m, 2H), 5.13-5.16 (m, 1H), 7.21-7.28 (m, 1H).

Intermediate 71 tert-Butyl N-(2-methyl-1-oxaspiro[2.3]hexan-5-yl) carbamate

To a solution of Intermediate 70 (1.50 g, 7.60 mmol) in DCM (80 mL) at 0° C. was added mCPBA (2.62 g, 15.20 mmol) portionwise. The reaction mixture was stirred at room temperature for 3 h, then quenched with saturated brine (50 mL) and extracted with DCM (2×50 mL). The organic layer was separated, then washed with saturated aqueous NaHCO$_3$ solution (50 mL) and brine (50 mL). The organic layer was separated, dried over anhydrous Na$_2$SO$_4$ and concentrated in vacuo. The crude residue was purified by column chromatography (silica, 100-200 mesh, 40% EtOAc in hexanes) to afford the title compound (1.1 g, 62%) as an off-white solid. LCMS (ESI, Method 1) m/e 213 [M+H]$^+$, RT 1.30 minutes.

Intermediate 72 tert-Butyl N-(3-ethyl-3-hydroxycyclobutyl)carbamate

To a solution of Intermediate 71 (0.85 g, 3.64 mmol) in THF (15 mL) at 0° C. was added LiAlH$_4$ (1M solution in THF, 5.46 mL, 5.46 mmol). The reaction mixture was stirred at 0° C. for 1 h, then quenched with EtOAc (20 mL) and washed with brine (20 mL). The organic layer was washed with H$_2$O (20 mL) and separated, then dried over anhydrous Na$_2$SO$_4$ and concentrated in vacuo. The crude residue was purified by column chromatography (silica, 100-200 mesh, 30% EtOAc in hexanes) to afford the title compound (0.71 g, 91%) as brown gum. $\delta_H$ (400 MHz, CDCl$_3$) 0.93 (t, J7.6 Hz, 3H), 1.44 (s, 9H), 1.59 (q, J6.8 Hz, 2H), 1.90 (q, J6.8 Hz, 2H), 2.51-2.55 (m, 3H), 3.70 (br s, 1H), 4.77 (br s, 1H).

Intermediate 73

3-Amino-1-ethyl-cyclobutanol hydrochloride

To a solution of Intermediate 72 (0.71 g, 3.30 mmol) in MeOH (15 mL) at 0° C. was added 4M HCl in 1,4-dioxane (3.30 mL, 13.2 mmol). The reaction mixture was stirred at room temperature for 6 h, then concentrated in vacuo. The crude residue was washed with diethyl ether (250 mL) and hexane (250 mL), then dried, to afford the title compound (0.48 g, 96%) as an off-white solid. $\delta_H$ (400 MHz, DMSO-d$_6$) 0.75-0.82 (m, 3H), 1.45-1.58 (m, 2H), 2.05-2.50 (m, 3H), 3.17-3.20 (m, 2H), 3.72-3.74 (m, 1H), 8.70 (br s, 3H).

Intermediate 74 tert-Butyl N-[(3-ethyl-3-hydroxycyclobutyl)carbamothioyl]carbamate

To a solution of tert-butyl N-(tert-butoxycarbonylcarbamothioyl)carbamate (0.71 g, 2.58 mmol) in THF (20 mL) at 0° C. was added 60% NaH (0.38 g, 9.50 mmol). The reaction mixture was stirred at 0° C. for 1 h, then TFAA (0.67 mL, 4.75 mmol) was added dropwise. The reaction mixture was further stirred at 0° C. for 1 h. A solution of Intermediate 73 (0.48 g, 3.17 mmol) in THF (5 mL) was added at 0° C. The reaction mixture was stirred at room temperature for 4 h, then quenched with H$_2$O (50 mL) and extracted with EtOAc (2×50 mL). The organic layer was washed with brine (50 mL) and separated, then dried over anhydrous Na$_2$SO$_4$ and concentrated in vacuo. The crude residue was purified by column chromatography (silica, 100-200 mesh, 10-20% EtOAc in hexanes) to afford the title compound (0.46 g, 48%) as an off-white solid. $\delta_H$ (400 MHz, CDCl$_3$) 0.90-0.98 (m, 2H), 1.51 (s, 9H), 1.59-1.67 (m, 3H), 2.00-2.05 (m, 2H), 2.52-2.71 (m, 2H), 4.11-4.81 (m, 2H), 7.91-7.94 (m, 1H), 9.79-9.86 (m, 1H). LCMS (ESI, Method 1) m/e 274 [M+H]$^+$, RT 1.92 minutes.

Intermediates 75 & 76 tert-Butyl (NE)-N-{(4S)-4-[3-(benzyloxycarbonylamino)-2-chlorophenyl]-1-(3-ethyl-3-hydroxycyclobutyl)-4-methyl-6-oxohexahydropyrimidin-2-ylidene}carbamate (trans and cis isomers)

Prepared from Intermediate 74 (1.50 g, 3.63 mmol) in accordance with the procedure described for Intermediate 61 to afford the title compounds (Peak 1: 0.2 g, 40%; and Peak 2: 0.18 g, 30%) as off-white solids.

Intermediate 75 (Peak 1, trans isomer): $\delta_H$ (400 MHz, DMSO-d$_6$) 1.14 (t, J7.6 Hz, 3H), 1.36-1.43 (m, 11H), 1.75 (s, 3H), 2.12-2.49 (m, 4H), 3.18 (d, J 16.4 Hz 1H), 3.59 (d, J 16.8 Hz, 1H), 4.01-4.19 (m, 1H), 4.54 (s, 1H), 5.14 (s, 2H), 7.18 (d, J7.6 Hz 1H), 7.32-7.36 (m, 6H), 7.58 (d, J7.2 Hz, 1H), 9.21 (s, 1H), 10.32 (s, 1H). LCMS (ESI, Method 1) m/e 585.25 [M+H]$^+$, RT 2.20 minutes.

Intermediate 76 (Peak 2, cis isomer): $\delta_H$ (400 MHz, DMSO-d$_6$) 1.14 (t, J7.6 Hz, 3H), 1.38-1.42 (m, 11H), 1.73 (s, 3H), 1.81-2.40 (m, 4H), 3.15 (d, J 16.4 Hz, 1H), 3.56 (d, J 16.8 Hz, 1H), 4.02 (q, J7.2 Hz 1H), 4.56 (s, 1H), 5.13 (s, 2H), 7.16 (d, J7.6 Hz 1H), 7.32-7.39 (m, 6H), 7.56 (d, J8.0 Hz, 1H), 9.21 (s, 1H), 10.32 (s, 1H). LCMS (ESI, Method 1) m/e 585.25 [M+H]$^+$, RT 2.14 minutes.

Intermediate 77 tert-Butyl (NE)-N-[(4S)-4-(3-amino-2-chlorophenyl)-1-(3-ethyl-3-hydroxycyclobutyl)-4-methyl-6-oxohexahydropyrimidin-2-ylidene]carbamate (trans isomer)

To a solution of Intermediate 75 (0.18 g, 0.32 mmol) in MeOH (10 mL) at 0° C. was added 10% Pd on charcoal (0.05 g, 0.48 mmol). The reaction mixture was stirred at room temperature for 30 minutes under $H_2$ pressure, then filtered through a pad of Celite® and washed with MeOH (20 mL). The filtrate was concentrated in vacuo. The crude residue was purified by column chromatography (silica, 100-200 mesh, 30% EtOAc in hexanes) to afford the title compound (0.082 g, 67%) as an off-white solid. $\delta_H$ (400 MHz, DMSO-$d_6$) 0.69 (t, J7.2 Hz, 3H), 1.41 (s, 11H), 1.59 (s, 3H), 1.85-2.39 (m, 4H), 3.07 (d, J16.0 Hz, 1H), 3.48 (d, J 15.6 Hz, 1H), 4.59 (s, 1H), 4.99-5.08 (m, 1H), 5.52 (s, 2H), 6.47 (d, J8.0 Hz, 1H), 6.78 (d, J8.0 Hz, 1H), 7.00 (t, J7.6 Hz, 1H), 10.30 (s, 1H). LCMS (ESI, Method 1) m/e 451.2 [M+H]$^+$, RT 1.93 minutes.

Intermediate 78 tert-Butyl (NE)-N-[(4S)-4-(3-amino-2-chlorophenyl)-1-(3-ethyl-3-hydroxycyclobutyl)-4-methyl-6-oxohexahydropyrimidin-2-ylidene]carbamate (cis isomer)

Prepared from Intermediate 76 (0.20 g, 0.32 mmol) in accordance with the procedure described for Intermediate 77 to afford the title compound (0.133 g, 90%) as a white solid. $\delta_H$ (400 MHz, DMSO-$d_6$) 0.78 (t, J7.2 Hz, 3H), 1.28-1.42 (m, 11H), 1.58 (s, 3H), 2.06-2.32 (m, 4H), 3.10 (d, J16.8 Hz, 1H), 3.51 (d, J16.4 Hz, 1H), 4.15-4.23 (m, 1H), 4.58 (s, 1H), 5.52 (s, 2H), 6.49 (d, J8.0 Hz, 1H), 6.79 (d, J7.6 Hz, 1H), 7.01 (t, J 8.0 Hz, 1H), 10.34 (s, 1H). LCMS (ESI, Method 1) m/e 451 [M+H]$^+$, RT 1.85 minutes.

Intermediate 79 rac-(2S,4S)-2-Methyltetrahydropyran-4-amine

To a stirred solution of 2-methyltetrahydropyran-4-one (10.0 g, 87.6 mmol) in MeOH (100 mL) were added benzylamine (14.3 mL, 131.4 mmol) and acetic acid (0.25 mL, 4.38 mmol) under a nitrogen atmosphere. The mixture was stirred for 4 h at room temperature, then sodium cyanoborohydride (8.27 g, 131.4 mmol) was added at r.t. The reaction mixture was stirred for 16 h, then concentrated under reduced pressure. The crude residue was purified by column chromatography (100-200 mesh silica gel, eluting with 30-100% EtOAc/hexane). The resulting pale brown liquid was dissolved in MeOH (100 mL), and 10% Pd/C (10.0 g) was added in a Parr shaker vessel. The reaction mixture was stirred at r.t. for 16 h, then passed through a celite pad and washed with 10% MeOH in DCM. The filtrate was concentrated under reduced pressure to obtain the title compound (4.0 g, 71%) as a brown liquid. $\delta_H$ (400 MHz, DMSO-$d_6$) 3.81-3.77 (m, 1H), 3.32-3.23 (m, 2H), 2.71-2.63 (m, 1H), 2.32-1.86 (br s, 2H), 1.71-1.58 (m, 2H), 1.14-1.05 (m 4H), 0.86 (q, J 12.3 Hz, 1H).

Intermediate 80 tert-Butyl N-{[rac-(2S,4S)-2-methyltetrahydropyran-4-yl]carbamothioyl}carbamate

Prepared from Intermediate 79 (3.16 g, 11.46 mmol) in accordance with the procedure described for Intermediate 6 to afford the title compound (2.1 g, 60%) as an off-white solid. $\delta_H$ (400 MHz, DMSO-$d_6$) 10.61 (s, 1H), 9.69 (d, J7.5 Hz, 1H), 4.34-4.30 (m, 1H), 3.86 (dd, J1.9, 10.8 Hz, 1H), 3.43-3.35 (m, 2H), 2.01 (d, J10.6 Hz, 1H), 1.93 (d, J12.2 Hz, 1H), 1.47 (s, 9H), 1.44-1.37 (m, 2H), 1.18-1.13 (m, 1H), 1.10 (d, J6.12 Hz, 3H).

Intermediate 81 tert-Butyl (NE)-N-{(4S)-4-[3-(benzyloxycarbonylamino)-2-chlorophenyl]-4-methyl-1-[(2SR,4SR)-2-methyltetrahydropyran-4-yl]-6-oxohexahydropyrimidin-2-ylidene}-carbamate Prepared from Intermediate 80 (2.0 g, 5.3 mmol) in accordance with the procedure described for Intermediate 61 to afford the title compound as an off-white solid. $\delta_H$ (400 MHz, DMSO-$d_6$) 10.51 (s, 1H), 9.25 (s, 1H), 7.58 (d, J7.8 Hz, 1H), 7.40-7.32 (m, 6H), 7.17 (d, J8.0 Hz, 1H), 5.13 (s, 2H), 4.68-4.62 (m, 1H), 3.82 (dd, J2.8, 11.6, 1H), 3.74-3.71 (m, 1H), 3.58 (dd, J2.8, 16.4 Hz, 1H), 3.29-3.17 (m, 3H), 2.35-2.21 (m, 1H), 1.75 (s, 3H), 1.44 (s, 9H), 1.07 (d, J 9.3 Hz, 2H), 1.05 (d, J 17.6 Hz, 2H).

Intermediates 82 & 83 tert-Butyl (NE)-N-{(4S)-4-(3-amino-2-chlorophenyl)-4-methyl-1-[(2S*,4S*)-2-methyl-tetrahydropyran-4-yl]-6-oxohexahydropyrimidin-2-ylidene}carbamate (isomers 1 and 2)

Prepared from Intermediate 81 (1.5 g, 2.5 mmol) in accordance with the procedure described for Intermediate 28. The resulting racemic mixture was separated using chiral HPLC purification (chiral HPLC conditions: column: Chiralpak IC (250×20 mm) 5μ; mobile phase: hexane/EtOH/DEA: 80/20/0.1 (v/v/v); flow rate: 18 mL/minute; uv: 242 nm; runtime: 15 minutes) to afford the title compounds (Peak 1 diastereomer 0.505 g; and Peak 2 diastereomer 0.523 g) as off-white solids.

Intermediate 82 (Peak 1): $\delta_H$ (400 MHz, DMSO-$d_6$) 10.47 (s, 1H), 7.01 (t, J7.9 Hz, 1H), 6.78 (d, J8.1 Hz, 1H), 6.46 (d, J7.7 Hz, 1H), 5.52 (s, 2H), 4.66-4.63 (m, 1H), 3.83 (dd, J 4.1, 11.3 Hz, 1H), 3.50 (d, J 16.1 Hz, 1H), 3.29-3.23 (m, 2H), 3.11 (d, J16.2 Hz, 1H), 2.35-2.32 (m, 1H), 2.00-1.97 (m, 1H), 1.72 (s, 3H), 1.44 (s, 9H), 1.33-1.30 (m, 1H), 1.08-1.05 (m, 1H), 0.99 (d, J6.0 Hz, 3H). LCMS (ESI, Method 5) m/e 451 [M+H]$^+$, RT 1.53 minutes.

Intermediate 83 (Peak 2): $\delta_H$ (400 MHz, DMSO-$d_6$) 10.47 (s, 1H), 7.00 (t, J7.9 Hz, 1H), 6.78 (d, J8.0 Hz, 1H), 6.46 (d, J7.8 Hz, 1H), 5.52 (s, 2H), 4.69-4.63 (m, 1H), 3.75 (dd, J 4.5, 11.2 Hz, 1H), 3.50 (d, J 16.3 Hz, 1H), 3.23-3.18 (m, 2H), 3.11 (d, J 16.2 Hz, 1H), 2.33-2.22 (m, 1H), 2.11-2.02 (m, 1H), 1.73 (s, 3H), 1.44 (s, 10H), 1.06 (d, J6.0 Hz, 3H), 0.85 (d, J7.0 Hz, 1H). LCMS (ESI, Method 5) m/e 451 [M+H]$^+$, RT 1.56 minutes.

Intermediate 84

3-Bromo-6-(difluoromethyl)pyridine-2-carbonitrile

5-Bromo-2-(difluoromethyl)pyridine (400 mg, 1.92 mmol) was dissolved in chloroform (16 mL) and mCPBA (398 mg, 2.31 mmol) was added. The reaction mixture was stirred at r.t. for 8 h, then partitioned between aqueous $K_2CO_3$ solution and DCM. The aqueous layer was separated, and washed with further DCM. The combined organic layers were dried with $Na_2SO_4$ and concentrated under reduced pressure. The resulting white solid was redissolved in acetonitrile (20 mL), then trimethylsilyl cyanide (1.1 mL, 8.9 mmol) and triethylamine (0.933 mL, 6.7 mmol) were added. The reaction mixture was heated at 100° C. and stirred for 16 h, then cooled to room temperature and partitioned between EtOAc and water. The organic layer was separated and dried with sodium sulfate. The solvent was removed under reduced pressure, and the resulting crude solid was purified with flash chromatography (eluting with 20% EtOAc in hexane) to afford the title compound (135 mg, 26%) as an off-white solid. $\delta_H$ (400 MHz, DMSO-d$_6$) 8.22 (d, J 8.4 Hz, 1H), 7.76 (d, J8.4 Hz, 1H), 6.63 (t, J53 Hz, 1H).

Intermediate 85

1-Bromo-4-fluoro-2-(methylsulfonyl)benzene

1-Bromo-4-fluoro-2-(methylsulfanyl)benzene (250 mg, 1.13 mmol) was dissolved in DCM (15 mL), and mCPBA (390 mg, 2.26 mmol) was added portionwise. The reaction mixture was stirred for 16 h, then the resulting suspension was filtered. The filtrate was diluted with DCM and washed with aqueous $NaHCO_3$ solution, then with water. The organic layer was dried over $Na_2SO_4$, and the solvent was removed. The crude solid was purified using flash column chromatography (eluting with 10% EtOAc in hexane) to afford the title compound (235 mg, 83%) as an off-white solid.

Intermediate 86 tert-Butyl N-[(3-oxocyclobutyl)carbamothioyl]carbamate

To a solution of N,N'-bis-tert-butoxycarbonylthiourea (3.33 g, 11.8 mmol) in THF (40 mL) at 0° C. was added 60% NaH (1.78 g, 44.4 mmol). The reaction mixture was stirred at 0° C. for 1 h, then TFAA (2.71 mL, 19.2 mmol) was added. The reaction mixture was further stirred at 0° C. for 1 h, then a solution of 3-aminocyclobutan-1-one hydrochloride (2.00 g, 14.8 mmol) in DMF (5 mL) was added at 0° C. The reaction mixture was stirred at room temperature for 4 h, then quenched with $H_2O$ (100 mL) and extracted with EtOAc (2×100 mL). The organic layer was washed with brine (100 mL) and separated, then dried over anhydrous $Na_2SO_4$ and concentrated in vacuo. The crude residue was purified by column chromatography (silica, 100-200 mesh, 10-20% EtOAc in hexanes) to afford the title compound (2.2 g, 53%) as a pale yellow solid. $\delta_H$ (400 MHz, DMSO-d$_6$) 1.54 (s, 9H), 3.13-3.20 (m, 2H), 3.53-3.61 (m, 2H), 4.76-4.82 (m, 1H), 7.91 (br s, 1H), 10.07 (br s, 1H). LCMS (ESI, Method 1) m/e 245 [M+H]$^+$, RT 1.85 minutes.

Intermediate 87 tert-Butyl (NE)-N-{(4S)-4-[3-(benzyloxycarbonylamino)-2-chlorophenyl]-4-methyl-6-oxo-1-(3-oxocyclobutyl)hexahydropyrimidin-2-ylidene}carbamate Prepared from Intermediate 86 (2.0 g, 5.3 mmol) in accordance with the procedure described for Intermediate 61 to afford the title compound as an off-white solid. $\delta_H$ (400 MHz, DMSO-d$_6$) 1.55 (s, 9H), 1.87 (s, 3H), 2.90 (d, J16.1 Hz, 1H), 3.07-3.18 (m, 1H), 3.25-3.36 (m, 2H), 3.51-3.59 (m, 1H), 3.70 (dd, J 16.1, 1.4 Hz, 1H), 5.24 (s, 2H), 5.49-5.62 (m, 1H), 7.05 (dd, J8.0, 1.2 Hz, 1H), 7.36-7.40 (m, 2H), 7.41-7.45 (m, 4H), 8.23 (d, J8.3 Hz, 1H), 10.64 (s, 1H) (1H submerged in solvent peak). LCMS (ESI, Method 1) m/e 455 [M+H]$^+$, RT 2.14 minutes.

Intermediate 88 tert-Butyl (NE)-N-{(4S)-4-[3-(benzyloxycarbonylamino)-2-chlorophenyl]-1-(3-hydroxy-3-isopropylcyclobutyl)-4-methyl-6-oxohexahydropyrimidin-2-ylidene}carbamate (cis isomer To a solution of Intermediate 87 (0.8 g, 1.41 mmol) in dry THF (25 mL) at −78° C. was added isopropylmagnesium chloride (2M solution in THF, 7.03 mL, 14.1 mmol). The reaction mixture was stirred at room temperature for 2 h, then diluted with $H_2O$ (100 mL) and extracted with EtOAc (2×100 mL). The organic layer was separated, dried over anhydrous $Na_2SO_4$ and concentrated in vacuo. The crude residue was purified by column chromatography (silica, 100-200 mesh, 50% EtOAc in hexanes) to afford the title compound (0.125 g, 15%) as an off-white solid. $\delta_H$ (400 MHz, CDCl$_3$) 0.90 (d, J6.8 Hz, 6H), 1.55 (s, 9H), 1.85 (s, 3H), 2.40-2.55 (m, 2H), 2.56-2.70 (m, 3H), 2.88 (d, J 16.6 Hz, 1H), 3.76 (d, J 16.6 Hz, 1H), 4.35 (s, 1H), 4.83-4.91 (m, 1H), 5.24 (s, 2H), 7.02 (dd, J7.8, 1.4 Hz, 1H), 7.35-7.46 (m, 7H), 8.21 (d, J8.3 Hz, 1H), 10.58 (s, 1H). LCMS (ESI, Method 1) m/e 599 [M+H]$^+$, RT 2.44 minutes.

Intermediate 89 tert-Butyl (NE)-N-[(4S)-4-(3-amino-2-chlorophenyl)-1-(3-hydroxy-3-isopropyl-cyclobutyl)-4-methyl-6-oxohexahydropyrimidin-2-ylidene]carbamate (cis isomer)

Prepared from Intermediate 88 (0.12 g, 0.2 mmol) in accordance with the procedure described for Intermediate 28 to afford the title compound (0.065 g, 69%) as an off-white solid. $\delta_H$ (400 MHz, DMSO-d$_6$) 0.77-0.80 (m, 6H), 1.43 (s, 9H), 1.47-1.52 (m, 1H), 1.73 (s, 3H), 2.20-2.36 (m, 4H), 3.12 (d, J 16.6 Hz, 1H), 3.54 (d, J 16.6 Hz, 1H), 4.27-4.36 (m, 1H), 4.49 (s, 1H), 5.53 (s, 2H), 6.49 (d, J7.8 Hz, 1H), 6.79 (d, J8.3 Hz, 1H), 6.98-7.05 (m, 1H), 10.36 (s, 1H). LCMS (ESI, Method 1) m/e 465 [M+H]$^+$, RT 2.08 minutes.

Intermediate 90 tert-Butyl N-[(4,4-difluorocyclohexyl)carbamothioyl]carbamate

Prepared from 4,4-difluorocyclohexanamine (4.09 g, 14.8 mmol) in accordance with the procedure described for Intermediate 6 to afford the title compound as a yellow solid.

δ$_H$ (400 MHz, CDCl$_3$) 1.50 (s, 9H), 1.62-1.81 (m, 2H), 1.84-2.01 (m, 2H), 2.05-2.24 (m, 4H), 4.30-4.44 (m, 1H), 7.87 (br s, 1H), 9.74 (d, J3.9 Hz, 1H).

Intermediate 91 tert-Butyl (NE)-N-{(4S)-4-[3-(benzyloxycarbo-nylamino)-2-chlorophenyl]-1-(4,4-difluorocyclo-hexyl)-4-methyl-6-oxohexahydropyrimidin-2-ylidene}carbamate Prepared from Intermediate 90 in accordance with the procedure described for Intermediate 61 to afford the title compound as an off-white solid. δ$_H$ (400 MHz, CDCl$_3$) 1.14 (d, J12.7 Hz, 1H), 1.55 (s, 9H), 1.65-1.70 (m, 3H), 1.72-1.79 (m, 1H), 1.83 (s, 3H), 1.98-2.14 (m, 2H), 2.43-2.54 (m, 1H), 2.56-2.66 (m, 1H), 2.84 (d, J 16.1 Hz, 1H), 3.65 (d, J16.6 Hz, 1H), 4.60-4.70 (m, 1H), 5.24 (s, 2H), 7.04 (dd, J7.8, 1.4 Hz, 1H), 7.36-7.40 (m, 2H), 7.40-7.46 (m, 4H), 8.21 (d, J7.8 Hz, 1H), 10.60 (br s, 1H). LCMS (ESI, Method 1) m/e 606 [M+H]$^+$, RT 2.35 minutes.

Intermediate 92 tert-Butyl (NE)-N-[(4S)-4-(3-amino-2-chlorophe-nyl)-1-(4,4-difluorocyclohexyl)-4-methyl-6-oxo-hexahydropyrimidin-2-ylidene]carbamate Prepared from Intermediate 91 (1.90 g, 3.03 mmol) in accordance with the procedure described for Intermediate 28 to afford the title compound (1.18 g, 83%) as an off-white solid. δ$_H$ (400 MHz, CDCl$_3$) 1.15-1.21 (m, 1H), 1.55 (s, 9H), 1.62-1.70 (m, 2H), 1.74-1.80 (m, 1H), 1.84 (s, 3H), 2.00-2.02 (m, 1H), 2.08-2.11 (m, 1H), 2.45-2.55 (m, 1H), 2.57-2.67 (m, 1H), 2.78-2.85 (m, 1H), 3.66 (d, J 16.6 Hz, 1H), 4.61-4.70 (m, 1H), 6.68 (dd, J7.8, 1.4 Hz, 1H), 6.76 (dd, J8.0, 1.2 Hz, 1H), 7.00-7.07 (m, 1H), 10.55 (br s, 1H) (both exchangeable protons of —NH$_2$ not observed as a consequence of moisture in the solvent). LCMS (ESI, Method 1) m/e 471.2 [M+H]$^+$, RT 2.12 minutes.

Intermediate 93 rac-(2R,4S)-2-Methyltetrahydropyran-4-amine

Isolated as a second product from the reaction described for Intermediate 79. δ$_H$ (400 MHz, DMSO-d$_6$) 3.81-3.76 (m, 1H), 3.74-3.71 (m, 1H), 3.54-3.51 (m, 1H), 3.20 (br s, 1H), 1.67-1.58 (m, 1H), 1.41-1.31 (m, 2H), 1.30-1.23 (m, 1H), 1.00 (d, J6.3 Hz, 3H).

Intermediate 94 tert-Butyl N-[(2,2-dimethyltetrahydropyran-4-yl)carbamothioyl]carbamate

Prepared from 2,2-dimethyltetrahydro-2H-pyran-4-amine (2.00 g, 15.5 mmol) in accordance with the procedure described for Intermediate 6 to afford the title compound (2.2 g, 45%) as a yellow solid. δ$_H$ (400 MHz, CDCl$_3$) 1.27 (s, 3H), 1.30 (s, 3H), 1.50 (s, 9H), 1.52-1.56 (m, 2H), 2.03-2.13 (m, 2H), 3.73-3.85 (m, 2H), 4.55-4.68 (m, 1H), 7.83 (br s, 1H), 9.57 (d, J5.9 Hz, 1H). LCMS (ESI, Method 1) m/e 233 [M+H−56]+, RT 1.98 minutes.

Intermediate 95 tert-Butyl (NE)-N-{(4S)-4-[3-(benzyloxycarbo-nylamino)-2-chlorophenyl]-1-(2,2-dimethyltetrahy-dropyran-4-yl)-4-methyl-6-oxohexahydropyrimidin-2-ylidene}carbamate Prepared from Intermediate 94 (2.30 g, 5.56 mmol) in accordance with the procedure described for Intermediate 61 to afford the title compound (mixture of diastereomers) (1.8 g, 98%) as an off-white solid. LCMS (ESI, Method 1) m/e 600 [M+H]$^+$, RT 2.25 & 2.26 minutes.

Intermediates 96 & 97 tert-Butyl (NE)-N-{(4S)-4-(3-amino-2-chlorophe-nyl)-1-[(4S*)-2,2-dimethyltetrahydro-pyran-4-yl]-4-methyl-6-oxohexahydropyrimidin-2-ylidene}carbamate (isomers 1 and 2)

To a solution of Intermediate 95 (1.80 g, 2.9 mmol) in MeOH (25 mL) at 0° C. was added 10% Pd/C (0.16 g, 1.48 mmol). The reaction mixture was stirred at room temperature for 2 h under H$_2$ pressure, then filtered through a pad of Celite® and washed with MeOH (150 mL). The filtrate was concentrated in vacuo. The crude residue was purified by column chromatography (silica, 100-200 mesh, 20% EtOAc in hexanes) to afford the title compounds (mixture of diastereomers) (1.3 g, 94%). The individual diastereomers were isolated using chiral HPLC SFC (column: Diacel Chiralpak-IC, 250 mm×4.6 mm, 5 g; mobile phase A: n-hexane+0.1% diethylamine; mobile phase B: ethanol; flow rate: 1.0 mL/minute; isocratic: 15% B).

Intermediate 96 (Peak 1): δ$_H$ (400 MHz, CDCl$_3$) 1.11 (d, J12.2 Hz, 1H), 1.24 (s, 3H), 1.27 (s, 3H), 1.45 (d, J 12.2 Hz, 1H), 1.54 (s, 9H), 1.84 (s, 3H), 2.41 (t, J 12.4 Hz, 1H), 2.50-2.59 (m, 1H), 2.80 (d, J 16.1 Hz, 1H), 3.58-3.65 (m, 1H), 3.67-3.74 (m, 2H), 4.98-5.06 (m, 1H), 6.70 (d, J7.8 Hz, 1H), 6.76 (d, J8.3 Hz, 1H), 7.03 (t, J7.8 Hz, 1H), 10.49 (br s, 1H) (two exchangeable protons not observed as a consequence of moisture in the solvent). LCMS (ESI, Method 1) m/e 465 [M+H]$^+$, RT 2.09 minutes.

Intermediate 97 (Peak 2): δ$_H$ (400 MHz, CDCl$_3$) 1.10 (dd, J12.2, 1.9 Hz, 1H), 1.18 (s, 3H), 1.23 (s, 3H), 1.45 (d, J 12.2 Hz, 1H), 1.55 (s, 9H), 1.84 (s, 3H), 2.39 (t, J 12.7 Hz, 1H), 2.56-2.65 (m, 1H), 2.80 (d, J 16.1 Hz, 1H), 3.67 (d, J 16.1 Hz, 1H), 3.72-3.81 (m, 2H), 5.01-5.04 (m, 1H), 6.70 (d, J7.8 Hz, 1H), 6.77 (d, J7.8 Hz, 1H), 7.05 (t, J7.8 Hz, 1H), 10.53 (br s, 1H) (two exchangeable protons not observed as a consequence of moisture in the solvent). LCMS (ESI, Method 1) m/e 465 [M+H]$^+$, RT 2.05 minutes.

Intermediate 98 tert-Butyl N-{[3-hydroxy-3-(trifluoromethyl)cy-clobutyl]carbamothioyl}carbamate

Prepared from 3-amino-1-(trifluoromethyl)cyclobutan-1-ol (5.00 g, 32.2 mmol) in accordance with the procedure described for Intermediate 6 to afford the title compound (5.5 g, 50%) as a yellow solid. δ$_H$ (400 MHz, CDCl$_3$) 1.51 (s, 9H), 3.12-2.25 (m, 4H), 4.95-4.49 (m 1H), 6.78 (br s, 1H), 7.90 (br s, 1H), 9.90 (br s, 1H).

Intermediates 99 & 100 tert-Butyl (NE)-N-{(4S)-4-[3-(benzyloxycarbonylamino)-2-chlorophenyl]-1-[3-hydroxy-3-(trifluoromethyl)cyclobutyl]-4-methyl-6-oxohexahydropyrimidin-2-ylidene}carbamate (cis and trans isomers)

Prepared from Intermediate 98 (5.50 g, 16.2 mmol) in accordance with the procedure described for Intermediate 61. The crude residue was purified by column chromatography (silica, 100-200 mesh, 20-25% EtOAc in hexanes) to afford the title compounds (cis isomer: 2.5 g, 13%; and trans isomer: 3.5 g, 18%) as off-white solids.

Intermediate 99 (cis isomer): $\delta_H$ (400 MHz, CDCl$_3$) 1.53 (s, 9H), 1.85 (s, 3H), 2.73-2.93 (m, 4H), 2.95-3.07 (m, 1H), 3.77 (d, J 16.1 Hz, 1H), 4.41 (br s, 1H), 5.06-5.14 (m, 1H), 5.22 (s, 2H), 6.98 (dd, J 8.1, 1.2 Hz, 1H), 7.33-7.46 (m, 6H), 8.22 (d, J 8.3 Hz, 1H), 10.56 (s, 1H) (one exchangeable proton not observed as a consequence of moisture in the solvent). LCMS (ESI, Method 1) m/e 625 [M+H]$^+$, RT 2.32 minutes.

Intermediate 100 (trans isomer): $\delta_H$ (400 MHz, CDCl$_3$) 1.52 (s, 9H), 1.83 (s, 3H), 2.30-2.45 (m, 2H), 2.57-2.68 (m, 2H), 2.82 (d, J 16.6 Hz, 1H), 3.67 (d, J 16.6 Hz, 1H), 4.99 (t, J 8.6 Hz, 1H), 5.23 (s, 2H), 7.02 (d, J 7.82 Hz, 1H), 7.33-7.45 (m, 6H), 8.22 (d, J 8.3 Hz, 1H), 10.40 (br s, 1H) (two exchangeable protons submerged within solvent peak). LCMS (ESI, Method 1) m/e 625 [M+H]$^+$, RT 2.24 minutes.

Intermediate 101 tert-Butyl N-(2-oxaspiro[3.3]heptan-6-ylcarbamothioyl)carbamate

Prepared from 2-oxaspiro[3.3]heptan-6-amine (1.00 g, 6.68 mmol) in accordance with the procedure described for Intermediate 6 to afford the title compound (0.65 g, 32%) as an off-white solid. $\delta_H$ (400 MHz, CDCl$_3$) 1.48 (s, 9H), 2.14-2.23 (m, 2H), 2.80-2.85 (m, 2H), 4.47-4.55 (m, 1H), 4.64 (s, 2H), 4.76 (s, 2H), 7.95 (br s, 1H), 9.77 (br s, 1H). LCMS (ESI, Method 1) m/e 273.2 [M+H]$^+$, RT 1.80 minutes.

Intermediate 102 tert-Butyl (NE)-N-{(4S)-4-[3-(benzyloxycarbonylamino)-2-chlorophenyl]-4-methyl-1-[(2SR,4RS)-2-methyltetrahydropyran-4-yl]-6-oxohexahydropyrimidin-2-ylidene}-carbamate Prepared from Intermediate 93 in accordance with the procedure described for Intermediate 6, then Intermediate 61, to afford the title compound. $\delta_H$ (400 MHz, CDCl$_3$) (signals for isomers are in italics) 1.03-1.07 (m, 1H), 1.24, 1.29 (d, J 6.8 Hz, 3H), 1.35-1.40 (m, 1H), 1.45-1.47 (m, 1H), 1.54, 1.57 (s, 9H), 1.83 (s, 3H), 2.54-2.70 (m, 2H), 2.83 (d, J 16.1 Hz, 1H), 3.63-3.68 (m, 1H), 3.72-3.77 (m, 1H), 4.13-4.28 (m, 1H), 4.98-5.09 (m, 1H), 5.24 (s, 2H), 7.05 (d, J 7.8 Hz, 1H), 7.36-7.40 (m, 3H), 7.41-7.46 (m, 3H), 8.21 (d, J 8.3 Hz, 1H), 10.53, 10.57 (br s, 1H). LCMS (ESI, Method 1) m/e 585.7 [M+H]$^+$, RT 2.28 minutes.

Intermediate 103 tert-Butyl (NE)-N-{(4S)-4-(3-amino-2-chlorophenyl)-4-methyl-1-[(2SR,4RS)-2-methyl-tetrahydropyran-4-yl]-6-oxohexahydropyrimidin-2-ylidene}carbamate Prepared from Intermediate 102 (1.50 g, 2.48 mmol) in accordance with the procedure described for Intermediate 28 to afford the title compound (1.18 g, 83%) as an off-white solid. $\delta_H$ (400 MHz, CDCl$_3$) 1.24 (d, J 6.8 Hz, 3H), 1.51 (s, 1H), 1.54 (s, 9H), 1.84 (s, 3H), 2.52-2.73 (m, 2H), 2.81 (d, J 16.6 Hz, 1H), 3.63-3.71 (m, 2H), 3.73-3.79 (m, 1H), 4.11-4.20 (m, 1H), 4.21-4.28 (m, 1H), 5.00-5.12 (m, 1H), 6.69 (d, J 7.8 Hz, 1H), 6.76 (d, J 8.3 Hz, 1H), 7.01-7.06 (m, 1H), 10.51 (d, J 17.1 Hz, 1H) (exchangeable —NH$_2$ protons not observed). LCMS (ESI, Method 1) m/e 451.4 [M+H]$^+$, RT 2.03 minutes.

Intermediate 104 tert-Butyl (NE)-N-[(4S)-4-(2-chloro-3-{[6-(difluoromethoxy)pyridin-3-yl]amino}phenyl)-4-methyl-1-[(2SR,4RS)-2-methyltetrahydropyran-4-yl]-6-oxohexahydropyrimidin-2-ylidene]carbamate Prepared from Intermediate 103 and 5-bromo-2-(difluoromethoxy)pyridine in accordance with the procedure described in General Method 4 to afford the title compound as an off-white solid. LCMS (ESI, Method 1) m/e 594.1 [M+H]$^+$, RT 2.28 minutes.

Intermediate 105 tert-Butyl (NE)-N-[(4S)-4-{2-chloro-3-[(6-cyclopropylpyridin-3-yl)amino]phenyl}-4-methyl-1-[(2SR,4RS)-2-methyltetrahydropyran-4-yl]-6-oxohexahydropyrimidin-2-ylidene]carbamate Prepared from Intermediate 103 and 5-bromo-2-cyclopropylpyridine in accordance with the procedure described in General Method 4 to afford the title compound as an off-white solid. LCMS (ESI, Method 1) m/e 568.1 [M+H]$^+$, RT 2.26 minutes.

Intermediate 106 tert-Butyl (NE)-N-[(4S)-4-{2-chloro-3-[(6-methylpyridin-3-yl)amino]phenyl}-4-methyl-1-[(2SR,4RS)-2-methyltetrahydropyran-4-yl]-6-oxohexahydropyrimidin-2-ylidene]-carbamate Prepared from Intermediate 103 and 5-bromo-2-methylpyridine in accordance with the procedure described in General Method 4 to afford the title compound as an off-white solid. LCMS (ESI, Method 1) m/e 541.2 [M+H]$^+$, RT 2.10 minutes.

Intermediate 107 tert-Butyl (NE)-N-{(4S)-4-(3-amino-2-chlorophenyl)-1-[3-hydroxy-3-(trifluoromethyl)-cyclobutyl]-4-methyl-6-oxohexahydropyrimidin-2-ylidene}carbamate (cis isomer)

Prepared from Intermediate 99 (2.5 g, 3.78 mmol) in accordance with the procedure described for Intermediate 28 to afford the title compound (1.6 g, 76%) as an off-white solid. 1.43 (s, 9H), 1.74 (s, 3H), 2.33-2.36 (m, 1H), 2.52-2.58 (m, 2H), 2.61-2.68 (m, 1H), 3 $\delta_H$ (400 MHz, DMSO-d$_6$). 13 (d, J 16.6 Hz, 1H), 3.54 (d, J 16.1 Hz, 1H), 4.40-4.45 (m, 1H), 5.54 (s, 2H), 6.39 (s, 1H), 6.50 (d, J 7.8 Hz, 1H), 6.80 (d, J 8.3 Hz, 1H), 6.99-7.04 (m, 1H), 10.33 (s, 1H). LCMS (ESI, Method 1) m/e 491.5 [M+H]$^+$, RT 2.12 minutes.

Intermediate 108 tert-Butyl (NE)-N-{(4S)-4-(3-amino-2-chlorophenyl)-1-[3-hydroxy-3-(trifluoromethyl)-cyclobutyl]-4-methyl-6-oxohexahydropyrimidin-2-ylidene}carbamate (trans isomer)

Prepared from Intermediate 100 (2.5 g, 3.78 mmol) in accordance with the procedure described for Intermediate 28 to afford the title compound (1.6 g, 76%) as an off-white solid. $\delta_H$ (400 MHz, DMSO-d$_6$) 1.43 (s, 9H), 1.72 (s, 3H), 2.03-2.10 (m, 1H), 2.13-2.21 (m, 1H), 2.54-2.66 (m, 2H), 3.11 (d, J 16.6 Hz, 1H), 3.52 (d, J 16.6 Hz, 1H), 4.91-4.96 (m, 1H), 5.54 (s, 2H), 6.41 (s, 1H), 6.48 (d, J7.3 Hz, 1H), 6.78 (d, J7.8 Hz, 1H), 6.97-7.03 (m, 1H), 10.29 (s, 1H). LCMS (ESI, Method 1) m/e 491 [M+H]$^+$, RT 2.07 minutes.

Intermediate 109

1,1,2,2-Tetramethyl-1,2-ethanediamino-N,N'-bis(3,5-di-tert-butylsallidene)cobalt(II)

A solution of 2,4-di-tert-butyl-6-[(E)-{2-[(E)-(3,5-di-tert-butyl-2-hydroxyphenyl)-methyleneamino]-1,1,2-trimethylpropyl}iminomethyl]phenol (1 g, 1.82 mmol) in EtOH (20 mL) was heated to reflux under an argon atmosphere for 10 minutes. Cobalt(II) acetate (0.45 g, 1.82 mmol) was added. The reaction mixture was heated under reflux for 2 h, then cooled to room temperature. The solvent was decanted and the residue was concentrated in vacuo. The crude residue was washed with diethyl ether (20 mL) to afford the title compound (0.16 g, 15%) as a red solid.

Intermediate 110 tert-Butyl N-(3-cyano-3-methylcyclobutyl)carbamate

To tert-butyl N-(3-methylenecyclobutyl)carbamate (1.00 g, 5.46 mmol) in EtOH (12 mL) under an argon atmosphere were added Intermediate 109 (0.01 g, 0.11 mmol), p-toluenesulfonyl cyanide (1.48 g, 8.19 mmol) tert-butyl hydroperoxide (5.5M solution in THF, 0.2 mL, 0.83 mmol), phenylsilane (1M solution in THF, 5.46 mL, 5.46 mmol) and EtOH (3 mL). The reaction mixture was stirred at room temperature for 2 h, then quenched with water (20 mL) and extracted with EtOAc (2×10 mL). The organic layer was separated, dried over anhydrous Na$_2$SO$_4$ and concentrated in vacuo. The crude residue was purified by column chromatography (silica, 100-200 mesh, 3-7% EtOAc in hexanes) to afford the title compound (0.93 g, 81%) as a colourless oil. $\delta_H$ (400 MHz, CDCl$_3$) 1.51 (s, 9H), 1.67-1.59 (m, 3H), 2.05-2.10 (m, 2H), 3.19-3.15 (m, 2H), 4.81-4.11 (m, 1H), 7.91 (br s, 1H).

Intermediate 111

3-Amino-1-methylcyclobutanecarbonitrile hydrochloride

To Intermediate 110 (0.92 g, 4.3 mmol) in MeOH (20 mL) at 0° C. was added 4M HCl in 1,4-dioxane (3.28 mL, 13.1 mmol). The reaction mixture was stirred at room temperature for 5 h, then concentrated in vacuo. The crude residue was washed with diethyl ether (250 mL) and hexane (250 mL), then dried, to afford the title compound (0.72 g) as a yellow solid. $\delta_H$ (400 MHz, DMSO-d$_6$) 1.12-1.19 (m, 3H), 2.84-2.61 (m, 2H), 2.23-2.15 (m, 2H), 3.90-3.45 (br s, 1H), 8.37 (br s, 3H).

Intermediate 112 tert-Butyl N-[(3-cyano-3-methylcyclobutyl)carbamothioyl]carbamate

Prepared from Intermediate 111 (1.14 g, 4.1 mmol) in accordance with the procedure described for Intermediate 6 to afford the title compound (0.56 g, 41%) as an off-white solid. $\delta_H$ (400 MHz, CDCl$_3$) 1.51 (s, 9H), 1.67-1.59 (m, 3H), 2.05-2.10 (m, 2H), 3.19-3.15 (m, 2H), 4.81-4.11 (m, 1H), 7.91 (br s, 1H), 9.83 (br s, 1H).

Intermediates 113 & 114 tert-Butyl (NE)-N-{(4S)-4-[3-(benzyloxycarbonylamino)-2-chlorophenyl]-1-(3-cyano-3-methylcyclobutyl)-4-methyl-6-oxohexahydropyrimidin-2-ylidene}carbamate (cis and trans isomers)

Prepared from Intermediate 112 (0.68 g, 1.65 mmol) in accordance with the procedure described for Intermediate 61 to afford the title compounds (separated diastereomers) after purification using flash column chromatography (gradient elution with 25-45% EtOAc in hexanes).

Intermediate 113 (trans isomer): $\delta_H$ (400 MHz, CDCl$_3$) 1.50 (s, 3H), 1.54 (s, 9H), 1.84 (s, 3H), 2.55-2.65 (m, 1H), 2.66-2.74 (m, 2H), 2.77-2.88 (m, 2H), 2.90-3.00 (m, 1H), 3.68 (d, J16.6 Hz, 1H), 5.24 (s, 2H), 7.00-7.04 (m, 1H), 7.37-7.40 (m, 5H), 7.42 (d, J5.8 Hz, 2H), 8.23 (d, J8.3 Hz, 1H), 10.47 (br s, 1H). LCMS (ESI, Method 1) m/e 580.6 [M+H]$^+$, RT 2.32 minutes.

Intermediate 114 (cis isomer): $\delta_H$ (400 MHz, CDCl$_3$) 1.50 (s, 3H), 1.54 (s, 9H), 1.86 (s, 3H), 2.34-2.39 (m, 1H), 2.43-2.48 (m, 1H), 2.52-2.56 (m, 1H), 2.80-2.85 (m, 1H), 2.87 (s, 1H), 3.51 (s, 1H), 3.69 (d, J 16.6 Hz, 1H), 4.85-4.94 (m, 1H), 5.24 (s, 2H), 7.05 (dd, J 8.07, 1.22 Hz, 1H), 7.29-7.35 (m, 1H), 7.36-7.47 (m, 5H), 8.25 (d, J7.83 Hz, 1H), 10.49 (br s, 1H). LCMS (ESI, Method 1) m/e 580.6 [M+H]$^+$, RT 2.28 minutes.

Intermediate 115 tert-Butyl (NE)-N-[(4S)-4-(3-amino-2-chlorophenyl)-1-(3-cyano-3-methylcyclobutyl)-4-methyl-6-oxohexahydropyrimidin-2-ylidene]carbamate (cis isomer)

Prepared from Intermediate 114 (0.15 g, 0.23 mmol) in accordance with the procedure described for Intermediate 28 to afford the title compound (0.11 g, 85%) as an off-white solid. $\delta_H$ (400 MHz, DMSO-d$_6$) 1.49 (s, 3H), 1.54 (s, 9H), 1.86 (s, 3H), 2.40-2.52 (m, 2H), 2.55 (d, J8.3 Hz, 2H), 2.68-2.74 (m, 1H), 2.81 (d, J 16.6 Hz, 1H), 3.25 (d, J17.6 Hz, 1H), 3.68-3.74 (m, 1H), 4.76-4.85 (m, 1H), 6.70 (dd, J7.8, 1.4 Hz, 1H), 6.81 (dd, J7.8, 1.4 Hz, 1H), 7.09 (t, J7.8 Hz, 1H), 10.41 (br s, 1H). LCMS (ESI, Method 1) m/e 446.1 [M+H]$^+$, RT 2.11 minutes.

Intermediate 116 tert-Butyl (NE)-N-[(4S)-4-(3-amino-2-chlorophenyl)-1-(3-cyano-3-methylcyclobutyl)-4-methyl-6-oxohexahydropyrimidin-2-ylidene]carbamate (trans isomer)

Prepared from Intermediate 113 (0.35 g, 0.58 mmol) in accordance with the procedure described for Intermediate 28 to afford the title compound (0.27 g, 99%) as an off-white solid. δ$_H$ (400 MHz, CDCl$_3$) 1.50 (s, 3H), 1.55 (s, 9H), 1.85 (s, 3H), 2.58-2.73 (m, 3H), 2.78-2.84 (m, 4H), 3.67-3.73 (m, 1H), 5.19-5.28 (m, 1H), 6.66 (d, J7.8 Hz, 1H), 6.75-6.80 (m, 1H), 7.04 (t, J7.8 Hz, 1H), 10.41 (br s, 1H). LCMS (ESI, Method 1) m/e 446.1 [M+H]$^+$, RT 2.16 minutes.

Intermediate 117

3-Bromo-6-(2,2,2-trifluoroethoxy)pyridazine

To a solution of 2,2,2-trifluoroethanol (0.25 mL, 4.20 mmol) in DMF (10 mL) was added NaH (0.15 g, 6.31 mmol) portionwise at 0-5° C. The reaction mixture was stirred at room temperature for 30 minutes, then 3,6-dibromopyridazine (0.50 g, 2.10 mmol) was added. The reaction mixture was stirred at room temperature for 16 h, then quenched with H$_2$O (100 mL) and extracted with EtOAc (3×100 mL). The organic layer was separated, washed with H$_2$O (100 mL) and brine (100 mL), then concentrated in vacuo. The crude residue was purified by column chromatography (silica, 100-200 mesh, 10% EtOAc in hexanes) to afford the title compound (0.30 g, 50%) as an off-white solid. δ$_H$ (400 MHz, CDCl$_3$) 4.92 (q, J8.3 Hz, 2H), 7.04 (d, J8.8 Hz, 1H), 7.61 (d, J8.8 Hz, 1H).

Intermediate 118

5-Bromo-2-(2,2-difluoroethoxy)pyridine

To a solution of 2,2-difluoroethanol (0.64 g, 7.84 mmol) in DMF (10 mL) was added NaH (0.08 g, 3.38 mmol) at 0° C. The reaction mixture was stirred for 10 minutes, then 2,5-dibromopyridine (1.00 g, 4.22 mmol) was added at 0° C. The reaction mixture was heated at 60° C. for 5 h, then quenched with H$_2$O (100 mL) and extracted with EtOAc (3×100 mL). The organic layer was separated, dried over anhydrous Na$_2$SO$_4$ and concentrated in vacuo. The crude residue was purified by column chromatography (silica, 100-200 mesh, 5% EtOAc in hexanes) to afford the title compound (0.20 g, 19%) as a white solid. δ$_H$ (400 MHz, DMSO-d$_6$) 4.58 (t, J12.5 Hz, 2H), 6.39 (t, J70 Hz, 1H), 6.92-6.98 (d, J7.8 Hz, 1H), 7.92-8.01 (d, J7.8 Hz, 1H), 8.21 (s, 1H). LCMS (ESI, Method 1) m/e 238 [M+H]$^+$, RT 2.11 minutes.

Intermediate 119 tert-Butyl N-{[rac-(1S,5R)-8-oxabicyclo[3.2.1]octan-3-yl]carbamothioyl}carbamate Prepared from rac-(1S,5R)-8-oxabicyclo[3.2.1]octan-3-amine (0.9 g, 7.1 mmol) in accordance with the procedure described for Intermediate 6 to afford the title compound (0.95 g, 39%) as a yellow solid. δ$_H$ (400 MHz, CDCl$_3$) 1.46 (s, 9H), 1.59-1.66 (m, 2H), 1.83-1.86 (m, 2H), 1.94-1.99 (m, 2H), 2.02 (d, J5.3 Hz, 1H), 2.05 (d, J5.3 Hz, 1H), 4.41-4.44 (m, 2H), 4.62-4.74 (m, 1H), 7.78 (br s, 1H), 9.52 (d, J5.6 Hz, 1H).

Intermediate 120 tert-Butyl (NE)-N-{(4S)-4-[3-(benzyloxycarbonylamino)-2-chlorophenyl]-4-methyl-1-[(1SR,5RS)-8-oxabicyclo[3.2.1]octan-3-yl]-6-oxohexahydropyrimidin-2-ylidene}-carbamate Prepared from Intermediate 119 in accordance with the procedure described for Intermediate 61 to afford the title compound as an off-white solid. LCMS (ESI, Method 1) m/e 597.60 [M+H]$^+$, RT 2.27 minutes.

Intermediate 121 tert-Butyl (NE)-N-{(4S)-4-(3-amino-2-chlorophenyl)-4-methyl-1-[(1SR,5RS)-8-oxabicyclo[3.2.1]octan-3-yl]-6-oxohexahydropyrimidin-2-ylidene}carbamate Prepared from Intermediate 120 (0.9 g, 1.46 mmol) in accordance with the procedure described for Intermediate 28 to afford the title compound (0.11 g, 85%) as an off-white solid. δ$_H$ (400 MHz, CDCl$_3$) 1.07 (dd, J 12.2, 5.3 Hz, 1H), 1.45 (dd, J 12.2, 4.8 Hz, 1H), 1.55 (s, 9H), 1.76-1.78 (m, 1H), 1.83 (s, 3H), 1.88-1.97 (m, 2H), 2.52-2.71 (m, 3H), 2.80 (d, J 16.6 Hz, 1H), 3.66 (d, J16.1 Hz, 1H), 4.34-4.37 (m, 1H), 4.42-4.45 (m, 1H), 4.98-5.05 (m, 1H), 6.69 (dd, J7.8, 1.4 Hz, 1H), 6.76 (dd, J8.0, 1.2 Hz, 1H), 7.03 (t, J7.8 Hz, 1H), 10.56 (br s, 1H) (exchangeable —NH$_2$ protons not observed). LCMS (ESI, Method 1) m/e 463.10 [M+H]$^+$, RT 2.10 minutes.

Intermediate 122

1-(2-Chloro-4-fluoro-3-nitrophenyl)ethanone

To a stirred solution of 1-bromo-2-chloro-4-fluoro-3-nitrobenzene (16.0 g, 62.99 mmol) in 1,4-dioxane (160 mL), degassed for 5 minutes, were added tributyl(1-ethoxy-vinyl)stannane (23.59 mL, 69.29 mmol) and bis(triphenylphosphine)palladium(II) dichloride (3.53 g, 5.03 mmol). The reaction mixture was stirred at 85° C. for 16 h under an inert atmosphere, then diluted with saturated KF solution, filtered through a celite pad and washed with ethyl acetate. The filtrate was collected and washed with water. The organic layer was separated and concentrated under reduced pressure. The resulting oil was dissolved in THF and 4M aqueous HCl (1:1) was added. The reaction mixture was stirred at room temperature for 16 h, then diluted with water and extracted into ethyl acetate. The organic layer was separated, dried over Na$_2$SO$_4$ and concentrated under reduced pressure. The crude residue was purified by column chromatography to afford the title compound (8.0 g, 58%). δ$_H$ (400 MHz, CDCl$_3$) 7.76-7.27 (m, 1H), 7.28 (t, J8.2 Hz, 1H), 2.66 (s, 3H).

Intermediate 123

(NE)-N-[1-(2-Chloro-4-fluoro-3-nitrophenyl)ethylidene]-(R)-2-methylpropane-2-sulfinamide To a stirred solution of Intermediate 122 (24.6 g, 113.36 mmol) in toluene (200.0 mL) were added (R)-(+)-2-methyl-2-propanesulfinamide (41.151 g, 340.09 mmol) and titanium (IV) ethoxide (118.6 mL, 566.8 mmol). The mixture was heated at 90° C. for 16 h, then quenched with ice-cold water. Ethyl acetate was added, and the mixture was filtered through a celite plug. The organic layer was separated, washed with brine and dried over anhydrous Na$_2$SO$_4$. The solution was evaporated to dryness under reduced pressure. The crude residue was purified by column chromatography (eluting with 30% ethyl acetate in hexane) to afford the title compound (10.0 g, 27.5%). δ$_H$ (400 MHz, CDCl$_3$) 7.50-7.47 (m 1H), 7.31-7.25 (m 1H), 2.71 (s, 3H), 1.28 (s, 9H).

Intermediate 124

Methyl (3S)-3-{[(R)-tert-butylsulfinyl]amino}-3-(2-chloro-4-fluoro-3-nitrophenyl)-butanoate A dry apparatus under an inert atmosphere was charged with zinc powder (66.84 g, 1078 mmol), CuCl (20.48 g, 215 mmol) and dry 2-methyltetrahydrofuran (90 mL). The resulting dark slurry was heated at 70° C. and stirred vigorously for 40 minutes, then cooled to 50° C. Methyl bromoacetate (41.23 mL, 431 mmol) was added dropwise at such a rate that reflux was re-initiated, and a control reflux was maintained. Once addition was complete, the reaction mixture was stirred at 50° C. for 30 minutes, then cooled to room temperature, whereupon a solution of Intermediate 123 (23.0 g, 71.87 mmol) in 2-methyltetrahydrofuran (60 mL) was added dropwise. The reaction mixture was stirred at room temperature for 16 h, then filtered through a celite pad and washed with ethyl acetate. The combined filtrate was washed with water. The organic layer was separated, dried over $Na_2SO_4$ and concentrated under reduced pressure. The crude residue was purified by combi-flash column chromatography (eluting with 30-70% ethyl acetate in hexane) to afford the title compound (8.0 g, 28%). $\delta_H$ (400 MHz, DMSO-$d_6$) 7.95-7.91 (m, 1H), 7.66 (t, J8.9 Hz, 1H), 5.57 (s, 1H), 3.48 (s, 3H), 3.44 (d, J 16.2 Hz, 1H), 3.28 (d, J16.2 Hz, 1H), 1.88 (s, 3H), 1.12 (s, 9H).

Intermediate 125

Methyl (3S)-3-(3-amino-2-chloro-4-fluorophenyl)-3-{[(R)-tert-butylsulfinyl]amino}-butanoate To a stirred solution of Intermediate 124 (8.0 g, 20.25 mmol) in MeOH (100 mL) was added Raney Ni (2 g) under a nitrogen atmosphere. The reaction mixture was stirred at r.t. for 5 h, then filtered through a celite pad. The solution was evaporated. The crude residue was purified by column chromatography (eluting with 30-70% ethyl acetate in hexane) to afford the title compound (4.0 g, 54%). $\delta_H$ (400 MHz, DMSO-$d_6$) 7.00 (t, J8.9 Hz, 1H), 6.78-6.75 (m, 1H), 5.33 (d, J6.4 Hz, 3H), 3.48 (s, 3H), 3.37-3.26 (m, 2H), 1.81 (s, 3H), 1.15 (s, 9H).

Intermediate 126

[(1S)-1-(3-Amino-2-chloro-4-fluorophenyl)-3-methoxy-1-methyl-3-oxopropyl]-ammonium chloride To a stirred solution of Intermediate 125 (4.0 g, 10.99 mmol) in DCM (40 mL) was added 4M HCl in 1,4-dioxane (20 mL). The reaction mixture was stirred for 16 h at r.t., then concentrated under vacuum and washed with pentane, to afford the title compound as an off-white solid. $\delta_H$ (400 MHz, DMSO-$d_6$) 8.87 (s, 3H), 7.12 (t, J9.5 Hz, 1H), 6.65-6.62 (m, 1H), 3.59 (d, J16 Hz, 1H), 3.48 (s, 3H), 3.31 (d, J 16 Hz, 1H), 1.80 (s, 3H).

Intermediate 127 tert-Butyl (NE)-N-[(4S)-4-(3-amino-2-chloro-4-fluorophenyl)-4-methyl-6-oxo-1-(tetrahydropyran-4-yl)hexahydropyrimidin-2-ylidene]carbamate Prepared from Intermediate 126 (3.0 g, 10.2 mmol) and Intermediate 6 (2.6 g, 10.1 mmol) in accordance with the procedure described for Intermediate 61 to afford the title compound as an off-white solid. $\delta_H$ (400 MHz, DMSO-$d_6$) 10.45 (s, 1H), 7.06 (t, J 10.4 Hz, 1H), 6.50-6.47 (m, 1H), 5.57 (s, 2H), 4.63 (br s, 1H), 3.83 (m, 1H), 3.77 (m, 1H), 3.5 (d, J 16.4 Hz, 1H), 3.29-3.11 (m, 3H), 2.44-2.33 (m, 2H), 1.72 (s, 3H), 1.45 (s, 9H), 1.33-1.24 (m, 1H), 1.01 (m, 1H).

Intermediate 128 tert-Butyl (NE)-N-{(4S)-4-[2-chloro-4-fluoro-3-(4-fluoroanilino)phenyl]-4-methyl-6-oxo-1-(tetrahydropyran-4-yl)hexahydropyrimidin-2-ylidene}carbamate To a solution of Intermediate 127 (0.06 g, 0.12 mmol) in toluene (2 mL) were added 1-bromo-4-fluorobenzene (0.02 g, 0.12 mmol), $K_3PO_4$ (0.05 g, 0.24 mmol) and XPhos (0.006 g, 0.01 mmol) at room temperature. The reaction mixture was purged with argon for 10 minutes, then $Pd_2(dba)_3$ (0.01 g, 0.02 mmol) was added. The reaction mixture was heated at 100° C. for 3 h, then diluted with $H_2O$ (20 mL) and extracted with EtOAc (2×30 mL). The organic layer was separated, washed with $H_2O$ (50 mL) and brine (60 mL), then dried over anhydrous $Na_2SO_4$ and concentrated in vacuo. The crude residue was purified by column chromatography (silica, 100-200 mesh, 50% EtOAc in hexanes) to afford the title compound (0.025 g, 37%) as an off-white solid. MS (ESI, Method 1) m/e 549.6 [M+H]$^+$, RT 2.25 minutes.

Intermediate 129 tert-Butyl (NE)-N-[(4S)-4-{2-chloro-4-fluoro-3-[(6-methylpyridin-3-yl)amino]phenyl}-4-methyl-6-oxo-1-(tetrahydropyran-4-yl)hexahydropyrimidin-2-ylidene]carbamate A mixture of Intermediate 127 (0.11 g, 0.24 mmol), 5-bromo-2-methylpyridine (0.04 g, 0.22 mmol), $K_3PO_4$ (0.10 g, 0.48 mmol), BrettPhos Pd G3 (0.02 g, 0.02 mmol) and BrettPhos (0.02 g, 0.04 mmol) was flushed with argon, followed by the addition of 1,4-dioxane (6 mL). The reaction mixture was purged with argon for 5 minutes and heated in a sealed tube at 90° C. for 3 h, then filtered through a pad of celite, and washed with EtOAc (10 mL) and $H_2O$ (10 mL). The organic layer was separated, dried over anhydrous $Na_2SO_4$ and concentrated in vacuo. The crude residue was purified by preparative HPLC to afford the title compound (0.08 g, 59%) as a white solid. MS (ESI, Method 1) m/e 546.6 [M+H]$^+$, RT 2.04 minutes.

Examples 1 to 14 (General Method 2)

To a solution of the relevant precursor (0.07 mmol, 1 equiv.) in DCM (4 mL, 0.01 mol/L) was added TFA (1.34 mmol, 19 equiv.) at 0° C. The reaction mixture was stirred at room temperature for 3 h, then concentrated in vacuo. The crude residue was purified by washing with diethyl ether (4 mL) and hexane (15 mL), then lyophilised with acetonitrile/water (3 mL) to afford Examples 1 to 14 (TFA salt) as off-white solids, as indicated in the following Table.

| Ex. | Precursor | Product | Structure | LCMS RT (min) | LCMS [MH]+ (method 3) |
|---|---|---|---|---|---|
| 1 | Int. 48 | (6S)-6-(3-Anilino-2-chloro-phenyl)-3-[(1-hydroxy-cyclopropyl)methyl]-2-imino-6-methylhexahydropyrimidin-4-one | 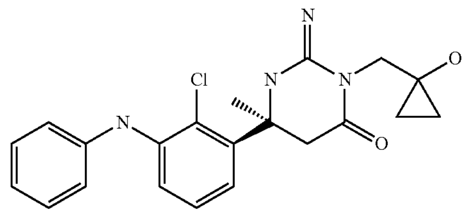 | 1.45 | 399.4 |
| 2 | Int. 36 | (6S)-6-(3-Anilino-2-chloro-phenyl)-2-imino-6-methyl-3-(tetrahydropyran-4-yl)-hexahydropyrimidin-4-one | 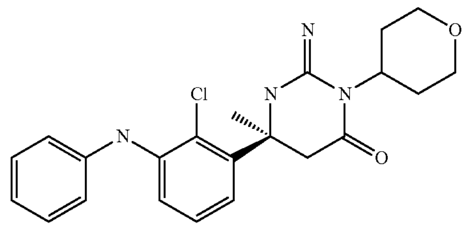 [SMILES: C[C@@]1(c2cccc(Nc3ccccc3)c2Cl)CC(=O)N(C2CCOCC2)C(=N)N1] | 1.35 | 413.4 |
| 3 | Int. 37 | (6S)-6-(3-Anilino-2-chloro-phenyl)-2-imino-6-methyl-3-(tetrahydropyran-4-ylmethyl)-hexahydropyrimidin-4-one | 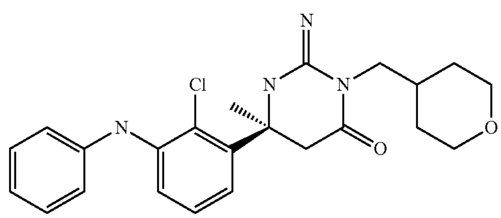 [SMILES: C[C@@]1(c2cccc(Nc3ccccc3)c2Cl)CC(=O)N(CC2CCOCC2)C(=N)N1] | 1.33 | 427.4 |
| 4 | Int. 38 | (6S)-6-(3-Anilino-2-chloro-phenyl)-3-cyclohexyl-2-imino-6-methylhexahydropyrimidin-4-one | 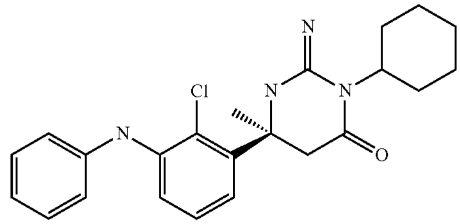 [SMILES: C[C@@]1(c2cccc(Nc3ccccc3)c2Cl)CC(=O)N(C2CCCCC2)C(=N)N1] | 1.67 | 411.1 |
| 5 | Int. 39 | (6S)-6-(3-Anilino-2-chloro-phenyl)-2-imino-6-methyl-3-[(3S or 3R*)-tetrahydrofuran-3-yl]hexahydropyrimidin-4-one | 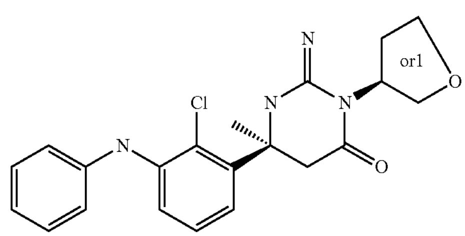 [SMILES: C[C@@]1(c2cccc(Nc3ccccc3)c2Cl)CC(=O)N([C@H]2CCOC2)C(=N)N1] | 1.34 | 399.1 |
| 6 | Int. 40 | (6S)-6-(3-Anilino-2-chloro-phenyl)-2-imino-6-methyl-3-[(3S or 3R*)-tetrahydrofuran-3-yl]hexahydropyrimidin-4-one | 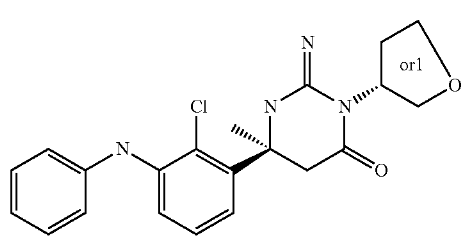 [SMILES: C[C@@]1(c2cccc(Nc3ccccc3)c2Cl)CC(=O)N([C@@H]2CCOC2)C(=N)N1] | 1.34 | 399.1 |

-continued

| Ex. | Precursor | Product | Structure | LCMS RT (min) | LCMS [MH]+ (method 3) |
|---|---|---|---|---|---|
| 7 | Int. 41 | (6S)-6-[2-Chloro-3-(3-chloro-anilino)phenyl]-2-imino-6-methyl-3-(tetrahydropyran-4-yl)hexahydropyrimidin-4-one | 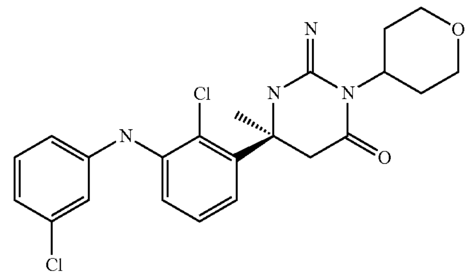 [SMILES: C[C@@]1(c2cccc(Nc3cccc(Cl)c3)c2Cl)CC(=O)N(C2CCOCC2)C(=N)N1] | 1.46 | 447.3 |
| 8 | Int. 42 | (6S)-6-[2-Chloro-3-(3-methyl-anilino)phenyl]-2-imino-6-methyl-3-(tetrahydropyran-4-yl)hexahydropyrimidin-4-one | 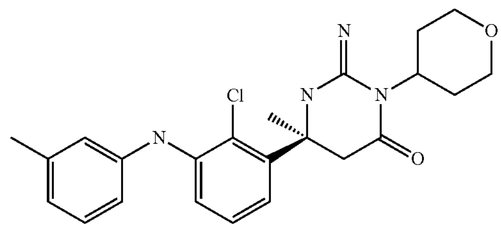 [SMILES: Cc1cccc(Nc2cccc([C@]3(C)CC(=O)N(C4CCOCC4)C(=N)N3)c2Cl)c1] | 1.45 | 427.3 |
| 9 | Int. 43 | 3-{2-Chloro-3-[(4S)-2-imino-4-methyl-6-oxo-1-(tetrahydro-pyran-4-yl)hexahydropyrimidin-4-yl]anilino}benzonitrile | 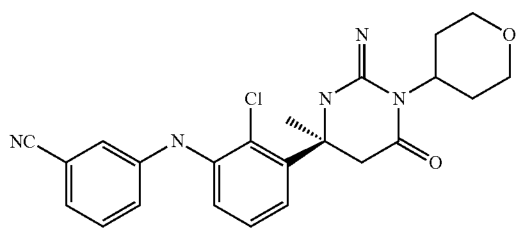 [SMILES: C[C@@]1(c2cccc(Nc3cccc(C#N)c3)c2Cl)CC(=O)N(C2CCOCC2)C(=N)N1] | 1.24 | 438.4 |
| 10 | Int. 44 | (6S)-6-[2-Chloro-3-(4-fluoro-3-methylanilino)phenyl]-2-imino-6-methyl-3-(tetrahydropyran-4-yl)hexahydropyrimidin-4-one | 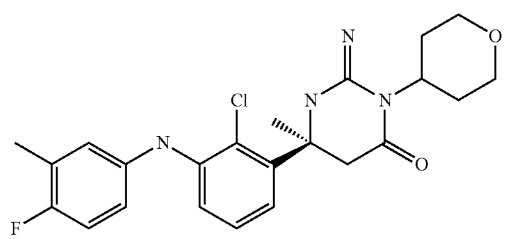 [SMILES: Cc1cc(Nc2cccc([C@]3(C)CC(=O)N(C4CCOCC4)C(=N)N3)c2Cl)ccc1F] | 1.47 | 445.4 |
| 11 | Int. 45 | (6S)-6-{2-Chloro-3-[4-(tri-fluoromethyl)anilino]phenyl}-2-imino-6-methyl-3-(tetrahydro-pyran-4-yl)hexahydropyrimidin-4-one | 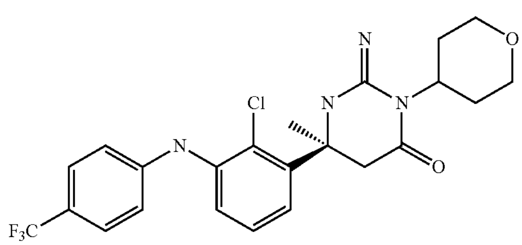 [SMILES: C[C@@]1(c2cccc(Nc3ccc(C(F)(F)F)cc3)c2Cl)CC(=O)N(C2CCOCC2)C(=N)N1] | 1.51 | 481.4 |
| 12 | Int. 46 | (6S)-6-[2-Chloro-3-(4-fluoro-anilino)phenyl]-2-imino-6-methyl-3-(tetrahydropyran-4-yl)hexahydropyrimidin-4-one | 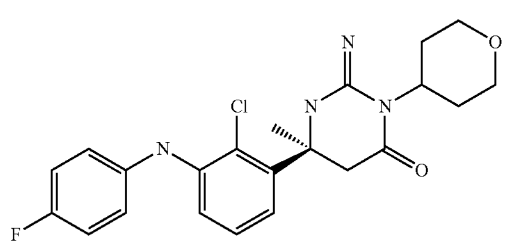 [SMILES: C[C@@]1(c2cccc(Nc3ccc(F)cc3)c2Cl)CC(=O)N(C2CCOCC2)C(=N)N1] | 1.36 | 431.3 |

| Ex. | Precursor | Product | Structure | LCMS RT (min) | LCMS [MH]+ (method 3) |
|---|---|---|---|---|---|
| 13 | Int. 47 | (6S)-6-(3-Anilino-2-chloro-phenyl)-3-(3-hydroxy-3-methyl-cyclobutyl)-2-imino-6-methyl-hexahydropyrimidin-4-one | 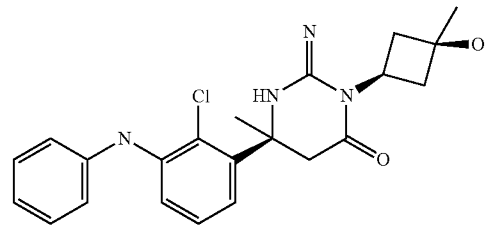 [SMILES: C[C@@]1(c2cccc(Nc3ccccc3)c2Cl)CC(=O)N([C@H]2C[C@@](C)(O)C2)C(=N)N1] | 1.25 | 413.3 |
| 14 | Int. 49 | (6S)-6-{2-Chloro-3-[(6-methyl-pyridin-3-yl)amino]phenyl}-2-imino-6-methyl-3-(tetrahydro-pyran-4-yl)hexahydropyrimidin-4-one | 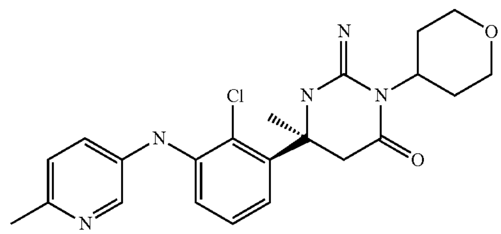 | 1.05 | 428.9 |

Examples 15 to 73 (General Method 3)

Intermediate 28 and the appropriate aryl halide were dissolved in a solvent, and a base (3 equiv.) was added. The solution was degassed, then a phosphine ligand (0.1 equiv.) and a transition metal catalyst (0.05 equiv.) were added. The reaction mixture was heated at 80° C. until the reaction was complete. The material was isolated using silica gel chromatography, then deprotected in accordance with General Method 2 to afford the title compounds. As necessary, final products were further purified by preparative reverse phase HPLC (pH 3) and the compounds were isolated as the TFA salt.

The solvent employed for Examples 15-34, 36-56, 72 and 73 was toluene. The solvent employed for Examples 35 and 57-71 was 1,4-dioxane.

The base employed for Examples 15-18, 20, 22-31, 33, 34 and 36-73 was $K_3PO_4$. The base employed for Examples 19, 21 and 35 was sodium tert-butoxide. The base employed for Example 32 was $Cs_2CO_3$.

The phosphine ligand employed for Examples 15-31 and 33-73 was XPhos. The phosphine ligand employed for Example 32 was rac-BINAP.

The transition metal catalyst employed for Examples 15-31, 33, 34, 36-56 and 72 was $Pd_2(dba)_3$. The transition metal catalyst employed for Example 32 was palladium(II) acetate. The transition metal catalyst employed for Example 35 was BrettPhos Pd G1.

The transition metal catalyst employed for Examples 57-71 and 73 was BrettPhos Pd G3.

The compounds identified in the following Table were prepared in accordance with General Method 3.

| Ex. | Aryl halide | Product | Structure | LCMS RT (min) | LCMS [MH]+ (method 3) |
|---|---|---|---|---|---|
| 15 | 1-Bromo-2-chloro-benzene | (6S)-6-[2-Chloro-3-(2-chloro-anilino)phenyl]-2-imino-6-methyl-3-(tetrahydropyran-4-yl)hexahydropyrimidin-4-one | 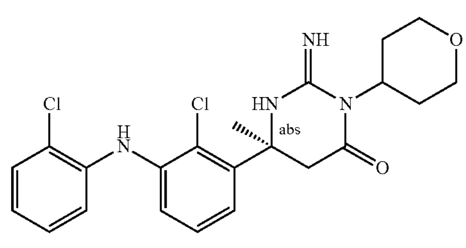 [SMILES: C[C@@]1(c2cccc(Nc3ccccc3Cl)c2Cl)CC(=O)N(C2CCOCC2)C(=N)N1] | 1.48 | 448 |
| 16 | 1-Bromo-2-(trifluoro-methyl)-benzene | (6S)-6-{2-Chloro-3-[2-(trifluoromethyl)anilino]-phenyl}-2-imino-6-methyl-3-(tetrahydropyran-4-yl)-hexahydropyrimidin-4-one | 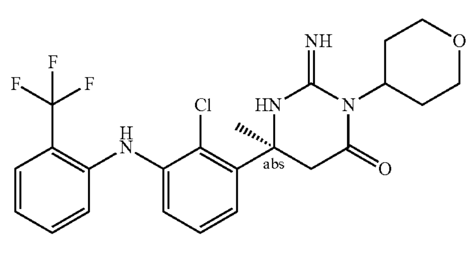 [SMILES: C[C@@]1(c2cccc(Nc3ccccc3C(F)(F)F)c2Cl)CC(=O)N(C2CCOCC2)C(=N)N1] | 1.52 | 481 |

-continued

| Ex. | Aryl halide | Product | Structure | LCMS RT (min) | LCMS [MH]+ (method 3) |
|---|---|---|---|---|---|
| 17 | 2-Bromo-benzonitrile | 2-{2-Chloro-3-[(4S)-2-imino-4-methyl-6-oxo-1-(tetrahydro-pyran-4-yl)hexahydropyrimidin-4-yl]anilino}benzonitrile | 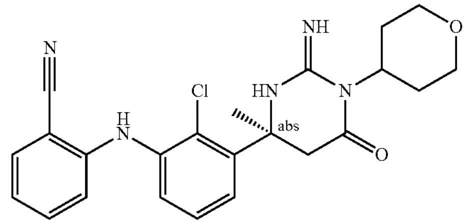 [SMILES: C[C@@]1(c2cccc(Nc3ccccc3C#N)c2Cl)CC(=O)N(C2CCOCC2)C(=N)N1] | 1.25 | 438 |
| 18 | 4-Bromo-benzonitrile | 4-{2-Chloro-3-[(4S)-2-imino-4-methyl-6-oxo-1-(tetrahydro-pyran-4-yl)hexahydropyrimidin-4-yl]anilino}benzonitrile | 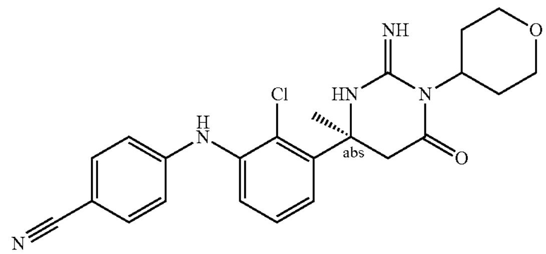 [SMILES: C[C@@]1(c2cccc(Nc3ccc(C#N)cc3)c2Cl)CC(=O)N(C2CCOCC2)C(=N)N1] | 1.19 | 438 |
| 19 | 5-Bromo-2-methyl-pyrimidine | (6S)-6-{2-Chloro-3-[(2-methyl-pyrimidin-5-yl)amino]phenyl}-2-imino-6-methyl-3-(tetrahydro-pyran-4-yl)hexahydropyrimidin-4-one | 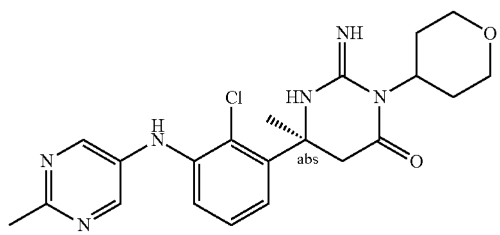 [SMILES: Cc1ncc(Nc2cccc([C@]3(C)CC(=O)N(C4CCOCC4)C(=N)N3)c2Cl)cn1] | 0.89 | 429 |
| 20 | 3-Bromo-pyridine | (6S)-6-[2-Chloro-3-(pyridin-3-ylamino)phenyl]-2-imino-6-methyl-3-(tetrahydropyran-4-yl)hexahydropyrimidin-4-one | 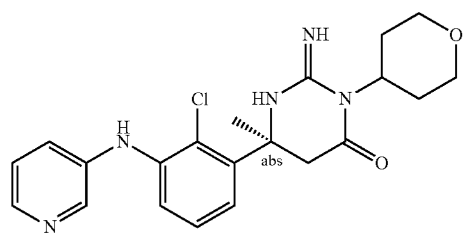 [SMILES: C[C@@]1(c2cccc(Nc3cccnc3)c2Cl)CC(=O)N(C2CCOCC2)C(=N)N1] | 0.98 | 414 |
| 21 | 5-Bromo-quinoline | (6S)-6-[2-Chloro-3-(quinolin-5-ylamino)phenyl]-2-imino-6-methyl-3-(tetrahydropyran-4-yl)hexahydropyrimidin-4-one | 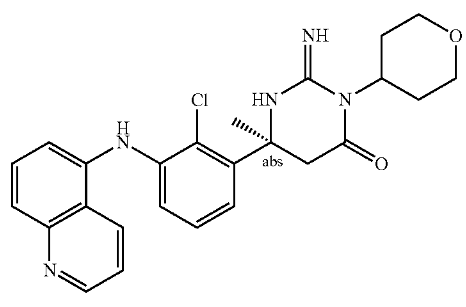 [SMILES: C[C@@]1(c2cccc(Nc3cccc4ncccc34)c2Cl)CC(=O)N(C2CCOCC2)C(=N)N1] | 1.15 | 464 |
| 22 | 2-Bromo-1-fluoro-4-(trifluoro-methoxy)-benzene | (6S)-6-{2-Chloro-3-[2-fluoro-5-(trifluoromethoxy)anilino]-phenyl}-2-imino-6-methyl-3-(tetrahydropyran-4-yl)-hexahydropyrimidin-4-one | 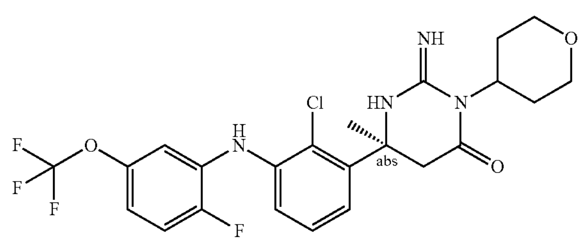 [SMILES: C[C@@]1(c2cccc(Nc3cc(OC(F)(F)F)ccc3F)c2Cl)CC(=O)N(C2CCOCC2)C(=N)N1] | 1.55 | 515 |

-continued

| Ex. | Aryl halide | Product | Structure | LCMS RT (min) | LCMS [MH]+ (method 3) |
|---|---|---|---|---|---|
| 23 | 1-Bromo-3-fluoro-5-methoxy-benzene | (6S)-6-[2-Chloro-3-(3-fluoro-5-methoxyanilino)phenyl]-2-imino-6-methyl-3-(tetrahydro-pyran-4-yl)hexahydropyrimidin-4-one | 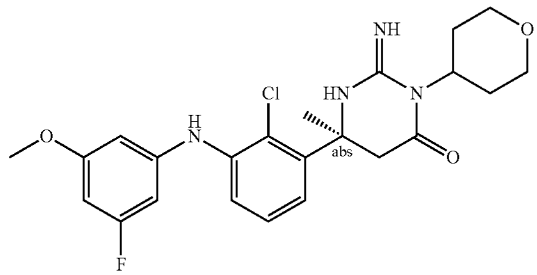 [SMILES: COc1cc(F)cc(Nc2cccc([C@]3(C)CC(=O)N(C4CCOCC4)C(=N)N3)c2Cl)c1] | 1.37 | 461 |
| 24 | 4-Bromo-2-chloro-benzonitrile | 2-Chloro-4-{2-chloro-3-[(4S)-2-imino-4-methyl-6-oxo-1-(tetrahydropyran-4-yl)-hexahydropyrimidin-4-yl]-anilino}benzonitrile | 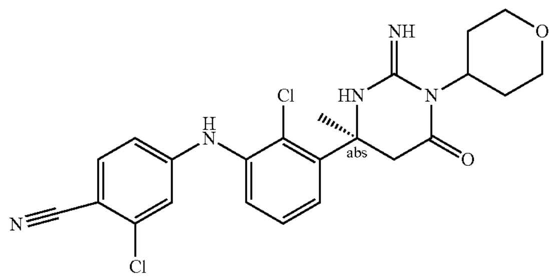 [SMILES: C[C@@]1(c2cccc(Nc3ccc(C#N)c(Cl)c3)c2Cl)CC(=O)N(C2CCOCC2)C(=N)N1] | 1.29 | 472 |
| 25 | 4-(5-Bromo-pyridin-2-yl)-morpholine | (6S)-6-(2-Chloro-3-{[6-(morpholin-4-yl)pyridin-3-yl]amino}phenyl)-2-imino-6-methyl-3-(tetrahydropyran-4-yl)hexahydropyrimidin-4-one | 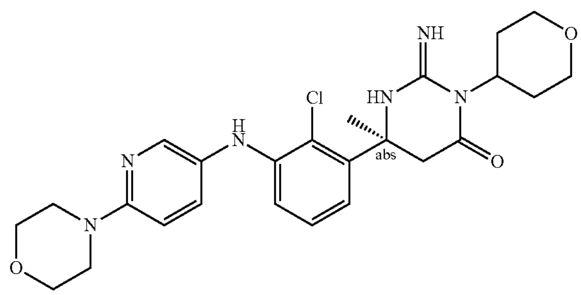 [SMILES: C[C@@]1(c2cccc(Nc3ccc(N4CCOCC4)nc3)c2Cl)CC(=O)N(C2CCOCC2)C(=N)N1] | 1.13 | 499 |
| 26 | 3-Bromo-2-(trifluoro-methyl)-pyridine | (6S)-6-(2-Chloro-3-{[2-(trifluoromethyl)pyridin-3-yl]amino}phenyl)-2-imino-6-methyl-3-(tetrahydropyran-4-yl)hexahydropyrimidin-4-one | 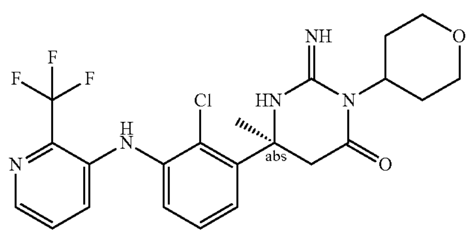 [SMILES: C[C@@]1(c2cccc(Nc3cccnc3C(F)(F)F)c2Cl)CC(=O)N(C2CCOCC2)C(=N)N1] | 1.24 | 482 |
| 27 | 2-Bromo-4-fluoro-anisole | (6S)-6-[2-Chloro-3-(5-fluoro-2-methoxyanilino)phenyl]-2-imino-6-methyl-3-(tetrahydro-pyran-4-yl)hexahydropyrimidin-4-one | 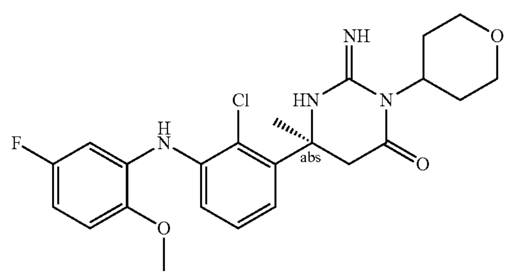 [SMILES: COc1ccc(F)cc1Nc1cccc([C@]2(C)CC(=O)N(C3CCOCC3)C(=N)N2)c1Cl] | 1.42 | 461 |

-continued

| Ex. | Aryl halide | Product | Structure | LCMS RT (min) | LCMS [MH]+ (method 3) |
|---|---|---|---|---|---|
| 28 | 3-Bromo-2-methyl-pyridine | (6S)-6-{2-Chloro-3-[(2-methyl-pyridin-3-yl)amino]phenyl}-2-imino-6-methyl-3-(tetrahydro-pyran-4-yl)hexahydropyrimidin-4-one | 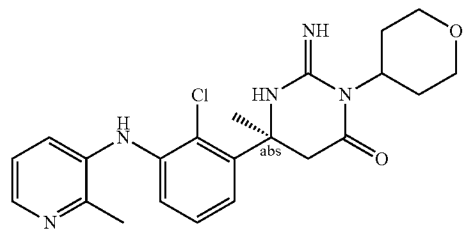 [SMILES: Cc1ncccc1Nc1cccc([C@]2(C)CC(=O)N(C3CCOCC3)C(=N)N2)c1Cl] | 1.03 | 428 |
| 29 | 4-Bromo-2-fluoro-pyridine | (6S)-6-{2-Chloro-3-[(2-fluoro-pyridin-4-yl)amino]phenyl}-2-imino-6-methyl-3-(tetrahydro-pyran-4-yl)hexahydropyrimidin-4-one | 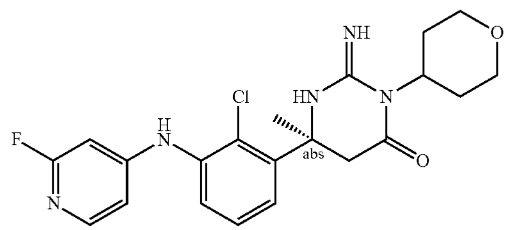 [SMILES: C[C@@]1(c2cccc(Nc3ccnc(F)c3)c2Cl)CC(=O)N(C2CCOCC2)C(=N)N1] | 1.01 | 432 |
| 30 | 3-Bromo-quinoline | (6S)-6-[2-Chloro-3-(quinolin-3-ylamino)phenyl]-2-imino-6-methyl-3-(tetrahydropyran-4-yl)hexahydropyrimidin-4-one | 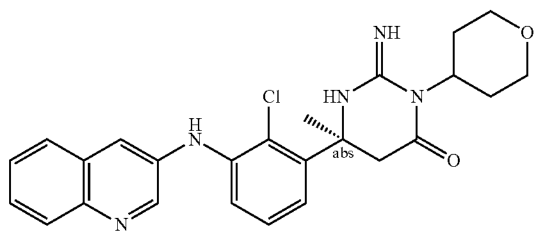 [SMILES: C[C@@]1(c2cccc(Nc3cnc4ccccc4c3)c2Cl)CC(=O)N(C2CCOCC2)C(=N)N1] | 1.21 | 464 |
| 31 | 5-Bromo-2-(trifluoro-methyl)-pyridine | (6S)-6-(2-Chloro-3-{[6-(trifluoromethyl)pyridin-3-yl]amino}phenyl)-2-imino-6-methyl-3-(tetrahydropyran-4-yl)hexahydropyrimidin-4-one | 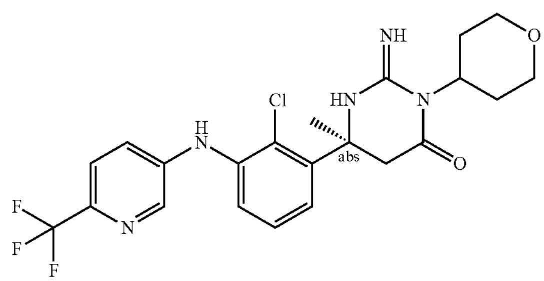 [SMILES: C[C@@]1(c2cccc(Nc3ccc(C(F)(F)F)nc3)c2Cl)CC(=O)N(C2CCOCC2)C(=N)N1] | 1.27 | 482 |
| 32 | 3-Bromo-2-chloro-5-(trifluoro-methyl)-pyridine | (6S)-6-(2-Chloro-3-{[2-chloro-5-(trifluoromethyl)pyridin-3-yl]amino}phenyl)-2-imino-6-methyl-3-(tetrahydropyran-4-yl)hexahydropyrimidin-4-one | 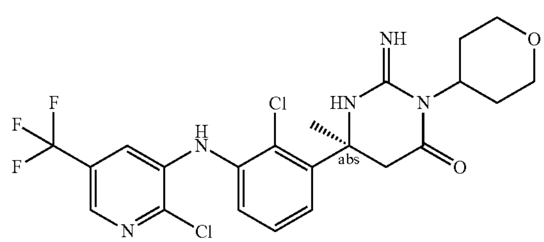 [SMILES: C[C@@]1(c2cccc(Nc3cc(C(F)(F)F)cnc3Cl)c2Cl)CC(=O)N(C2CCOCC2)C(=N)N1] | 1.41 | 516 |
| 33 | 4-Bromo-1-chloro-2-fluoro-benzene | (6S)-6-[2-Chloro-3-(4-chloro-3-fluoroanilino)phenyl]-2-imino-6-methyl-3-(tetrahydropyran-4-yl)hexahydropyrimidin-4-one | 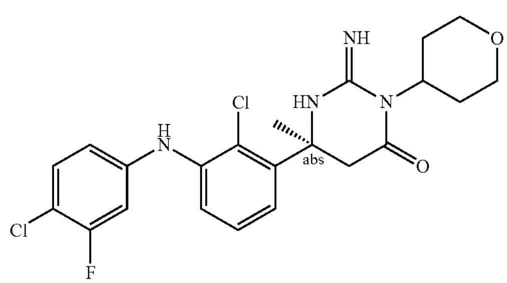 [SMILES: C[C@@]1(c2cccc(Nc3ccc(Cl)c(F)c3)c2Cl)CC(=O)N(C2CCOCC2)C(=N)N1] | 1.48 | 465 |

| Ex. | Aryl halide | Product | Structure | LCMS RT (min) | LCMS [MH]+ (method 3) |
|---|---|---|---|---|---|
| 34 | 3-Bromo-5-chloro-benzonitrile | 3-Chloro-5-{2-chloro-3-[(4S)-2-imino-4-methyl-6-oxo-1-(tetrahydropyran-4-yl)-hexahydropyrimidin-4-yl]-anilino}benzonitrile | 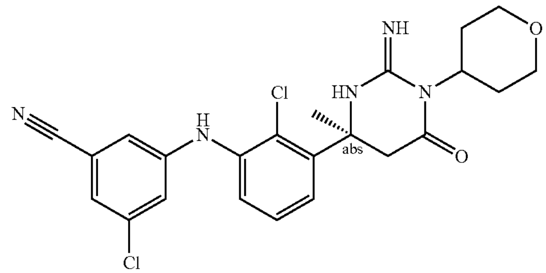 [SMILES: C[C@@]1(c2cccc(Nc3cc(Cl)cc(C#N)c3)c2Cl)CC(=O)N(C2CCOCC2)C(=N)N1] | 1.39 | 472 |
| 35 | 2-Bromo-imidazo-[1,2-a]-pyridine | (6S)-6-[2-Chloro-3-(imidazo-[1,2-a]pyridin-2-ylamino)-phenyl]-2-imino-6-methyl-3-(tetrahydropyran-4-yl)-hexahydropyrimidin-4-one | 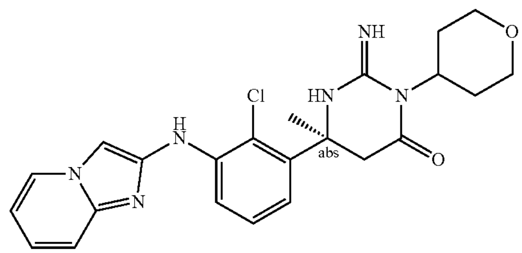 [SMILES: C[C@@]1(c2cccc(Nc3cn4ccccc4n3)c2Cl)CC(=O)N(C2CCOCC2)C(=N)N1] | 1.07 | 453 |
| 36 | 1-Bromo-2-fluoro-benzene | (6S)-6-[2-Chloro-3-(2-fluoro-anilino)phenyl]-2-imino-6-methyl-3-(tetrahydropyran-4-yl)hexahydropyrimidin-4-one | 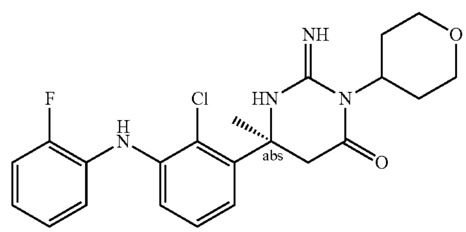 [SMILES: C[C@@]1(c2cccc(Nc3ccccc3F)c2Cl)CC(=O)N(C2CCOCC2)C(=N)N1] | 1.34 | 431 |
| 37 | Int. 50 | (6S)-6-{2-Chloro-3-[4-(difluoro-methoxy)anilino]phenyl}-2-imino-6-methyl-3-(tetrahydro-pyran-4-yl)hexahydropyrimidin-4-one | 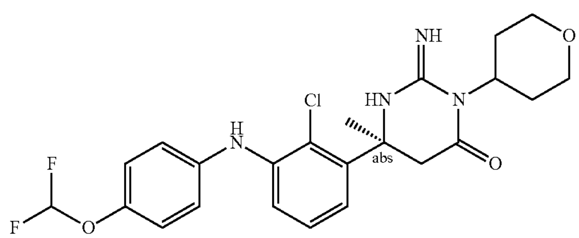 [SMILES: C[C@@]1(c2cccc(Nc3ccc(OC(F)F)cc3)c2Cl)CC(=O)N(C2CCOCC2)C(=N)N1] | 1.39 | 479 |
| 38 | 1-Bromo-2,4,5-trifluoro-benzene | (6S)-6-[2-Chloro-3-(2,4,5-trifluoroanilino)phenyl]-2-imino-6-methyl-3-(tetrahydro-pyran-4-yl)hexahydropyrimidin-4-one | 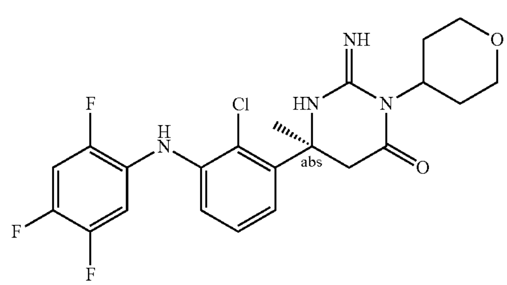 [SMILES: C[C@@]1(c2cccc(Nc3cc(F)c(F)cc3F)c2Cl)CC(=O)N(C2CCOCC2)C(=N)N1] | 1.24 | 449 |
| 39 | 4-Bromo-phenyl-methyl-sulfone | (6S)-6-[2-Chloro-3-(4-methyl-sulfonylanilino)phenyl]-2-imino-6-methyl-3-(tetrahydro-pyran-4-yl)hexahydropyrimidin-4-one | 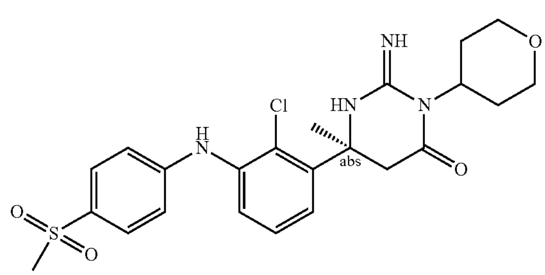 [SMILES: C[C@@]1(c2cccc(Nc3ccc(S(C)(=O)=O)cc3)c2Cl)CC(=O)N(C2CCOCC2)C(=N)N1] | 1.04 | 491 |

-continued

| Ex. | Aryl halide | Product | Structure | LCMS RT (min) | LCMS [MH]+ (method 3) |
|---|---|---|---|---|---|
| 40 | 5-Bromo-2-cyano-pyridine | 5-{2-Chloro-3-[(4S)-2-imino-4-methyl-6-oxo-1-(tetrahydro-pyran-4-yl)hexahydropyrimidin-4-yl]anilino}pyridine-2-carbo-nitrile | 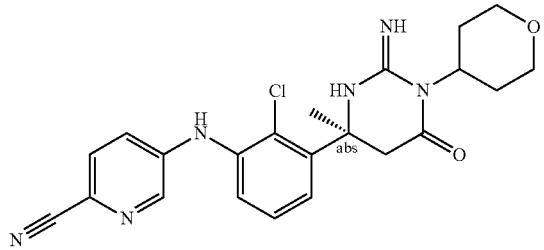 [SMILES: C[C@@]1(c2cccc(Nc3ccc(C#N)nc3)c2Cl)CC(=O)N(C2CCOCC2)C(=N)N1] | 1.05 | 439 |
| 41 | 3-Bromo-phenyl-methyl-sulfone | (6S)-6-[2-Chloro-3-(3-methyl-sulfonylanilino)phenyl]-2-imino-6-methyl-3-(tetrahydro-pyran-4-yl)hexahydropyrimidin-4-one | 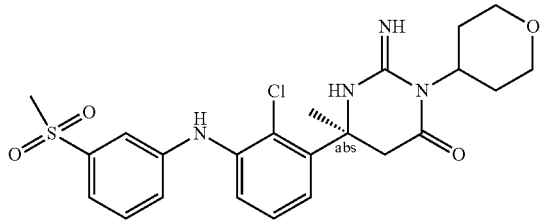 [SMILES: C[C@@]1(c2cccc(Nc3cccc(S(C)(=O)=O)c3)c2Cl)CC(=O)N(C2CCOCC2)C(=N)N1] | 1.08 | 491 |
| 42 | 5-Bromo-2-(difluoro-methoxy)-pyridine | (6S)-6-(2-Chloro-3-{[6-(difluoromethoxy)pyridin-3-yl]-amino}phenyl)-2-imino-6-methyl-3-(tetrahydropyran-4-yl)hexahydropyrimidin-4-one | 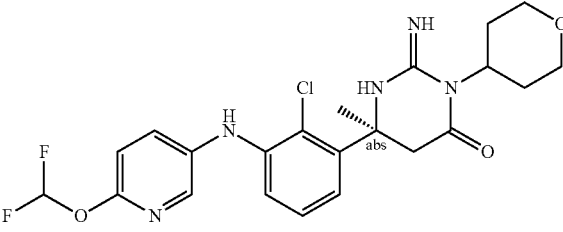 | 1.32 | 480 |
| 43 | 2-Bromo phenyl-methyl-sulfone | (6S)-6-[2-Chloro-3-(2-methyl-sulfonylanilino)phenyl]-2-imino-6-methyl-3-(tetrahydro-pyran-4-yl)hexahydropyrimidin-4-one | 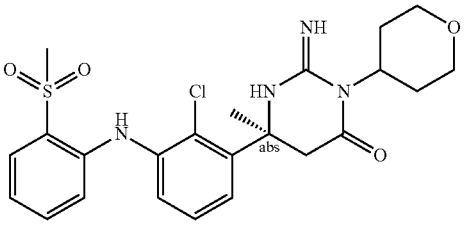 [SMILES: C[C@@]1(c2cccc(Nc3ccccc3S(C)(=O)=O)c2Cl)CC(=O)N(C2CCOCC2)C(=N)N1] | 1.21 | 491 |
| 44 | 2-Bromo-5-methyl-pyrazine | (6S)-6-{2-Chloro-3-[(5-methyl-pyrazin-2-yl)amino]phenyl}-2-imino-6-methyl-3-(tetrahydro-pyran-4-yl)hexahydropyrimidin-4-one | 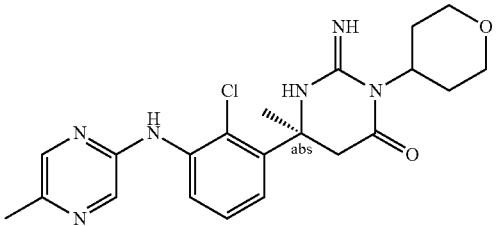 [SMILES: Cc1cnc(Nc2cccc([C@]3(C)CC(=O)N(C4CCOCC4)C(=N)N3)c2Cl)cn1] | 1.04 | 429 |
| 45 | 5-Bromo-2-(trifluoro-methoxy)-pyridine | (6S)-6-(2-Chloro-3-{[6-(trifluoromethoxy)pyridin-3-yl]-amino}phenyl)-2-imino-6-methyl-3-(tetrahydropyran-4-yl)hexahydropyrimidin-4-one | 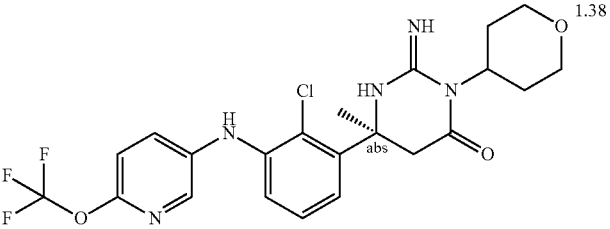 | 1.38 | 498 |

-continued

| Ex. | Aryl halide | Product | Structure | LCMS RT (min) | LCMS [MH]+ (method 3) |
|---|---|---|---|---|---|
| 46 | 4-Bromo-isoquinoline | (6S)-6-[2-Chloro-3-(isoquinolin-4-ylamino)phenyl]-2-imino-6-methyl-3-(tetrahydropyran-4-yl)hexahydropyrimidin-4-one | 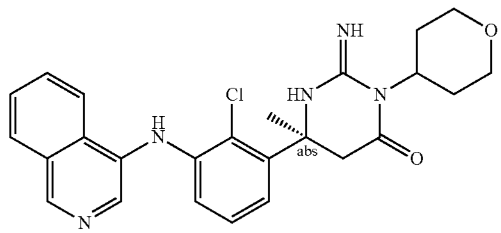 [SMILES: C[C@@]1(c2cccc(Nc3cncc4ccccc34)c2Cl)CC(=O)N(C2CCOCC2)C(=N)N1] | 1.18 | 464 |
| 47 | 4-Bromo-3-methoxy-benzonitrile | 4-{2-Chloro-3-[(4S)-2-imino-4-methyl-6-oxo-1-(tetrahydro-pyran-4-yl)hexahydropyrimidin-4-yl]anilino}-3-methoxy-benzonitrile | 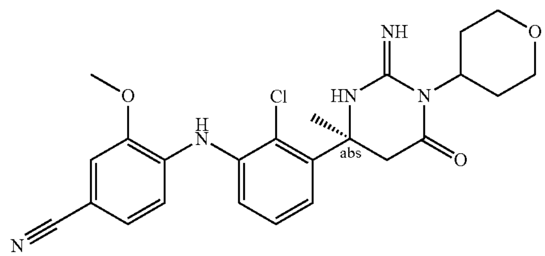 [SMILES: COc1cc(C#N)ccc1Nc1cccc([C@]2(C)CC(=O)N(C3CCOCC3)C(=N)N2)c1Cl] | 1.3 | 468 |
| 48 | 3-Bromo-4-cyano-pyridine | 3-{2-Chloro-3-[(4S)-2-imino-4-methyl-6-oxo-1-(tetrahydro-pyran-4-yl)hexahydropyrimidin-4-yl]anilino}pyridine-4-carbonitrile | 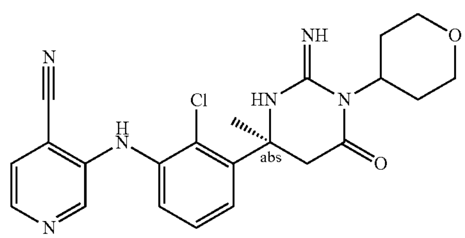 [SMILES: C[C@@]1(c2cccc(Nc3cnccc3C#N)c2Cl)CC(=O)N(C2CCOCC2)C(=N)N1] | 0.99 | 439 |
| 49 | 5-Bromo-3-fluoro-2-methoxy-pyridine | (6S)-6-{2-Chloro-3-[(5-fluoro-6-methoxypyridin-3-yl)amino]-phenyl}-2-imino-6-methyl-3-(tetrahydropyran-4-yl)-hexahydropyrimidin-4-one | 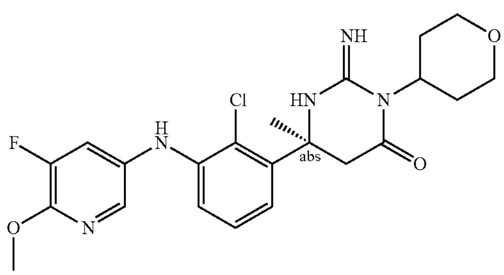 [SMILES: COc1ncc(Nc2cccc([C@]3(C)CC(=O)N(C4CCOCC4)C(=N)N3)c2Cl)cc1F] | 1.24 | 462 |
| 50 | 3-Bromo-2-methoxy-pyridine | (6S)-6-{2-Chloro-3-[(2-methoxypyridin-3-yl)amino]-phenyl}-2-imino-6-methyl-3-(tetrahydropyran-4-yl)-hexahydropyrimidin-4-one | 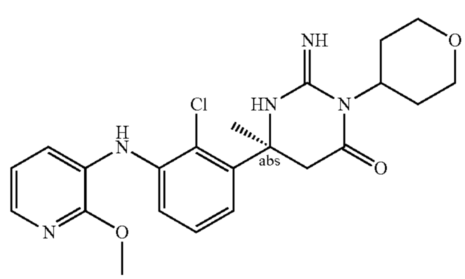 [SMILES: COc1ncccc1Nc1cccc([C@]2(C)CC(=O)N(C3CCOCC3)C(=N)N2)c1Cl] | 1.21 | 444 |
| 51 | 3-Bromo-pyridine-2-carbonitrile | 3-{2-Chloro-3-[(4S)-2-imino-4-methyl-6-oxo-1-(tetrahydro-pyran-4-yl)hexahydropyrimidin-4-yl]anilino}pyridine-2-carbonitrile | 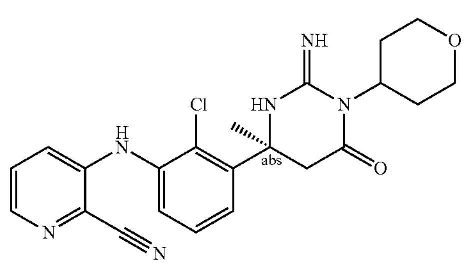 [SMILES: C[C@@]1(c2cccc(Nc3cccnc3C#N)c2Cl)CC(=O)N(C2CCOCC2)C(=N)N1] | 1.02 | 439 |

-continued

| Ex. | Aryl halide | Product | Structure | LCMS RT (min) | LCMS [MH]+ (method 3) |
|---|---|---|---|---|---|
| 52 | 5-Bromo-2-(trifluoro-methyl)-pyrimidine | (6S)-6-(2-Chloro-3-{[2-(trifluoromethyl)pyrimidin-5-yl]amino}phenyl)-2-imino-6-methyl-3-(tetrahydropyran-4-yl)hexahydropyrimidin-4-one | 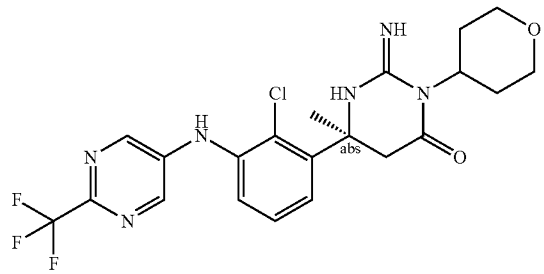 [SMILES: C[C@@]1(c2cccc(Nc3cnc(C(F)(F)F)nc3)c2Cl)CC(=O)N(C2CCOCC2)C(=N)N1] | 1.16 | 483 |
| 53 | 1-Bromo-2-(trifluoro-methoxy)-benzene | (6S)-6-{2-Chloro-3-[2-(trifluoromethoxy)anilino]-phenyl}-2-imino-6-methyl-3-(tetrahydropyran-4-yl)-hexahydropyrimidin-4-one | 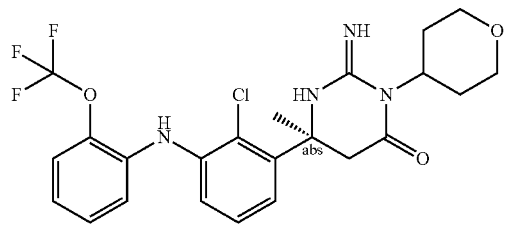 [SMILES: C[C@@]1(c2cccc(Nc3ccccc3OC(F)(F)F)c2Cl)CC(=O)N(C2CCOCC2)C(=N)N1] | 1.51 | 497 |
| 54 | 3-Bromo-4-methoxy-pyridine | (6S)-6-{2-Chloro-3-[(4-methoxypyridin-3-yl)amino]-phenyl}-2-imino-6-methyl-3-(tetrahydropyran-4-yl)-hexahydropyrimidin-4-one | 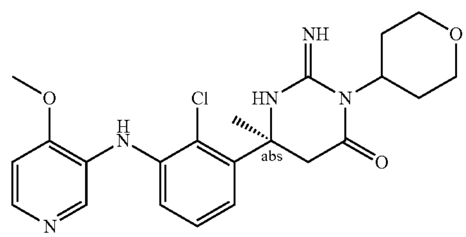 [SMILES: COc1ccncc1Nc1cccc([C@]2(C)CC(=O)N(C3CCOCC3)C(=N)N2)c1Cl] | 0.97 | 444 |
| 55 | 3-Bromo-2-methoxy-6-methyl-pyridine | (6S)-6-{2-Chloro-3-[(2-methoxy-6-methylpyridin-3-yl)-amino]phenyl}-2-imino-6-methyl-3-(tetrahydropyran-4-yl)hexahydropyrimidin-4-one | 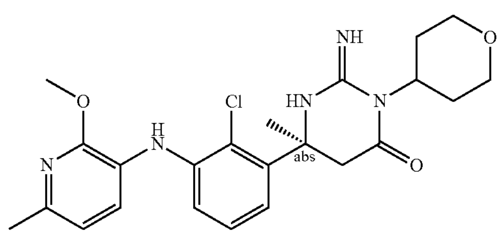 [SMILES: COc1nc(C)ccc1Nc1cccc([C@]2(C)CC(=O)N(C3CCOCC3)C(=N)N2)c1Cl] | 1.38 | 458 |
| 56 | 3-Bromo-4-(trifluoro-methyl)-pyridine | (6S)-6-(2-Chloro-3-{[4-(trifluoromethyl)pyridin-3-yl]-amino}phenyl)-2-imino-6-methyl-3-(tetrahydropyran-4-yl)hexahydropyrimidin-4-one | 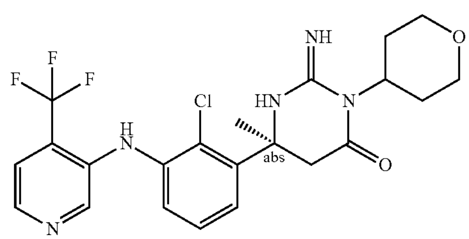 [SMILES: C[C@@]1(c2cccc(Nc3cnccc3C(F)(F)F)c2Cl)CC(=O)N(C2CCOCC2)C(=N)N1] | 1.21 | 482 |
| 57 | 1-Bromo-naphtha-lene | (6S)-6-[2-Chloro-3-(1-naphthyl-amino)phenyl]-2-imino-6-methyl-3-(tetrahydropyran-4-yl)hexahydropyrimidin-4-one | 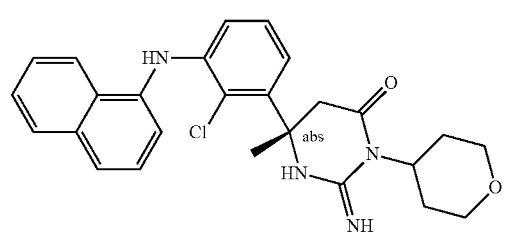 [SMILES: C[C@@]1(c2cccc(Nc3cccc4ccccc34)c2Cl)CC(=O)N(C2CCOCC2)C(=N)N1] | 1.53 | 463 |

| Ex. | Aryl halide | Product | Structure | LCMS RT (min) | LCMS [MH]+ (method 3) |
|---|---|---|---|---|---|
| 58 | 3-Bromo-biphenyl | (6S)-6-[2-Chloro-3-(3-phenyl-anilino)phenyl]-2-imino-6-methyl-3-(tetrahydropyran-4-yl)hexahydropyrimidin-4-one | 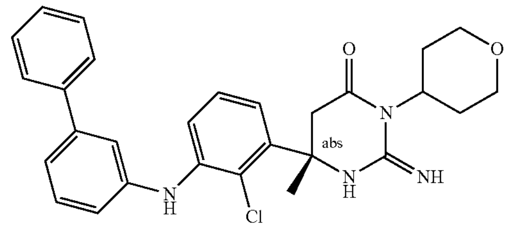 [SMILES: C[C@@]1(c2cccc(Nc3cccc(-c4ccccc4)c3)c2Cl)CC(=O)N(C2CCOCC2)C(=N)N1] | 1.64 | 489 |
| 59 | 4-Bromo-1,2-(methyl-enedioxy)-benzene | (6S)-6-[3-(1,3-Benzodioxol-5-ylamino)-2-chlorophenyl]-2-imino-6-methyl-3-(tetrahydro-pyran-4-yl)hexahydropyrimidin-4-one | 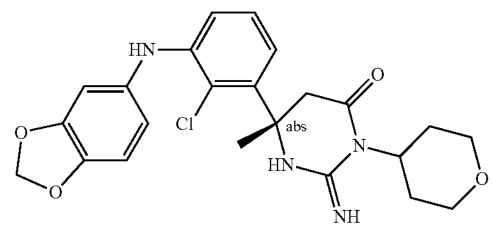 [SMILES: C[C@@]1(c2cccc(Nc3ccc4c(c3)OCO4)c2Cl)CC(=O)N(C2CCOCC2)C(=N)N1] | 1.26 | 457 |
| 60 | 5-Bromo-2-chloro-pyridine | (6S)-6-{2-Chloro-3-[(6-chloro-pyridin-3-yl)amino]phenyl}-2-imino-6-methyl-3-(tetrahydro-pyran-4-yl)hexahydropyrimidin-4-one | 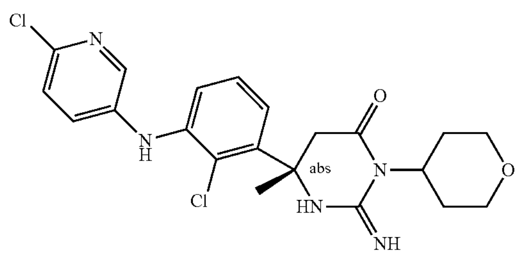 [SMILES: C[C@@]1(c2cccc(Nc3ccc(Cl)nc3)c2Cl)CC(=O)N(C2CCOCC2)C(=N)N1] | 1.15 | 448 |
| 61 | 5-(3-Bromo-phenyl)-isoxazole | (6S)-6-{2-Chloro-3-[3-(isoxazol-5-yl)anilino]phenyl}-2-imino-6-methyl-3-(tetrahydro-pyran-4-yl)hexahydropyrimidin-4-one | 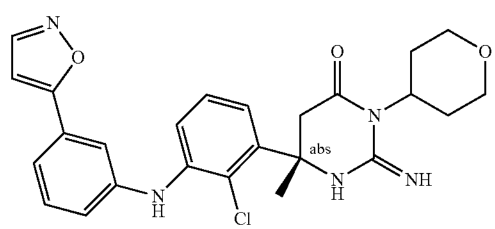 [SMILES: C[C@@]1(c2cccc(Nc3cccc(-c4ccno4)c3)c2Cl)CC(=O)N(C2CCOCC2)C(=N)N1] | 1.31 | 480 |
| 62 | 5-Bromo-2-tert-butyl-pyrimidine | (6S)-6-{3-[(2-tert-Butyl-pyrimidin-5-yl)amino]-2-chloro-phenyl}-2-imino-6-methyl-3-(tetrahydropyran-4-yl)-hexahydropyrimidin-4-one | 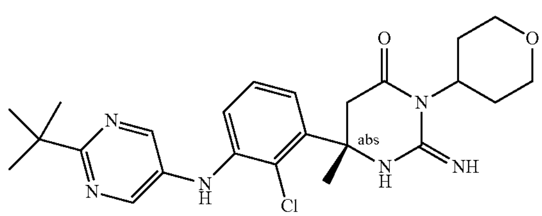 [SMILES: CC(C)(C)c1ncc(Nc2cccc([C@]3(C)CC(=O)N(C4CCOCC4)C(=N)N3)c2Cl)cn1] | 1.33 | 471 |
| 63 | 3-(Difluoro-methoxy)-bromo-benzene | (6S)-6-{2-Chloro-3-[3-(difluoro-methoxy)anilino]phenyl}-2-imino-6-methyl-3-(tetrahydro-pyran-4-yl)hexahydropyrimidin-4-one | 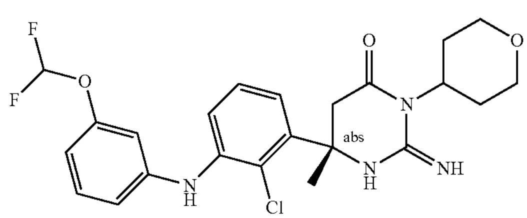 [SMILES: C[C@@]1(c2cccc(Nc3cccc(OC(F)F)c3)c2Cl)CC(=O)N(C2CCOCC2)C(=N)N1] | 1.40 | 479 |

| Ex. | Aryl halide | Product | Structure | LCMS RT (min) | LCMS [MH]+ (method 3) |
|---|---|---|---|---|---|
| 64 | 1-Bromo-4-(trifluoro-methoxy)-benzene | (6S)-6-{2-Chloro-3-[4-(trifluoromethoxy)anilino]-phenyl}-2-imino-6-methyl-3-(tetrahydropyran-4-yl)-hexahydropyrimidin-4-one | 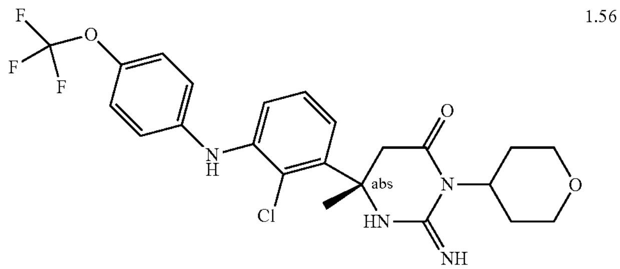 | 1.56 | 497 |
| 65 | 1-Acetyl-5-bromo-indoline | (6S)-6-{3-[(1-Acetylindolin-5-yl)amino]-2-chlorophenyl}-2-imino-6-methyl-3-(tetrahydro-pyran-4-yl)hexahydropyrimidin-4-one | 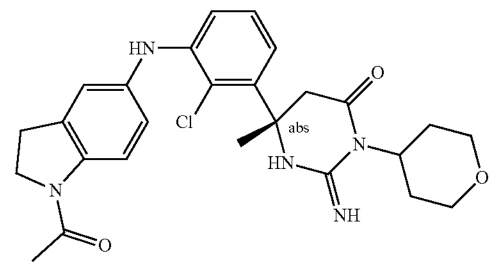 [SMILES: CC(=O)N1CCc2cc(Nc3cccc([C@]4(C)CC(=O)N(C5CCOCC5)C(=N)N4)c3Cl)ccc21] | 1.09 | 496 |
| 66 | 2-(Difluoro-methoxy)-bromo-benzene | (6S)-6-{2-Chloro-3-[2-(difluoro-methoxy)anilino]phenyl}-2-imino-6-methyl-3-(tetrahydro-pyran-4-yl)hexahydropyrimidin-4-one | 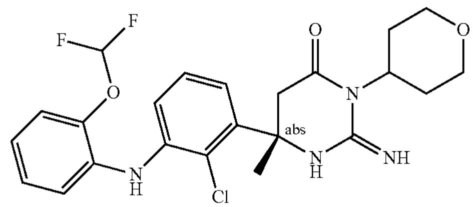 [SMILES: C[C@@]1(c2cccc(Nc3ccccc3OC(F)F)c2Cl)CC(=O)N(C2CCOCC2)C(=N)N1] | 1.38 | 479 |
| 67 | 1-Bromo-4-tert-butyl-benzene | (6S)-6-[3-(4-tert-Butylanilino)-2-chlorophenyl]-2-imino-6-methyl-3-(tetrahydropyran-4-yl)hexahydropyrimidin-4-one | 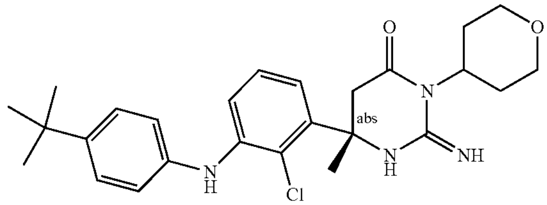 [SMILES: CC(C)(C)c1ccc(Nc2cccc([C@]3(C)CC(=O)N(C4CCOCC4)C(=N)N3)c2Cl)cc1] | 1.74 | 469 |
| 68 | 1-Bromo-2,3-[(difluoro-methyl-ene)dioxy]-benzene | (6S)-6-{2-Chloro-3-[(2,2-difluoro-1,3-benzodioxol-4-yl)amino]phenyl}-2-imino-6-methyl-3-tetrahydropyran-4-yl-hexahydropyrimidin-4-one | 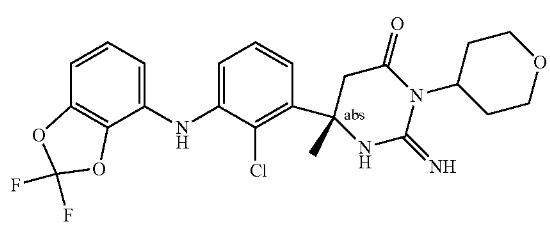 [SMILES: C[C@@]1(c2cccc(Nc3cccc4c3OC(F)(F)O4)c2Cl)CC(=O)N(C2CCOCC2)C(=N)N1] | 1.48 | 493 |
| 69 | 2-Bromo-m-xylene | (6S)-6-[2-Chloro-3-(2,6-dimethylanilino)phenyl]-2-imino-6-methyl-3-(tetrahydro-pyran-4-yl)hexahydropyrimidin-4-one | 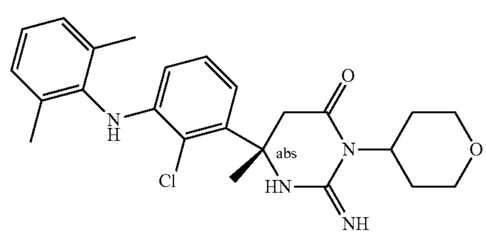 [SMILES: Cc1cccc(C)c1Nc1cccc([C@]2(C)CC(=O)N(C3CCOCC3)C(=N)N2)c1Cl] | 1.50 | 441 |

| Ex. | Aryl halide | Product | Structure | LCMS RT (min) | LCMS [MH]+ (method 3) |
|---|---|---|---|---|---|
| 70 | 6-Bromo-4-fluoro-pyrazolo-[1,5-a]-pyridine | (6S)-6-{2-Chloro-3-[(4-fluoro-pyrazolo[1,5-a]pyridin-6-yl)-amino]phenyl}-2-imino-6-methyl-3-(tetrahydropyran-4-yl)hexahydropyrimidin-4-one | 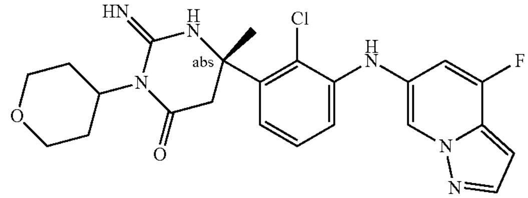 [SMILES: C[C@@]1(c2cccc(Nc3cc(F)c4ccnn4c3)c2Cl)CC(=O)N(C2CCOCC2)C(=N)N1] | 1.25 | 471 |
| 71 | 4-Bromo-biphenyl | (6S)-6-[2-Chloro-3-(4-phenyl-anilino)phenyl]-2-imino-6-methyl-3-(tetrahydropyran-4-yl)hexahydropyrimidin-4-one | 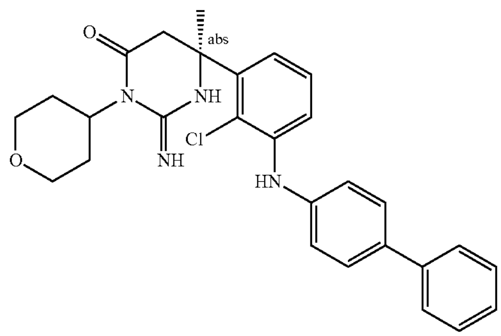 [SMILES: C[C@@]1(c2cccc(Nc3ccc(-c4ccccc4)cc3)c2Cl)CC(=O)N(C2CCOCC2)C(=N)N1] | 1.61 | 489 |
| 72 | 5-Bromo-N,N-dimethyl-pyridin-2-amine | (6S)-6-(2-Chloro-3-{[6-(dimethylamino)pyridin-3-yl]-amino}phenyl)-2-imino-6-methyl-3-(tetrahydropyran-4-yl)hexahydropyrimidin-4-one | 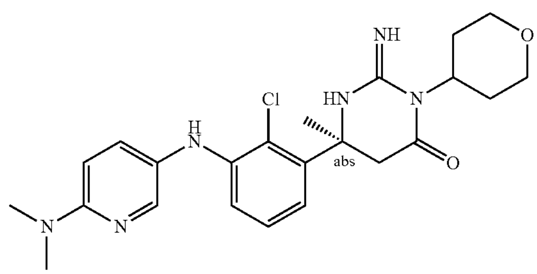 [SMILES: CN(C)c1ccc(Nc2cccc([C@]3(C)CC(=O)N(C4CCOCC4)C(=N)N3)c2Cl)cn1] | 1.22 | 457 |
| 73 | 4-Bromo-1-methyl-pyridin-2-one | (6S)-6-{2-Chloro-3-[(1-methyl-2-oxopyridin-4-yl)amino]-phenyl}-2-imino-6-methyl-3-(tetrahydropyran-4-yl)-hexahydropyrimidin-4-one | 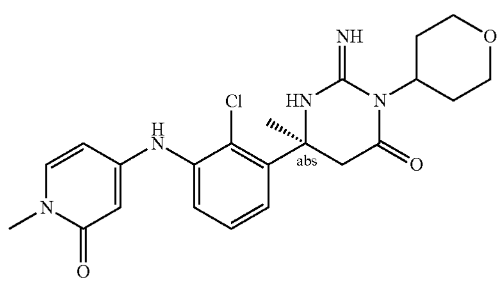 [SMILES: Cn1ccc(Nc2cccc([C@]3(C)CC(=O)N(C4CCOCC4)C(=N)N3)c2Cl)cc1=O] | 0.77 | 444 |

Examples 74 to 119 (General Method 4)

The appropriate aniline and the appropriate aryl halide were dissolved in a solvent, and a base (3 equiv.) was added. The solution was degassed, then a transition metal catalyst (0.05 equiv.) and a phosphine ligand (0.10 equiv.) were added. The reaction mixture was heated at 80° C. for 3 h, or until the reaction was complete. The solution was filtered, and the material was isolated using silica gel chromatography or reverse phase HPLC, then deprotected in accordance with General Method 2, to afford the title compounds. As necessary, final products were further purified by preparative reverse phase HPLC and isolated as the TFA salt.

The solvent employed for Examples 74-80, 85-99 and 101-117 was 1,4-dioxane. The solvent employed for Examples 81-84, 100, 118 and 119 was toluene.

The base employed for Examples 74-83, 86-89, 92, 94, 96, 100, 102, 104, 110, 118 and 119 was $K_3PO_4$. The base employed for Examples 84, 85, 90, 91, 93, 95, 97-99, 101, 103, 105-109 and 111-117 was sodium tert-butoxide.

The transition metal catalyst employed for Examples 74-80, 84-88, 90, 91, 93, 95, 97-99, 101, 103-109 and 111-117 was BrettPhos Pd G3. The transition metal catalyst employed for Examples 81-83, 89, 92, 94, 96, 100, 102, 110, 118 and 119 was $Pd_2(dba)_3$.

The phosphine ligand employed for Examples 74-80, 85-88, 90, 91, 93, 95, 97-99, 101, 103-109 and 111-117 was BrettPhos. The phosphine ligand employed for Examples 81-83, 89, 92, 94, 96, 100, 118 and 119 was XPhos. The phosphine ligand employed for Examples 84, 102 and 110 was XantPhos.

The compounds identified in the following Table were prepared in accordance with General Method 4, utilising Intermediate 28 as the aniline.

| Ex. | Aryl halide | Product | Structure | LCMS RT (min) | LCMS [MH]+ (method 4) |
|---|---|---|---|---|---|
| 74 | 1-Bromo-3-isopropoxy-benzene | (6S)-6-[2-Chloro-3-(3-isopropoxyanilino)phenyl]-2-imino-6-methyl-3-(tetrahydro-pyran-4-yl)hexahydropyrimidin-4-one | 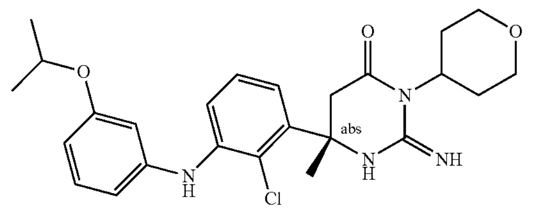 [SMILES: CC(C)Oc1cccc(Nc2cccc([C@]3(C)CC(=O)N(C4CCOCC4)C(=N)N3)c2Cl)c1] | 0.97 | 471 |
| 75 | 1-Bromo-3-phenoxy-benzene | (6S)-6-[2-Chloro-3-(3-phenoxy-anilino)phenyl]-2-imino-6-methyl-3-(tetrahydropyran-4-yl)hexahydropyrimidin-4-one | 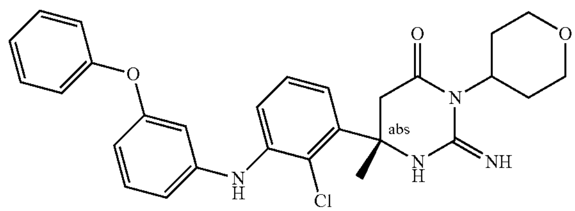 [SMILES: C[C@@]1(c2cccc(Nc3cccc(Oc4ccccc4)c3)c2Cl)CC(=O)N(C2CCOCC2)C(=N)N1] | 1.04 | 505 |
| 76 | 1-Bromo-2-isopropoxy-benzene | (6S)-6-[2-Chloro-3-(2-isopropoxyanilino)phenyl]-2-imino-6-methyl-3-(tetrahydro-pyran-4-yl)hexahydropyrimidin-4-one | 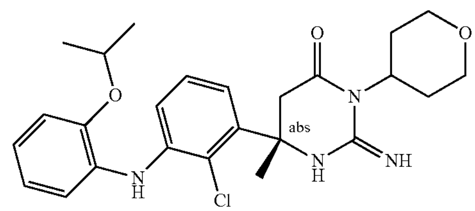 [SMILES: CC(C)Oc1ccccc1Nc1cccc([C@]2(C)CC(=O)N(C3CCOCC3)C(=N)N2)c1Cl] | 0.99 | 471 |
| 77 | 4-Bromo-2-methyl-2H-indazole | (6S)-6-{2-Chloro-3-[(2-methyl-indazol-4-yl)amino]phenyl}-2-imino-6-methyl-3-(tetrahydro-pyran-4-yl)hexahydropyrimidin-4-one | 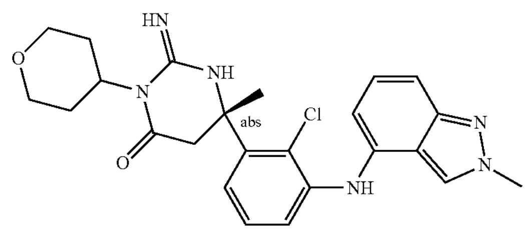 [SMILES: Cn1cc2c(Nc3cccc([C@]4(C)CC(=O)N(C5CCOCC5)C(=N)N4)c3Cl)cccc2n1] | 0.86 | 467 |
| 78 | 5-Bromo-2-methyl-2H-indazole | (6S)-6-{2-Chloro-3-[(2-methyl-indazol-5-yl)amino]phenyl}-2-imino-6-methyl-3-(tetrahydro-pyran-4-yl)hexahydropyrimidin-4-one | 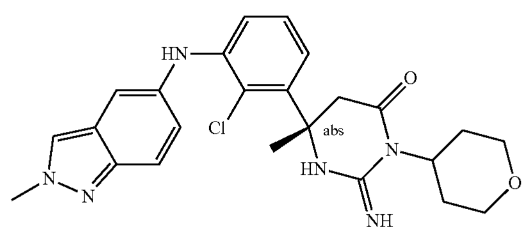 [SMILES: Cn1cc2cc(Nc3cccc([C@]4(C)CC(=O)N(C5CCOCC5)C(=N)N4)c3Cl)ccc2n1] | 0.91 | 467 |
| 79 | 1-(3-Bromo-phenyl)-pyrrolidine-2-one | (6S)-6-{2-Chloro-3-[3-(2-oxo-pyrrolidin-1-yl)anilino]phenyl}-2-imino-6-methyl-3-(tetrahydro-pyran-4-yl)hexahydropyrimidin-4-one | 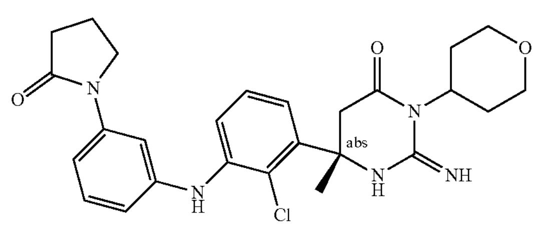 [SMILES: C[C@@]1(c2cccc(Nc3cccc(N4CCCC4=O)c3)c2Cl)CC(=O)N(C2CCOCC2)C(=N)N1] | 0.75 | 496 |
| 80 | 2-(4-Bromo-phenyl)-5-methyl-1,3,4-oxadiazole | (6S)-6-{2-Chloro-3-[4-(5-methyl-1,3,4-oxadiazol-2-yl)-anilino]phenyl}-2-imino-6-methyl-3-(tetrahydropyran-4-yl)hexahydropyrimidin-4-one | 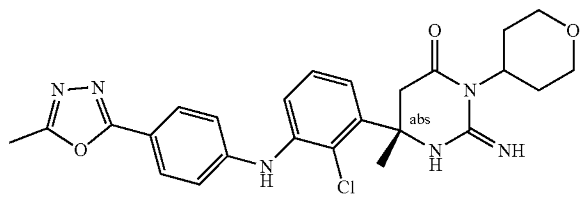 [SMILES: Cc1nnc(-c2ccc(Nc3cccc([C@]4(C)CC(=O)N(C5CCOCC5)C(=N)N4)c3Cl)cc2)o1] | 0.72 | 495 |

| Ex. | Aryl halide | Product | Structure | LCMS RT (min) | LCMS [MH]+ (method 4) |
|---|---|---|---|---|---|
| 81 | 5-Bromo-2-(difluoro-methyl)-pyridine | (6S)-6-(2-Chloro-3-{[6-(difluoromethyl)pyridin-3-yl]-amino}phenyl)-2-imino-6-methyl-3-tetrahydropyran-4-yl-hexahydropyrimidin-4-one | 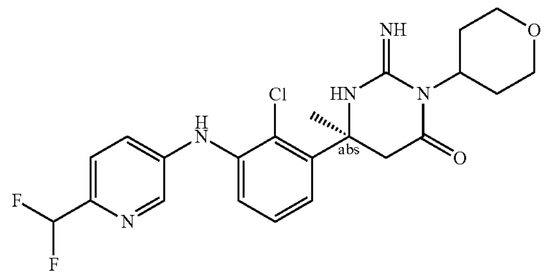 [SMILES: C[C@@]1(c2cccc(Nc3ccc(C(F)F)nc3)c2Cl)CC(=O)N(C2CCOCC2)C(=N)N1] | 0.71 | 464 |
| 82 | 2-Bromo-5-fluoro-benzonitrile | 2-{2-Chloro-3-[(4S)-2-imino-4-methyl-6-oxo-1-(tetrahydro-pyran-4-yl)hexahydropyrimidin-4-yl]anilino}-5-fluorobenzo-nitrile | 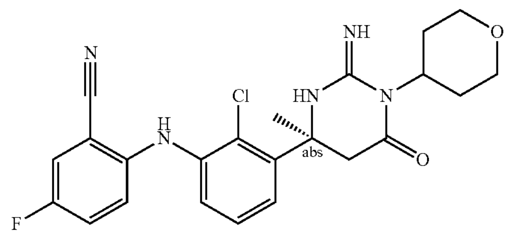 [SMILES: C[C@@]1(c2cccc(Nc3ccc(F)cc3C#N)c2Cl)CC(=O)N(C2CCOCC2)C(=N)N1] | 0.78 | 456 |
| 83 | 2-Bromo-5-(trifluoro-methyl)-benzonitrile | 2-{2-Chloro-3-[(4S)-2-imino-4-methyl-6-oxo-1-(tetrahydro-pyran-4-yl)hexahydropyrimidin-4-yl]anilino}-5-(trifluoro-methyl)benzonitrile | 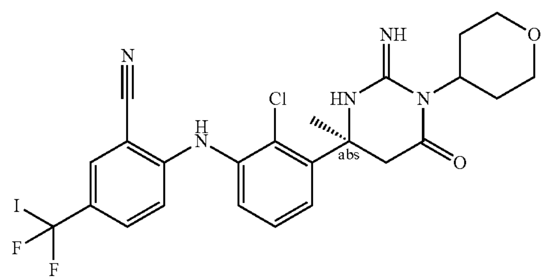 [SMILES: C[C@@]1(c2cccc(Nc3ccc(C(F)(F)I)cc3C#N)c2Cl)CC(=O)N(C2CCOCC2)C(=N)N1] | 0.87 | 506 |
| 84 | 3-Iodo-6-methyl-pyridazine | (6S)-6-{2-Chloro-3-[(6-methyl-pyridazin-3-yl)amino]phenyl}-2-imino-6-methyl-3-(tetrahydro-pyran-4-yl)hexahydropyrimidin-4-one | 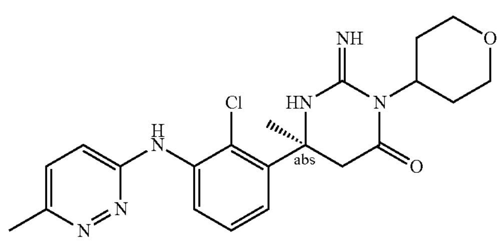 [SMILES: Cc1ccc(Nc2cccc([C@]3(C)CC(=O)N(C4CCOCC4)C(=N)N3)c2Cl)nn1] | 0.39 | 429 |
| 85 | 6-Bromo-[1,2,4]-triazolo-[1,5-a]-pyridine | (6S)-6-[2-Chloro-3-([1,2,4]-triazolo[1,5-a]pyridin-6-yl-amino)phenyl]-2-imino-6-methyl-3-(tetrahydropyran-4-yl)hexahydropyrimidin-4-one | 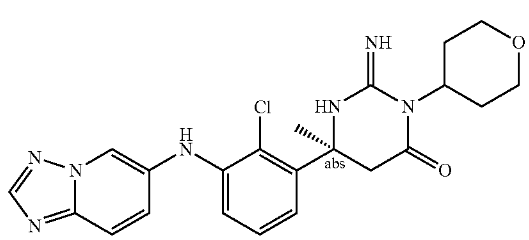 [SMILES: C[C@@]1(c2cccc(Nc3ccc4ncnn4c3)c2Cl)CC(=O)N(C2CCOCC2)C(=N)N1] | 0.56 | 454 |

-continued

| Ex. | Aryl halide | Product | Structure | LCMS RT (min) | LCMS [MH]+ (method 4) |
|---|---|---|---|---|---|
| 86 | 7-Bromo-4-methyl-3,4-dihydro-2H-1,4-benzoxazine | (6S)-6-{2-Chloro-3-[(4-methyl-2,3-dihydro-1,4-benzoxazin-7-yl)amino]phenyl}-2-imino-6-methyl-3-(tetrahydropyran-4-yl)hexahydropyrimidin-4-one | 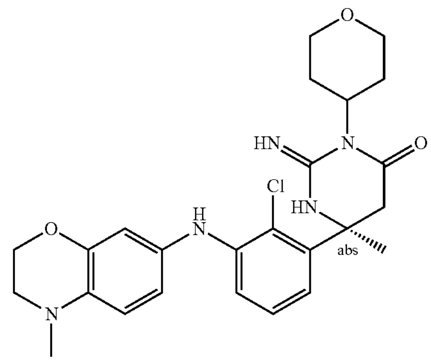 [SMILES: CN1CCOc2cc(Nc3cccc([C@]4(C)CC(=O)N(C5CCOCC5)C(=N)N4)c3Cl)ccc21] | 0.83 | 484 |
| 87 | 4-Bromo-2-methoxypyridine | (6S)-6-{2-Chloro-3-[(2-methoxypyridin-4-yl)amino]phenyl}-2-imino-6-methyl-3-(tetrahydropyran-4-yl)-hexahydropyrimidin-4-one | 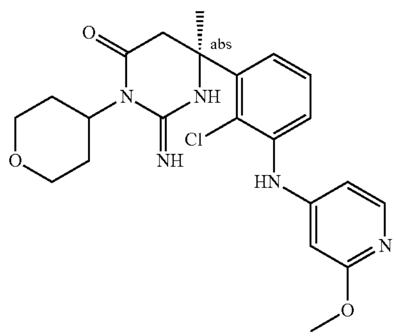 [SMILES: COc1cc(Nc2cccc([C@]3(C)CC(=O)N(C4CCOCC4)C(=N)N3)c2Cl)ccn1] | 0.37 | 444 |
| 88 | Int. 52 | 3-{2-Chloro-3-[(4S)-2-imino-4-methyl-6-oxo-1-(tetrahydropyran-4-yl)hexahydropyrimidin-4-yl]anilino}-6-methylpyridine-2-carbonitrile | 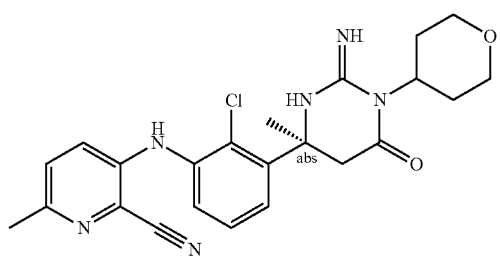 [SMILES: Cc1ccc(Nc2cccc([C@]3(C)CC(=O)N(C4CCOCC4)C(=N)N3)c2Cl)c(C#N)n1] | 0.68 | 453 |
| 89 | Int. 53 | 3-{2-Chloro-3-[(4S)-2-imino-4-methyl-6-oxo-1-(tetrahydropyran-4-yl)hexahydropyrimidin-4-yl]anilino}quinoline-4-carbonitrile | 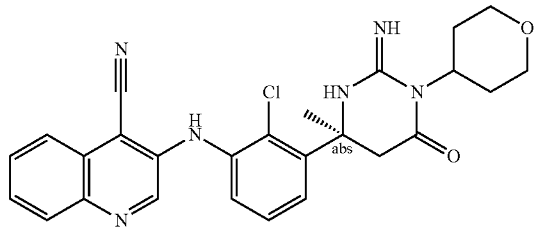 [SMILES: C[C@@]1(c2cccc(Nc3cnc4ccccc4c3C#N)c2Cl)CC(=O)N(C2CCOCC2)C(=N)N1] | 0.83 | 489 |
| 90 | 4-Bromo-1-methylisoquinoline | (6S)-6-{2-Chloro-3-[(1-methylisoquinolin-4-yl)amino]phenyl}-2-imino-6-methyl-3-(tetrahydropyran-4-yl)hexahydropyrimidin-4-one | 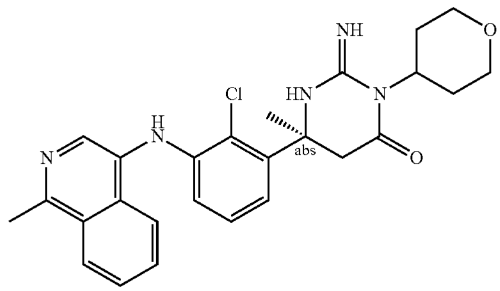 [SMILES: Cc1ncc(Nc2cccc([C@]3(C)CC(=O)N(C4CCOCC4)C(=N)N3)c2Cl)c2ccccc12] | 0.52 | 478 |

-continued

| Ex. | Aryl halide | Product | Structure | LCMS RT (min) | LCMS [MH]+ (method 4) |
|---|---|---|---|---|---|
| 91 | 5-Bromo-pyrazolo-[1,5,a]-pyridine | (6S)-6-[2-Chloro-3-(pyrazolo-[1,5-a]pyridin-5-ylamino)-phenyl]-2-imino-6-methyl-3-(tetrahydropyran-4-yl)-hexahydropyrimidin-4-one | 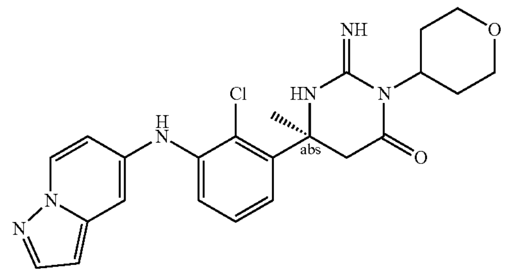 [SMILES: C[C@@]1(c2cccc(Nc3ccn4nccc4c3)c2Cl)CC(=O)N(C2CCOCC2)C(=N)N1] | 0.67 | 453 |
| 92 | 1-Bromo-2-(difluoro-methoxy)-4-fluoro-benzene | (6S)-6-{2-Chloro-3-[2-(difluoro-methoxy)-4-fluoro-anilino]-phenyl}-2-imino-6-methyl-3-(tetrahydropyran-4-yl)-hexahydropyrimidin-4-one | 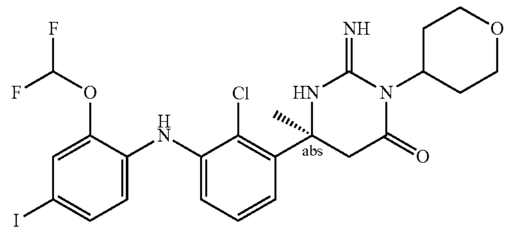 [SMILES: C[C@@]1(c2cccc(Nc3ccc(I)cc3OC(F)F)c2Cl)CC(=O)N(C2CCOCC2)C(=N)N1] | 0.89 | 497 |
| 93 | 5-Bromo-2-methyl-3-(trifluoro-methyl)-pyridine | (6S)-6-(2-Chloro-3-{[6-methyl-5-(trifluoromethyl)pyridin-3-yl]-amino}phenyl)-2-imino-6-methyl-3-(tetrahydropyran-4-yl)hexahydropyrimidin-4-one | 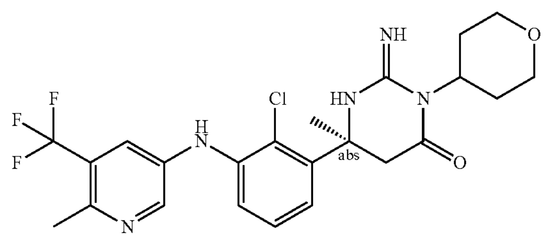 [SMILES: Cc1ncc(Nc2cccc([C@]3(C)CC(=O)N(C4CCOCC4)C(=N)N3)c2Cl)cc1C(F)(F)F] | 0.79 | 496 |
| 94 | Int. 54 | (6S)-6-(2-Chloro-3-{[2-(difluoromethoxy)-6-methyl-pyridin-3-yl]amino}phenyl)-2-imino-6-methyl-3-(tetrahydro-pyran-4-yl)hexahydropyrimidin-4-one | 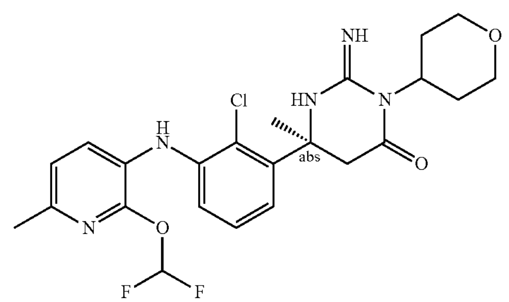 [SMILES: Cc1ccc(Nc2cccc([C@]3(C)CC(=O)N(C4CCOCC4)C(=N)N3)c2Cl)c(OC(F)F)n1] | 0.89 | 494 |
| 95 | Int. 55 | (6S)-6-(2-Chloro-3-{[1-(difluoromethoxy)isoquinolin-4-yl]amino}phenyl)-2-imino-6-methyl-3-(tetrahydropyran-4-yl)hexahydropyrimidin-4-one | 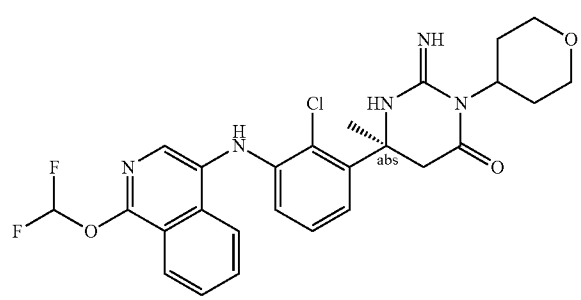 [SMILES: C[C@@]1(c2cccc(Nc3cnc(OC(F)F)c4ccccc34)c2Cl)CC(=O)N(C2CCOCC2)C(=N)N1] | 0.94 | 530 |

-continued

| Ex. | Aryl halide | Product | Structure | LCMS RT (min) | LCMS [MH]+ (method 4) |
|---|---|---|---|---|---|
| 96 | Int. 56 | 4-{2-Chloro-3-[(4S)-2-imino-4-methyl-6-oxo-1-(tetrahydro-pyran-4-yl)hexahydropyrimidin-4-yl]anilino}-3-(difluoro-methoxy)benzonitrile | 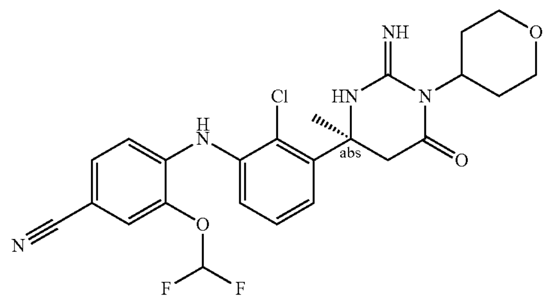 [SMILES: C[C@@]1(c2cccc(Nc3ccc(C#N)cc3OC(F)F)c2Cl)CC(=O)N(C2CCOCC2)C(=N)N1] | 0.81 | 504 |
| 97 | 3-Bromo-2-(difluoro-methoxy)-pyridine | (6S)-6-(2-Chloro-3-{[2-(difluoromethoxy)pyridin-3-yl]-amino}phenyl)-2-imino-6-methyl-3-(tetrahydropyran-4-yl)hexahydropyrimidin-4-one | 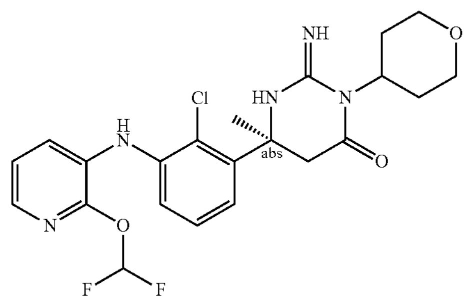 [SMILES: C[C@@]1(c2cccc(Nc3cccnc3OC(F)F)c2Cl)CC(=O)N(C2CCOCC2)C(=N)N1] | 0.80 | 480 |
| 98 | 3-Bromo-2-(difluoro-methoxy)-quinoline | (6S)-6-(2-Chloro-3-{[2-(difluoromethoxy)quinolin-3-yl]amino}phenyl)-2-imino-6-methyl-3-(tetrahydropyran-4-yl)hexahydropyrimidin-4-one | 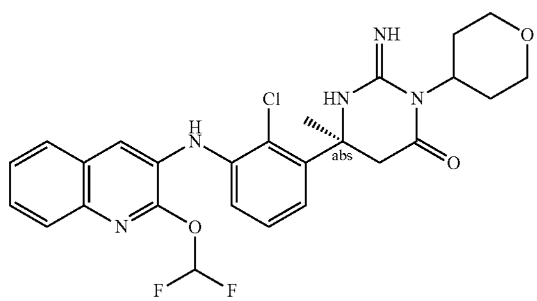 [SMILES: C[C@@]1(c2cccc(Nc3cc4ccccc4nc3OC(F)F)c2Cl)CC(=O)N(C2CCOCC2)C(=N)N1] | 0.96 | 530 |
| 99 | 5-Bromo-2-cyclo-propyl-pyridine | (6S)-6-{2-Chloro-3-[(6-cyclo-propylpyridin-3-yl)amino]-phenyl}-2-imino-6-methyl-3-(tetrahydropyran-4-yl)-hexahydropyrimidin-4-one | 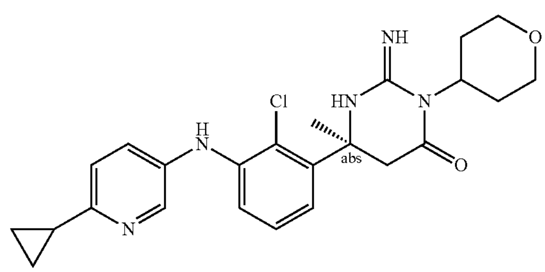 [SMILES: C[C@@]1(c2cccc(Nc3ccc(C4CC4)nc3)c2Cl)CC(=O)N(C2CCOCC2)C(=N)N1] | 0.52 | 454 |
| 100 | Int. 84 | 3-{2-Chloro-3-[(4S)-2-imino-4-methyl-6-oxo-1-(tetrahydro-pyran-4-yl)hexahydropyrimidin-4-yl]anilino}-6-(difluoro-methyl)pyridine-2-carbonitrile | 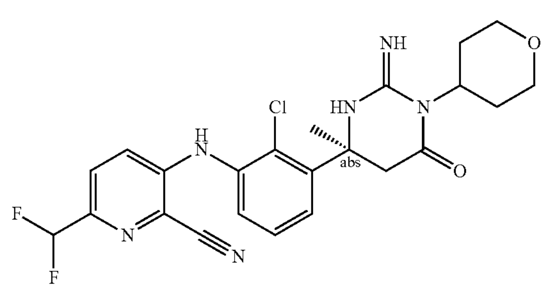 [SMILES: C[C@@]1(c2cccc(Nc3ccc(C(F)F)nc3C#N)c2Cl)CC(=O)N(C2CCOCC2)C(=N)N1] | 0.71 | 489 |

-continued

| Ex. | Aryl halide | Product | Structure | LCMS RT (min) | LCMS [MH]+ (method 4) |
|---|---|---|---|---|---|
| 101 | 2-Chloro-3-(difluoromethoxy)-pyrazine | (6S)-6-(2-Chloro-3-{[3-(difluoromethoxy)pyrazin-2-yl]-amino}phenyl)-2-imino-6-methyl-3-(tetrahydropyran-4-yl)hexahydropyrimidin-4-one | 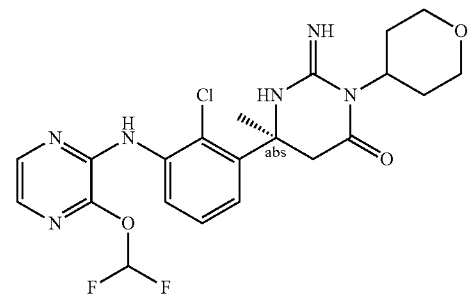 [SMILES: C[C@@]1(c2cccc(Nc3nccnc3OC(F)F)c2Cl)CC(=O)N(C2CCOCC2)C(=N)N1] | 0.76 | 481 |
| 102 | 2-Bromo-3-(difluoromethoxy)-pyridine | (6S)-6-(2-Chloro-3-{[3-(difluoromethoxy)pyridin-2-yl]-amino}phenyl)-2-imino-6-methyl-3-(tetrahydropyran-4-yl)hexahydropyrimidin-4-one | 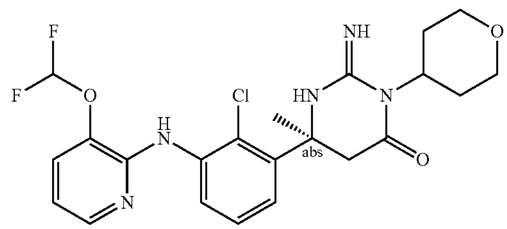 [SMILES: C[C@@]1(c2cccc(Nc3ncccc3OC(F)F)c2Cl)CC(=O)N(C2CCOCC2)C(=N)N1] | 0.76 | 480 |
| 103 | 1-(5-Bromo-pyridin-2-yl)cyclo-butane-carbonitrile | 1-(5-{2-Chloro-3-[(4S)-2-imino-4-methyl-6-oxo-1-(tetrahydro-pyran-4-yl)hexahydropyrimidin-4-yl]anilino}pyridin-2-yl)-cyclobutanecarbonitrile | 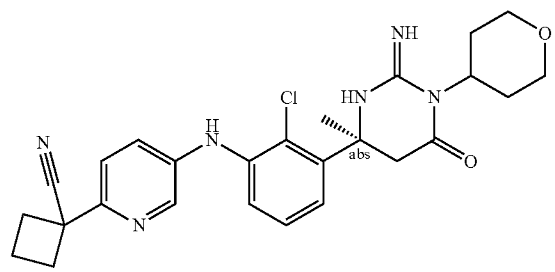 [SMILES: C[C@@]1(c2cccc(Nc3ccc(C4(C#N)CCC4)nc3)c2Cl)CC(=O)N(C2CCOCC2)C(=N)N1] | 0.74 | 493 |
| 104 | Int. 85 | (6S)-6-{2-Chloro-3-[4-fluoro-2-(methylsulfonyl)anilino]-phenyl}-2-imino-6-methyl-3-(tetrahydropyran-4-yl)-hexahydropyrimidin-4-one | 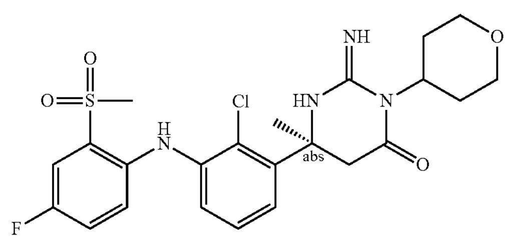 [SMILES: C[C@@]1(c2cccc(Nc3ccc(F)cc3S(C)(=O)=O)c2Cl)CC(=O)N(C2CCOCC2)C(=N)N1] | 0.72 | 509 |
| 105 | 5-Bromo-2-tert-butyl-pyridine | (6S)-6-{3-[(6-tert-Butylpyridin-3-yl)amino]-2-chlorophenyl}-2-imino-6-methyl-3-(tetrahydro-pyran-4-yl)hexahydropyrimidin-4-one | 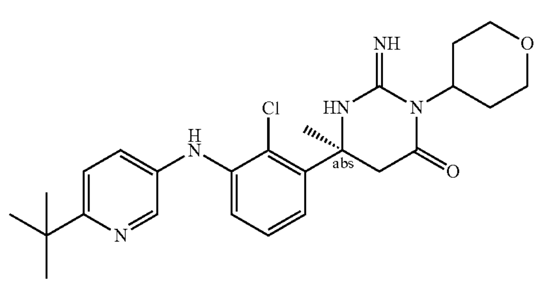 [SMILES: CC(C)(C)c1ccc(Nc2cccc([C@]3(C)CC(=O)N(C4CCOCC4)C(=N)N3)c2Cl)cn1] | 0.63 | 470 |

-continued

| Ex. | Aryl halide | Product | Structure | LCMS RT (min) | LCMS [MH]+ (method 4) |
|---|---|---|---|---|---|
| 106 | 5-Bromo-2-cyclobutyl-pyridine | (6S)-6-{2-Chloro-3-[(6-cyclo-butylpyridin-3-yl)amino]-phenyl}-2-imino-6-methyl-3-(tetrahydropyran-4-yl)-hexahydropyrimidin-4-one | 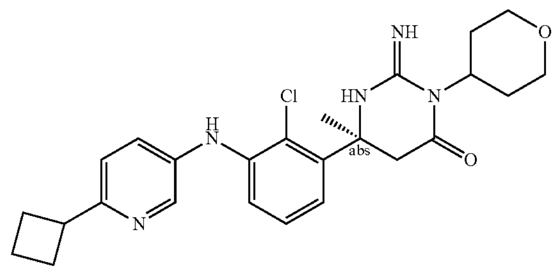 [SMILES: C[C@@]1(c2cccc(Nc3ccc(C4CCC4)nc3)c2Cl)CC(=O)N(C2CCOCC2)C(=N)N1] | 0.56 | 468 |
| 107 | 5-Bromo-2-tert-butyl-pyrazine | (6S)-6-{3-[(5-tert-Butylpyrazin-2-yl)amino]-2-chlorophenyl}-2-imino-6-methyl-3-(tetrahydro-pyran-4-yl)hexahydropyrimidin-4-one | 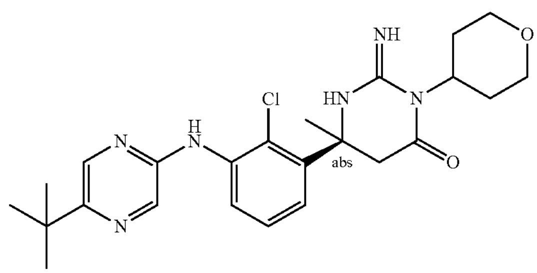 [SMILES: CC(C)(C)c1cnc(Nc2cccc([C@]3(C)CC(=O)N(C4CCOCC4)C(=N)N3)c2Cl)cn1] | 0.85 | 471 |
| 108 | 7-Bromo-imidazo-[1,2-a]-pyridine | (6S)-6-[2-Chloro-3-(imidazo-[1,2-a]pyridin-7-ylamino)-phenyl]-2-imino-6-methyl-3-(tetrahydropyran-4-yl)-hexahydropyrimidin-4-one | 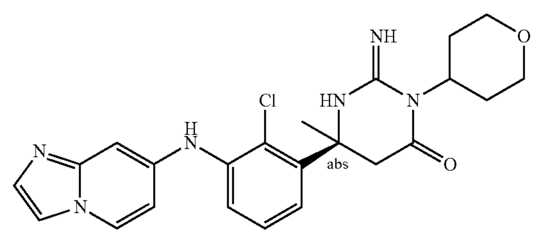 [SMILES: C[C@@]1(c2cccc(Nc3ccn4ccnc4c3)c2Cl)CC(=O)N(C2CCOCC2)C(=N)N1] | 0.25 | 453 |
| 109 | [(2-Bromo-phenyl)-imino]-(dimethyl)-(oxo)-λ6-sulfane | (6S)-6-[2-Chloro-3-(2-{[dimethyl(oxo)-λ6-sulfanylidene]amino}anilino)-phenyl]-2-imino-6-methyl-3-(tetrahydropyran-4-yl)-hexahydropyrimidin-4-one | 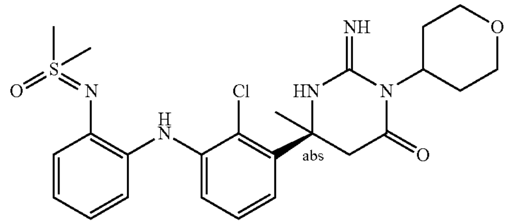 [SMILES: C[C@@]1(c2cccc(Nc3ccccc3N=S(C)(C)=O)c2Cl)CC(=O)N(C2CCOCC2)C(=N)N1] | 0.69 | 504 |
| 110 | 5-Bromo-4-chloro-2-methyl-pyridine | (6S)-6-{2-Chloro-3-[(4-chloro-6-methylpyridin-3-yl)amino]-phenyl}-2-imino-6-methyl-3-(tetrahydropyran-4-yl)-hexahydropyrimidin-4-one | 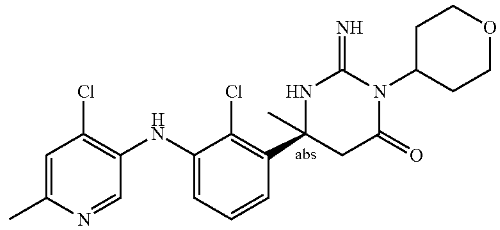 [SMILES: Cc1cc(Cl)c(Nc2cccc([C@]3(C)CC(=O)N(C4CCOCC4)C(=N)N3)c2Cl)cn1] | 0.68 | 462 |
| 111 | 5-Bromo-2-ethyl-pyridine | (6S)-6-{2-Chloro-3-[(6-ethyl-pyridin-3-yl)amino]phenyl}-2-imino-6-methyl-3-(tetrahydro-pyran-4-yl)hexahydropyrimidin-4-one | 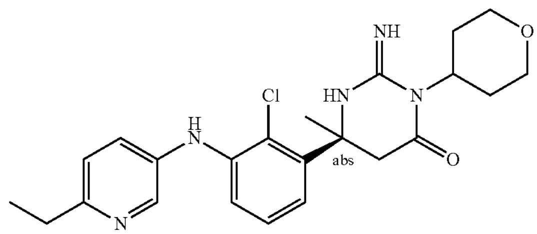 [SMILES: CCc1ccc(Nc2cccc([C@]3(C)CC(=O)N(C4CCOCC4)C(=N)N3)c2Cl)cn1] | 0.48 | 442 |

-continued

| Ex. | Aryl halide | Product | Structure | LCMS RT (min) | LCMS [MH]+ (method 4) |
|---|---|---|---|---|---|
| 112 | 5-Bromo-2-(2,2,2-trifluoro-ethoxy)-pyridine | (6S)-6-(2-Chloro-3-{[6-(2,2,2-trifluoroethoxy)pyridin-3-yl]-amino}phenyl)-2-imino-6-methyl-3-(tetrahydropyran-4-yl)hexahydropyrimidin-4-one | 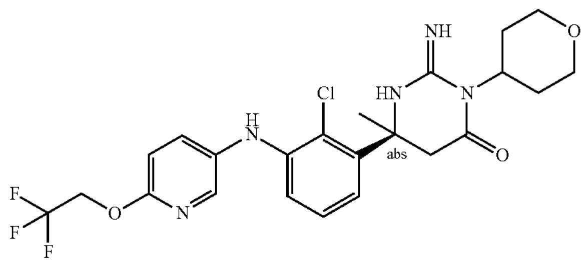 [SMILES: C[C@@]1(c2cccc(Nc3ccc(OCC(F)(F)F)nc3)c2Cl)CC(=O)N(C2CCOCC2)C(=N)N1] | 0.92 | 512 |
| 113 | 2-(Azetidin-1-yl)-5-bromo-pyridine | (6S)-6-(3-{[6-(Azetidin-1-yl)-pyridin-3-yl]amino}-2-chloro-phenyl)-2-imino-6-methyl-3-(tetrahydropyran-4-yl)-hexahydropyrimidin-4-one | 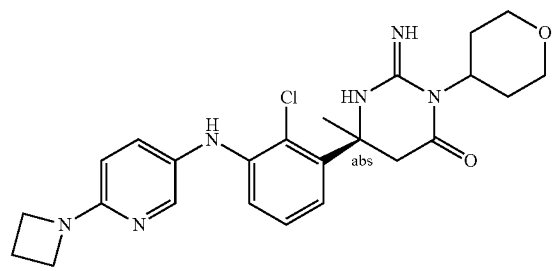 [SMILES: C[C@@]1(c2cccc(Nc3ccc(N4CCC4)nc3)c2Cl)CC(=O)N(C2CCOCC2)C(=N)N1] | 0.48 | 469 |
| 114 | 5-Bromo-2-(1,2,4-triazol-1-yl)pyridine | (6S)-6-(2-Chloro-3-{[6-(1,2,4-triazol-1-yl)pyridin-3-yl]-amino}phenyl)-2-imino-6-methyl-3-(tetrahydropyran-4-yl)hexahydropyrimidin-4-one | 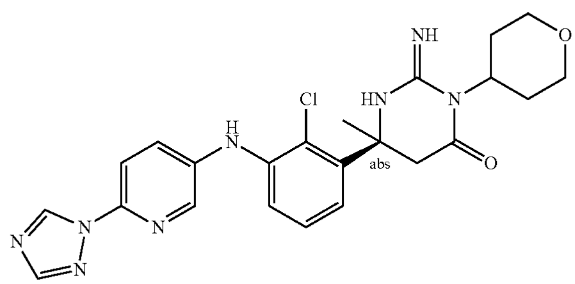 [SMILES: C[C@@]1(c2cccc(Nc3ccc(-n4cncn4)nc3)c2Cl)CC(=O)N(C2CCOCC2)C(=N)N1] | 0.63 | 481 |
| 115 | 5-Bromo-1-methyl-pyrazolo-[3,4-b]-pyridine | (6S)-6-{2-Chloro-3-[(1-methyl-pyrazolo[3,4-b]pyridin-5-yl)-amino]phenyl}-2-imino-6-methyl-3-(tetrahydropyran-4-yl)hexahydropyrimidin-4-one | 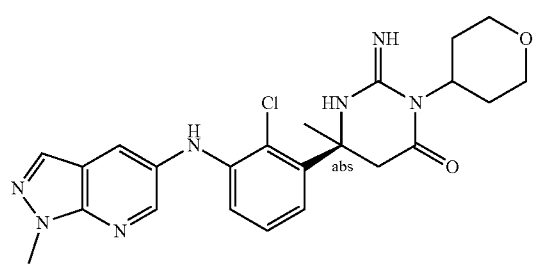 [SMILES: Cn1ncc2cc(Nc3cccc([C@]4(C)CC(=O)N(C5CCOCC5)C(=N)N4)c3Cl)cnc21] | 0.67 | 468 |
| 116 | 6-Bromo-3-methyl-imidazo-[4,5-b]-pyridine | (6S)-6-{2-Chloro-3-[(3-methyl-imidazo[4,5-b]pyridin-6-yl)-amino]phenyl}-2-imino-6-methyl-3-(tetrahydropyran-4-yl)hexahydropyrimidin-4-one | 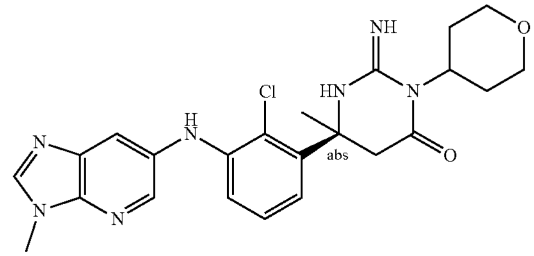 [SMILES: Cn1cnc2cc(Nc3cccc([C@]4(C)CC(=O)N(C5CCOCC5)C(=N)N4)c3Cl)cnc21] | 0.54 | 468 |

-continued

| Ex. | Aryl halide | Product | Structure | LCMS RT (min) | LCMS [MH]+ (method 4) |
|---|---|---|---|---|---|
| 117 | 5-Bromo-2-(2-methyl-tetrazol-5-yl)pyridine | (6S)-6-(2-Chloro-3-{[6-(2-methyltetrazol-5-yl)pyridin-3-yl]amino}phenyl)-2-imino-6-methyl-3-(tetrahydropyran-4-yl)hexahydropyrimidin-4-one | 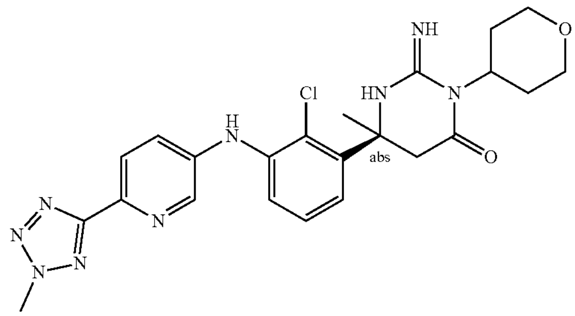 [SMILES: Cn1nnc(-c2ccc(Nc3cccc([C@]4(C)CC(=O)N(C5CCOCC5)C(=N)N4)c3Cl)cn2)n1] | 0.63 | 496 |
| 118 | 1-Bromo-4-chloro-2-(methyl-sulfonyl)-benzene | (6S)-6-{2-Chloro-3-[4-chloro-2-(methylsulfonyl)anilino]phenyl}-2-imino-6-methyl-3-(tetrahydropyran-4-yl)-hexahydropyrimidin-4-one | 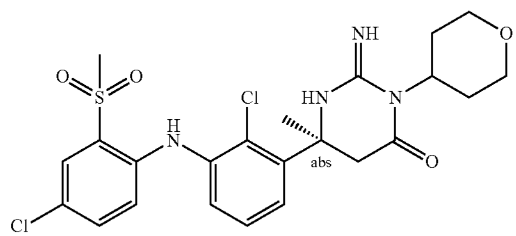 [SMILES: C[C@@]1(c2cccc(Nc3ccc(Cl)cc3S(C)(=O)=O)c2Cl)CC(=O)N(C2CCOCC2)C(=N)N1] | 0.80 | 525 |
| 119 | 3-Bromo-6-(2,2,2-trifluoro-ethyl)-pyridine | (6S)-6-(2-Chloro-3-{[6-(2,2,2-trifluoroethyl)pyridin-3-yl]-amino}phenyl)-2-imino-6-methyl-3-(tetrahydropyran-4-yl)hexahydropyrimidin-4-one | 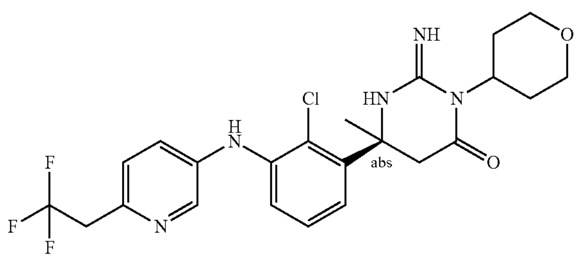 [SMILES: C[C@@]1(c2cccc(Nc3ccc(CC(F)(F)F)nc3)c2Cl)CC(=O)N(C2CCOCC2)C(=N)N1] | 0.76 | 496 |

Examples 120 to 158

The compounds identified in the following Table were prepared from the appropriate aniline and the appropriate aryl halide in accordance with General Method 4.

The solvent employed for Examples 120-158 was 1,4-dioxane.

The base employed for Examples 120-141 and 143-158 was $K_3PO_4$. The base employed for Example 142 was sodium tert-butoxide.

The transition metal catalyst employed for Examples 120-125, 127-132 and 134-158 was BrettPhos Pd G3. The transition metal catalyst employed for Example 126 was BrettPhos Pd G1. The transition metal catalyst employed for Example 133 was $Pd_2(dba)_3$.

The phosphine ligand employed for Examples 120-132, 134-149 and 151-158 was BrettPhos. The phosphine ligand employed for Example 133 was XPhos. The phosphine ligand employed for Example 150 was XantPhos.

| Ex. | Reagents | Product | Structure | LCMS RT (min) | LCMS [MH]+ (method 3) |
|---|---|---|---|---|---|
| 120 | 1-Bromo-2,4-difluoro-benzene & Int. 34 | (6S)-6-[2-Chloro-3-(2,4-difluoroanilino)phenyl]-3-(3-hydroxy-3-methylcyclobutyl)-2-imino-6-methylhexahydro-pyrimidin-4-one | 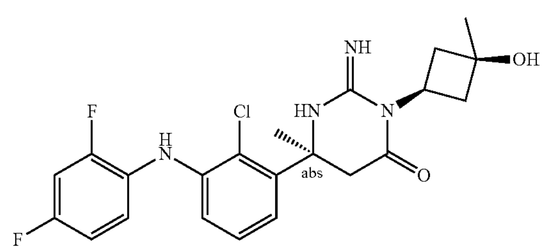 [SMILES: C[C@@]1(c2cccc(Nc3ccc(F)cc3F)c2Cl)CC(=O)N([C@H]2C[C@@](C)(O)C2)C(=N)N1] | 1.24 | 449 |

-continued

| Ex. | Reagents | Product | Structure | LCMS RT (min) | LCMS [MH]+ (method 3) |
|---|---|---|---|---|---|
| 121 | 4-Bromo-2-fluoro-benzonitrile & Int. 34 | 4-{2-Chloro-3-[(4S)-1-(3-hydroxy-3-methylcyclobutyl)-2-imino-4-methyl-6-oxo-hexahydropyrimidin-4-yl]-anilino}-2-fluorobenzonitrile | 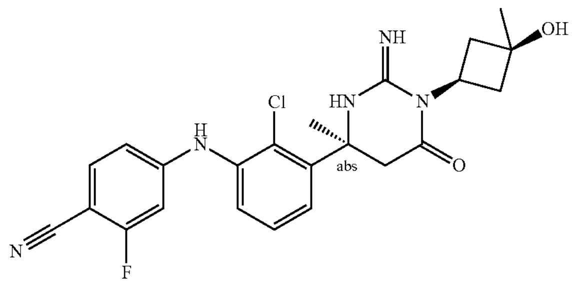 [SMILES: C[C@@]1(c2cccc(Nc3ccc(C#N)c(F)c3)c2Cl)CC(=O)N([C@H]2C[C@@](C)(O)C2)C(=N)N1] | 1.16 | 456 |
| 122 | 5-Bromo-pyridine-2-carbonitrile & Int. 34 | 5-{2-Chloro-3-[(4S)-1-(3-hydroxy-3-methylcyclobutyl)-2-imino-4-methyl-6-oxo-hexahydropyrimidin-4-yl]-anilino}pyridine-2-carbonitrile | 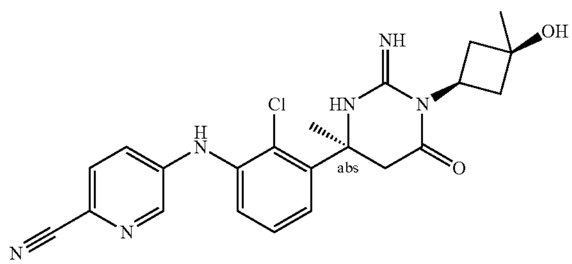 [SMILES: C[C@@]1(c2cccc(Nc3ccc(C#N)nc3)c2Cl)CC(=O)N([C@H]2C[C@@](C)(O)C2)C(=N)N1] | 0.96 | 439 |
| 123 | 4-Bromo-benzonitrile & Int. 34 | 4-{2-Chloro-3-[(4S)-1-(3-hydroxy-3-methylcyclobutyl)-2-imino-4-methyl-6-oxo-hexahydropyrimidin-4-yl]-anilino}benzonitrile | 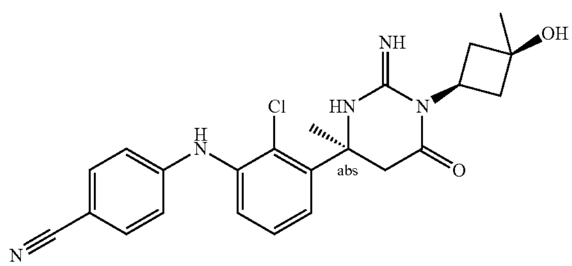 [SMILES: C[C@@]1(c2cccc(Nc3ccc(C#N)cc3)c2Cl)CC(=O)N([C@H]2C[C@@](C)(O)C2)C(=N)N1] | 1.10 | 438 |
| 124 | 5-Bromo-2-(trifluoro-methyl)-pyridine & Int. 34 | (6S)-6-(2-Chloro-3-{[6-(trifluoromethyl)pyridin-3-yl]-amino}phenyl)-3-(3-hydroxy-3-methylcyclobutyl)-2-imino-6-methylhexahydropyrimidin-4-one | 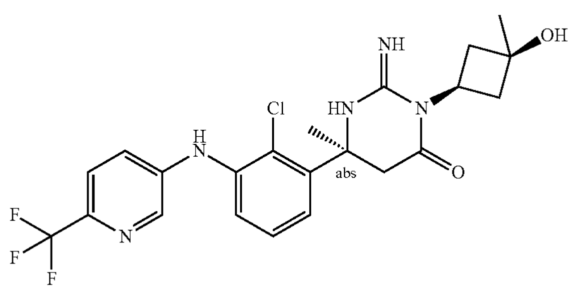 [SMILES: C[C@@]1(c2cccc(Nc3ccc(C(F)(F)F)nc3)c2Cl)CC(=O)N([C@H]2C[C@@](C)(O)C2)C(=N)N1] | 1.19 | 482 |
| 125 | 5-Bromo-2-methyl-pyridine & Int. 34 | (6S)-6-{2-Chloro-3-[(6-methyl-pyridin-3-yl)amino]phenyl}-3-(3-hydroxy-3-methylcyclo-butyl)-2-imino-6-methyl-hexahydropyrimidin-4-one | 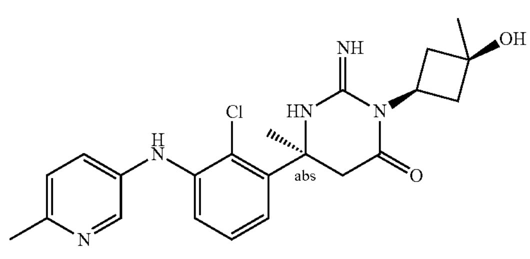 [SMILES: Cc1ccc(Nc2cccc([C@]3(C)CC(=O)N([C@H]4C[C@@](C)(O)C4)C(=N)N3)c2Cl)cn1] | 0.98 | 428 |

-continued

| Ex. | Reagents | Product | Structure | LCMS RT (min) | LCMS [MH]+ (method 3) |
|---|---|---|---|---|---|
| 126 | 2-Bromo-5-fluoro-pyridine & Int. 34 | (6S)-6-{2-Chloro-3-[(5-fluoro-pyridin-2-yl)amino]phenyl}-3-(3-hydroxy-3-methylcyclo-butyl)-2-imino-6-methyl-hexahydropyrimidin-4-one | 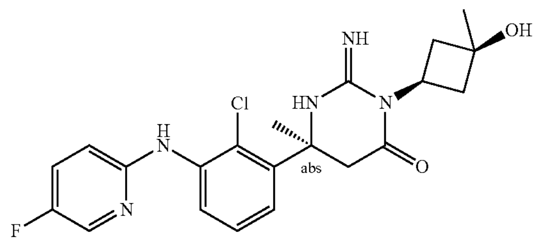 [SMILES: C[C@@]1(c2cccc(Nc3ccc(F)cn3)c2Cl)CC(=O)N([C@H]2C[C@@](C)(O)C2)C(=N)N1] | 1.04 | 432 |
| 127 | 2-Bromo-5-fluoro-benzonitrile & Int. 34 | 2-{2-Chloro-3-[(4S)-1-(3-hydroxy-3-methylcyclobutyl)-2-imino-4-methyl-6-oxo-hexahydropyrimidin-4-yl]-anilino}-5-fluorobenzonitrile | 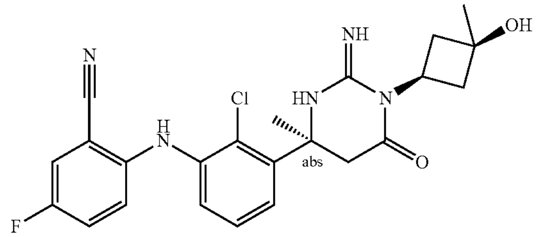 [SMILES: C[C@@]1(c2cccc(Nc3ccc(F)cc3C#N)c2Cl)CC(=O)N([C@H]2C[C@@](C)(O)C2)C(=N)N1] | 0.71* | 459 |
| 128 | 5-Bromo-2-(difluoro-methoxy)-pyridine & Int. 34 | (6S)-6-(2-Chloro-3-{[6-(difluoromethoxy)pyridin-3-yl]-amino}phenyl)-3-(3-hydroxy-3-methylcyclobutyl)-2-imino-6-methylhexahydropyrimidin-4-one | 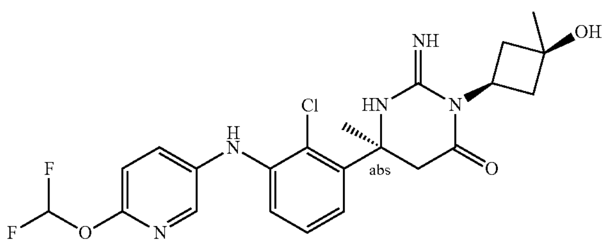 [SMILES: C[C@@]1(c2cccc(Nc3ccc(OC(F)F)nc3)c2Cl)CC(=O)N([C@H]2C[C@@](C)(O)C2)C(=N)N1] | 0.70* | 480 |
| 129 | 2-Bromo-5-methyl-pyrazine & Int. 34 | (6S)-6-{2-Chloro-3-[(5-methyl-pyrazin-2-yl)amino]phenyl}-3-(3-hydroxy-3-methylcyclo-butyl)-2-imino-6-methyl-hexahydropyrimidin-4-one | 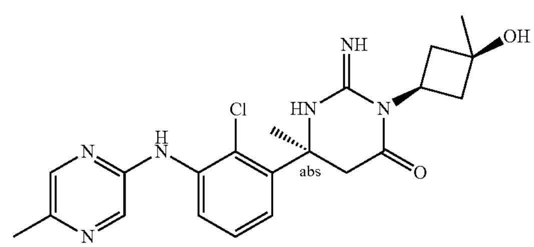 [SMILES: Cc1cnc(Nc2cccc([C@]3(C)CC(=O)N([C@H]4C[C@@](C)(O)C4)C(=N)N3)c2Cl)cn1] | 0.52* | 429 |
| 130 | 5-Bromo-2-(trifluoro-methoxy)-pyridine & Int. 34 | (6S)-6-(2-Chloro-3-{[6-(trifluoromethoxy)pyridin-3-yl]-amino}phenyl)-3-(3-hydroxy-3-methylcyclobutyl)-2-imino-6-methylhexahydropyrimidin-4-one | 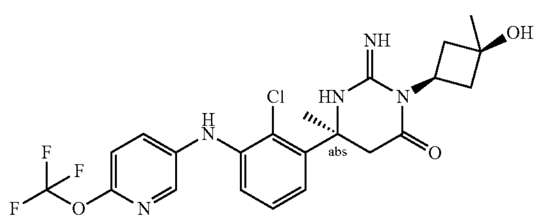 [SMILES: C[C@@]1(c2cccc(Nc3ccc(OC(F)(F)F)nc3)c2Cl)CC(=O)N([C@H]2C[C@@](C)(O)C2)C(=N)N1] | 0.74* | 498 |
| 131 | 4-Bromo-2-(trifluoro-methyl)-pyridine & Int. 34 | (6S)-6-(2-Chloro-3-{[2-(trifluoromethyl)pyridin-4-yl]amino}phenyl)-3-(3-hydroxy-3-methylcyclobutyl)-2-imino-6-methylhexahydropyrimidin-4-one | 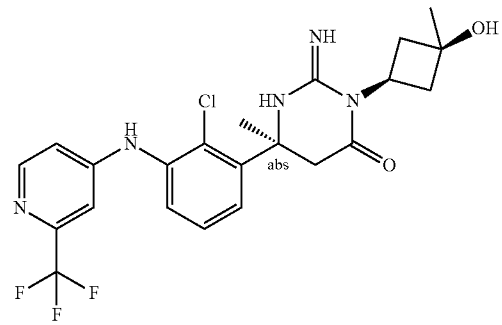 [SMILES: C[C@@]1(c2cccc(Nc3ccnc(C(F)(F)F)c3)c2Cl)CC(=O)N([C@H]2C[C@@](C)(O)C2)C(=N)N1] | 0.58* | 482 |

| Ex. | Reagents | Product | Structure | LCMS RT (min) | LCMS [MH]+ (method 3) |
|---|---|---|---|---|---|
| 132 | 5-Bromo-pyrazolo-[1,5-a]-pyridine & Int. 34 | (6S)-6-[2-Chloro-3-(pyrazolo-[1,5-a]pyridin-5-ylamino)-phenyl]-3-(3-hydroxy-3-methyl-cyclobutyl)-2-imino-6-methyl-hexahydropyrimidin-4-one | 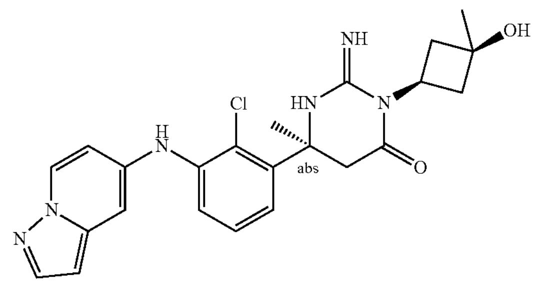 [SMILES: C[C@@]1(c2cccc(Nc3ccn4nccc4c3)c2Cl)CC(=O)N([C@H]2C[C@@](C)(O)C2)C(=N)N1] | 0.60* | 453 |
| 133 | Int. 56 & Int. 34 | 4-{2-Chloro-3-[(4S)-1-(3-hydroxy-3-methylcyclobutyl)-2-imino-4-methyl-6-oxo-hexahydropyrimidin-4-yl]-anilino}-3-(difluoromethoxy)-benzonitrile | 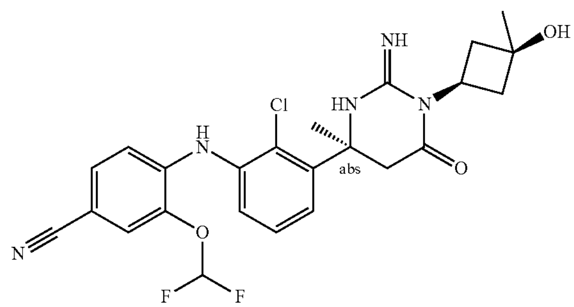 [SMILES: C[C@@]1(c2cccc(Nc3ccc(C#N)cc3OC(F)F)c2Cl)CC(=O)N([C@H]2C[C@@](C)(O)C2)C(=N)N1] | 0.75* | 504 |
| 134 | 5-Bromo-2-methyl-pyridine & Int. 89 | (6S)-6-{2-Chloro-3-[(6-methyl-pyridin-3-yl)amino]phenyl}-3-(3-hydroxy-3-isopropylcyclo-butyl)-2-imino-6-methyl-hexahydropyrimidin-4-one | 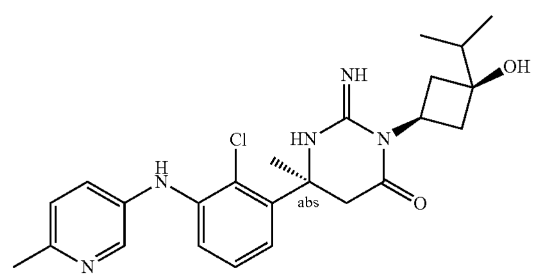 [SMILES: Cc1ccc(Nc2cccc([C@]3(C)CC(=O)N([C@H]4C[C@](O)(C(C)C)C4)C(=N)N3)c2Cl)cn1] | 1.11 | 456 |
| 135 | 5-Bromo-2-methyl-pyridine & Int. 83 | (6S)-6-{2-Chloro-3-[(6-methyl-pyridin-3-yl)amino]phenyl}-2-imino-6-methyl-3-[(cis)-2-methyltetrahydropyran-4-yl]-hexahydropyrimidin-4-one | ISOMER 1 | 1.09 | 442 |
| 136 | 5-Bromo-2-methyl-pyridine & Int. 82 | (6S)-6-{2-Chloro-3-[(6-methyl-pyridin-3-yl)amino]phenyl}-2-imino-6-methyl-3-[(cis)-2-methyltetrahydropyran-4-yl]-hexahydropyrimidin-4-one | ISOMER 1 | 1.08 | 442 |

-continued

| Ex. | Reagents | Product | Structure | LCMS RT (min) | LCMS [MH]+ (method 3) |
|---|---|---|---|---|---|
| 137 | 6-Bromo-4-fluoro-pyrazolo-[1,5-a]-pyridine & Int. 83 | (6S)-6-{2-Chloro-3-[(4-fluoro-pyrazolo[1,5-a]pyridin-6-yl)-amino]phenyl}-2-imino-6-methyl-3-[(cis)-2-methyl-tetrahydropyran-4-yl]-hexahydropyrimidin-4-one | 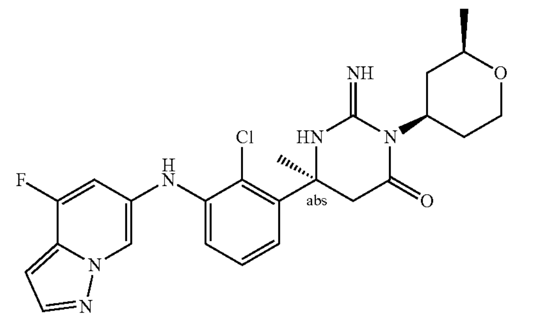 [SMILES: C[C@@H]1C[C@H](N2C(=N)N[C@](C)(c3cccc(Nc4cc(F)c5ccnn5c4)c3Cl)CC2=O)CCO1] | 0.79* | 485 |
| 138 | 5-Bromo-2-(difluoro-methoxy)-pyridine & Int. 83 | (6S)-6-(2-Chloro-3-{[6-(difluoromethoxy)pyridin-3-yl]-amino}phenyl)-2-imino-6-methyl-3-[(cis)-2-methyl-tetrahydropyran-4-yl]-hexahydropyrimidin-4-one | 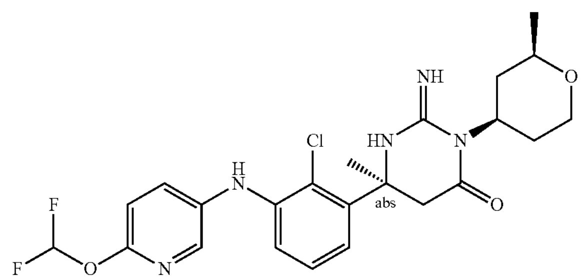 [SMILES: C[C@@H]1C[C@H](N2C(=N)N[C@](C)(c3cccc(Nc4ccc(OC(F)F)nc4)c3Cl)CC2=O)CCO1] | 0.84* | 494 |
| 139 | 5-Bromo-2-methyl-pyridine & Int. 92 | (6S)-6-{2-Chloro-3-[(6-methyl-pyridin-3-yl)amino]phenyl}-3-(4,4-difluorocyclohexyl)-2-imino-6-methylhexahydro-pyrimidin-4-one | 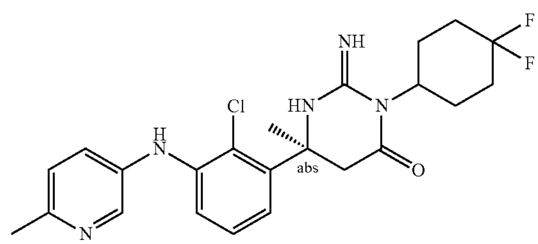 [SMILES: Cc1ccc(Nc2cccc([C@]3(C)CC(=O)N(C4CCC(F)(F)CC4)C(=N)N3)c2Cl)cn1] | 0.56* | 462 |
| 140 | 5-Bromo-2-(difluoro-methoxy)-pyridine & Int. 92 | (6S)-6-(2-Chloro-3-{[6-(difluoromethoxy)pyridin-3-yl]-amino}phenyl)-3-(4,4-difluoro-cyclohexyl)-2-imino-6-methyl-hexahydropyrimidin-4-one | 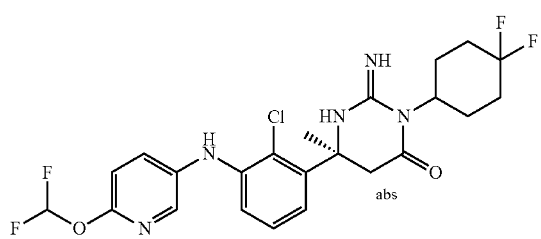 [SMILES: C[C@@]1(c2cccc(Nc3ccc(OC(F)F)nc3)c2Cl)CC(=O)N(C2CCC(F)(F)CC2)C(=N)N1] | 0.94* | 514 |
| 141 | 2-tert-Butyl-5-bromo-pyrimidine & Int. 92 | (6S)-6-{3-[(2-tert-Butyl-pyrimidin-5-yl)amino]-2-chloro-phenyl]-3-(4,4-difluoro-cyclohexyl)-2-imino-6-methyl-hexahydropyrimidin-4-one | 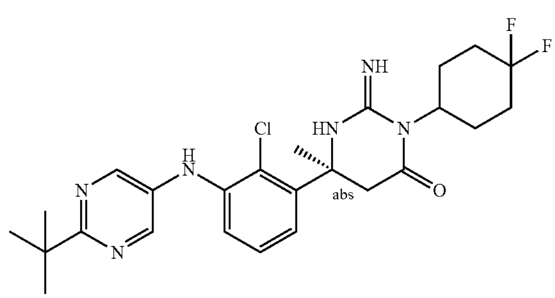 [SMILES: CC(C)(C)c1ncc(Nc2cccc([C@]3(C)CC(=O)N(C4CCC(F)(F)CC4)C(=N)N3)c2Cl)cn1] | 0.96* | 505 |

-continued

| Ex. | Reagents | Product | Structure | LCMS RT (min) | LCMS [MH]+ (method 3) |
|---|---|---|---|---|---|
| 142 | 5-Bromo-2-cyclopropyl-pyridine & Int. 92 | (6S)-6-{2-Chloro-3-[(6-cyclopropylpyridin-3-yl)amino]phenyl}-3-(4,4-difluorocyclohexyl)-2-imino-6-methylhexahydropyrimidin-4-one | 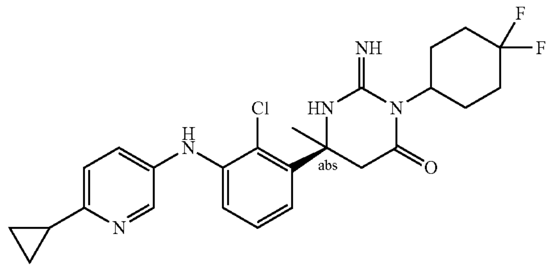 [SMILES: C[C@@]1(c2cccc(Nc3ccc(C4CC4)nc3)c2Cl)CC(=O)N(C2CCC(F)(F)CC2)C(=N)N1] | 0.75* | 488 |
| 143 | 5-Bromo-2-(difluoromethoxy)-pyridine & Int. 96 | (6S)-6-(2-Chloro-3-{[6-(difluoromethoxy)pyridin-3-yl]amino}phenyl)-3-[(4R*)-2,2-dimethyltetrahydropyran-4-yl]-2-imino-6-methylhexahydropyrimidin-4-one | ISOMER 2 | 0.85* | 508 |
| 144 | 5-Bromo-2-(difluoromethoxy)-pyridine & Int. 97 | (6S)-6-(2-Chloro-3-{[6-(difluoromethoxy)pyridin-3-yl]amino}phenyl)-3-[(4S*)-2,2-dimethyltetrahydropyran-4-yl]-2-imino-6-methylhexahydropyrimidin-4-one | ISOMER 2 | 0.90* | 508 |
| 145 | 5-Bromo-2-methyl-pyridine & Int. 96 | (6S)-6-{2-Chloro-3-[(6-methylpyridin-3-yl)amino]phenyl}-3-[(4R*)-2,2-dimethyltetrahydropyran-4-yl]-2-imino-6-methylhexahydropyrimidin-4-one | ISOMER 2 | 0.47* | 456 |
| 146 | 5-Bromo-2-methyl-pyridine & Int. 97 | (6S)-6-{2-Chloro-3-[(6-methylpyridin-3-yl)amino]phenyl}-3-[(4S*)-2,2-dimethyltetrahydropyran-4-yl]-2-imino-6-methylhexahydropyrimidin-4-one | ISOMER 2 | 0.47* | 456 |

| Ex. | Reagents | Product | Structure | LCMS RT (min) | LCMS [MH]+ (method 3) |
|---|---|---|---|---|---|
| 147 | 5-Bromo-2-cyclopropyl-pyridine & Int. 97 | (6S)-6-{2-Chloro-3-[(6-cyclopropylpyridin-3-yl)amino]-phenyl}-3-[(4S*)-2,2-dimethyl-tetrahydropyran-4-yl]-2-imino-6-methylhexahydropyrimidin-4-one ISOMER 1 | 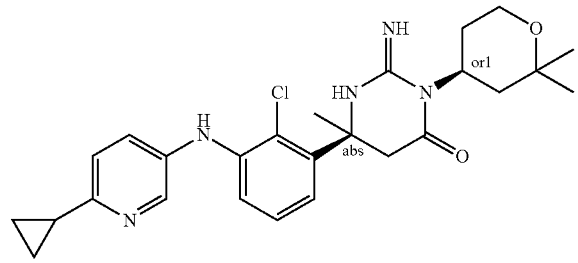 | 0.65* | 482 |
| 148 | 5-Bromo-2-tert-butyl-pyridine & Int. 97 | (6S)-6-{3-[(6-tert-Butylpyridin-3-yl)amino]-2-chlorophenyl}-3-[(4S*)-2,2-dimethyltetrahydro-pyran-4-yl]-2-imino-6-methyl-hexahydropyrimidin-4-one ISOMER 1 | 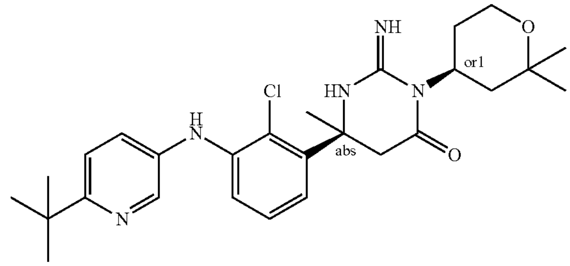 | 0.76* | 498 |
| 149 | 2-Bromo-5-tert-butyl-pyrazine & Int. 97 | (6S)-6-{3-[(5-tert-Butylpyrazin-2-yl)amino]-2-chlorophenyl}-3-[(4S*)-2,2-dimethyltetrahydro-pyran-4-yl]-2-imino-6-methyl-hexahydropyrimidin-4-one ISOMER 1 | 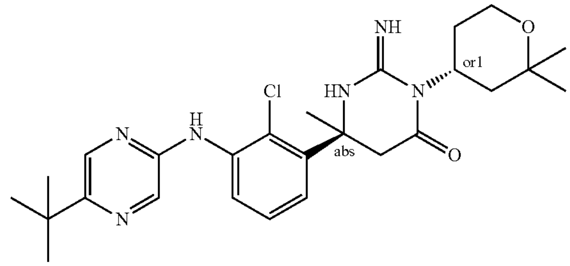 | 0.97* | 499 |
| 150 | 3-Bromo-6-cyclopropyl-pyridazine & Int. 97 | (6S)-6-{2-Chloro-3-[(6-cyclopropylpyridazin-3-yl)amino]-phenyl}-3-[(4S*)-2,2-dimethyl-tetrahydropyran-4-yl]-2-imino-6-methylhexahydropyrimidin-4-one ISOMER 1 | 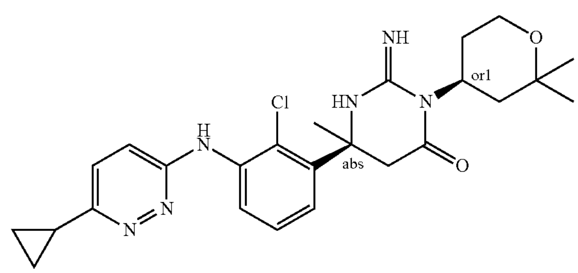 | 0.63* | 483 |
| 151 | 2-Bromo-5-cyclopropyl-pyrazine & Int. 97 | (6S)-6-{2-Chloro-3-[(5-cyclopropylpyrazin-2-yl)amino]-phenyl}-3-[(4S*)-2,2-dimethyl-tetrahydropyran-4-yl]-2-imino-6-methylhexahydropyrimidin-4-one ISOMER 2 | 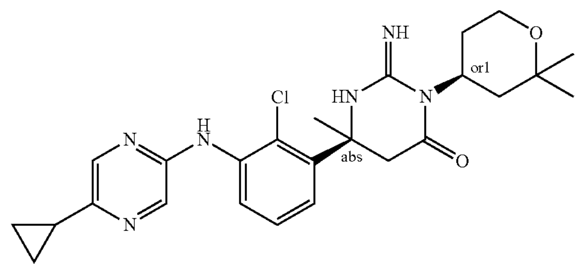 | 0.85* | 483 |

| Ex. | Reagents | Product | Structure | LCMS RT (min) | LCMS [MH]+ (method 3) |
|---|---|---|---|---|---|
| 152 | 5-Bromo-2-methyl-pyridine & Int. 107 | (6S)-6-{2-Chloro-3-[(6-methyl-pyridin-3-yl)amino]phenyl}-3-[3-hydroxy-3-(trifluoromethyl)-cyclobutyl]-2-imino-6-methyl-hexahydropyrimidin-4-one (cis isomer) | 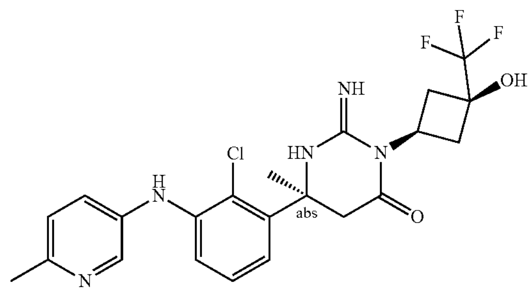 [SMILES: Cc1ccc(Nc2cccc([C@]3(C)CC(=O)N([C@H]4C[C@](O)(C(F)(F)F)C4)C(=N)N3)c2Cl)cn1] | 0.37* | 482 |
| 153 | 5-Bromo-2-methyl-pyridine & Int. 108 | (6S)-6-{2-Chloro-3-[(6-methyl-pyridin-3-yl)amino]phenyl}-3-[3-hydroxy-3-(trifluoromethyl)-cyclobutyl]-2-imino-6-methyl-hexahydropyrimidin-4-one (trans isomer) | 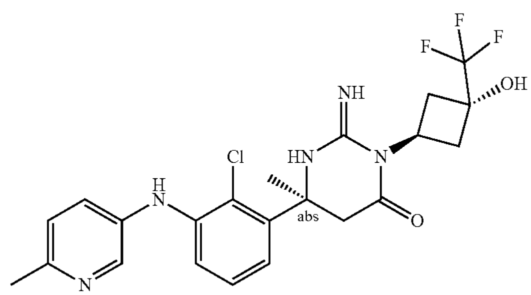 [SMILES: Cc1ccc(Nc2cccc([C@]3(C)CC(=O)N([C@H]4C[C@@](O)(C(F)(F)F)C4)C(=N)N3)c2Cl)cn1] | 0.47* | 482 |
| 154 | 5-Bromo-2-cyclo-propyl-pyridine & Int. 107 | (6S)-6-{2-Chloro-3-[(6-cyclo-propylpyridin-3-yl)amino]-phenyl}-3-[3-hydroxy-3-(trifluoromethyl)cyclobutyl]-2-imino-6-methylhexahydro-pyrimidin-4-one (cis isomer) | 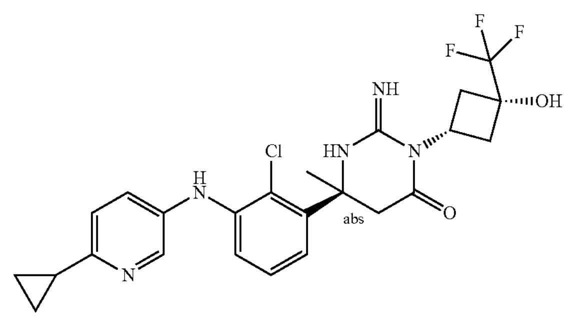 [SMILES: C[C@@]1(c2cccc(Nc3ccc(C4CC4)nc3)c2Cl)CC(=O)N([C@H]2C[C@](O)(C(F)(F)F)C2)C(=N)N1] | 0.57* | 508 |
| 155 | 1-Bromo-4-chloro-benzene & Int. 83 | (6S)-6-[2-Chloro-3-(4-chloro-anilino)phenyl]-2-imino-6-methyl-3-[(2R*,4R*)-2-methyl-tetrahydropyran-4-yl]-hexahydropyrimidin-4-one | 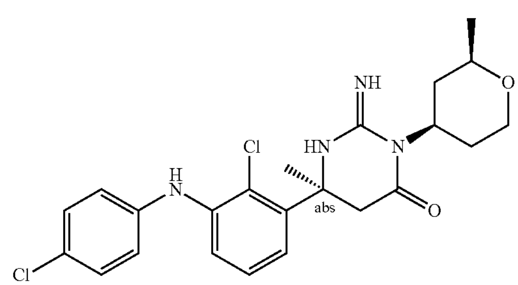 [SMILES: C[C@@H]1C[C@H](N2C(=N)N[C@](C)(c3cccc(Nc4ccc(Cl)cc4)c3Cl)CC2=O)CCO1] | 0.96* | 461 |
| 156 | 5-Bromo-2-(difluoro-methoxy)-pyridine & Int. 121 | (6S)-6-(2-Chloro-3-{[6-(difluoromethoxy)pyridin-3-yl]-amino}phenyl)-2-imino-6-methyl-3-[(1SR,5RS)-8-oxa-bicyclo[3.2.1]octan-3-yl]-hexahydropyrimidin-4-one | 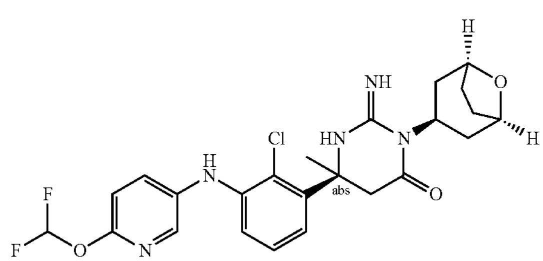 [SMILES: C[C@@]1(c2cccc(Nc3ccc(OC(F)F)nc3)c2Cl)CC(=O)N([C@@H]2C[C@H]3CC[C@@H](C2)O3)C(=N)N1] | 0.80* | 506 |

-continued

| Ex. | Reagents | Product | Structure | LCMS RT (min) | LCMS [MH]+ (method 3) |
|---|---|---|---|---|---|
| 157 | 5-Bromo-2-methyl-pyridine & Int. 121 | (6S)-6-{2-Chloro-3-[(6-methyl-pyridin-3-yl)amino]phenyl}-2-imino-6-methyl-3-[(1SR,5RS)-8-oxabicyclo[3.2.1]octan-3-yl]-hexahydropyrimidin-4-one | 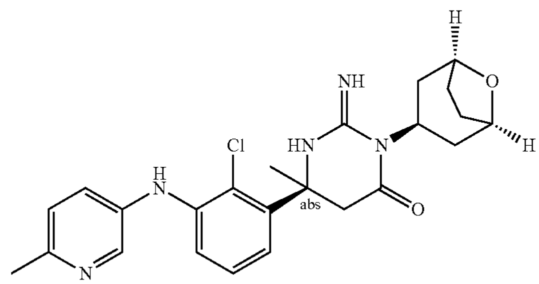 [SMILES: Cc1ccc(Nc2cccc([C@]3(C)CC(=O)N([C@@H]4C[C@H]5CC[C@@H](C4)O5)C(=N)N3)c2Cl)cn1] | 0.42* | 454 |
| 158 | 5-Bromo-2-cyclo-propyl-pyridine & Int. 96 | (6S)-6-{2-Chloro-3-[(6-cyclo-propylpyridin-3-yl)amino]-phenyl}-3-[(4S*)-2,2-dimethyl-tetrahydropyran-4-yl]-2-imino-6-methylhexahydropyrimidin-4-one ISOMER 2 | 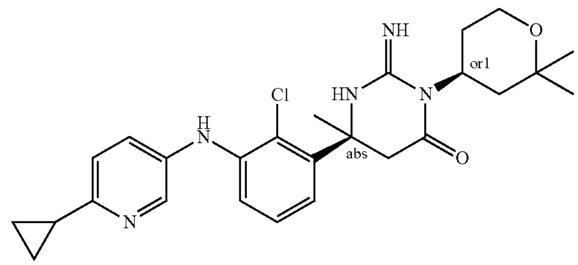 | 0.66* | 482 |

*Method 4

Examples 159 to 168

The compounds identified in the following Table were prepared from Intermediate 28 and the appropriate aryl boronic in accordance with General Method 1, followed by General Method 2. As necessary, final products were further purified by preparative reverse phase HPLC (pH 3).

| Ex. | Aryl boronic acid | Product | Structure | LCMS RT (min) | LCMS [MH]+ (method 3) |
|---|---|---|---|---|---|
| 159 | 4-Methoxy-phenyl-boronic acid | (6S)-6-[2-Chloro-3-(4-methoxy-anilino)phenyl]-2-imino-6-methyl-3-(tetrahydropyran-4-yl)hexahydropyrimidin-4-one | 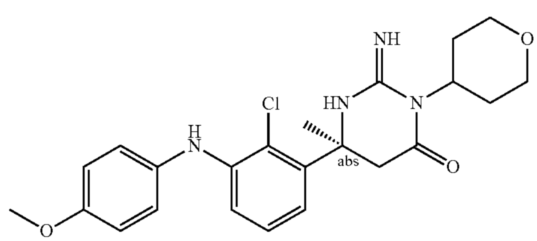 [SMILES: COc1ccc(Nc2cccc([C@]3(C)CC(=O)N(C4CCOCC4)C(=N)N3)c2Cl)cc1] | 1.32 | 443 |
| 160 | 4-Methyl-phenyl-boronic acid | (6S)-6-[2-Chloro-3-(4-methyl-anilino)phenyl]-2-imino-6-methyl-3-(tetrahydropyran-4-yl)hexahydropyrimidin-4-one | 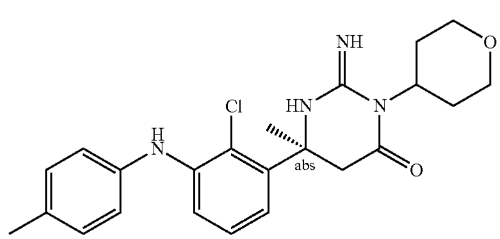 [SMILES: Cc1ccc(Nc2cccc([C@]3(C)CC(=O)N(C4CCOCC4)C(=N)N3)c2Cl)cc1] | 1.46 | 427 |

| Ex. | Aryl boronic acid | Product | Structure | LCMS RT (min) | LCMS [MH]+ (method 3) |
|---|---|---|---|---|---|
| 161 | 3,5-Dimethoxyphenylboronic acid | (6S)-6-[2-Chloro-3-(3,5-dimethoxyanilino)phenyl]-2-imino-6-methyl-3-(tetrahydropyran-4-yl)hexahydropyrimidin-4-one | 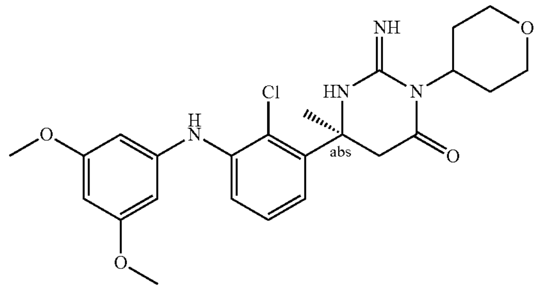 [SMILES: COc1cc(Nc2cccc([C@]3(C)CC(=O)N(C4CCOCC4)C(=N)N3)c2Cl)cc(OC)c1] | 1.32 | 473 |
| 162 | 4-Chlorophenylboronic acid | (6S)-6-[2-Chloro-3-(4-chloroanilino)phenyl]-2-imino-6-methyl-3-(tetrahydropyran-4-yl)hexahydropyrimidin-4-one | 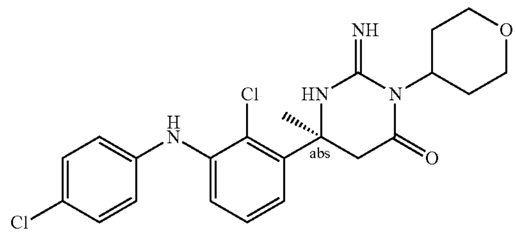 [SMILES: C[C@@]1(c2cccc(Nc3ccc(Cl)cc3)c2Cl)CC(=O)N(C2CCOCC2)C(=N)N1] | 1.47 | 447 |
| 163 | 3-(Trifluoromethyl)phenylboronic acid | (6S)-6-{2-Chloro-3-[3-(trifluoromethyl)anilino]-phenyl}-2-imino-6-methyl-3-(tetrahydropyran-4-yl)-hexahydropyrimidin-4-one | 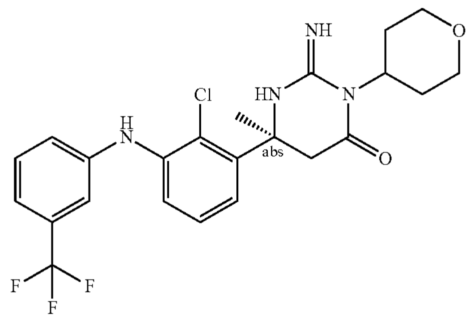 [SMILES: C[C@@]1(c2cccc(Nc3cccc(C(F)(F)F)c3)c2Cl)CC(=O)N(C2CCOCC2)C(=N)N1] | 1.51 | 481 |
| 164 | 3,4-Dimethoxyphenylboronic acid | (6S)-6-[2-Chloro-3-(3,4-dimethoxyanilino)phenyl]-2-imino-6-methyl-3-(tetrahydropyran-4-yl)hexahydropyrimidin-4-one | 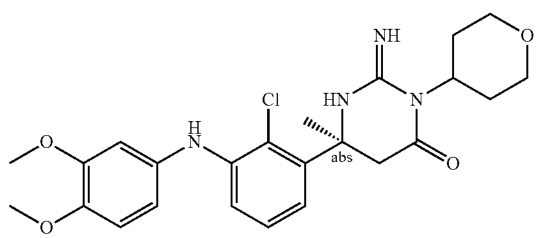 [SMILES: COc1ccc(Nc2cccc([C@]3(C)CC(=O)N(C4CCOCC4)C(=N)N3)c2Cl)cc1OC] | 1.22 | 473 |
| 165 | 2-Methylphenylboronic acid | (6S)-6-[2-Chloro-3-(2-methylanilino)phenyl]-2-imino-6-methyl-3-(tetrahydropyran-4-yl)hexahydropyrimidin-4-one | 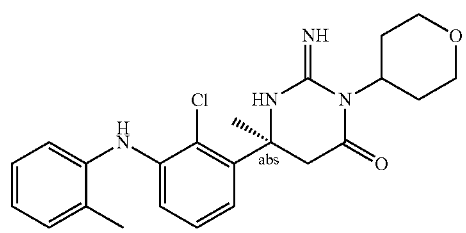 [SMILES: Cc1ccccc1Nc1cccc([C@]2(C)CC(=O)N(C3CCOCC3)C(=N)N2)c1Cl] | 1.45 | 427 |
| 166 | Methoxycarbonyl)phenylboronic acid | Methyl 3-{2-chloro-3-[(4S)-2-imino-4-methyl-6-oxo-1-(tetrahydropyran-4-yl)-hexahydropyrimidin-4-yl]-anilino}benzoate | 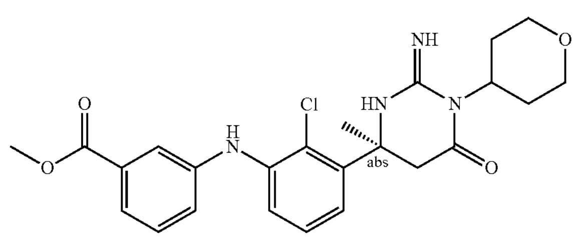 [SMILES: COC(=O)c1cccc(Nc2cccc([C@]3(C)CC(=O)N(C4CCOCC4)C(=N)N3)c2Cl)c1] | 1.31 | 471 |

-continued

| Ex. | Aryl boronic acid | Product | Structure | LCMS RT (min) | LCMS [MH]+ (method 3) |
|---|---|---|---|---|---|
| 167 | (3-Chloro-4-fluoro-phenyl)-boronic acid | (6S)-6-[2-Chloro-3-(3-chloro-4-fluoroanilino)phenyl]-2-imino-6-methyl-3-(tetrahydropyran-4-yl)hexahydropyrimidin-4-one | 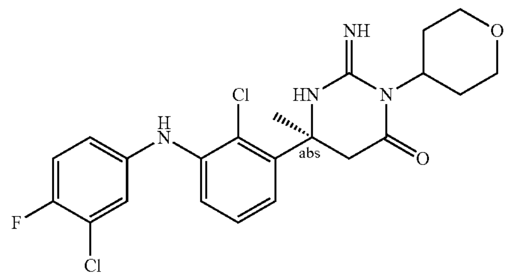 [SMILES: C[C@@]1(c2cccc(Nc3ccc(F)c(Cl)c3)c2Cl)CC(=O)N(C2CCOCC2)C(=N)N1] | 1.47 | 465 |
| 168 | (3-Fluoro-phenyl)-boronic acid | (6S)-6-[2-Chloro-3-(3-fluoro-anilino)phenyl]-2-imino-6-methyl-3-(tetrahydropyran-4-yl)hexahydropyrimidin-4-one | 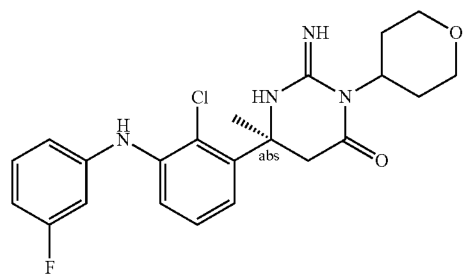 [SMILES: C[C@@]1(c2cccc(Nc3cccc(F)c3)c2Cl)CC(=O)N(C2CCOCC2)C(=N)N1] | 1.35 | 431 |

Examples 169 to 181

The compounds identified in the following Table were prepared from the appropriate aniline and the appropriate aryl boronic acid in accordance with General Method 1, followed by General Method 2. As necessary, final products were further purified by preparative reverse phase HPLC (pH 3).

| Ex. | Reagents | Product | Structure | LCMS RT (min) | LCMS [MH]+ (method 3) |
|---|---|---|---|---|---|
| 169 | 4-Fluoro-phenyl-boronic acid & Int. 33 | (6S)-6-[2-Chloro-3-(4-fluoro-anilino)phenyl]-2-imino-6-methyl-3-[(3R*)-tetrahydro-furan-3-yl]hexahydropyrimidin-4-one | 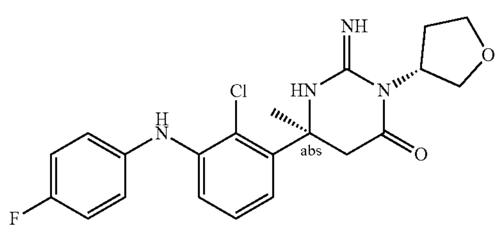 [SMILES: C[C@@]1(c2cccc(Nc3ccc(F)cc3)c2Cl)CC(=O)N([C@@H]2CCOC2)C(=N)N1] | 1.36 | 417 |
| 170 | 4-Fluoro-phenyl-boronic acid & Int. 31 | (6S*)-6-[2-Chloro-3-(4-fluoro-anilino)phenyl]-2-imino-6-methyl-3-(tetrahydropyran-4-ylmethyl)hexahydropyrimidin-4-one | 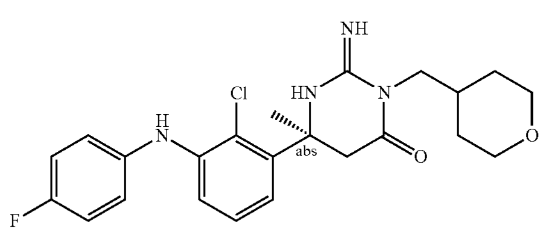 [SMILES: C[C@@]1(c2cccc(Nc3ccc(F)cc3)c2Cl)CC(=O)N(CC2CCOCC2)C(=N)N1] | 1.33 | 445 |

-continued

| Ex. | Reagents | Product | Structure | LCMS RT (min) | LCMS [MH]+ (method 3) |
|---|---|---|---|---|---|
| 171 | 4-Fluoro-phenyl-boronic acid & Int. 62 | (6S)-6-[2-Chloro-3-(4-fluoro-anilino)phenyl]-2-imino-6-methyl-3-(2-oxaspiro[3.3]-heptan-6-yl)hexahydro-pyrimidin-4-one | 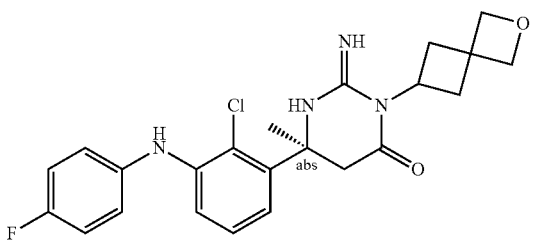 [SMILES: C[C@@]1(c2cccc(Nc3ccc(F)cc3)c2Cl)CC(=O)N(C2CC3(COC3)C2)C(=N)N1] | 1.29 | 443 |
| 172 | 4-Fluoro-phenyl-boronic acid & Int. 34 | (6S)-6-[2-Chloro-3-(4-fluoro-anilino)phenyl]-3-(3-hydroxy-3-methylcyclobutyl)-2-imino-6-methylhexahydropyrimidin-4-one | 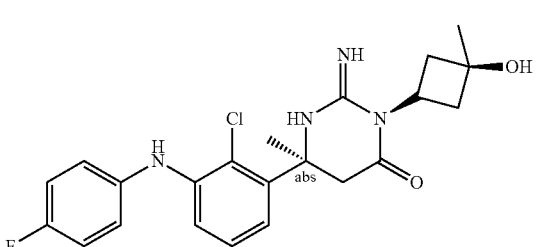 | 1.22 | 431 |
| 173 | 4-(Trifluoro-methyl)-phenyl-boronic acid & Int. 31 | (6S)-6-{2-Chloro-3-[4-(trifluoromethyl)anilino]-phenyl}-2-imino-6-methyl-3-(tetrahydropyran-4-ylmethyl)-hexahydropyrimidin-4-one | 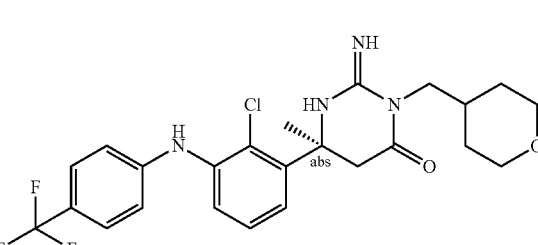 | 1.49 | 495 |
| 174 | 4-(Trifluoro-methyl)-phenyl-boronic acid & Int. 34 | (6S)-6-{2-Chloro-3-[4-(trifluoromethyl)anilino]-phenyl}-3-(3-hydroxy-3-methyl-cyclobutyl)-2-imino-6-methyl-hexahydropyrimidin-4-one | 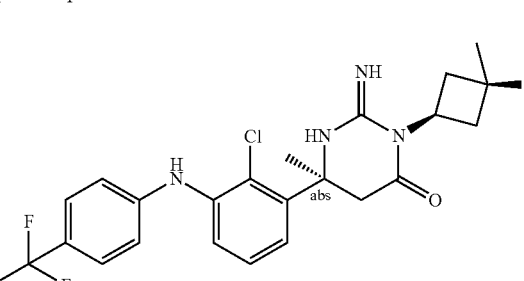 | 1.38 | 481 |
| 175 | 4-Fluoro-phenyl-boronic acid & Int. 69 | (6S)-6-[2-Chloro-3-(4-fluoro-anilino)phenyl]-2-imino-6-methyl-3-[(3-methyloxetan-3-yl)methyl]hexahydropyrimidin-4-one | 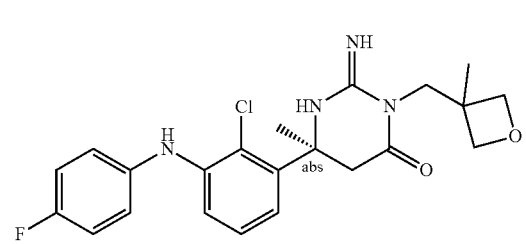 [SMILES: CC1(CN2C(=N)N[C@](C)(c3cccc(Nc4ccc(F)cc4)c3Cl)CC2=O)COC1] | 1.31 | 431 |
| 176 | 4-Chloro-phenyl-boronic acid & Int. 34 | (6S)-6-[2-Chloro-3-(4-chloro-anilino)phenyl]-3-(3-hydroxy-3-methylcyclobutyl)-2-imino-6-methylhexahydropyrimidin-4-one | 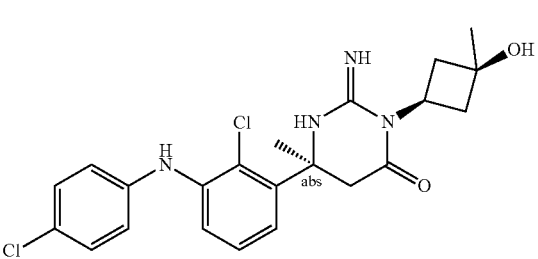 [SMILES: C[C@@]1(c2cccc(Nc3ccc(Cl)cc3)c2Cl)CC(=O)N([C@H]2C[C@@](C)(O)C2)C(=N)N1] | 0.82* | 447 |

| Ex. | Reagents | Product | Structure | LCMS RT (min) | LCMS [MH]+ (method 3) |
|---|---|---|---|---|---|
| 177 | 4-Fluoro-phenyl-boronic acid & Int. 77 | (6S)-6-[2-Chloro-3-(4-fluoro-anilino)phenyl]-3-(3-ethyl-3-hydroxycyclobutyl)-2-imino-6-methylhexahydropyrimidin-4-one (trans isomer) | 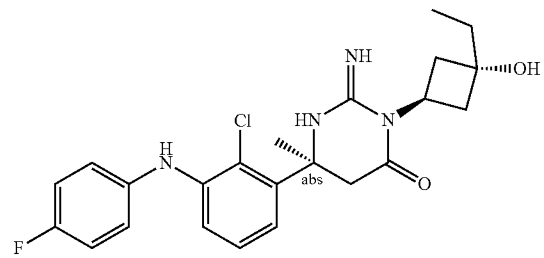 [SMILES: CC[C@]1(O)C[C@H](N2C(=N)N[C@](C)(c3cccc(Nc4ccc(F)cc4)c3Cl)CC2=O)C1] | 1.35 | 445 |
| 178 | 4-Fluoro-phenyl-boronic acid & Int. 78 | (6S)-6-[2-Chloro-3-(4-fluoro-anilino)phenyl]-3-(3-ethyl-3-hydroxycyclobutyl)-2-imino-6-methylhexahydropyrimidin-4-one (cis isomer) | 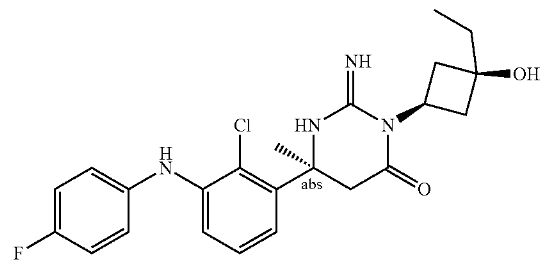 [SMILES: CC[C@]1(O)C[C@@H](N2C(=N)N[C@](C)(c3cccc(Nc4ccc(F)cc4)c3Cl)CC2=O)C1] | 1.36 | 445 |
| 179 | 4-Fluoro-phenyl-boronic acid & Int. 107 | (6S)-6-[2-Chloro-3-(4-fluoro-anilino)phenyl]-3-[3-hydroxy-3-(trifluoromethyl)cyclobutyl]-2-imino-6-methyl-hexahydro-pyrimidin-4-one (cis isomer) | 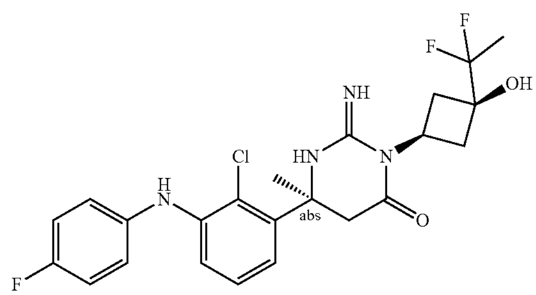 [SMILES: CC(F)(F)[C@]1(O)C[C@@H](N2C(=N)N[C@](C)(c3cccc(Nc4ccc(F)cc4)c3Cl)CC2=O)C1] | 0.85* | 485 |
| 180 | 4-Fluoro-phenyl-boronic acid & Int. 116 | 3-{(4S)-4-[2-Chloro-3-(4-fluoroanilino)phenyl]-2-imino-4-methyl-6-oxohexahydro-pyrimidin-1-yl}-1-methyl-cyclobutanecarbonitrile (trans isomer) | 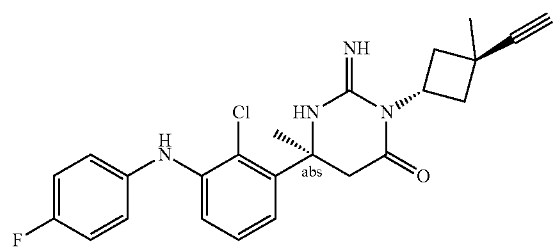 [SMILES: C#C[C@]1(C)C[C@@H](N2C(=N)N[C@](C)(c3cccc(Nc4ccc(F)cc4)c3Cl)CC2=O)C1] | 0.89* | 440 |
| 181 | 4-Fluoro-phenyl-boronic acid & Int. 115 | 3-{(4S)-4-[2-Chloro-3-(4-fluoroanilino)phenyl]-2-imino-4-methyl-6-oxohexahydro-pyrimidin-1-yl}-1-methyl-cyclobutanecarbonitrile (cis isomer) | 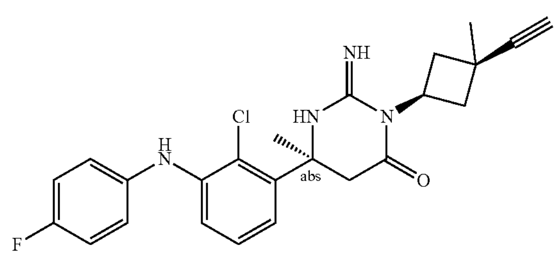 [SMILES: C#C[C@]1(C)C[C@H](N2C(=N)N[C@](C)(c3cccc(Nc4ccc(F)cc4)c3Cl)CC2=O)C1] | 0.88* | 440 |

*Method 4

Examples 182 to 184 (General Method 5)

A solution of Intermediate 28 in THF was cooled to −78° C. and treated with tert-butyllithium (1.6M in hexane, 5 equiv.). The solution was stirred for 1 h, then the appropriate aryl halide (1.5 equiv.) in THF was added. Once the reaction was complete, the mixture was quenched with brine and extracted with EtOAc. The organic layer was washed with water and brine, then dried with sodium sulfate. The solvent was removed. The crude material was purified by preparative HPLC, then deprotected in accordance with General Method 2. As necessary, final products were further purified by preparative reverse phase HPLC (pH 3).

The compounds identified in the following Table were prepared in accordance with General Method 5.

| Ex. | Aryl halide | Product | Structure | LCMS RT (min) | LCMS [MH]+ (method 3) |
|---|---|---|---|---|---|
| 182 | 5-Chloro-2-fluoro-pyridine | (6S)-6-{2-Chloro-3-[(5-chloro-pyridin-2-yl)amino]phenyl}-2-imino-6-methyl-3-(tetrahydro-yran-4-yl)-hexahydropyrimidin-4-one | 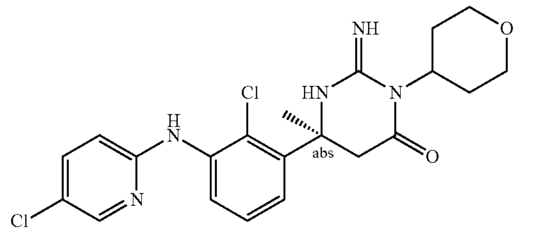 [SMILES: C[C@@]1(c2cccc(Nc3ccc(Cl)cn3)c2Cl)CC(=O)N(C2CCOCC2)C(=N)N1] | 1.32 | 448 |
| 183 | 3-Cyano-6-fluoro-pyridine | 6-{2-Chloro-3-[(4S)-2-imino-4-methyl-6-oxo-1-(tetrahydro-pyran-4-yl)hexahydropyrimidin-4-yl]anilino}pyridine-3-carbo-nitrile | 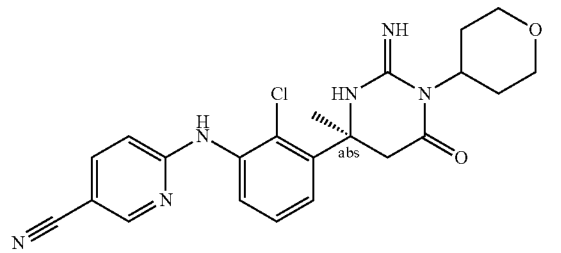 [SMILES: C[C@@]1(c2cccc(Nc3ccc(C#N)cn3)c2Cl)CC(=O)N(C2CCOCC2)C(=N)N1] | 1.07 | 439 |
| 184 | 3-Cyano-2-fluoro-pyridine | 2-{2-Chloro-3-[(4S)-2-imino-4-methyl-6-oxo-1-(tetrahydro-pyran-4-yl)hexahydropyrimidin-4-yl]anilino}pyridine-3-carbo-nitrile | 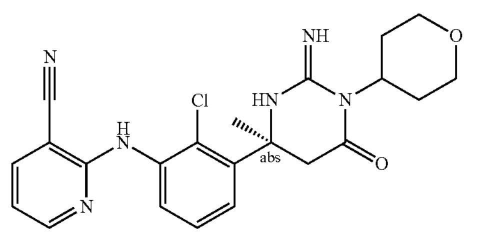 [SMILES: C[C@@]1(c2cccc(Nc3ncccc3C#N)c2Cl)CC(=O)N(C2CCOCC2)C(=N)N1] | 1.10 | 439 |

Examples 185 to 187 (General Method 6)

Intermediate 51 and the appropriate aryl amine were dissolved in 1,4 dioxane and sodium tert-butoxide (3 equiv.) was added. The solution was degassed, and XantPhos (0.10 equiv.) and a transition metal catalyst (0.10 equiv.) were added. The reaction mixture was heated at 90° C. for 3 h or until the reaction was complete, then filtered. The material was isolated using silica gel chromatography or reverse phase HPLC, then deprotected in accordance with General Method 2 to afford the title compounds. As necessary, final products were further purified by preparative reverse phase HPLC (pH 3).

The transition metal catalyst employed for Examples 185 and 187 was $Pd_2(dba)_3$. The transition metal catalyst employed for Example 186 was RuPhos Pd G3.

The compounds identified in the following Table were prepared in accordance with General Method 6.

| Ex. | Aryl amine | Product | Structure | LCMS RT (min) | LCMS [MH]+ (method 4) |
|---|---|---|---|---|---|
| 185 | 3-Amino-imidazo-[1,2-a]-pyridine | (6S)-6-[2-Chloro-3-(imidazo-[1,2-a]pyridin-3-ylamino)-phenyl]-2-imino-6-methyl-3-(tetrahydropyran-4-yl)-hexahydropyrimidin-4-one | 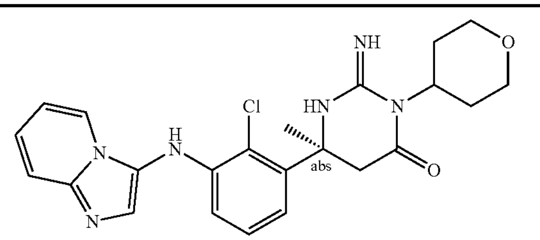 | 0.37 | 453 |

-continued

| Ex. | Aryl amine | Product | Structure | LCMS RT (min) | LCMS [MH]+ (method 4) |
|---|---|---|---|---|---|
| 186 | 3,5-Dimethyl-1-phenyl-pyrazol-4-amine | (6S)-6-{2-Chloro-3-[(3,5-dimethyl-1-phenylpyrazol-4-yl)-amino]phenyl}-2-imino-6-methyl-3-(tetrahydropyran-4-yl)hexahydropyrimidin-4-one | 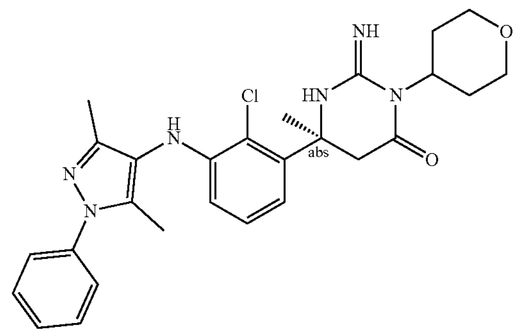 [SMILES: Cc1nn(-c2ccccc2)c(C)c1Nc1cccc([C@]2(C)CC(=O)N(C3CCOCC3)C(=N)N2)c1Cl] | 0.86 | 507 |
| 187 | Imidazo-[1,5-a]-pyridin-3-amine | (6S)-6-[2-Chloro-3-(imidazo-[1,5-a]pyridin-3-ylamino)-phenyl]-2-imino-6-methyl-3-(tetrahydropyran-4-yl)-hexahydropyrimidin-4-one | 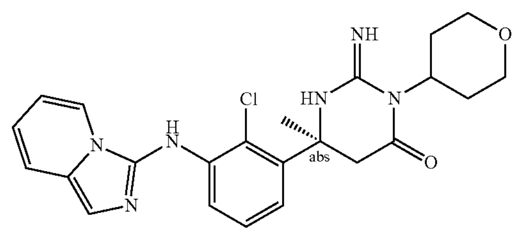 [SMILES: C[C@@]1(c2cccc(Nc3ncc4ccccn34)c2Cl)CC(=O)N(C2CCOCC2)C(=N)N1] | 0.62 | 453 |

Examples 188 to 190

The compounds identified in the following Table were prepared from the relevant precursor in accordance with General Method 2. As necessary, final products were further purified by preparative reverse phase HPLC (pH 3).

| Ex. | Precursor | Product | Structure | LCMS RT (min) | LCMS [MH]+ (method 3) |
|---|---|---|---|---|---|
| 188 | Int. 66 | (6S)-6-[2-Chloro-3-(4-fluoro-anilino)phenyl]-2-imino-6-methyl-3-[(1RS,2SR,4SR)-7-oxabicyclo[2.2.1]heptan-3-yl]-hexahydropyrimidin-4-one | ISOMER 1 | 1.38 | 443 |
| 189 | Int. 59 | (6S)-6-[2-Chloro-3-(4-fluoro-anilino)phenyl]-2-imino-6-methyl-3-[(3S*)-tetrahydro-pyran-3-yl]hexahydropyrimidin-4-one | 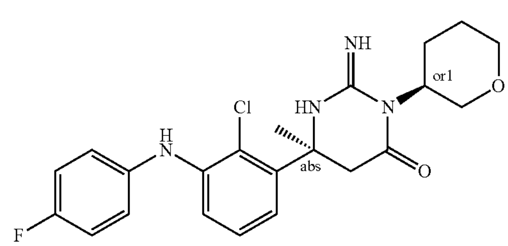 [SMILES: C[C@@]1(c2cccc(Nc3ccc(F)cc3)c2Cl)CC(=O)N([C@H]2CCCOC2)C(=N)N1] | 1.42 | 431 |

-continued

| Ex. | Precursor | Product | Structure | LCMS RT (min) | LCMS [MH]+ (method 3) |
|---|---|---|---|---|---|
| 190 | Int. 60 | (6S)-6-[2-Chloro-3-(4-fluoro-anilino)phenyl]-2-imino-6-methyl-3-[(3R* or 3S)-tetrahydropyran-3-yl]-hexahydropyrimidin-4-one | 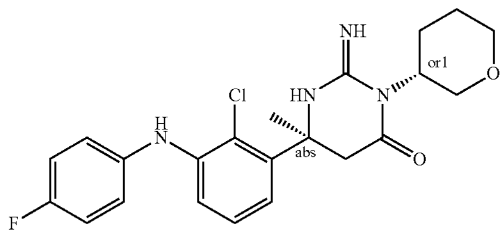 [SMILES: C[C@@]1(c2cccc(Nc3ccc(F)cc3)c2Cl)CC(=O)N([C@@H]2CCCOC2)C(=N)N1] | 1.42 | 431 |

Examples 191 to 196

The compounds identified in the following Table were prepared from the relevant precursor in accordance with General Method 2. Diastereomeric final products were separated by preparative chiral reverse phase HPLC (pH 3).

| Ex. | Precursor | Product | Structure | LCMS RT (min) | LCMS [MH]+ (method 4) |
|---|---|---|---|---|---|
| 191 | Int. 104 | (6S)-6-(2-Chloro-3-{[6-(difluoromethoxy)pyridin-3-yl]-amino}phenyl)-2-imino-6-methyl-3-[(2R*,4S*)-2-methyl-tetrahydropyran-4-yl]-hexahydropyrimidin-4-one (Peak 1) | ISOMER 1 | 0.85 | 494 |
| 192 | Int. 104 | (6S)-6-(2-Chloro-3-{[6-(difluoromethoxy)pyridin-3-yl]-amino}phenyl)-2-imino-6-methyl-3-[(2S*,4R*)-2-methyl-tetrahydropyran-4-yl]-hexahydropyrimidin-4-one (Peak 2) | ISOMER 1 | 0.85 | 494 |
| 193 | Int. 105 | (6S)-6-{2-Chloro-3-[(6-cyclo-propylpyridin-3-yl)amino]-phenyl}-2-imino-6-methyl-3-[(2R*,4S*)-2-methyltetrahydro-pyran-4-yl]hexahydropyrimidin-4-one (Peak 1) | ISOMER 1 | 0.61 | 468 |

| Ex. | Precursor | Product | Structure | LCMS RT (min) | LCMS [MH]+ (method 4) |
|---|---|---|---|---|---|
| 194 | Int. 105 | (6S)-6-{2-Chloro-3-[(6-cyclo-propylpyridin-3-yl)amino]-phenyl}-2-imino-6-methyl-3-[(2S*,4R*)-2-methyltetrahydro-pyran-4-yl]hexahydropyrimidin-4-one (Peak 2) | 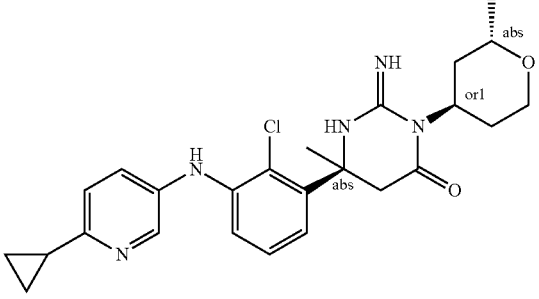<br>ISOMER 1 | 0.61 | 468 |
| 195 | Int. 106 | (6S)-6-(2-Chloro-3-[(6-methyl-pyridin-3-yl)amino]phenyl}-2-imino-6-methyl-3-[(2R*,4S*)-2-methyltetrahydropyran-4-yl]-hexahydropyrimidin-4-one (Peak 1) | 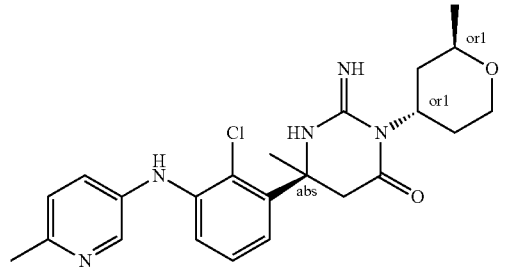<br>ISOMER 1 | 0.42 | 441 |
| 196 | Int. 106 | (6S)-6-{2-Chloro-3-[(6-methyl-pyridin-3-yl)amino]phenyl}-2-imino-6-methyl-3-[(2S*,4R*)-2-methyltetrahydropyran-4-yl]-hexahydropyrimidin-4-one (Peak 2) | 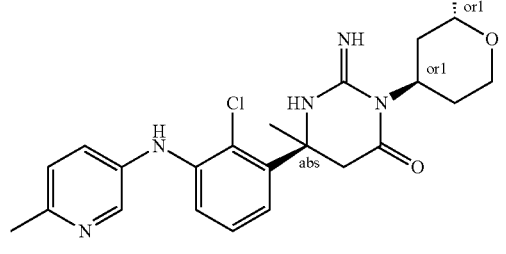<br>ISOMER 1 | 0.41 | 441 |

Examples 197 to 205 (General Method 7)

The appropriate aryl halide and the appropriate aniline were dissolved in 1,4 dioxane, and K₃PO₄ (3 equiv.) was added. The solution was degassed, then a transition metal catalyst (0.05 equiv.) and a phosphine ligand (0.10 equiv.) were added. The reaction mixture was heated at 80° C. for 3 h or until the reaction was complete. The solution was filtered. The material was isolated using silica gel chromatography or reverse phase HPLC, then deprotected in accordance with General Method 2. As necessary, the material was further purified by preparative reverse phase HPLC. The resulting solid was dissolved in DCM, and 4M HCl in 1,4-dioxane (6 equiv.) was added. The mixture was stirred for 30 minutes. The solvent was removed under reduced pressure, and the title compound (HCl salt) was isolated after trituration with diethyl ether or DCM/pentane.

The transition metal catalyst employed for Examples 197 and 200 was Pd₂(dba)₃. The transition metal catalyst employed for Examples 198, 199 and 201-205 was Brett-Phos Pd G3.

The phosphine ligand employed for Examples 197 and 200 was XantPhos. The phosphine ligand employed for Examples 198, 199 and 201-205 was BrettPhos.

The compounds identified in the following Table were prepared in accordance with General Method 7.

| Ex. | Reagents | Product | Structure | LCMS RT (min) | LCMS [MH]+ (method 3) |
|---|---|---|---|---|---|
| 197 | 3-Bromo-6-cyclo-propyl-pyridazine & Int. 28 | (6S)-6-{2-Chloro-3-[(6-cyclo-propylpyridazin-3-yl)amino]-phenyl}-2-imino-6-methyl-3-(tetrahydropyran-4-yl)-hexahydropyrimidin-4-one | 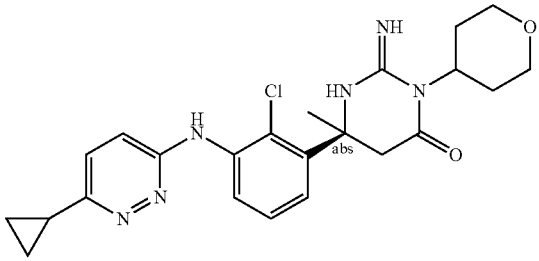 [SMILES: C[C@@]1(c2cccc(Nc3ccc(C4CC4)nn3)c2Cl)CC(=O)N(C2CCOCC2)C(=N)N1] | 0.54 | 455 |
| 198 | 5-Bromo-2-cyclo-propyl-pyridine & Int. 83 | (6S)-6-{2-Chloro-3-[(6-cyclo-propylpyridin-3-yl)amino]-phenyl}-2-imino-6-methyl-3-[(2R*,4R*)-2-methyltetrahydro-pyran-4-yl]hexahydropyrimidin-4-one | 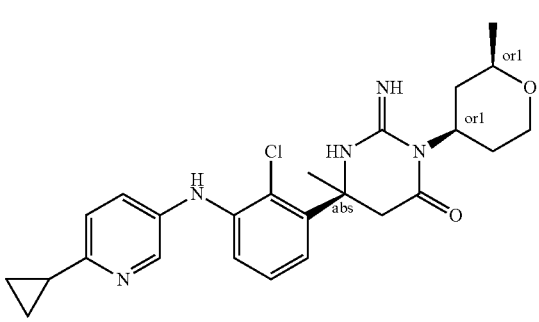  ISOMER 1 | 0.62* | 468 |
| 199 | 5-Bromo-2-cyclo-propyl-pyridine & Int. 82 | (6S)-6-{2-Chloro-3-[(6-cyclo-propylpyridin-3-yl)amino]-phenyl}-2-imino-6-methyl-3-[(2S*,4S*)-2-methyltetrahydro-pyran-4-yl]hexahydropyrimidin-4-one | 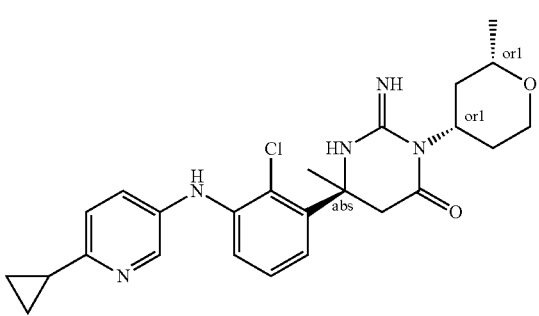  ISOMER 2 | 0.63* | 468 |
| 200 | 3-Bromo-6-cyclo-propyl-pyridazine & Int. 83 | (6S)-6-{2-Chloro-3-[(6-cyclo-propylpyridazin-3-yl)amino]-phenyl}-2-imino-6-methyl-3-[(2R*,4R*)-2-methyltetrahydro-pyran-4-yl]hexahydropyrimidin-4-one | 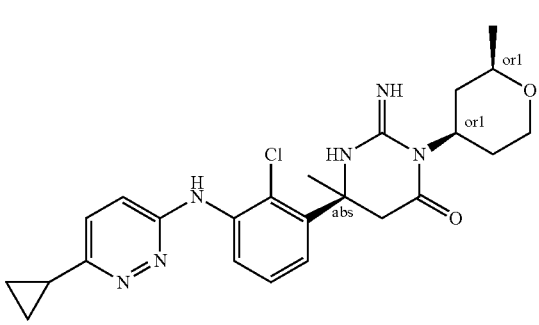  ISOMER 2 | 0.60* | 469 |

-continued

| Ex. | Reagents | Product | Structure | LCMS RT (min) | LCMS [MH]+ (method 3) |
|---|---|---|---|---|---|
| 201 | 5-Bromo-2-(2,2,2-trifluoro-ethoxy)-pyridine & Int. 83 | (6S)-6-(2-Chloro-3-{[6-(2,2,2-trifluoroethoxy)pyridin-3-yl]-amino}phenyl)-2-imino-6-methyl-3-[(2R*,4R*)-2-methyl-tetrahydropyran-4-yl]-hexahydropyrimidin-4-one | ISOMER 1 | 0.96* | 526 |
| 202 | Int. 117 & Int. 83 | (6S)-6-(2-Chloro-3-{[6-(2,2,2-trifluoroethoxy)pyridazin-3-yl]-amino}phenyl)-2-imino-6-methyl-3-[(2R*,4R*)-2-methyl-tetrahydropyran-4-yl]-hexahydropyrimidin-4-one | ISOMER 1 | 0.82* | 527 |
| 203 | Int. 118 & Int. 83 | (6S)-6-(2-Chloro-3-{[6-(2,2-difluoroethoxy)pyridin-3-yl]-amino}phenyl)-2-imino-6-methyl-3-[(2R*,4R*)-2-methyl-tetrahydropyran-4-yl]-hexahydropyrimidin-4-one | ISOMER 1 | 0.87* | 508 |
| 204 | 5-Bromo-2-cyclopropyl-pyrimidine & Int. 83 | (6S)-6-{2-Chloro-3-[(2-cyclopropylpyrimidin-5-yl)amino]-phenyl}-2-imino-6-methyl-3-[(2R*,4R*)-2-methyltetrahydro-pyran-4-yl]hexahydropyrimidin-4-one | ISOMER 1 | 0.74* | 469 |

| Ex. | Reagents | Product | Structure | LCMS RT (min) | LCMS [MH]+ (method 3) |
|---|---|---|---|---|---|
| 205 | 4-Bromo-1-cyclopropyl-pyridin-2-one & Int. 97 | (6S)-6-{2-Chloro-3-[(1-cyclopropyl-2-oxopyridin-4-yl)-amino]phenyl}-3-[(4R*)-2,2-dimethyltetrahydropyran-4-yl]-2-imino-6-methylhexahydro-pyrimidin-4-one | 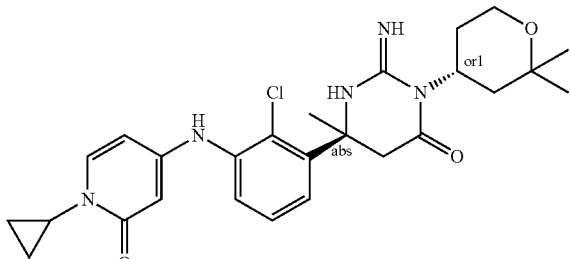 ISOMER 1 | 0.62* | 498 |

*Method 4

Example 206

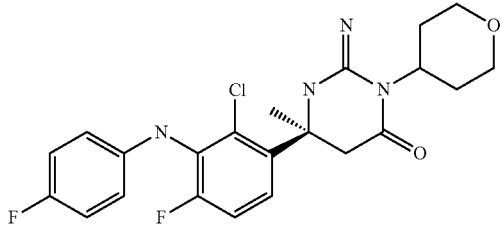

(6S)-6-[2-Chloro-4-fluoro-3-(4-fluoroanilino)phenyl]-2-imino-6-methyl-3-(tetrahydro-pyran-4-yl)hexahydropyrimidin-4-one To a solution of Intermediate 128 (0.02 g, 0.04 mmol) in DCM (10 mL) was added TFA (0.03 mL, 0.35 mmol) at 0° C. The reaction mixture was stirred at room temperature for 1 h, then concentrated in vacuo. The crude residue was purified by washing with diethyl ether:n-pentane (1:9, 30 mL) to afford the title compound (TFA salt) (0.014 g, 70%) as an off-white solid. $\delta_H$ (400 MHz, DMSO-d$_6$) 0.84 (d, J 10.8 Hz, 1H), 1.67 (d, J11.8 Hz, 1H), 1.76 (s, 3H), 2.15-2.19 (m, 1H), 2.32-2.41 (m, 1H), 3.15 (t, J11.0 Hz, 1H), 3.68-3.74 (m, 1H), 3.75-3.81 (m, 1H), 3.82-3.89 (m, 2H), 6.59-6.62 (m, 2H), 6.97-7.02 (m, 2H), 7.18-7.21 (m, 1H), 7.35 (t, J9.3 Hz, 1H), 7.86 (s, 1H), 8.83 (br s, 1H), 10.56 (s, 1H) (2 proton signals submerged in solvent peak). MS (ESI, Method 1) m/e 449.0 [M+H]+, RT 2.46 minutes.

Example 207

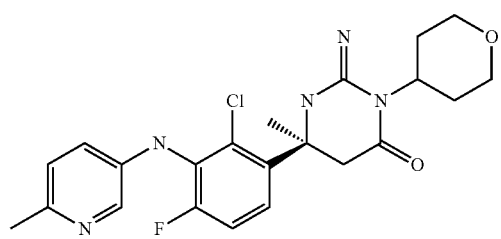

(6S)-6-{2-Chloro-4-fluoro-3-[(6-methylpyridin-3-yl)amino]phenyl}-2-imino-6-methyl-3-(tetrahydropyran-4-yl)hexahydropyrimidin-4-one To a solution of Intermediate 129 (0.08 g, 0.13 mmol) in DCM (10 mL) was added TFA (0.10 mL, 1.34 mmol) at 0° C. The reaction mixture was stirred at room temperature for 1 h, then concentrated in vacuo. The crude residue was purified by washing with diethyl ether:n-pentane (1:9, 30 mL) to afford the title compound (TFA salt) (0.054 g, 72%) as an off-white solid. $\delta_H$ (400 MHz, DMSO-d$_6$) 0.89 (d, J11.2 Hz, 1H), 1.67 (d, J11.2 Hz, 1H), 1.76 (s, 3H), 2.14-2.23 (m, 1H), 2.31-2.42 (m, 1H), 3.15 (t, J 11.2 Hz, 1H), 3.30-3.37 (m, 2H), 3.71 (d, J 16.6 Hz, 1H), 3.75-3.80 (m, 1H), 3.80-3.88 (m, 2H), 7.33 (dd, J 9.0, 5.6 Hz, 1H), 7.40-7.48 (m, 2H), 7.51-7.55 (m, 1H), 7.97 (d, J 1.9 Hz, 1H), 8.73 (br s, 1H), 9.17 (br s, 1H), 11.02 (s, 1H) (3 proton signals submerged in solvent peak). MS (ESI, Method 1) m/e 446.0 [M+H]+, RT 2.01 minutes.

The invention claimed is:
1. A compound of formula (I) or a pharmaceutically acceptable salt thereof:

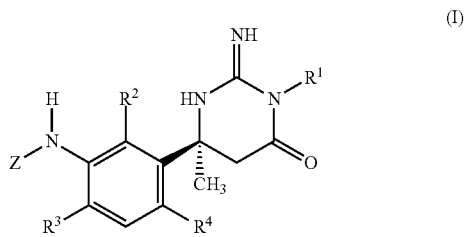

wherein
W represents C(O) or S(O)$_2$;
Z represents aryl or heteroaryl, either of which groups may be optionally substituted by one or more substituents;
R$^1$ represents C$_{2-6}$ alkyl, optionally substituted by hydroxy; or R$^1$ represents C$_{3-7}$ cycloalkyl, C$_{3-7}$ cycloalkyl(C$_{1-6}$)alkyl, aryl(C$_{1-6}$)alkyl, C$_{3-7}$ heterocycloalkyl, C$_{3-7}$ heterocycloalkyl(C$_{1-6}$)alkyl, C$_{4-9}$ heterobicycloalkyl, C$_{4-9}$ spiroheterocycloalkyl or heteroaryl($C_{1-6}$)alkyl, any of which groups may be optionally substituted by one or more substituents; and $R^2$, $R^3$ and $R^4$ independently represent hydrogen, halogen or trifluoromethyl.

2. A compound as claimed in claim 1 wherein Z represents phenyl, naphthyl, 2,3-dihydroindolyl, 2,3-dihydrobenzoxazinyl, pyrazolyl, pyrazolo[1,5-a]pyridinyl, pyrazolo-[3,4-b]pyridinyl, indazolyl, imidazo[1,2-a]pyridinyl, imidazo[1,5-a]pyridinyl, imidazo-[4,5-b]pyridinyl, [1,2,4]triazolo[1,5-a]pyridinyl, pyridinyl, quinolinyl, isoquinolinyl, pyridazinyl, pyrimidinyl or pyrazinyl, any of which groups may be optionally substituted by one, two or three substituents independently selected from halogen, cyano, $C_{1-6}$ alkyl, difluoromethyl, trifluoromethyl, trifluoroethyl, cyclopropyl, cyclobutyl, cyanocyclobutyl, phenyl, azetidinyl, oxopyrrolidinyl, morpholinyl, oxazolyl, methyloxadiazolyl, triazolyl, methyltetrazolyl, oxo, $C_{1-6}$ alkoxy, difluoromethoxy, trifluoromethoxy, difluoroethoxy, trifluoroethoxy, phenoxy, methylenedioxy, difluoromethylenedioxy, $C_{1-6}$ alkylsulfonyl, di($C_{1-6}$)alkylamino, $C_{2-6}$ alkylcarbonyl, $C_{2-6}$ alkoxycarbonyl and di($C_{1-6}$)alkylsulfoximino.

3. A compound as claimed in claim 1 represented by formula (IIA), or a pharmaceutically acceptable salt thereof:

(IIA)

wherein
$R^{15}$ and $R^{16}$ independently represent hydrogen, halogen, cyano, nitro, $C_{1-6}$ alkyl, difluoromethyl, trifluoromethyl, phenyl, oxopyrrolidinyl, oxazolyl, methyloxadiazolyl, hydroxy, hydroxy($C_{1-6}$)alkyl, $C_{1-6}$ alkoxy, difluoromethoxy, trifluoromethoxy, phenoxy, $C_{1-6}$ alkylthio, $C_{1-6}$ alkylsulfinyl, $C_{1-6}$ alkylsulfonyl, amino, $C_{1-6}$ alkylamino, amino, amino($C_{1-6}$)alkyl, di($C_{1-6}$)alkylamino($C_{1-6}$)alkyl, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl, di($C_{1-6}$)alkylaminosulfonyl or di($C_{1-6}$)alkylsulfoximino; and $R^1$, $R^2$ and $R^3$ are as defined in claim 1.

4. A compound as claimed in claim 3 wherein $R^{15}$ represents hydrogen, halogen, cyano, $C_{1-6}$ alkyl, trifluoromethyl, phenyl, oxopyrrolidinyl, oxazolyl, methyloxadiazolyl, $C_{1-6}$ alkoxy, difluoromethoxy, trifluoromethoxy, phenoxy, $C_{1-6}$ alkylsulfonyl, $C_{2-6}$ alkoxycarbonyl or di($C_{1-6}$)alkylsulfoximino.

5. A compound as claimed in claim 3 wherein $R^{16}$ represents hydrogen, halogen, cyano, $C_{1-6}$ alkyl, trifluoromethyl or $C_{1-6}$ alkoxy.

6. A compound as claimed in claim 1 represented by formula (IIB), or a pharmaceutically acceptable salt thereof:

(IIB)

wherein
V represents N or CH;
$R^{25}$ represents methyl, cyclopropyl, difluoromethoxy or difluoroethoxy; and
$R^1$, $R^2$ and $R^3$ are as defined in claim 1.

7. A compound as claimed in claim 1 wherein $R^1$ represents $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, $C_{4-9}$ heterobicycloalkyl or $C_{4-9}$ spiroheterocycloalkyl, any of which groups may be optionally substituted by one, two or three substituents independently selected from halogen, cyano, $C_{1-6}$ alkyl, trifluoromethyl and hydroxy.

8. A compound as claimed in claim 1 represented by formula (IIC), or a pharmaceutically acceptable salt thereof:

(IIC)

wherein
$R^{11}$ represents hydrogen or methyl;
$R^{12}$ represents hydrogen or methyl; and
Z, $R^2$ and $R^3$ are as defined in claim 1.

9. A compound as claimed in claim 1 wherein $R^2$ represents chloro.

10. A compound as claimed in claim 1 which is
(6S)-6-(3-Anilino-2-chloro-phenyl)-3-[(1-hydroxy-cyclopropyl)methyl]-2-imino-6-methylhexahydropyrimidin-4-one;
(6S)-6-(3-Anilino-2-chloro-phenyl)-2-imino-6-methyl-3-(tetrahydropyran-4-yl)-hexahydropyrimidin-4-one;
(6S)-6-(3-Anilino-2-chloro-phenyl)-2-imino-6-methyl-3-(tetrahydropyran-4-ylmethyl)-hexahydropyrimidin-4-one;
(6S)-6-(3-Anilino-2-chloro-phenyl)-3-cyclohexyl-2-imino-6-methylhexahydropyrimidin-4-one;
(6S)-6-(3-Anilino-2-chloro-phenyl)-2-imino-6-methyl-3-[(3S or 3R*)-tetrahydrofuran-3-yl]hexahydropyrimidin-4-one;
(6S)-6-(3-Anilino-2-chloro-phenyl)-2-imino-6-methyl-3-[(3S or 3R*)-tetrahydrofuran-3-yl]hexahydropyrimidin-4-one;
(6S)-6[2-Chloro-3-(3-chloro-anilino)phenyl]-2-imino-6-methyl-3-(tetrahydropyran-4-yl)hexahydropyrimidin-4-one;
(6S)-6[2-Chloro-3-(3-methyl-anilino)phenyl]-2-imino-6-methyl-3-(tetrahydropyran-4-yl)hexahydropyrimidin-4-one;

3-{2-Chloro-3-[(4S)-2-imino-4-methyl-6-oxo-1-(tetra-hydro-pyran-4-yl)hexahydropyrimidin-4-yl]anilino}benzonitrile;

(6S)-6[2-Chloro-3-(4-fluoro-3-methylanilino)phenyl]-2-imino-6-methyl-3-(tetrahydropyran-4-yl)hexahydropyrimidin-4-one;

(6S)-6-{2-Chloro-3-[4-(tri-fluoromethyl)anilino]phenyl}-2-imino-6-methyl-3-(tetrahydro-pyran-4-yl)hexahydropyrimidin-4-one;

(6S)-6-[2-Chloro-3-(4-fluoro-anilino)phenyl]-2-imino-6-methyl-3-(tetrahydropyran-4-yl)hexahydropyrimidin-4-one;

(6S)-6-(3-Anilino-2-chloro-phenyl)-3-(3-hydroxy-3-methyl-cyclobutyl)-2-imino-6-methyl-hexahydropyrimidin-4-one;

(6S)-6-{2-Chloro-3-[(6-methyl-pyridin-3-yl)amino]phenyl}-2-imino-6-methyl-3-(tetrahydro-pyran-4-yl)hexahydropyrimidin-4-one;

(6S)-6-[2-Chloro-3-(2-chloro-anilino)phenyl]-2-imino-6-methyl-3-(tetrahydropyran-4-yl)hexahydropyrimidin-4-one;

(6S)-6-{2-Chloro-3-[2-(trifluoromethyl)anilino]-phenyl}-2-imino-6-methyl-3-(tetrahydropyran-4-yl)-hexahydropyrimidin-4-one;

2-{2-Chloro-3-[(4S)-2-imino-4-methyl-6-oxo-1-(tetra-hydro-pyran-4-yl)hexahydropyrimidin-4-yl]anilino}benzonitrile;

4-{2-Chloro-3-[(4S)-2-imino-4-methyl-6-oxo-1-(tetra-hydro-pyran-4-yl)hexahydropyrimidin-4-yl]anilino}benzonitrile;

(6S)-6-{2-Chloro-3-[(2-methyl-pyrimidin-5-yl)amino]phenyl}-2-imino-6-methyl-3-(tetrahydro-pyran-4-yl)hexahydropyrimidin-4-one;

(6S)-6-[2-Chloro-3-(pyridin-3-ylamino)phenyl]-2-imino-6-methyl-3-(tetrahydropyran-4-yl)hexahydropyrimidin-4-one;

(6S)-6-[2-Chloro-3-(quinolin-5-ylamino)phenyl]-2-imino-6-methyl-3-(tetrahydropyran-4-yl)hexahydropyrimidin-4-one;

(6S)-6-{2-Chloro-3-[2-fluoro-5-(trifluoromethoxy)anilino]-phenyl}-2-imino-6-methyl-3-(tetrahydropyran-4-yl)-hexahydropyrimidin-4-one;

(6S)-6-[2-Chloro-3-(3-fluoro-5-methoxyanilino)phenyl]-2-imino-6-methyl-3-(tetrahydro-pyran-4-yl)hexahydropyrimidin-4-one;

2-Chloro-4-{2-chloro-3-[(4S)-2-imino-4-methyl-6-oxo-1-(tetrahydropyran-4-yl)-hexahydropyrimidin-4-yl]-anilino}benzonitrile;

(6S)-6-(2-Chloro-3-{[6-(morpholin-4-yl)pyridin-3-yl]amino}phenyl)-2-imino-6-methyl-3-(tetrahydropyran-4-yl)hexahydropyrimidin-4-one;

(6S)-6-(2-Chloro-3-{[2-(trifluoromethyl)pyridin-3-yl]amino}phenyl)-2-imino-6-methyl-3-(tetrahydropyran-4-yl)hexahydropyrimidin-4-one;

(6S)-6-[2-Chloro-3-(5-fluoro-2-methoxyanilino)phenyl]-2-imino-6-methyl-3-(tetrahydro-pyran-4-yl)hexahydropyrimidin-4-one;

(6S)-6-{2-Chloro-3-[(2-methyl-pyridin-3-yl)amino]phenyl}-2-imino-6-methyl-3-(tetrahydro-pyran-4-yl)hexahydropyrimidin-4-one;

(6S)-6-{2-Chloro-3-[(2-fluoro-pyridin-4-yl)amino]phenyl}-2-imino-6-methyl-3-(tetrahydro-pyran-4-yl)hexahydropyrimidin-4-one;

(6S)-6-[2-Chloro-3-(quinolin-3-ylamino)phenyl]-2-imino-6-methyl-3-(tetrahydropyran-4-yl)hexahydropyrimidin-4-one;

(6S)-6-(2-Chloro-3-{[6-(trifluoromethyl)pyridin-3-yl]amino}phenyl)-2-imino-6-methyl-3-(tetrahydropyran-4-yl)hexahydropyrimidin-4-one;

(6S)-6-(2-Chloro-3-{[2-chloro-5-(trifluoromethyl)pyridin-3-yl]amino}phenyl)-2-imino-6-methyl-3-(tetrahydropyran-4-yl)hexahydropyrimidin-4-one;

(6S)-6-[2-Chloro-3-(4-chloro-3-fluoroanilino)phenyl]-2-imino-6-methyl-3-(tetrahydropyran-4-yl)hexahydropyrimidin-4-one;

3-Chloro-5-{2-chloro-3-[(4S)-2-imino-4-methyl-6-oxo-1-(tetrahydropyran-4-yl)-hexahydropyrimidin-4-yl]-anilino}benzonitrile;

(6S)-6-[2-Chloro-3-(imidazo-[1,2-a]pyridin-2-ylamino)-phenyl]-2-imino-6-methyl-3-(tetrahydropyran-4-yl)-hexahydropyrimidin-4-one;

(6S)-6-[2-Chloro-3-(2-fluoro-anilino)phenyl]-2-imino-6-methyl-3-(tetrahydropyran-4-yl)hexahydropyrimidin-4-one;

(6S)-6-{2-Chloro-3-[4-(difluoro-methoxy)anilino]phenyl}-2-imino-6-methyl-3-(tetrahydro-pyran-4-yl)hexahydropyrimidin-4-one;

(6S)-6-[2-Chloro-3-(2,4,5-trifluoroanilino)phenyl]-2-imino-6-methyl-3-(tetrahydro-pyran-4-yl)hexahydropyrimidin-4-one;

(6S)-6-[2-Chloro-3-(4-methyl-sulfonylanilino)phenyl]-2-imino-6-methyl-3-(tetrahydro-pyran-4-yl)hexahydropyrimidin-4-one;

5-{2-Chloro-3-[(4S)-2-imino-4-methyl-6-oxo-1-(tetra-hydro-pyran-4-yl)hexahydropyrimidin-4-yl]anilino}pyridine-2-carbonitrile;

(6S)-6-[2-Chloro-3-(3-methyl-sulfonylanilino)phenyl]-2-imino-6-methyl-3-(tetrahydro-pyran-4-yl)hexahydropyrimidin-4-one;

(6S)-6-(2-Chloro-3-{[6-(difluoromethoxy)pyridin-3-yl]amino}phenyl)-2-imino-6-methyl-3-(tetrahydropyran-4-yl)hexahydropyrimidin-4-one;

(6S)-6-[2-Chloro-3-(2-methyl-sulfonylanilino)phenyl]-2-imino-6-methyl-3-(tetrahydro-pyran-4-yl)hexahydropyrimidin-4-one;

(6S)-6-{2-Chloro-3-[(5-methyl-pyrazin-2-yl)amino]phenyl}-2-imino-6-methyl-3-(tetrahydro-pyran-4-yl)hexahydropyrimidin-4-one;

(6S)-6-(2-Chloro-3-{[6-(trifluoromethoxy)pyridin-3-yl]amino}phenyl)-2-imino-6-methyl-3-(tetrahydropyran-4-yl)hexahydropyrimidin-4-one;

(6S)-6-[2-Chloro-3-(isoquinolin-4-ylamino)phenyl]-2-imino-6-methyl-3-(tetrahydropyran-4-yl)hexahydropyrimidin-4-one;

4-{2-Chloro-3-[(4S)-2-imino-4-methyl-6-oxo-1-(tetra-hydro-pyran-4-yl)hexahydropyrimidin-4-yl]anilino}-3-methoxy-benzonitrile;

3-{2-Chloro-3-[(4S)-2-imino-4-methyl-6-oxo-1-(tetra-hydro-pyran-4-yl)hexahydropyrimidin-4-yl]anilino}pyridine-4-carbonitrile;

(6S)-6-{2-Chloro-3-[(5-fluoro-6-methoxypyridin-3-yl)amino]-phenyl}-2-imino-6-methyl-3-(tetrahydropyran-4-yl)-hexahydropyrimidin-4-one;

(6S)-6-{2-Chloro-3-[(2-methoxypyridin-3-yl)amino]-phenyl}-2-imino-6-methyl-3-(tetrahydropyran-4-yl)-hexahydropyrimidin-4-one;

3-{2-Chloro-3-[(4S)-2-imino-4-methyl-6-oxo-1-(tetra-hydro-pyran-4-yl)hexahydropyrimidin-4-yl]anilino}pyridine-2-carbo-nitrile;

(6S)-6-(2-Chloro-3-{[2-(trifluoromethyl)pyrimidin-5-yl]amino}phenyl)-2-imino-6-methyl-3-(tetrahydropyran-4-yl)hexahydropyrimidin-4-one;

(6S)-6-{2-Chloro-3-[2-(trifluoromethoxy)anilino]-phenyl}-2-imino-6-methyl-3-(tetrahydropyran-4-yl)-hexahydropyrimidin-4-one;
(6S)-6-{2-Chloro-3-[(4-methoxypyridin-3-yl)amino]phenyl}-2-imino-6-methyl-3-(tetrahydropyran-4-yl)-hexahydropyrimidin-4-one;
(6S)-6-{2-Chloro-3-[(2-methoxy-6-methylpyridin-3-yl)amino]phenyl}-2-imino-6-methyl-3-(tetrahydropyran-4-yl)hexahydropyrimidin-4-one;
(6S)-6-(2-Chloro-3-{[4-(trifluoromethyl)pyridin-3-yl]amino}phenyl)-2-imino-6-methyl-3-(tetrahydropyran-4-yl)hexahydropyrimidin-4-one;
(6S)-6-[2-Chloro-3-(1-naphthyl-amino)phenyl]-2-imino-6-methyl-3-(tetrahydropyran-4-yl)hexahydropyrimidin-4-one;
(6S)-6-[2-Chloro-3-(3-phenyl-anilino)phenyl]-2-imino-6-methyl-3-(tetrahydropyran-4-yl)hexahydropyrimidin-4-one;
(6S)-6-[3-(1,3-Benzodioxol-5-ylamino)-2-chlorophenyl]-2-imino-6-methyl-3-(tetrahydro-pyran-4-yl)hexahydropyrimidin-4-one;
(6S)-6-{2-Chloro-3-[(6-chloro-pyridin-3-yl)amino]phenyl}-2-imino-6-methyl-3-(tetrahydro-pyran-4-yl)hexahydropyrimidin-4-one;
(6S)-6-{2-Chloro-3-[3-(isoxazol-5-yl)anilino]phenyl}-2-imino-6-methyl-3-(tetrahydro-pyran-4-yl)hexahydropyrimidin-4-one;
(6S)-6-{3-[(2-tert-Butyl-pyrimidin-5-yl)amino]-2-chloro-phenyl}-2-imino-6-methyl-3-(tetrahydropyran-4-yl)-hexahydropyrimidin-4-one;
(6S)-6-{2-Chloro-3-[3-(difluoro-methoxy)anilino]phenyl}-2-imino-6-methyl-3-(tetrahydro-pyran-4-yl)hexahydropyrimidin-4-one;
(6S)-6-{2-Chloro-3-[4-(trifluoromethoxy)anilino]-phenyl}-2-imino-6-methyl-3-(tetrahydropyran-4-yl)-hexahydropyrimidin-4-one;
(6S)-6-{3-[(1-Acetylindolin-5-yl)amino]-2-chlorophenyl}-2-imino-6-methyl-3-(tetrahydro-pyran-4-yl)hexahydropyrimidin-4-one;
(6S)-6-{2-Chloro-3-[2-(difluoro-methoxy)anilino]phenyl}-2-imino-6-methyl-3-(tetrahydro-pyran-4-yl)hexahydropyrimidin-4-one;
(6S)-6-[3-(4-tert-Butylanilino)-2-chlorophenyl]-2-imino-6-methyl-3-(tetrahydropyran-4-yl)hexahydropyrimidin-4-one;
(6S)-6-[3-(4-tert-Butylanilino)-2-chlorophenyl]-2-imino-6-methyl-3-(tetrahydropyran-4-yl)hexahydropyrimidin-4-one;
(6S)-6-{2-Chloro-3-[(2,2-difluoro-1,3-benzodioxol-4-yl)amino]phenyl}-2-imino-6-methyl-3-tetrahydropyran-4-yl-hexahydropyrimidin-4-one;
(6S)-6-[2-Chloro-3-(2,6-dimethylanilino)phenyl]-2-imino-6-methyl-3-(tetrahydro-pyran-4-yl)hexahydropyrimidin-4-one;
(6S)-6-{2-Chloro-3-[(4-fluoro-pyrazolo[1,5-a]pyridin-6-yl)-amino]phenyl}2-imino-6-methyl-3-(tetrahydropyran-4-yl)hexahydropyrimidin-4-one;
(6S)-6-{2-Chloro-3-[(4-phenyl-anilino]phenyl}-2-imino-6-methyl-3-(tetrahydropyran-4-yl)hexahydropyrimidin-4-one;
(6S)-6-(2-Chloro-3-{[6-(dimethylamino)pyridin-3-yl]amino}phenyl)-2-imino-6-methyl-3-(tetrahydropyran-4-yl)hexahydropyrimidin-4-one;
(6S)-6-{2-Chloro-3-[(1-methyl-2-oxopyridin-4-yl)amino]-phenyl}-2-imino-6-methyl-3-(tetrahydropyran-4-yl)-hexahydropyrimidin-4-one;
(6S)-6-[2-Chloro-3-(2-isopropoxyanilino)phenyl]-2-imino-6-methyl-3-(tetrahydro-pyran-4-yl)hexahydropyrimidin-4-one;
(6S)-6-[2-Chloro-3-(3-phenoxy-anilino)phenyl]-2-imino-6-methyl-3-(tetrahydropyran-4-yl)hexahydropyrimidin-4-one;
(6S)-6-[2-Chloro-3-(2-isopropoxyanilino)phenyl]-2-imino-6-methyl-3-(tetrahydro-pyran-4-yl)hexahydropyrimidin-4-one;
(6S)-6-{2-Chloro-3-[(2-methyl-indazol-4-yl)amino]phenyl}-2-imino-6-methyl-3-(tetrahydro-pyran-4-yl)hexahydropyrimidin-4-one;
(6S)-6-{2-Chloro-3-[(2-methyl-indazol-5-yl)amino]phenyl}-2-imino-6-methyl-3-(tetrahydro-pyran-4-yl)hexahydropyrimidin-4-one;
(6S)-6-{2-Chloro-3-[3-(2-oxo-pyrrolidin-1-yl)anilino]phenyl}-2-imino-6-methyl-3-(tetrahydro-pyran-4-yl)hexahydropyrimidin-4-one;
(6S)-6-{2-Chloro-3-[4-(5-methyl-1,3,4-oxadiazol-2-yl)-anilino]phenyl}-2-imino-6-methyl-3-(tetrahydropyran-4-yl)hexahydropyrimidin-4-one;
(6S)-6-(2-Chloro-3-{[6-(difluoromethyl)pyridin-3-yl]-amino}phenyl)-2-imino-6-methyl-3-tetrahydropyran-4-yl-hexahydropyrimidin-4-one;
2-{2-Chloro-3-[(4S)-2-imino-4-methyl-6-oxo-1-(tetrahydro-pyran-4-yl)hexahydropyrimidin-4-yl]anilino}-5-fluorobenzo-nitrile;
2-{2-Chloro-3-[(4S)-2-imino-4-methyl-6-oxo-1-(tetrahydro-pyran-4-yl)hexahydropyrimidin-4-yl]anilino}-5-(trifluoro-methy)benzonitrile;
(6S)-6-{2-Chloro-3-[(6-methyl-pyridazin-3-yl)amino]phenyl}-2-imino-6-methyl-3-(tetrahydro-pyran-4-yl)hexahydropyrimidin-4-one;
(6S)-6-[2-Chloro-3-([1,2,4]-triazolo[1,5-a]pyridin-6-ylamino)phenyl]-2-imino-6-methyl-3-(tetrahydropyran-4-yl)hexahydropyrimidin-4-one;
(6S)-6-{2-Chloro-3-[(4-methyl-2,3-dihydro-1,4-benzoxazin-7-yl)amino]phenyl}-2-imino-6-methyl-3-(tetrahydropyran-4-yl)hexahydropyrimidin-4-one;
(6S)-6-{2-Chloro-3-[(2-methoxypyridin-4-yl)amino]phenyl}-2-imino-6-methyl-3-(tetrahydropyran-4-yl)-hexahydropyrimidin-4-one;
3-{2-Chloro-3-[(4S)-2-imino-4-methyl-6-oxo-1-(tetrahydro-pyran-4-yl)hexahydropyrimidin-4-yl]anilino}-6-methylpyridine-2-carbonitrile;
3-{2-Chloro-3-[(4S)-2-imino-4-methyl-6-oxo-1-(tetrahydro-pyran-4-yl)hexahydropyrimidin-4-yl]anilino}quinoline-4-carbonitrile;
(6S)-6-{2-Chloro-3-[(1-methyl-isoquinolin-4-yl)amino]phenyl}-2-imino-6-methyl-3-(tetrahydro-pyran-4-yl)hexahydropyrimidin-4-one;
(6S)-6-[2-Chloro-3-(pyrazolo-[1,5-a]pyridin-5-ylamino)-phenyl]-2-imino-6-methyl-3-(tetrahydropyran-4-yl)-hexahydropyrimidin-4-one;
(6S)-6-{2-Chloro-3-[2-(difluoro-methoxy)-4-fluoro-anilino]-phenyl}-2-imino-6-methyl-3-(tetrahydropyran-4-yl)-hexahydropyrimidin-4-one;
(6S)-6-(2-Chloro-3-{[6-methyl-5-(trifluoromethyl)pyridin-3-yl]-amino}phenyl)-2-imino-6-methyl-3-(tetrahydropyran-4-yl)hexahydropyrimidin-4-one;
(6S)-6-(2-Chloro-3-{[2-(difluoromethoxy)-6-methylpyridin-3-yl]amino}phenyl)-2-imino-6-methyl-3-(tetrahydro-pyran-4-yl)hexahydropyrimidin-4-one;
(6S)-6-(2-Chloro-3-{[1-(difluoromethoxy)isoquinolin-4-yl]amino}phenyl)-2-imino-6-methyl-3-(tetrahydropyran-4-yl)hexahydropyrimidin-4-one;

4-{2-Chloro-3-[(4S)-2-imino-4-methyl-6-oxo-1-(tetra-hydro-pyran-4-yl)hexahydropyrimidin-4-yl]anilino}-3-(difluoro-methoxy)benzonitrile;

(6S)-6-(2-Chloro-3-{[2-(difluoromethoxy)pyridin-3-yl]-amino}phenyl)-2-imino-6-methyl-3-(tetrahydropyran-4-yl)hexahydropyrimidin-4-one;

(6S)-6-(2-Chloro-3-{[2-(difluoromethoxy)quinolin-3-yl]amino}phenyl)-2-imino-6-methyl-3-(tetrahydropyran-4-yl)hexahydropyrimidin-4-one;

(6S)-6-{2-Chloro-3-[(6-cyclo-propylpyridin-3-yl)amino]-phenyl}-2-imino-6-methyl-3-(tetrahydropyran-4-yl)-hexahydropyrimidin-4-one;

3-{2-Chloro-3-[(4S)-2-imino-4-methyl-6-oxo-1-(tetra-hydro-pyran-4-yl)hexahydropyrimidin-4-yl]anilino}-6-(difluoro-methyl)pyridine-2-carbonitrile;

(6S)-6-(2-Chloro-3-{[3-(difluoromethoxy)pyrazin-2-yl]-amino}phenyl)-2-imino-6-methyl-3-(tetrahydropyran-4-yl)hexahydropyrimidin-4-one;

(6S)-6-(2-Chloro-3-{[3-(difluoromethoxy)pyridin-2-yl]-amino}phenyl)-2-imino-6-methyl-3-(tetrahydropyran-4-yl)hexahydropyrimidin-4-one;

1-(5-{2-Chloro-3-[(4S)-2-imino-4-methyl-6-oxo-1-(tet-rahydro-pyran-4-yl)hexahydropyrimidin-4-yl]anilino}pyridin-2-yl)-cyclobutanecarbonitrile;

(6S)-6-{2-Chloro-3-[4-fluoro-2-(methylsulfonyl)an-ilino]-phenyl}-2-imino-6-methyl-3-(tetrahydropyran-4-yl)-hexahydropyrimidin-4-one;

(6S)-6-{3-[(6-tert-Butylpyridin-3-yl)amino]-2-chloro-phenyl}-2-imino-6-methyl-3-(tetrahydro-pyran-4-yl)hexahydropyrimidin-4-one;

(6S)-6-{2-Chloro-3-[(6-cyclo-butylpyridin-3-yl)amino]-phenyl}-2-imino-6-methyl-3-(tetrahydropyran-4-yl)-hexahydropyrimidin-4-one;

(6S)-6-{3-[(5-tert-Butylpyrazin-2-yl)amino]-2-chloro-phenyl}-2-imino-6-methyl-3-(tetrahydro-pyran-4-yl)hexahydropyrimidin-4-one;

(6S)-6-[2-Chloro-3-(imidazo-[1,2-a]pyridin-7-ylamino)-phenyl]-2-imino-6-methyl-3-(tetrahydropyran-4-yl)-hexahydropyrimidin-4-one;

(6S)-6-[2-Chloro-3-(2-{[dimethyl(oxo)-λ6-sulfa-nylidene]amino}anilino)-phenyl]-2-imino-6-methyl-3-(tetrahydropyran-4-yl)-hexahydropyrimidin-4-one;

(6S)-6-{2-Chloro-3-[(4-chloro-6-methylpyridin-3-yl)amino]-phenyl}-2-imino-6-methyl-3-(tetrahydropyran-4-yl)-hexahydropyrimidin-4-one;

(6S)-6-{2-Chloro-3-[(6-ethyl-pyridin-3-yl)amino]phenyl}-2-imino-6-methyl-3-(tetrahydro-pyran-4-yl)hexa-hydropyrimidin-4-one;

(6S)-6-(2-Chloro-3-{[6-(2,2,2-trifluoroethoxy)pyridin-3-yl]-amino}phenyl)-2-imino-6-methyl-3-(tetrahydropyran-4-yl)hexahydropyrimidin-4-one;

(6S)-6-(3-{[6-(Azetidin-1-yl)-pyridin-3-yl]amino}-2-chloro-phenyl)-2-imino-6-methyl-3-(tetrahydropyran-4-yl)-hexahydropyrimidin-4-one;

(6S)-6-(2-Chloro-3-{[6-(1,2,4-triazol-1-yl)pyridin-3-yl]-amino}phenyl)-2-imino-6-methyl-3-(tetrahydropyran-4-yl)hexahydropyrimidin-4-one;

(6S)-6-{2-Chloro-3-[(1-methyl-pyrazolo[3,4-b]pyridin-5-yl)-amino]phenyl}-2-imino-6-methyl-3-(tetrahydro-pyran-4-yl)hexahydropyrimidin-4-one;

(6S)-6-{2-Chloro-3-[(3-methyl-imidazo[4,5-b]pyridin-6-yl)-amino]phenyl}-2-imino-6-methyl-3-(tetrahydropyran-4-yl)hexahydropyrimidin-4-one;

(6S)-6-(2-Chloro-3-{[6-(2-methyltetrazol-5-yl)pyridin-3-yl]amino}phenyl)-2-imino-6-methyl-3-(tetrahydropyran-4-yl)hexahydropyrimidin-4-one;

(6S)-6-{2-Chloro-3-[4-chloro-2-(methylsulfonyl)an-ilino]-phenyl}-2-imino-6-methyl-3-(tetrahydropyran-4-yl)-hexahydropyrimidin-4-one;

(6S)-6-(2-Chloro-3-{[6-(2,2,2-trifluoroethyl)pyridin-3-yl]-amino}phenyl)-2-imino-6-methyl-3-(tetrahydropyran-4-yl)hexahydropyrimidin-4-one;

(6S)-6-[2-Chloro-3-(2,4-difluoroanilino)phenyl]-3-(3-hy-droxy-3-methylcyclobutyl)-2-imino-6-methylhexa-hydro-pyrimidin-4-one;

4-{2-Chloro-3-[(4S)-1-(3-hydroxy-3-methylcyclobutyl)-2-imino-4-methyl-6-oxo-hexahydropyrimidin-4-yl]-anilino}-2-fluorobenzonitrile;

5-{2-Chloro-3-[(4S)-1-(3-hydroxy-3-methylcyclobutyl)-2-imino-4-methyl-6-oxo-hexahydropyrimidin-4-yl]-anilino}pyridine-2-carbonitrile;

4-{2-Chloro-3-[(4S)-1-(3-hydroxy-3-methylcyclobutyl)-2-imino-4-methyl-6-oxo-hexahydropyrimidin-4-yl]-anilino}benzonitrile;

(6S)-6-(2-Chloro-3-{[6-(trifluoromethyl)pyridin-3-yl]-amino}phenyl)-3-(3-hydroxy-3-methylcyclobutyl)-2-imino-6-methylhexahydropyrimidin-4-one;

(6S)-6-{2-Chloro-3-[(6-methyl-pyridin-3-yl)amino]phe-nyl}-3-(3-hydroxy-3-methylcyclo-butyl)-2-imino-6-methyl-hexahydropyrimidin-4-one;

(6S)-6-{2-Chloro-3-[(5-fluoro-pyridin-2-yl)amino]phe-nyl}-3-(3-hydroxy-3-methylcyclo-butyl)-2-imino-6-methyl-hexahydropyrimidin-4-one;

2-{2-Chloro-3-[(4S)-1-(3-hydroxy-3-methylcyclobutyl)-2-imino-4-methyl-6-oxo-hexahydropyrimidin-4-yl]-anilino}-5-fluorobenzonitrile;

(6S)-6-(2-Chloro-3-{[6-(difluoromethoxy)pyridin-3-yl]-amino}phenyl)-3-(3-hydroxy-3-methylcyclobutyl)-2-imino-6-methylhexahydropyrimidin-4-one;

(6S)-6-{2-Chloro-3-[(5-methyl-pyrazin-2-yl)amino]phe-nyl}-3-(3-hydroxy-3-methylcyclo-butyl)-2-imino-6-methyl-hexahydropyrimidin-4-one;

(6S)-6-(2-Chloro-3-{[6-(trifluoromethoxy)pyridin-3-yl]-amino}phenyl)-3-(3-hydroxy-3-methylcyclobutyl)-2-imino-6-methylhexahydropyrimidin-4-one;

(6S)-6-(2-Chloro-3-{[2-(trifluoromethyl)pyridin-4-yl]amino}phenyl)-3-(3-hydroxy-3-methylcyclobutyl)-2-imino-6-methylhexahydropyrimidin-4-one;

(6S)-6-[2-Chloro-3-(pyrazolo-[1,5-a]pyridin-5-ylamino)-phenyl]-3-(3-hydroxy-3-methyl-cyclobutyl)-2-imino-6-methyl-hexahydropyrimidin-4-one;

4-{2-Chloro-3-[(4S)-1-(3-hydroxy-3-methylcyclobutyl)-2-imino-4-methyl-6-oxo-hexahydropyrimidin-4-yl]-anilino}-3-(difluoromethoxy)-benzonitrile;

(6S)-6-{2-Chloro-3-[(6-methyl-pyridin-3-yl)amino]phe-nyl}-3-(3-hydroxy-3-isopropylcyclo-butyl)-2-imino-6-methyl-hexahydropyrimidin-4-one;

(6S)-6-{2-Chloro-3-[(6-methyl-pyridin-3-yl)amino]phe-nyl}-2-imino-6-methyl-3-[(cis)-2-methyltetrahydropy-ran-4-yl]-hexahydropyrimidin-4-one;

(6S)-6-{2-Chloro-3-[(6-methyl-pyridin-3-yl)amino]phe-nyl}-2-imino-6-methyl-3-[(cis)-2-methyltetrahydropy-ran-4-yl]-hexahydropyrimidin-4-one;

(6S)-6-{2-Chloro-3-[(4-fluoro-pyrazolo[1,5-a]pyridin-6-yl)-amino]phenyl}-2-imino-6-methyl-3-[(cis)-2-methyl-tetrahydropyran-4-yl]-hexahydropyrimidin-4-one;

(6S)-6-(2-Chloro-3-{[6-(difluoromethoxy)pyridin-3-yl]-amino}phenyl)-2-imino-6-methyl-3-[(cis)-2-methyl-tetrahydropyran-4-yl]-hexahydropyrimidin-4-one;

(6S)-6-{2-Chloro-3-[(6-methyl-pyridin-3-yl)amino]phe-nyl}-3-(4,4-difluorocyclohexyl)-2-imino-6-methyl-hexahydro-pyrimidin-4-one;

(6S)-6-(2-Chloro-3-{[6-(difluoromethoxy)pyridin-3-yl]-amino}phenyl)-3-(4,4-difluoro-cyclohexyl)-2-imino-6-methyl-hexahydropyrimidin-4-one;
(6S)-6-{3-[(2-tert-Butyl-pyrimidin-5-yl)amino]-2-chloro-phenyl}-3-(4,4-difluoro-cyclohexyl)-2-imino-6-methyl-hexahydropyrimidin-4-one;
(6S)-6-{2-Chloro-3-[(6-cyclo-propylpyridin-3-yl)amino]-phenyl}-3-(4,4-difluoro-cyclohexyl)-2-imino-6-methyl-hexahydropyrimidin-4-one;
(6S)-6-(2-Chloro-3-{[6-(difluoromethoxy)pyridin-3-yl]-amino}phenyl)-3-[(4R*)-2,2-dimethyltetrahydropyran-4-yl]-2-imino-6-methylhexahydro-pyrimidin-4-one;
(6S)-6-(2-Chloro-3-{[6-(difluoromethoxy)pyridin-3-yl]-amino}phenyl)-3-[(4S*)-2,2-dimethyltetrahydropyran-4-yl]-2-imino-6-methylhexahydro-pyrimidin-4-one;
(6S)-6-{2-Chloro-3-[(6-methyl-pyridin-3-yl)amino]phenyl}-3-[(4R*)-2,2-dimethyltetrahydro-pyran-4-yl]-2-imino-6-methyl-hexahydropyrimidin-4-one;
(6S)-6-{2-Chloro-3-[(6-methyl-pyridin-3-yl)amino]phenyl}-3-[(4S*)-2,2-dimethyltetrahydro-pyran-4-yl]-2-imino-6-methyl-hexahydropyrimidin-4-one;
(6S)-6-{2-Chloro-3-[(6-cyclo-propylpyridin-3-yl)amino]-phenyl}-3-[(4S*)-2,2-dimethyl-tetrahydropyran-4-yl]-2-imino-6-methylhexahydropyrimidin-4-one;
(6S)-6-{3-[(6-tert-Butylpyridin-3-yl)amino]-2-chloro-phenyl}-3-[(4S*)-2,2-dimethyltetrahydro-pyran-4-yl]-2-imino-6-methyl-hexahydropyrimidin-4-one;
(6S)-6-{3-[(5-tert-Butylpyrazin-2-yl)amino]-2-chloro-phenyl}-3-[(4S*)-2,2-dimethyltetrahydro-pyran-4-yl]-2-imino-6-methyl-hexahydropyrimidin-4-one;
(6S)-6-{2-Chloro-3-[(6-cyclo-propylpyridazin-3-yl)amino]-phenyl}-3-[(4S*)-2,2-dimethyl-tetrahydropyran-4-yl]-2-imino-6-methylhexahydropyrimidin-4-one;
(6S)-6-{2-Chloro-3-[(5-cyclo-propylpyrazin-2-yl)amino]-phenyl}-3-[(4S*)-2,2-dimethyl-tetrahydropyran-4-yl]-2-imino-6-methylhexahydropyrimidin-4-one;
(6S)-6-{2-Chloro-3-[(6-methyl-pyridin-3-yl)amino]phenyl}-3-[3-hydroxy-3-(trifluoromethyl)-cyclobutyl]-2-imino-6-methyl-hexahydropyrimidin-4-one (cis isomer);
(6S)-6-{2-Chloro-3-[(6-methyl-pyridin-3-yl)amino]phenyl}-3-[3-hydroxy-3-(trifluoromethyl)-cyclobutyl]-2-imino-6-methyl-hexahydropyrimidin-4-one (trans isomer);
(6S)-6-{2-Chloro-3-[(6-cyclo-propylpyridin-3-yl)amino]-phenyl}-3-[3-hydroxy-3-(trifluoromethyl)cyclobutyl]-2-imino-6-methylhexahydro-pyrimidin-4-one (cis isomer);
(6S)-6-{2-Chloro-3-[(4-chloro-anilino]phenyl}-2-imino-6-methyl-3-[(2R*,4R*)-2-methyl-tetrahydropyran-4-yl]-hexahydropyrimidin-4-one;
(6S)-6-(2-Chloro-3-{[6-(difluoromethoxy)pyridin-3-yl]-amino}phenyl)-2-imino-6-methyl-3-[(1SR,5RS)-8-oxa-bicyclo[3.2.1]octan-3-yl]-hexahydropyrimidin-4-one;
(6S)-6-{2-Chloro-3-[(6-methyl-pyridin-3-yl)amino]phenyl}-2-imino-6-methyl-3-[(1SR,5RS)-8-oxabicyclo[3.2.1]octan-3-yl]-hexahydropyrimidin-4-one;
(6S)-6-{2-Chloro-3-[(6-cyclo-propylpyridin-3-yl)amino]-phenyl}-3-[(4S*)-2,2-dimethyltetrahydropyran-4-yl]-2-imino-6-methylhexahydropyrimidin-4-one;
(6S)-6-[2-Chloro-3-(4-methoxy-anilino)phenyl]-2-imino-6-methyl-3-(tetrahydropyran-4-yl)hexahydropyrimidin-4-one;
(6S)-6-[2-Chloro-3-(4-methyl-anilino)phenyl]-2-imino-6-methyl-3-(tetrahydropyran-4-yl)hexahydropyrimidin-4-one;
(6S)-6-[2-Chloro-3-(3,5-dimethoxyanilino)phenyl]-2-imino-6-methyl-3-(tetrahydro-pyran-4-yl)hexahydropyrimidin-4-one;
(6S)-6-[2-Chloro-3-(4-chloro-anilino)phenyl]-2-imino-6-methyl-3-(tetrahydropyran-4-yl)hexahydropyrimidin-4-one;
(6S)-6-{2-Chloro-3-[3-(trifluoromethyl)anilino]-phenyl}-2-imino-6-methyl-3-(tetrahydropyran-4-yl)-hexahydropyrimidin-4-one;
(6S)-6-[2-Chloro-3-(3,4-dimethoxyanilino)phenyl]-2-imino-6-methyl-3-(tetrahydro-pyran-4-yl)hexahydropyrimidin-4-one;
(6S)-6-[2-Chloro-3-(2-methyl-anilino)phenyl]-2-imino-6-methyl-3-(tetrahydropyran-4-yl)hexahydropyrimidin-4-one;
Methyl 3-{2-chloro-3-[(4S)-2-imino-4-methyl-6-oxo-1-(tetrahydropyran-4-yl)-hexahydropyrimidin-4-yl]-anilino}benzoate;
(6S)-6-[2-Chloro-3-(3-chloro-4-fluoroanilino)phenyl]-2-imino-6-methyl-3-(tetrahydropyran-4-yl)hexahydropyrimidin-4-one;
(6S)-6-[2-Chloro-3-(3-fluoro-anilino)phenyl]-2-imino-6-methyl-3-(tetrahydropyran-4-yl)hexahydropyrimidin-4-one;
(6S)-6-[2-Chloro-3-(4-fluoro-anilino)phenyl]-2-imino-6-methyl-3-[(3R*)-tetrahydro-furan-3-yl]hexahydropyrimidin-4-one;
(6S*)-6-[2-Chloro-3-(4-fluoro-anilino)phenyl]-2-imino-6-methyl-3-(tetrahydropyran-4-ylmethyl)hexahydropyrimidin-4-one;
(6S)-6-[2-Chloro-3-(4-fluoro-anilino)phenyl]-2-imino-6-methyl-3-(2-oxaspiro[3.3]-heptan-6-yl)hexahydro-pyrimidin-4-one;
(6S)-6-[2-Chloro-3-(4-fluoro-anilino)phenyl]-3-(3-hydroxy-3-methylcyclobutyl)-2-imino-6-methylhexahydropyrimidin-4-one;
(6S)-6-{2-Chloro-3-[4-(trifluoromethyl)anilino]-phenyl}-2-imino-6-methyl-3-(tetrahydropyran-4-ylmethyl)-hexahydropyrimidin-4-one;
(6S)-6-{2-Chloro-3-[4-(trifluoromethyl)anilino]-phenyl}-3-(3-hydroxy-3-methyl-cyclobutyl)-2-imino-6-methyl-hexahydropyrimidin-4-one;
(6S)-6-[2-Chloro-3-(4-fluoro-anilino)phenyl]-2-imino-6-methyl-3-[(3-methyloxetan-3-yl)methyl]hexahydropyrimidin-4-one;
(6S)-6-[2-Chloro-3-(4-chloro-anilino)phenyl]-3-(3-hydroxy-3-methylcyclobutyl)-2-imino-6-methylhexahydropyrimidin-4-one;
(6S)-6-[2-Chloro-3-(4-fluoro-anilino)phenyl]-3-(3-ethyl-3-hydroxycyclobutyl)-2-imino-6-methylhexahydropyrimidin-4-one (trans isomer);
(6S)-6-[2-Chloro-3-(4-fluoro-anilino)phenyl]-3-(3-ethyl-3-hydroxycyclobutyl)-2-imino-6-methylhexahydropyrimidin-4-one (cis isomer);
(6S)-6-[2-Chloro-3-(4-fluoro-anilino)phenyl]-3-[3-hydroxy-3-(trifluoromethyl)cyclobutyl]-2-imino-6-methyl-hexahydro-pyrimidin-4-one (cis isomer);
3-{(4S)-4-[2-Chloro-3-(4-fluoroanilino)phenyl]-2-imino-4-methyl-6-oxohexahydro-pyrimidin-1-yl}-1-methyl-cyclobutanecarbonitrile (trans isomer);

3-{(4S)-4-[2-Chloro-3-(4-fluoroanilino)phenyl]-2-imino-4-methyl-6-oxohexahydro-pyrimidin-1-yl}-1-methyl-cyclobutanecarbonitrile (cis isomer);

(6S)-6-{2-Chloro-3-[(5-chloro-pyridin-2-yl)amino]phenyl}-2-imino-6-methyl-3-(tetrahydro-yran-4-yl)-hexahydropyrimidin-4-one;

6-{2-Chloro-3-[(4S)-2-imino-4-methyl-6-oxo-1-(tetrahydro-pyran-4-yl)hexahydropyrimidin-4-yl]anilino}pyridine-3-carbonitrile;

2-{2-Chloro-3-[(4S)-2-imino-4-methyl-6-oxo-1-(tetrahydro-pyran-4-yl)hexahydropyrimidin-4-yl]anilino}pyridine-3-carbonitrile;

(6S)-6-[2-Chloro-3-(imidazo-[1,2-a]pyridin-3-ylamino)-phenyl]-2-imino-6-methyl-3-(tetrahydropyran-4-yl)-hexahydropyrimidin-4-one;

(6S)-6-{2-Chloro-3-[(3,5-dimethyl-1-phenylpyrazol-4-yl)-amino]phenyl}-2-imino-6-methyl-3-(tetrahydropyran-4-yl)hexahydropyrimidin-4-one;

(6S)-6-[2-Chloro-3-(imidazo-[1,5-a]pyridin-3-ylamino)-phenyl]-2-imino-6-methyl-3-(tetrahydropyran-4-yl)-hexahydropyrimidin-4-one;

(6S)-6-[2-Chloro-3-(4-fluoro-anilino)phenyl]-2-imino-6-methyl-3-[(1RS,2SR,4SR)-7-oxabicyclo[2.2.1]heptan-3-yl]-hexahydropyrimidin-4-one;

(6S)-6-[2-Chloro-3-(4-fluoro-anilino)phenyl]-2-imino-6-methyl-3-[(3S*)-tetrahydro-pyran-3-yl]hexahydropyrimidin-4-one;

(6S)-6-[2-Chloro-3-(4-fluoro-anilino)phenyl]-2-imino-6-methyl-3-[(3R* or 3S)-tetrahydropyran-3-yl]-hexahydropyrimidin-4-one;

(6S)-6-(2-Chloro-3-{[6-(difluoromethoxy)pyridin-3-yl]-amino}phenyl)-2-imino-6-methyl-3-[(2R*,4S*)-2-methyl-tetrahydropyran-4-yl]-hexahydropyrimidin-4-one (Peak 1);

(6S)-6-(2-Chloro-3-{[6-(difluoromethoxy)pyridin-3-yl]-amino}phenyl)-2-imino-6-methyl-3-[(2S*,4R*)-2-methyl-tetrahydropyran-4-yl]-hexahydropyrimidin-4-one (Peak 2);

(6S)-6-{2-Chloro-3-[(6-cyclo-propylpyridin-3-yl)amino]-phenyl}-2-imino-6-methyl-3-[(2R*,4S*)-2-methyltetrahydro-pyran-4-yl]hexahydropyrimidin-4-one (Peak 1);

(6S)-6-{2-Chloro-3-[(6-cyclo-propylpyridin-3-yl)amino]-phenyl}-2-imino-6-methyl-3-[(2S*,4R*)-2-methyltetrahydro-pyran-4-yl]hexahydropyrimidin-4-one (Peak 2);

(6S)-6-{2-Chloro-3-[(6-methyl-pyridin-3-yl)amino]phenyl}-2-imino-6-methyl-3-[(2R*,4S*)-2-methyltetrahydropyran-4-yl]-hexahydropyrimidin-4-one (Peak 1);

(6S)-6-{2-Chloro-3-[(6-methyl-pyridin-3-yl)amino]phenyl}-2-imino-6-methyl-3-[(2S*,4R*)-2-methyltetrahydropyran-4-yl]-hexahydropyrimidin-4-one (Peak 2);

(6S)-6-{2-Chloro-3-[(6-cyclo-propylpyridazin-3-yl)amino]phenyl}-2-imino-6-methyl-3-(tetrahydropyran-4-yl)-hexahydropyrimidin-4-one;

(6S)-6-{2-Chloro-3-[(6-cyclo-propylpyridin-3-yl)amino]-phenyl}-2-imino-6-methyl-3-[(2R*,4R*)-2-methyltetrahydro-pyran-4-yl]hexahydropyrimidin-4-one;

(6S)-6-{2-Chloro-3-[(6-cyclo-propylpyridin-3-yl)amino]phenyl}-2-imino-6-methyl-3-[(2S*,4R*)-2-methyltetrahydro-pyran-4-yl]hexahydropyrimidin-4-one;

(6S)-6-{2-Chloro-3-[(6-cyclo-propylpyridazin-3-yl)amino]-phenyl}-2-imino-6-methyl-3-[(2R*,4R*)-2-methyltetrahydro-pyran-4-yl]hexahydropyrimidin-4-one;

(6S)-6-(2-Chloro-3-{[6-(2,2,2-trifluoroethoxy)pyridin-3-yl]-amino}phenyl)-2-imino-6-methyl-3-[(2R*,4R*)-2-methyl-tetrahydropyran-4-yl]-hexahydropyrimidin-4-one;

(6S)-6-(2-Chloro-3-{[6-(2,2,2-trifluoroethoxy)pyridazin-3-yl]-amino}phenyl)-2-imino-6-methyl-3-[(2R*,4R*)-2-methyl-tetrahydropyran-4-yl]-hexahydropyrimidin-4-one;

(6S)-6-(2-Chloro-3-{[6-(2,2-difluoroethoxy)pyridin-3-yl]-amino}phenyl)-2-imino-6-methyl-3-[(2R*,4R*)-2-methyl-tetrahydropyran-4-yl]-hexahydropyrimidin-4-one;

(6S)-6-{2-Chloro-3-[(2-cyclo-propylpyrimidin-5-yl)amino]-phenyl}-2-imino-6-methyl-3-[(2R*,4R*)-2-methyltetrahydro-pyran-4-yl]hexahydropyrimidin-4-one;

(6S)-6-{2-Chloro-3-[(1-cyclo-propyl-2-oxopyridin-4-yl)-amino]phenyl}-3-[(4R*)-2,2-dimethyltetrahydropyran-4-yl]-2-imino-6-methylhexahydro-pyrimidin-4-one;

(6S)-6-[2-Chloro-4-fluoro-3-(4-fluoroanilino)phenyl]-2-imino-6-methyl-3-(tetrahydro-pyran-4-yl)hexahydro-pyrimidin-4-one;

(6S)-6-{2-Chloro-4-fluoro-3-[(6-methylpyridin-3-yl)amino]phenyl}-2-imino-6-methyl-3-(tetrahydropyran-4-yl)hexahydropyrimidin-4-one; or a pharmaceutically acceptable salt thereof.

11. A pharmaceutical composition comprising a compound of formula (I) as defined in claim 1 or a pharmaceutically acceptable salt thereof in association with a pharmaceutically acceptable carrier.

12. A method for the treatment and/or prevention of malaria, which comprises administering to a patient in need of such treatment an effective amount of a compound of formula (I) as defined in claim 1 or a pharmaceutically acceptable salt thereof.

13. A compound as claimed in claim 4 wherein $R^{16}$ represents hydrogen, halogen, cyano, $C_{1-6}$ alkyl, trifluoromethyl or $C_{1-6}$ alkoxy.

14. A compound as claimed in claim 3 wherein $R^2$ represents chloro.

15. A compound as claimed in claim 6 wherein $R^2$ represents chloro.

16. A compound as claimed in claim 8 wherein $R^2$ represents chloro.

17. A compound as claimed in claim 3 wherein $R^1$ represents $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, $C_{4-9}$ heterobicycloalkyl or $C_{4-9}$ spiroheterocycloalkyl, any of which groups may be optionally substituted by one, two or three substituents independently selected from halogen, cyano, $C_{1-6}$ alkyl, trifluoromethyl and hydroxy.

18. A compound as claimed in claim 6 wherein $R^1$ represents $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, $C_{4-9}$ heterobicycloalkyl or $C_{4-9}$ spiroheterocycloalkyl, any of which groups may be optionally substituted by one, two or three substituents independently selected from halogen, cyano, $C_{1-6}$ alkyl, trifluoromethyl and hydroxy.

* * * * *